(12) United States Patent
O'Riordan et al.

(10) Patent No.: US 12,201,698 B2
(45) Date of Patent: Jan. 21, 2025

(54) GENE THERAPY FOR RETINITIS PIGMENTOSA

(71) Applicant: Genzyme Corporation, Cambridge, MA (US)

(72) Inventors: Catherine O'Riordan, Bridgewater, NJ (US); Matthew Adamowicz, Bridgewater, NJ (US)

(73) Assignee: GENZYME CORPORATION, Cambridge, MA (US)

( * ) Notice: Subject to any disclaimer, the term of this patent is extended or adjusted under 35 U.S.C. 154(b) by 792 days.

(21) Appl. No.: 17/383,052

(22) Filed: Jul. 22, 2021

(65) Prior Publication Data
US 2022/0054657 A1    Feb. 24, 2022

Related U.S. Application Data

(62) Division of application No. 16/503,091, filed on Jul. 3, 2019, now Pat. No. 11,103,598, which is a division of application No. 15/127,757, filed as application No. PCT/US2015/021896 on Mar. 20, 2015, now Pat. No. 10,383,953.

(60) Provisional application No. 61/969,027, filed on Mar. 21, 2014.

(51) Int. Cl.
| A61K 48/00 | (2006.01) |
| A61K 9/00 | (2006.01) |
| A61K 31/7105 | (2006.01) |
| A61K 38/17 | (2006.01) |
| C12N 15/113 | (2010.01) |
| C12N 15/86 | (2006.01) |

(52) U.S. Cl.
CPC ........ *A61K 48/0058* (2013.01); *A61K 9/0019* (2013.01); *A61K 9/0048* (2013.01); *A61K 31/7105* (2013.01); *A61K 38/1709* (2013.01); *C12N 15/113* (2013.01); *C12N 15/86* (2013.01); *C12N 2310/141* (2013.01); *C12N 2320/34* (2013.01); *C12N 2330/51* (2013.01); *C12N 2750/14143* (2013.01)

(58) Field of Classification Search
None
See application file for complete search history.

(56) References Cited

U.S. PATENT DOCUMENTS

| 5,262,529 | A | 11/1993 | Dryja et al. |
| 5,985,583 | A | 11/1999 | Sealfon |
| 6,566,118 | B1 | 5/2003 | Atkinson et al. |
| 6,596,535 | B1 | 7/2003 | Carter |
| 6,989,264 | B2 | 1/2006 | Atkinson et al. |
| 6,995,006 | B2 | 2/2006 | Atkinson et al. |
| 7,125,717 | B2 | 10/2006 | Carter |
| 7,765,583 | B2 | 7/2010 | Kalonji et al. |
| 7,785,888 | B2 | 8/2010 | Carter |
| 7,790,154 | B2 | 9/2010 | Samulski et al. |
| 7,846,729 | B2 | 12/2010 | Carter |
| 8,093,054 | B2 | 1/2012 | Carter |
| 8,283,151 | B2 | 10/2012 | Schmidt et al. |
| 8,361,457 | B2 | 1/2013 | Samulski et al. |
| 8,617,876 | B2 | 12/2013 | Farrar et al. |
| 8,741,650 | B2 | 6/2014 | Iida et al. |
| 8,999,380 | B2 | 4/2015 | Bancel et al. |
| 9,078,914 | B2 | 7/2015 | Velin |
| 9,512,425 | B2 | 12/2016 | Mittal et al. |
| 10,383,953 | B2 | 8/2019 | O'Riordan et al. |
| 11,103,598 | B2 | 8/2021 | O'Riordan et al. |
| 2009/0214478 | A1 | 8/2009 | Auricchio |
| 2010/0186103 | A1 | 7/2010 | Gao |
| 2010/0190841 | A1 | 7/2010 | Farrar et al. |
| 2012/0066783 | A1 | 3/2012 | Kay et al. |
| 2012/0164106 | A1 | 6/2012 | Schaffer et al. |
| 2013/0323226 | A1 | 12/2013 | Wilson et al. |
| 2015/0105317 | A1 | 4/2015 | Lin |
| 2020/0046851 | A1 | 2/2020 | O'riordan et al. |
| 2020/0325493 | A1 | 10/2020 | Muramatsu |

FOREIGN PATENT DOCUMENTS

| CN | 101952307 A | 1/2011 |
| CN | 102573856 A | 7/2012 |
| EP | 1486567 A1 | 12/2004 |
| JP | 2013-517798 A | 5/2013 |
| JP | 6669664 B | 3/2020 |
| WO | WO-2003/042397 A2 | 5/2003 |
| WO | WO-2008/125846 A2 | 10/2008 |
| WO | WO-2010/138263 A2 | 12/2010 |
| WO | WO-2011/094198 A1 | 8/2011 |
| WO | WO-2012/057363 A1 | 5/2012 |
| WO | WO-2013/018612 A1 | 2/2013 |
| WO | WO-2013/093870 A1 | 6/2013 |
| WO | 2013123503 A1 | 8/2013 |

(Continued)

OTHER PUBLICATIONS

Powell, S. et al., Mol. Ther., 2020, vol. 28: pp. 1373-1380.*
Adamowicz, M. et al. (2012). "Development of a Cellular Model of Rod Opsin Retinitis Pigmentosa," Chapter 73 *in Retinal Degenerative Diseases, Advances in Experimental Medicine and Biology*, M.M. LaVail et al. (eds.), Springer Science+Business Media, LLC 723:573-579.
Bartel, D.P. (Jan. 23, 2004). "MicroRNAs: Genomics, Biogenesis, Mechanism, and Function" *Cell* 116(2):281-297.
Behrman, S. et al. (Mar. 14, 2011). "A CHOP-Regulated MicroRNA Controls Rhodopsin Expression" *J. Cell Biol.* 192(6):919-927.

(Continued)

*Primary Examiner* — Michael D Burkhart
(74) *Attorney, Agent, or Firm* — MORRISON & FOERSTER LLP

(57) ABSTRACT

Provided herein are methods for treating retinitis pigmentosa using an AAV particles encoding miR-708. In one aspect, viral particles are administered to the eye of a human subject; for example, by subretinal injection. Viral particles comprising AAV5 capsids or mutants thereof are contemplated.

16 Claims, 28 Drawing Sheets

Specification includes a Sequence Listing.

(56) References Cited

FOREIGN PATENT DOCUMENTS

| WO | 2013163430 A2 | 10/2013 |
|---|---|---|
| WO | WO-2013/176772 A1 | 11/2013 |
| WO | WO-2014/011210 A1 | 1/2014 |
| WO | WO-2015/143418 A2 | 9/2015 |

OTHER PUBLICATIONS

Bossis, I. et al. (Jun. 2003). "Cloning of an Avian Adeno-Associated Virus (AAAV) and Generation of Recombinant AAAV Particles," *J. Virol.* 77(12):6799-6810.

Clark, K.R. et al. (Apr. 10, 1999). "Highly Purified Recombinant Adeno-Associated Virus Vectors are Biologically Active and Free of Detectable Helper and Wild-Type Viruses," *Hum. Gene Ther.* 10(6):1031-1039.

Davidson, B.L. et al. (Mar. 28, 2000; e-pub Feb. 25, 2000). "Recombinant Adeno-Associated Virus Type 2, 4, and 5 Vectors: Transduction of Variant Cell Types and Regions in the Mammalian Central Nervous System," *PNAS* 97(7):3428-3432.

Dryja, T.P. et al. (Jan. 25, 1990). "A Point Mutation of the Rhodopsin Gene in One Form of Retinitis Pigmentosa," *Nature* 343:364-366.

Dryja, T.P. et al. (Oct. 1995). "Mutations in the Gene Encoding the α Subunit of the Rod cGMP-gated Channel in Autosomal Recessive Retinitis Pigmentosa," *Proc. Natl. Acad. Sci. U.S.A.* 92(22):10177-10181.

Farrar, G.J. et al. (Mar. 1, 2002). "On the Genetics of Retinitis Pigmentosa and on Mutation-Independent Approaches to Therapeutic Intervention," *EMBO J.* 21(5):857-864.

Farrar, G.J. et al. (Sep. 1990). "Autosomal Dominant Retinitis Pigmentosa: Linkage to Rhodopsin and Evidence for Genetic Heterogeneity," *Genomics* 8(1):35-40.

Fisher, K.J. et al. (Jan. 1996). "Transduction with Recombinant Adeno-Associated Virus for Gene Therapy is Limited by Leading-Strand Synthesis," *J. Virol.* 70(1):520-532.

Gao, G-P et al. (May 13, 2003). "Adeno-Associated Viruses Undergo Substantial Evolution in Primates During Natural Infections," *PNAS* 100(10):6081-6086.

Gao, G-P. et al. (Sep. 3, 2002). "Novel Adeno-Associated Viruses from Rhesus Monkeys as Vectors for Human Gene Therapy," *PNAS* 99(18):11854-11859.

Georgiadis, A. et al. (Apr. 2010, e-pub. Dec. 10, 2009). "AAV-mediated knockdown of Peripherin-2 in vivo using miRNA-based hairpins," 17(4):486-493.

Gray S. J. et al. (Sep. 2011). "Optimizing Promoters for Recombinant Adeno-Associated Virus-Mediated Gene Expression in the Peripheral and Central Nervous System Using Self-Complementary Vectors," *Hum. Gen. Ther.* 22(9):1143-1153.

Greenwald D. L. et al. (Apr. 2013). "Mutation-independent Rescue of a Novel Mouse Model of Retinitis Pigmentosa," *Gene Ther.* 20(4):425-434.

Gregersen, N. et al. (2006, e-pub. May 24, 2006). "Protein Misfolding and Human Disease," *Annu. Rev. Genomics Hum. Genet.* 7:103-124.

Griciuc, A. et al. (Aug. 2011, e-pub May 27, 2011). "ER Stress in Retinal Degeneration: A Target for Rational Therapy?", *Trends Mol Med* 17(8):442-451.

Guo, Z.S. et al. (Sep. 1996). "Evaluation of Promoter Strength for Hepatic Gene Expression In Vivo Following Adenovirus-Mediated Gene Transfer," *Gene Ther.* 3(9):802-810.

Humphries, M.M. et al. (Feb. 15, 1997). "Retinopathy Induced in Mice by Targeted Disruption of the Rhodopsin Gene," *Nat. Genet.* 15(2):216-219.

International Search Report mailed on Sep. 14, 2015 for PCT Application No. PCT/US2015/021896, filed on Mar. 20, 2015, 7 pages.

Kalloniatis, M. et al. (Mar. 8, 2004). "Retinitis Pigmentosa: Understanding the Clinical Presentation, Mechanisms and Treatment Options," *Clin. Exp. Optom.* 87(2):65-80.

Kay, C.N. et al. (2013). "Targeting Photoreceptors via Intravitreal Delivery Using Novel, Capsid-Mutated AAV Vectors," *PLoS ONE* 8(4): e62097.

Khani, S.C. et al. (Sep. 2007). "AAV-Mediated Expression Targeting of Rod and Cone Photoreceptors with a Human Rhodopsin Kinase Promoter," *Invest. Ophthalmol. Vis. Sci.* 48(9):3954-3961.

Kim, D.W. et al. (Jul. 16, 1990). "Use of the Human Elongation Factor 1 α Promoter as a Versatile and Efficient Expression System," *Gene* 91(2):217-223.

Kotin, R.M. (Jul. 1994). "Prospects for the Use of Adeno-Associated Virus as a Vector for Human Gene Therapy," *Hum. Gene Ther.* 5(7):793-801.

Le, Y.Z. et al. (Apr. 18, 2006). "Mouse Opsin Promoter-Directed Cre Recombinase Expression in Transgenic Mice," *Mol. Vis.* 12:389-398.

Lee, E.S. et al. (2007, e-pub Aug. 14, 2007). "The Double-Strand RNA-Dependent Protein Kinase PKR Plays a Significant Role in a Sustained ER Stress-Induced Apoptosis," *FEBS Lett.* 581(22):4325-4332.

Li, T. et al. (Nov. 1996). "Transgenic Mice Carrying the Dominant Rhodopsin Mutation P347S: Evidence for Defective Vectorial Transport of Rhodopsin to the Outer Segments," *Proc. Natl. Acad. Sci.* 93(24):14176-14181.

Mao, H. et al. (Apr. 2012). "Long-Term Rescue of Retinal Structure and Function by Rhodopsin RNA Replacement with a Single Adeno-Associated Viral Vector in P23H *RHO* Transgenic Mice," *Hum. Gen. Ther.* 23(4):356-366.

McLaughlin, S.K. et al. (Jun. 1988). "Adeno-Associated Virus General Transduction Vectors: Analysis of Proviral Structures," *J. Virol.* 62(6):1963-1973.

McWilliam, P. et al. (Oct. 1989). "Autosomal Dominant Retinitis Pigmentosa (ADRP): Localization of an ADRP Gene to the Long Arm of Chromosome 3," *Genomics* 5(3):619-622.

Niwa, H. et al. (1991). "Efficient Selection for High-Expression Transfectants with a Novel Eukaryotic Vector," *Gene* 108(2):193-200.

Olsson, J.E. et al. (Nov. 1992). "Transgenic Mice with a Rhodopsin Mutation (Pro23His): A Mouse Model of Autosomal Dominant Retinitis Pigmentosa," *Neuron* 9(5):815-830.

Passini, M.A. et al. (Jun. 2003). "Intraventricular Brain Injection of Adeno-Associated Virus Type 1 (AAV1) in Neonatal Mice Results in Complementary Patterns of Neuronal Transduction to AAV2 and Total Long-Term Correction of Storage Lesions in the Brains of β-Glucuronidase-Deficient Mice," *J. Virol.* 77(12):7034-7040.

Pechan, P. et al. (2009, e-pub Jul. 17, 2008). "Novel anti-VEGF Chimeric Molecules Delivered by AAV Vectors for Inhibition of Retinal Neovascularization," *Gene Ther.* 16:10-16.

Quiambao, A.B. et al. (Jul.-Aug. 1997). "A 221-bp Fragment of the Mouse Opsin Promoter Directs Expression Specifically to the Rod Photoreceptors of Transgenic Mice," *Vis. Neurosci.* 14(4):617-625.

Saliba, R.S. et al. (2002). "The Cellular Fate of Mutant Rhodopsin: Quality Control, Degradation and Aggresome Formation," *J. Cell Sci.* 115(14):2907-2918.

Skarnes, W.C. et al. (Jun. 15, 2011). "A Conditional Knockout Resource for the Genome-Wide Study of Mouse Gene Function," *Nature* 474(7351):337-342.

Tam, B.M. et al. (Aug. 2006). "Characterization of Rhodopsin P23H-Induced Retinal Degeneration in a *Xenopus laevis* Model of Retinitis Pigmentosa" *Invest. Ophthalmol. Vis. Sci.* 47(8):3234-3241.

Veldwijk, M.R. et al. (Aug. 2002). "Development and Optimization of a Real-Time Quantitative PCR-Based Method for the Titration of AAV-2 Vector Stocks," *Mol. Ther.* 6(2):272-278.

Wang, Z. et al. (2003). "Rapid and Highly Efficient Transduction by Double-Stranded Adeno-Associated Virus Vectors in Vitro and in Vivo," *Gene Ther* 10:2105-2111.

Woltczak, A. (Dec. 2000). "Glossary of Medical Education Terms," Institute of International Medical Education, as retrieved on Mar. 2013 from http://www.iime.org/glossary.htm, 23 pages.

Written Opinion of the International Search Authority mailed on Sep. 14, 2015 for PCT Application No. PCT/US2015/021896, filed on Mar. 20, 2015, 10 pages.

(56) References Cited

OTHER PUBLICATIONS

Xiao, X. et al. (Mar. 1, 1997). "Gene Transfer by Adeno-Associated Virus Vectors into the Central Nervous System," *Exp. Neurobiol.* 144(1):113-124.

Young, J.E. et al. (Sep. 2003). "A Short, Highly Active Photoreceptor-Specific Enhancer/Promoter Region Upstream of the Human Rhodopsin Kinase Gene," *Invest. Ophthalmol. Vis. Sci.* 44(9):4076-4085.

Zhong, L. et al. (Jun. 3, 2008; e-pub May 29, 2008). "Next Generation of Adeno-Associated Virus 2 Vectors: Point Mutations in Tyrosines Lead to High-Efficiency Transduction at Lower Doses," *Proc Natl Acad Sci* 105(22):7827-7832.

McClements, M.E. et al. (Apr. 2013, e-pub. Jan. 8, 2013). "Gene Therapy for Retinal Disease," Translational Research 161(4):241-254, 23 pages.

\* cited by examiner

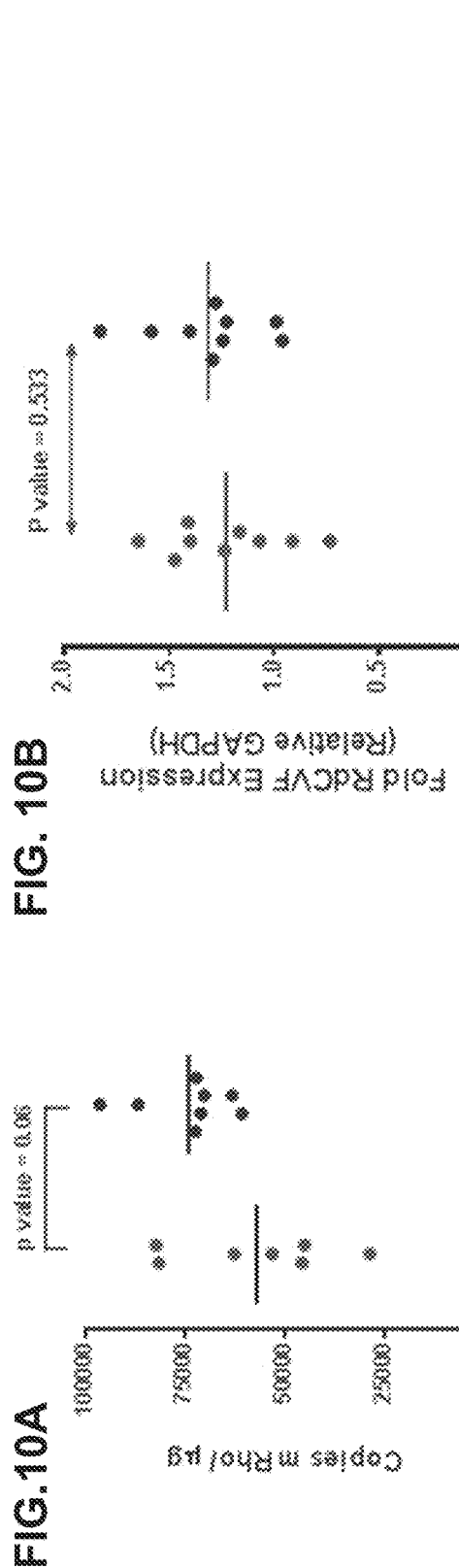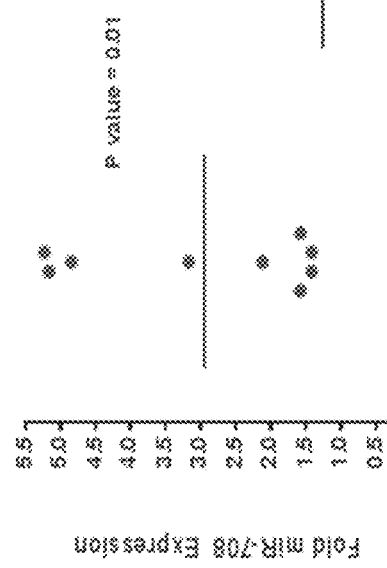
FIG. 10A
FIG. 10B
FIG. 10C

Animal # 45595

Animal # 45596

Animal # 45599

Animal # 45595

Animal # 45596

Animal # 45599 miR-155

Derived from miR-155 miR-708

SEQUENCE LISTING

<160> NUMBER OF SEQ ID NOS: 30

<210> SEQ ID NO 1
<211> LENGTH: 88
<212> TYPE: DNA
<213> ORGANISM: Homo sapiens

<400> SEQUENCE: 1
aactgccctc aaggagctta caatctagct gggggtaaat gacttgcaca tgaacacaac    60
tagactgtga gcttctagag ggcaggga                                      88

<210> SEQ ID NO 2
<211> LENGTH: 348
<212> TYPE: PRT
<213> ORGANISM: Homo sapiens

<400> SEQUENCE: 2

Met Asn Gly Thr Glu Gly Pro Asn Phe Tyr Val Pro Phe Ser Asn Ala
1               5                   10                  15

Thr Gly Val Val Arg Ser Pro Phe Glu Tyr Pro Gln Tyr Tyr Leu Ala
            20                  25                  30

Glu Pro Trp Gln Phe Ser Met Leu Ala Ala Tyr Met Phe Leu Leu Ile
        35                  40                  45

Val Leu Gly Phe Pro Ile Asn Phe Leu Thr Leu Tyr Val Thr Val Gln
    50                  55                  60

His Lys Lys Leu Arg Thr Pro Leu Asn Tyr Ile Leu Leu Asn Leu Ala
65                  70                  75                  80

Val Ala Asp Leu Phe Met Val Leu Gly Gly Phe Thr Ser Thr Leu Tyr
                85                  90                  95

Thr Ser Leu His Gly Tyr Phe Val Phe Gly Pro Thr Gly Cys Asn Leu
            100                 105                 110

Glu Gly Phe Phe Ala Thr Leu Gly Gly Glu Ile Ala Leu Trp Ser Leu
        115                 120                 125

Val Val Leu Ala Ile Glu Arg Tyr Val Val Val Cys Lys Pro Met Ser
    130                 135                 140

Asn Phe Arg Phe Gly Glu Asn His Ala Ile Met Gly Val Ala Phe Thr
145                 150                 155                 160

Trp Val Met Ala Leu Ala Cys Ala Ala Pro Pro Leu Ala Gly Trp Ser
                165                 170                 175

Arg Tyr Ile Pro Glu Gly Leu Gln Cys Ser Cys Gly Ile Asp Tyr Tyr
            180                 185                 190

Thr Leu Lys Pro Glu Val Asn Asn Glu Ser Phe Val Ile Tyr Met Phe
        195                 200                 205

Val Val His Phe Thr Ile Pro Met Ile Ile Ile Phe Phe Cys Tyr Gly
    210                 215                 220

```
Gln Leu Val Phe Thr Val Lys Glu Ala Ala Gln Gln Gln Glu Ser
225                 230                 235                 240

Ala Thr Thr Gln Lys Ala Glu Lys Glu Val Thr Arg Met Val Ile Ile
            245                 250                 255

Met Val Ile Ala Phe Leu Ile Cys Trp Val Pro Tyr Ala Ser Val Ala
        260                 265                 270

Phe Tyr Ile Phe Thr His Gln Gly Ser Asn Phe Gly Pro Ile Phe Met
    275                 280                 285

Thr Ile Pro Ala Phe Phe Ala Lys Ser Ala Ala Ile Tyr Asn Pro Val
        290                 295                 300

Ile Tyr Ile Met Met Asn Lys Gln Phe Arg Asn Cys Met Leu Thr Thr
305                 310                 315                 320

Ile Cys Cys Gly Lys Asn Pro Leu Gly Asp Asp Glu Ala Ser Ala Thr
                325                 330                 335

Val Ser Lys Thr Glu Thr Ser Gln Val Ala Pro Ala
                340                 345

<210> SEQ ID NO 3
<211> LENGTH: 1044
<212> TYPE: DNA
<213> ORGANISM: Homo sapiens

<400> SEQUENCE: 3
atgaatggca cagaaggccc taacttctac gtgcccttct ccaatgcgac gggtgtggta     60
cgcagcccct tcgagtaccc acagtactac ctggctgagc catggcagtt ctccatgctg    120
gccgcctaca tgtttctgct gatcgtgctg ggcttcccca tcaacttcct cacgctctac    180
gtcaccgtcc agcacaagaa gctgcgcacg cctctcaact acatcctgct caacctagcc    240
gtggctgacc tcttcatggt cctaggtggc ttcaccagca ccctctacac ctctctgcat    300
ggatacttcg tcttcgggcc acaggatgca aatttggagg gcttctttgc caccctgggc    360
ggtgaaattg ccctgtggtc cttggtggtc ctggccatcg agcggtacgt ggtggtgtgt    420
aagcccatga gcaacttccg cttcggggag aaccatgcca tcatgggcgt tgccttcacc    480
tgggtcatgg cgctggcctg cgccgcaccc ccactcgccg ctggtccagg tacatcccc     540 gagggcctgc agtgctcgtg tggaatcgac tactacacgc tcaagccgga ggtcaacaac    600
gagtcttttg tcatctacat gttcgtggtc cacttccaca tccccatgat tatcatcttt    660
ttctgctatg gcagctcgtc ttcaccgtc aaggaggccg ctgcccagca gcaggagtca    720
gccaccacac agaaggcaga gaaggaggtc acccgcatgg tcatcatcat ggtcatcgct    780
ttcctgatct gctgggtgcc ctacgccagc gtggcattct acatcttcac ccaccagggc    840
tccaacttcg gtcccatctt catgaccatc ccagcgttct ttgccaagag cgccgccatc    900
tacaaccctg tcatctatat catgatgaac aagcagttcc ggaactgcat gctcaccacc    960
atctgctgcg gcaagaaccc actgggtgac gatgaggcct tgctaccgt gtccaagacg   1020 gagacgagcc aggtggcccc ggcc                                          1044

<210> SEQ ID NO 4
<211> LENGTH: 2768
<212> TYPE: DNA
<213> ORGANISM: Homo sapiens

<400> SEQUENCE: 4
agagtcatcc agctggagcc ctgagtggct gagctcaggc cttcgcagca ttcttgggtg     60
```

```
ggagcagcca cgggtcagcc acaagggcca cagccatgaa tggcacagaa ggccctaact    120
tctacgtgcc cttctccaat gcgacgggtg tggtacgcag cccctttcgag tacccacagt    180 actacctggc tgagccatgg cagttctcca tgctggccgc ctacatgttt ctgctgatcg    240
tgctgggctt ccccatcaac ttcctcacgc tctacgtcac cgtccagcac aagaagctgc    300
gcacgcctct caactacatc ctgctcaacc tagccgtggc tgacctcttc atggtcctag    360
gtggcttcac cagcacccetc tacacctctc tgcatggata cttcgtcttc gggcccacag    420 gatgcaatt ggagggcttc tttgccaccc tgggcggtga aattgccctg tggtccttgg    480
tggtcctggc catcgagcgg tacgtggtgg tgtgtaagcc catgagcaac ttccgcttcg    540
gggagaacca tgccatcatg ggcgttgcct tcacctgggt catggcgctg gcctgcgccg    600 caccccact cgccggctgg tccaggtaca tccccgaggg cctgcagtgc tcgtgtggaa    660
tcgactacta cacgctcaag ccggaggtca caacgagtc ttttgtcatc tacatgttcg    720
tggtccactt caccatcccc atgattatca tcttttttctg ctatgggcag ctcgtcttca    780
ccgtcaagga ggccgctgcc cagcagcagg agtcagccac cacacagaag gcagagaagg    840
aggtcacccg catggtcatc atcatggtca tcgctttcct gatctgctgg gtgccctacg    900
ccagcgtggc attctacatc ttcacccacc agggctccaa cttcggtccc atcttcatga    960
ccatcccagc gttctttgcc aagagcgccg ccatctacaa ccctgtcatc tatatcatga   1020
tgaacaagca gttccggaac tgcatgctca ccaccatctg ctgcggcaag aacccactgg   1080
gtgacgatga ggcctctgct accgtgtcca agacggagac gagccaggtg ccccggcct    1140 aagacctgcc taggactctg tggccgacta taggcgtctc ccatccccta caccttcccc   1200
cagccacagc catcccacca ggagcagcgc ctgtgcagaa tgaacgaagt cacataggct   1260
ccttaatttt tttttttttt ttaagaaata attaatgagg ctcctcactc acctgggaca   1320
gcctgagaag ggacatccac caagacctac tgatctggag tcccacgttc cccaaggcca   1380
gcgggatgtg tgcccctcct cctcccaact catctttcag gaacacgagg attcttgctt   1440
tctggaaaag tgtcccagct tagggataag tgtctagcac agaatggggc acacagtagg   1500
tgcttaataa atgctggatg gatgcaggaa ggaatggagg aatgaatggg aagggagaac   1560
atatctatcc tctcagaccc tcgcagcagc agcaactcat acttggctaa tgatatggag   1620
cagttgtttt tccctccctg ggcctcactt tcttctccta taaatggaa atcccagatc   1680 cctggtcctg ccgacacgca gctactgaga agaccaaaag aggtgtgtgt gtgtctatgt   1740
gtgtgtttca gcactttgta aatagcaaga agctgtacag attctagtta atgttgtgaa   1800
taacatcaat taatgtaact agttaattac tatgattatc acctcctgat agtgaacatt   1860
ttgagattgg gcattcagat gatggggttt cacccaacct tggggcaggt ttttaaaaat   1920
tagctaggca tcaaggccag accagggctg ggggttgggc tgtaggcagg gacagtcaca   1980
ggaatgcaga atgcagtcat cagacctgaa aaaacaacac tggggagggg ggacggtgaa   2040
ggccaagttc ccaatgaggg tgagattggg cctggggtct caccctagt gtggggcccc    2100 aggtcccgtg cctcccctttc ccaatgtggc ctatggagag acaggccttt ctctcagcct   2160
ctggaagcca cctgctcttt tgctctagca cctgggtccc agcatctaga gcatggagcc   2220
tctagaagcc atgctcaccc gcccacattt aattaacagc tgagtccctg atgtcatcct   2280
tatctcgaag agcttagaaa caaagagtgg gaaattccac tgggcctacc ttccttgggg   2340
atgttcatgg gccccagttt ccagtttccc ttgccagaca agcccatctt cagcagttgc   2400
tagtccattc tccattctgg agaatctgct ccaaaaagct ggccacatct ctgaggtgtc   2460
```

-continued

```
agaattaagc tgcctcagta actgctcccc cttctccata taagcaaagc cagaagctct    2520
agctttaccc agctctgcct ggagactaag gcaaattggg ccattaaaag ctcagctcct    2580
atgttggtat taacggtggt gggttttgtt gctttcacac tctatccaca ggatagattg    2640
aaactgccag cttccacctg atccctgacc ctgggatggc tggattgagc aatgagcaga    2700
gccaagcagc acagagtccc ctggggctag aggtggagga ggcagtcctg ggaatgggaa    2760
aaacccca                                                              2768
```

<210> SEQ ID NO 5
<211> LENGTH: 1512
<212> TYPE: DNA
<213> ORGANISM: Artificial Sequence
<220> FEATURE:
<223> OTHER INFORMATION: Synthetic Construct

<400> SEQUENCE: 5

```
ggccccagaa gcctggtggt tgtttgtcct tctcagggga aaagtgaggc ggccccttgg      60 aggaagggc cgggcagaat gatctaatcg gattccaagc agctcagggg attgtctttt     120
tctagcacct tcttgccact cctaagcgtc ctccgtgacc ccggctggga tttagcctgg     180
tgctgtgtca gccccggtct cccaggggct tcccagtggt ccccaggaac cctcgacagg     240
gcccggtctc tctcgtccag caagggcagg gacgggccac aggccaaggg cggagtcgct     300
gcgacgctgc cttcgccccg tgccccgctc cgccgccgcc tcgcgccgcc cgccccggct     360
ctgactgacc gcgttactcc cacaggtgag cgggcgggac ggcccttctc ctccgggctg     420
taattagcgc ttggtttaat dacggcttgt ttcttttctg tggctgcgtg aaagccttga     480
ggggctccgg gagggccctt tgtgcggggg gagcggctcg gggggtgcgt gcgtgtgtgt     540
gtgcgtgggg agcgccgcgt gcggctccgc gctgcccggc ggctgtgagc gctgcgggcg     600
cggcgcgggg ctttgtgcgc tccgcagtgt gcgcgagggg agcgcggccg ggggcggtgc     660
cccgcggtgc ggggggggct gcgaggggaa caaaggctgc gtgcggggtg tgtgcgtggg     720
ggggtgagca ggggggtgtgg gcgcgtcggt cgggctgcaa ccccccctgc acccccctcc     780
ccgagttgct gagcacggcc cggcttcggg tgcggggctc cgtacggggc gtggcgcggg     840
gctcgccgtg ccgggcgggg ggtggcggca ggtggggtg ccggcgggg cggggccgcc      900 tcgggccggg gagggctcgg gggaggggcg cggcggcccc cggagcgccg gcggctgtcg     960
aggcgcggcg agccgcagcc attgcctttt atggtaatcg tgcgagaggg cgcagggact    1020
tcctttgtcc caaatctgtg cggagccgaa atctgggagg cgccgccgca ccccctctag    1080
cgggcgcggg gcgaagcggt gcggcgccgg caggaaggaa atgggcgggg agggccttcg    1140
tgcgtcgccg cgccgccgtc cccttctccc tctccagcct cggggctgtc cgcggggga    1200 cggctgcctt cggggggac ggggcagggc ggggttcggc ttctggcgtg tgaccggcgg     1260
ctctagagcc tctgctaacc atgttcatgc cttcttcttt ttcctacagc tcctgggcaa    1320
cgtgctggtt attgtgctgt ctcatcattt tggcaaagaa ttcttcgaaa gatcctggag    1380
gcttgctgaa ggctgtatgc tgaaggagct tacaatctag ctggggttt ggccactgac    1440 tgaccccagc tagtgtaagc tccttcagga cacaaggcct gttactagca ctcacatgga    1500
acaaatggcc ca                                                         1512
```

<210> SEQ ID NO 6
<211> LENGTH: 3444
<212> TYPE: DNA

<213> ORGANISM: Artificial Sequence
<220> FEATURE:
<223> OTHER INFORMATION: Synthetic Construct

<400> SEQUENCE: 6

```
caatctccca gatgctgatt cagccaggaa ctagttatta atagtaatca attacggggt      60
cattagttca tagcccatat atggagttcc gcgttacata acttacggta aatggcccgc     120
ctggctgacc gcccaacgac ccccgcccat tgacgtcaat aatgacgtat gttcccatag     180
taacgccaat agggactttc cattgacgtc aatgggtgga gtatttacgg taaactgccc     240
acttggcagt acatcaagtg tatcatatgc caagtacgcc ccctattgac gtcaatgacg     300
gtaaatggcc cgcctggcat tatgcccagt acatgacctt atgggacttt cctacttggc     360
agtacatcta cgtattagtc atcgctatta ccacaaatag ttatcgagcc gctgagccgg     420
ggggcggggg gtgtgagact ggaggcgatg gacggagctg acggcacaca cagctcagat     480
ctgtcaagtg agccattgtc agggcttggg gactggataa gtcaggggt ctcctgggaa      540
gagatgggat aggtgagttc aggaggagac attgtcaact ggagccatgt ggagaagtga     600
atttagggcc caaaggttcc agtcgcagcc tgaggccacc agactgacat ggggaggaat     660
tcccagagga ctctggggca gacaagatga gacaccctt cctttcttta cctaagggcc      720
tccacccgat gtcaccttgg cccctctgca agccaattag gccccggtgg cagcagtggg     780
attagcgtta gtatgatatc tcgcggatgc tgaatcagcc tctggcttag ggagagaagg     840
tcactttata agggtctggg gggggtcagt gcctggagtt gcgctgtggg agccgtcagt     900
ggctgagctc aagaggtaag ggtttaaggg atggttggtt ggtggggtat taatgtttaa     960
ttacctgttt tacaggcctg aaatcacttg gttttaggtt ggtacatctg cagaattcag    1020
ccaccaccgg cacaatgaat ggcacagaag gccctaactt ctacgtgccc ttctccaatg    1080
cgacgggtgt ggtacgcagc cccttcgagt acccacagta ctacctggct gagccatggc    1140
agttctccat gctggccgcc tacatgtttc tgctgatcgt gctgggcttc cccatcaact    1200
tcctcacgct ctacgtcacc gtccagcaca agaagctgcg cacgcctctc aactacatcc    1260
tgctcaacct agccgtggct gacctcttca tggtcctagg tggcttcacc agcaccctct    1320
acacctctct gcatggatac ttcgtcttcg ggcccacagg atgcaatttg gagggcttct    1380
ttgccaccct gggcggtgaa attgccctgt ggtccttggt ggtcctggcc atcgagcggt    1440
acgtggtggt gtgtaagccc atgagcaact tccgcttcgg ggagaaccat gccatcatgg    1500
gcgttgcctt cacctgggtc atggcgctgg cctgcgccgc accccactc gccggctggt     1560
ccaggtacat ccccgagggc ctgcagtgct cgtgtggaat cgactactac acgctcaagc    1620
cggaggtcaa caacgagtct tttgtcatct acatgttcgt ggtccacttc accatcccca    1680
tgattatcat cttttttctgc tatgggcagc tcgtcttcac cgtcaaggag gccgctgccc    1740
agcagcagga gtcagccacc acacagaagg cagagaagga ggtcacccgc atggtcatca    1800
tcatggtcat cgctttcctg atctgctggg tgccctacgc cagcgtggca ttctacatct    1860
tcacccacca gggctccaac ttcggtccca tcttcatgac catcccagcg ttctttgcca    1920
agagcgccgc catctacaac cctgtcatct atatcatgat gaacaagcag ttccggaact    1980
gcatgctcac caccatctgc tgcggcaaga acccactggg tgacgatgag gcctctgcta    2040
ccgtgtccaa gacggagacg agccaggtgg ccccggccta accaagaaag cttaagtttg    2100
tgtcccggct tagggctaaa tgtctaggac agaatggaac acatagtagc tgattaataa    2160
atgctagctg gatgaaggga ggaatgagtg actgactgag tggatatatg agtgaaggga    2220
```

```
ttaatggaag ggaacatgga tgtcctcagg tgcccaacct ggcagatcca gtcatgtctg    2280
gctggaatct ataagcagtt ttacatacct gccctgagct ttattgcggt agtttatcac    2340
agttaaattg ctaacgcagt cagtgcttct gacacaacag tctcgaactt aagctgcagt    2400
gactctctta aggtagcctt gcagaagttg gtcgtgaggc actgggcagg taagtatcaa    2460
ggttacaaga caggtttaag gagaccaata gaaactgggc ttgtcgagac agagaaaaac    2520
ctaaccccca tggttggcga gggactgctg tgtgtgaaat ggtaactgcc tcaaggagc     2580 ttacaatcta gctgggggta aatgacttgc acatgaacac aactagactg tgagcttcta    2640
gagggcaggg accttaccct agtcatctct cttctcaccc tgcacaccct ccctgaggga    2700
tctcatgact cttgcgtttc tgataggcac ctattggtct tactgacatc cactttgcct    2760
ttctctccac aggtgtccac tcccagttca caccggcaca atgaatggca cagaaggccc    2820
taacttctac gtgcccttct ccaatgcgac gggtgtggta cgcagcccct tcgagtaccc    2880
acagtcagag ataaatgaca gtgacagcaa cgtgagctgc agcccttagg actgagaaag    2940
catcgagacc aggggtctcc ggcaaggcct aggtcctccc ttcagtatgg aaaccttgcc    3000
tcatgtctct cagcctcctt ggcctgtgga gatccagccc ttcctcttgg cttctggata    3060
catttgctct tctacaccag caaccaagtg gcaacagttc caggccagta tggagtttta    3120
gaagccatgc caatatgccc accttcaggg agcagctgag tccttgatgc cacccttgtt    3180
ctgaagagtt cagaaacaca gtgcaagaca tgaccaggcc tcatccttag gatgctcatg    3240
gatccagttc ttagctccct tgttggatat gctgttttcc ttggcctttg gtcttttctt    3300
tatcccagag ggttttggct ttaaggccaa caggaactat ggggtaccag aattgagcag    3360
cctcagtctg catccctcct ctatagaacc acagctgggc cctcagcagg cccaactctg    3420
catggggaca gaggcattaa aagc                                           3444

<210> SEQ ID NO 7
<211> LENGTH: 3014
<212> TYPE: DNA
<213> ORGANISM: Artificial Sequence
<220> FEATURE:
<223> OTHER INFORMATION: Synthetic Construct

<400> SEQUENCE: 7
gggccccaga agcctggtgg ttgtttgtcc ttctcagggg aaaagtgagg cggccccttg      60
gaggaagggg ccgggcagaa tgatctaatc ggattccaag cagctcaggg gattgtcttt     120
ttctagcacc ttcttgccac tcctaagcgt cctccgtgac cccggctggg atttagcctg     180
gtgctgtgtc agccccggtc tcccaggggc ttcccagtgg tccccaggaa ccctcgacag     240
ggcccggtct ctctcgtcca gcaagggcag ggacgggcca caggccaagg gcggagtcgc     300 tgccgacgctg ccttcgcccc gtgccccgct ccgccgccgc ctcgcgccgc ccgccccggc    360
tctgactgac cgcgttactc ccacaggtga gcggcgggga cggcccttct cctccgggct    420
gtaattagca agaggtaagg gtttaaggga tggttggttg gtggggtatt aatgtttaat    480
tacctgtttt acaggcctga aatcacttgg ttttaggttg gggatccggt acccaattgc    540
catgggctag catgcatgag ctccctgcag ggtttatctg cagaattcag ccaccaccgg    600
cacaatgaat ggcacagaag gccctaactt ctacgtgccc ttctccaatg cgacgggtgt    660
ggtacgcagc cccttcgagt acccacagta ctacctggct gagccatggc agttctccat    720
gctggccgcc tacatgtttc tgctgatcgt gctgggcttc cccatcaact tcctcacgct    780
```

```
ctacgtcacc gtccagcaca agaagctgcg cacgcctctc aactacatcc tgctcaacct    840
agccgtggct gacctcttca tggtcctagg tggcttcacc agcaccctct acacctctct    900
gcatggatac ttcgtcttcg ggcccacagg atgcaatttg gagggcttct tgccaccct    960
gggcggtgaa attgccctgt ggtccttggt ggtcctggcc atcgagcggt acgtggtggt   1020
gtgtaagccc atgagcaact tccgcttcgg ggagaaccat gccatcatgg gcgttgcctt   1080
cacctgggtc atggcgctgg cctgcgccgc acccccactc gccggctggt ccaggtacat   1140
ccccgagggc ctgcagtgct cgtgtggaat cgactactac acgctcaagc cggaggtcaa   1200
caacgagtct tttgtcatct acatgttcgt ggtccacttc accatcccca tgattatcat   1260
cttttctgc tatgggcagc tcgtcttcac cgtcaaggag gccgctgccc agcagcagga   1320
gtcagccacc acacagaagg cagagaagga ggtcacccgc atggtcatca tcatggtcat   1380
cgctttcctg atctgctggg tgccctacgc cagcgtggca ttctacatct tcacccacca   1440
gggctccaac ttcggtccca tcttcatgac catcccagcg ttctttgcca agagcgccgc   1500
catctacaac cctgtcatct atatcatgat gaacaagcag ttccggaact gcatgctcac   1560
caccatctgc tgcggcaaga acccactggg tgacgatgag gcctctgcta ccgtgtccaa   1620
gacggagacg agccaggtgg ccccggccta accaagaaag cttaagtttg tgtcccggct   1680
tagggctaaa tgtctaggac agaatggaac acatagtagc tgattaataa atgctagctg   1740
gatgaaggga ggaatgagtg actgactgag tggatatatg agtgaaggga ttaatgaaag   1800
ggaacatgga tgtcctcagg tgcccaacct ggcagatcca gtcatgtctg ctggaatct    1860
ataagcagtt ttacatacct gccctgagct ttattgcggt agtttatcac agttaaattg   1920
ctaacgcagt cagtgcttct gacacaacag tctcgaactt aagctgcagt gactctctta   1980
aggtagcctt gcagaagttg gtcgtgaggc actgggcagg taagtatcaa ggttacaaga   2040
caggtttaag gagaccaata gaaactgggc ttgtcgagac agagaaaaac ctaaccccca   2100
tggttggcga gggactgctg tgtgtgaaat ggtaactgcc ctcaaggagc ttacaatcta   2160
gctgggggta aatgacttgc acatgaacac aactagactg tgagcttcta gagggcaggg   2220
accttaccct agtcatctct cttctcaccc tgcacaccct ccctgaggga tctcatgact   2280
cttgcgtttc tgataggcac ctattggtct tactgacatc cactttgcct ttctctccac   2340
aggtgtccac tccagttca caccggcaca atgaatggca cagaaggccc taacttctac   2400
gtgcccttct ccaatgcgac gggtgtggta cgcagcccct tcgagtaccc acagtcagag   2460
ataaatgaca gtgacagcaa cgtgagctgc agcccttagg actgagaaag catcgagacc   2520
aggggtctcc ggcaaggcct aggtcctccc ttcagtatgg aaaccttgcc tcatgtctct   2580
cagcctcctt ggcctgtgga gatccagccc ttcctcttgg cttctggata catttgctct   2640
tctacaccag caaccaagtg gcaacagttc caggccagta tggagtttta gaagccatgc   2700
caatatgccc accttcaggg agcagctgag tccttgatgc cacccttgtt ctgaagagtt   2760
cagaaacaca gtgcaagaca tgaccaggcc tcatccttag gatgctcatg gatccagttc   2820
ttagctccct tgttggatat gctgttttcc ttggcctttg gtcttttctt tatcccagag   2880
ggttttggct ttaaggccaa caggaactat ggggtaccag aattgagcag cctcagtctg   2940
catccctcct ctatagaacc acagctgggc cctcagcagg cccaactctg catgggagca   3000
gaggcattaa aagc                                                    3014

<210> SEQ ID NO 8
<211> LENGTH: 1826
```

<212> TYPE: DNA
<213> ORGANISM: Artificial Sequence
<220> FEATURE:
<223> OTHER INFORMATION: Synthetic Construct

<400> SEQUENCE: 8

```
gggccccaga agcctggtgg ttgtttgtcc ttctcagggg aaaagtgagg cggccccttg      60
gaggaagggg ccgggcagaa tgatctaatc ggattccaag cagctcaggg gattgtcttt     120
ttctagcacc ttcttgccac tcctaagcgt cctccgtgac cccggctggg atttagcctg     180
gtgctgtgtc agccccggtc tcccaggggc ttcccagtgg tccccaggaa ccctcgacag     240
ggcccggtct ctctcgtcca gcaagggcag ggacgggcca caggccaagg cactagaag      300
ctttattgcg gtagtttatc acagttaaat tgctaacgca gtcagtgctt ctgacacaac     360
agtctcgaac ttaagctgca gtgactctct taaggtagcc ttgcagaagt tggtcgtgag     420
gcactgggca ggtaagtatc aaggttacaa dacaggttta aggagaccaa tagaaactgg     480
gcttgtcgag acagagaaaa acctaacccc catggttggc gagggactgc tgtgtgtgaa     540
atggtaactg ccctcaagga gcttacaatc tagctggggg taaatgactt gcacatgaac     600
acaactagac tgtgagcttc tagagggcag ggaccttacc ctagtcatct ctcttctcac     660
cctgcacacc ctccctgagg gatctcatga ctcttgcgtt tctgataggc acctattggt     720
cttactgaca tccactttgc cttttctctcc acaggtgtcc actcccagtt cacaccggca     780
caatgaatgg cacagaaggc cctaacttct acgtgcccct ctccaatgcg acgggtgtgg     840
tacgcagccc cttcgagtac ccacagtact acctggctga gccatggcag ttctccatgc     900
tggccgccta catgtttctg ctgatcgtgc tgggcttccc catcaacttc ctcacgctct     960
acgtcaccgt ccagcacaag aagctgcgca cgcctctcaa ctacatcctg ctcaacctag    1020
ccgtggctga cctcttcatg gtcctaggtg gcttcaccag caccctctac acctctctgc    1080
atggatactt cgtcttcggg cccacaggat gcaatttgga gggcttcttt gccaccctgg    1140
gcggtgaaat tgccctgtgg tccttggtgg tcctggccat cgagcggtac gtggtggtgt    1200
gtaagcccat gagcaacttc cgcttcgggg agaaccatgc catcatgggc gttgccttca    1260
cctgggtcat ggcgctggcc tgcgccgcac ccccactcgc cggctggtcc aggtacatcc    1320
ccgagggcct gcagtgctcg tgtggaatcg actactacac gctcaagccg gaggtcaaca    1380
acgagtcttt tgtcatctac atgttcgtgg tccacttcac catccccatg attatcatct    1440
ttttctgcta tgggcagctc gtcttcaccg tcaaggaggc cgctgcccag cagcaggagt    1500
cagccaccac acagaaggca gagaaggagg tcacccgcat ggtcatcatc atggtcatcg    1560
ctttcctgat ctgctgggtg ccctacgcca gcgtggcatt ctacatcttc acccaccagg    1620
gctccaactt cggtcccatc ttcatgacca tcccagcgtt ctttgccaag agcgccgcca    1680
tctacaaccc tgtcatctat atcatgatga acaagcagtt ccggaactgc atgctcacca    1740
ccatctgctg cggcaagaac ccactgggtg acgatgaggc ctctgctacc gtgtccaaga    1800
cggagacgag ccaggtggcc ccggcc                                         1826
```

<210> SEQ ID NO 9
<211> LENGTH: 3444
<212> TYPE: DNA
<213> ORGANISM: Artificial Sequence
<220> FEATURE:
<223> OTHER INFORMATION: Synthetic Construct

<400> SEQUENCE: 9

```
caatctccca gatgctgatt cagccaggaa ctagttatta atagtaatca attacggggt      60
cattagttca tagcccatat atggagttcc gcgttacata acttacggta aatggcccgc     120
ctggctgacc gcccaacgac ccccgcccat tgacgtcaat aatgacgtat gttcccatag    180
taacgccaat agggactttc cattgacgtc aatgggtgga gtatttacgg taaactgccc    240
acttggcagt acatcaagtg tatcatatgc caagtacgcc ccctattgac gtcaatgacg    300
gtaaatggcc cgcctggcat tatgcccagt acatgacctt atgggacttt cctacttggc    360
agtacatcta cgtattagtc atcgctatta ccacaaatag ttatcgagcc gctgagccgg    420
ggggcggggg gtgtgagact ggaggcgatg gacggagctg acggcacaca cagctcagat    480
ctgtcaagtg agccattgtc agggcttggg gactggataa gtcaggggggt ctcctgggaa   540
gagatgggat aggtgagttc aggaggagac attgtcaact ggagccatgt ggagaagtga    600
atttagggcc caaaggttcc agtcgcagcc tgaggccacc agactgacat ggggaggaat    660
tcccagagga ctctggggca gacaagatga gacacccttt cctttcttta cctaagggcc    720
tccacccgat gtcaccttgg cccctctgca agccaattag gccccggtgg cagcagtggg    780
attagcgtta gtatgatatc tcgcggatgc tgaatcagcc tctggcttag ggagagaagg    840
tcactttata agggtctggg gggggtcagt gcctggagtt gcgctgtggg agccgtcagt    900
ggctgagctc aagaggtaag ggtttaaggg atggttggtt ggtggggtat taatgtttaa    960
ttacctgttt tacaggcctg aaatcacttg gttttaggtt ggtacatctg cagaattcag   1020
ccaccaccgg cacaatgaat ggcacagaag gccctaactt ctacgtgccc ttctccaatg   1080
cgacgggtgt ggtacgcagc cccttcgagt acccacagta ctacctggct gagccatggc   1140
agttctccat gctggccgcc tacatgtttc tgctgatcgt gctgggcttc cccatcaact   1200
tcctcacgct ctacgtcacc gtccagcaca gaaagctgcg cacgcctctc aactacatcc   1260
tgctcaacct agccgtggct gacctcttca tggtcctagg tggcttcacc agcacccctct 1320
acacctctct gcatggatac ttcgtcttcg ggcccacagg atgcaatttg gagggcttct   1380
ttgccaccct gggcggtgaa attgccctgt ggtccttggt ggtcctggcc atcgagcggt   1440
acgtggtggt gtgtaagccc atgagcaact tccgcttcgg ggagaaccat gccatcatgg   1500
gcgttgcctt cacctgggtc atggcgctgg cctgcgccgc acccccactc gccggctggt   1560
ccaggtacat ccccgagggc ctgcagtgct cgtgtggaat cgactactac acgctcaagc   1620
cggaggtcaa caacgagtct tttgtcatct acatgttcgt ggtccacttc accatcccca   1680
tgattatcat ctttttctgc tatgggcagc tcgtcttcac cgtcaaggag gccgctgccc   1740
agcagcagga gtcagccacc acacagaagg cagagaagga ggtcacccgc atggtcatca   1800
tcatggtcat cgcttttcctg atctgctggg tgccctacgc cagcgtggca ttctacatct   1860
tcacccacca gggctccaac ttcggtccca tcttcatgac catcccagcg ttctttgcca   1920
agagcgccgc catctacaac cctgtcatct atatcatgat gaacaagcag ttccggaact   1980
gcatgctcac caccatctgc tgcggcaaga acccactggg tgacgatgag gcctctgcta   2040
ccgtgtccaa gacggagacg agccaggtgg cccccggccta accaagaaag cttaagtttg   2100
tgtcccggct tagggctaaa tgtctaggac agaatggaac acatagtagc tgattaataa   2160
atgctagctg gatgaaggga ggaatgagtg actgactgag tggatatatg agtgaaggga   2220
ttaatggaag ggaacatgga tgtcctcagg tgcccaacct ggcagatcca gtcatgtctg   2280
gctggaatct ataagcagtt ttacatacct gccctgagct ttattgcggt agtttatcac   2340
agttaaattg ctaacgcagt cagtgcttct gacacaacag tctcgaactt aagctgcagt   2400
```

```
gactctctta aggtagcctt gcagaagttg gtcgtgaggc actgggcagg taagtatcaa    2460
ggttacaaga caggtttaag gagaccaata gaaactgggc ttgtcgagac agagaaaaac    2520
ctaaccccca tggttggcga gggactgctg tgtgtgaaat ggtaactgcc ctcaaggagc    2580
ttacaatcta gctggggta aatgacttgc acatgaacac aactagactg tgagcttcta    2640
gagggcaggg accttaccct agtcatctct cttctcaccc tgcacaccct ccctgaggga    2700
tctcatgact cttgcgtttc tgataggcac ctattggtct tactgacatc cactttgcct    2760
ttctctccac aggtgtccac tcccagttca caccggcaca atgaatggca cagaaggccc    2820
taacttctac gtgcccttct ccaatgcgac gggtgtggta cgcagcccct tcgagtaccc    2880
acagtcagag ataaatgaca gtgacagcaa cgtgagctgc agcccttagg actgagaaag    2940
catcgagacc aggggtctcc ggcaaggcct aggtcctccc ttcagtatgg aaaccttgcc    3000
tcatgtctct cagcctcctt ggcctgtgga gatccagccc ttcctcttgg cttctggata    3060
catttgctct tctacaccag caaccaagtg gcaacagttc caggccagta tggagtttta    3120
gaagccatgc caatatgccc accttcaggg agcagctgag tccttgatgc cacccttgtt    3180
ctgaagagtt cagaaacaca gtgcaagaca tgaccaggcc tcatccttag gatgctcatg    3240
gatccagttc ttagctccct tgttggatat gctgttttcc ttggcctttg gtcttttctt    3300
tatcccagag ggttttggct ttaaggccaa caggaactat ggggtaccag aattgagcag    3360
cctcagtctg catccctcct ctatagaacc acagctgggc cctcagcagg cccaactctg    3420
catggggaca gaggcattaa aagc                                          3444
```

<210> SEQ ID NO 10
<211> LENGTH: 1017
<212> TYPE: DNA
<213> ORGANISM: Artificial Sequence
<220> FEATURE:
<223> OTHER INFORMATION: Synthetic Construct

<400> SEQUENCE: 10

```
ggagtcgctg cgacgctgcc ttcgccccgt gcccgctcc gccgccgcct cgcgccgccc       60
gccccggctc tgactgaccg cgttactccc acaggtgagc gggcgggacg gcccttctcc     120
tccgggctgt aattagcgct tggtttaatg acggcttgtt tctttctgt ggctgcgtga     180 aagccttgag gggctccggg agggcccttt gtgcgggggg agcggctcgg ggggtgcgtg     240
cgtgtgtgtg tgcgtgggga gcgccgcgtg cggctccgcg ctgcccggcg gctgtgagcg     300 ctgcggggcgc ggcgcggggc tttgtgcgct ccgcagtgtg cgcgagggga gcgcggccgg     360
gggcggtgcc ccgcggtgcg gggggggctg cgagggaac aaaggctgcg tgcggggtgt     420
gtgcgtgggg gggtgagcag ggggtgtggg cgcgtcggtc gggctgcaac ccccctgca     480 ccccctcc cgagttgctg agcacggccc ggcttcgggt gcgggctcc gtacgggcg       540 tggcgcgggg ctcgccgtgc cgggcggggg gtggcggcag gtggggtgc cgggcggggc     600 ggggccgcct cgggccgggg agggctcggg ggaggggcgc ggcggccccc ggagcgccgg     660
cggctgtcga ggcgcggcga gccgcagcca ttgccttttta tggtaatcgt gcgagagggc     720
gcagggactt cctttgtccc aaatctgtgc ggagccgaaa tctgggaggc gccgccgcac     780
cccctctagc gggcgcgggg cgaagcggtg cggcgccggc aggaaggaaa tgggcggga     840 gggccttcgt gcgtcgccgc gccgccgtcc ccttctcctt ctccagcctc ggggctgtcc     900
gcggggggac ggctgccttc gggggggacg gggcagggcg gggttcggct tctggcgtgt     960
```
gaccggcggc tctagagcct ctgctaacca tgttcatgcc ttcttctttt tcctaca    1017

<210> SEQ ID NO 11
<211> LENGTH: 2239
<212> TYPE: DNA
<213> ORGANISM: Artificial Sequence
<220> FEATURE:
<223> OTHER INFORMATION: Synthetic Construct

<400> SEQUENCE: 11
aagcttgaaa tgccacctcc tctgatattc taggtgtcct ggaagcctgt ctcatcttgc     60
cctgtagtgt tgggtcacct ggcccccagc ctgtaacatc cccagggccc tacacccaga    120
gaaacacggg gctggtggca gtgcccagtg acaaccgttt agtggataag agaagagtga    180
ccacaccagg ctgagtgctc ctctctggtt ttccatgggg agacaatgcc accctgagca    240
gggtctggtg tgagcggcag ctggctctgg gctctctgat ccgttaccct ctcagcctct    300
ttgttctttc tcaaccccctg gagcagagac ctcaggaggt gctggcatgg aacagagaaa    360
ttccagcctc gattcctatt atgaacccga caccttttgt attttcatct tggttttaca    420
gtgtacaaaa cgaactagat cagcagggca tgggcataat cacgaatgca cacacataca    480
ctaatgtgtg gctcatgttt aagtatcact tactacagga cacccaatct aacagcaccg    540
ataaagtgac agagaaacgc aagccttctg cgaacatggc ctggctgttc caattccgaa    600
ccttgctttt ctgggccttg ccacacaggc tcttcccccg tcccccaggg acattctac     660
ccttgaactc cacactccac tgctgccttt gccaggaagc ccatctgttc cttttggtt     720
ctgccagaac gtgtggtggt gctgctgtcc ctgccttggg cactggatat tgggaaggga    780
cagtgtccac actggagtgg gaagttccca gggacgagac ctttacctcc tcaccctggg    840
tactgttctc ctcatggagc atggacgcg ctgcctgaac tcagtggtgg cctcattctg     900
gaagccaagt ttatacagag tagcagtgac ccagggatgt ggggttcacc ctcctcagcc    960
ctctggccag tcctgatggg cctcagtccc aacatggcta agaggtgtgg gcagcttctt   1020
ggtcaccctc aggttgggga atcaccttct gtcttcattt tccaggaact tggtgatgat   1080
atcgtgggtg agttcattta ccaggtgctg tagtttcccc tcatcaggca ggaagaagat   1140
ggcggtggca ttgcccaggt atttcatcag cagcacccag ctggacagct tcttacagtg   1200
ctggatgtta aacatgccta aacgcttcat cataggcacc ttcacggtgg tcacctggtc   1260
cacgtggaag tcctcttcct cggtgtcctt gacttcaaag ggtctctccc atttgcctgg   1320
agagagggga aggtgggcat caccaggggt gagtgaaggt ttggaagagt gtagcagaat   1380
aagaaaccat gagtcccctc cctgagaagc cctgagcccc cttgacgaca cacatccctc   1440
gaggctcagc ttcatcatct gtaaaaggtg ctgaaactga ccatccaagc tgccgaaaaa   1500
gattgtgtgg ggataattca aaactagagg aagatgcaga atttctacat cgtggcgatg   1560
tcaggctaag agatgccatc gtggctgtgc attttattg gaatcatatg tttatttgag   1620
ggtgtcttgg atattacaaa taaaatgttg gagcatcagg catatttggt accttctgtc   1680
taaggctccc tgccccttgt taattggcag ctcagttatt catccagggc aaacattctg   1740
cttactattc ctgagagctt tcctcatcct ctagattggc aggggaaatg cagatgcctg   1800
agcagcctcc cctctgccat accaacagag cttcaccatc gaggcatgca gagtggacag   1860
gggcctcagg gaccctgat cccagctttc tcattggaca aaggaggag actgggctg      1920
gagagggacc tgggccccca ctaaggccac agcagagcca ggactttagc tgtgctgact   1980
gcagcctggc ttgcctccac tgccctcctt tgcctcaaga gcaagggagc ctcagagtgg   2040

| aggaagcagc cctggcctt gcctcccacc tccctcccc tatgctgttt tcctgggaca | 2100 |
| gtgggagctg gcttagaatg ccctggggcc cccaggaccc tggcatttta accctcagg | 2160 |
| ggcaggaagg cagcctgaga tacagaagag tccatcacct gctgtatgcc acacaccatc | 2220 |
| cccacagtta cgtactagt | 2239 |

<210> SEQ ID NO 12
<211> LENGTH: 6408
<212> TYPE: DNA
<213> ORGANISM: Artificial Sequence
<220> FEATURE:
<223> OTHER INFORMATION: Synthetic Construct

<400> SEQUENCE: 12

| gaattcggac cgtcgacatt gattattgac tagttattaa tagtaatcaa ttacggggtc | 60 |
| attagttcat agcccatata tggagttccg cgttacataa cttacggtaa atggcccgcc | 120 |
| tggctgaccg cccaacgacc cccgcccatt gacgtcaata atgacgtatg ttcccatagt | 180 |
| aacgccaata gggactttcc attgacgtca atgggtggag tatttacggt aaactgccca | 240 |
| cttggcagta catcaagtgt atcatatgcc aagtacgccc cctattgacg tcaatgacgg | 300 |
| taaatggccc gcctggcatt atgcccagta catgacctta tgggactttc ctacttggca | 360 |
| gtacatctac gtattagtca tcgctattac catggtcgag gtgagcccca cgttctgctt | 420 |
| cactctcccc atctccccc cctccccacc cccaattttg tatttattta ttttttaatt | 480 |
| attttgtgca gcgatggggg cggggggggg ggggggcgc gcgccaggcg gggcggggcg | 540 |
| gggcgagggg cggggcgggg cgaggcggag aggtgcggcg gcagccaatc agagcggcgc | 600 |
| gctccgaaag tttccttta tggcgaggcg cggcggcgg cggccctata aaaagcgaag | 660 |
| cgcgcggcg gcggggagtc gctgcgacgc tgccttcgcc ccgtgccccg ctccgccgcc | 720 |
| gcctcgcgcc gcccgccccg gctctgactg accgcgttac tcccacaggt gagcgggcgg | 780 |
| gacggccctt ctcctccggg ctgtaattag cgcttggttt aatgacggct tgtttctttt | 840 |
| ctgtggctgc gtgaaagcct tgaggggctc cgggagggcc ctttgtgcgg gggagcggc | 900 |
| tcggggggtg cgtgcgtgtg tgtgtgcgtg gggagcgccg cgtgcggctc cgcgctgccc | 960 |
| ggcggctgtg agcgctgcgg gcgcggcgcg gggctttgtg cgctccgcag tgtgcgcgag | 1020 |
| gggagcgcgc ccggggcgg tgcccgcgcg tgcgggggg gctgcgaggg gaacaaaggc | 1080 |
| tgcgtgcggg gtgtgtgcgt gggggggtga gcaggggtg tgggcgcgtc ggtcgggctg | 1140 |
| caaccccccc tgcaccccc tccccgagtt gctgagcacg gcccggcttc gggtgcgggg | 1200 |
| ctccgtacgg ggcgtggcgc ggggctcgcc gtgccgggcg gggggtggcg gcaggtgggg | 1260 |
| gtgccgggcg gggcggggcc gcctcgggcc ggggagggct cggggagggg gcgcggcggc | 1320 |
| ccccggagcg ccggcggctg tcgaggcgcg gcgagccgca gccattgcct tttatggtaa | 1380 |
| tcgtgcgaga gggcgcaggg acttcctttg tcccaaatct gtgcggagcc gaaatctggg | 1440 |
| aggcgccgcc gcaccccctc tagcgggcgc ggggcgaagc ggtgcggcgc cggcaggaag | 1500 |
| gaaatgggcg gggagggcct tcgtgcgtcg ccgcgccgcc gtcccttct cctctccag | 1560 |
| cctcggggct gtccgcgggg ggacggctgc cttcggggg gacggggcag ggcggggttc | 1620 |
| ggcttctggc gtgtgaccgg cggctctaga gcctctgcta accatgttca tgccttcttc | 1680 |
| tttttcctac agctcctggg caacgtgctg gttattgtgc tgtctcatca ttttggcaaa | 1740 |
| gaattcttcg aaagatctgc tagcttaatt aacccaaacg ggccctctag actcgagcgg | 1800 |

-continued

| | |
|---|---|
| ccgccactgt gctggatatc tgcagaattc agccaccacc ggcacaatga atggcacaga | 1860 |
| aggccctaac ttctacgtgc ccttctccaa tgcgacgggt gtggtacgca gcccttcga | 1920 |
| gtacccacag tactacctgg ctgagccatg gcagttctcc atgctggccg cctacatgtt | 1980 |
| tctgctgatc gtgctgggct tccccatcaa cttcctcacg ctctacgtca ccgtccagca | 2040 |
| caagaagctg cgcacgcctc tcaactacat cctgctcaac ctagccgtgg ctgacctctt | 2100 |
| catggtccta ggtggcttca ccagcaccct ctacacctct ctgcatggat acttcgtctt | 2160 |
| cgggcccaca ggatgcaatt tggagggctt ctttgccacc ctgggcggtg aaattgccct | 2220 |
| gtggtccttg gtggtcctgg ccatcgagcg gtacgtggtg gtgtgtaagc ccatgagcaa | 2280 |
| cttccgcttc ggggagaacc atgccatcat gggcgttgcc ttcacctggg tcatggcgct | 2340 |
| ggcctgcgcc gcaccccac tcgccggctg gtccaggtac atccccgagg gcctgcagtg | 2400 |
| ctcgtgtgga atcgactact acacgctcaa gccggaggtc aacaacgagt cttttgtcat | 2460 |
| ctacatgttc gtggtccact tcaccatccc catgattatc atcttttct gctatgggca | 2520 |
| gctcgtcttc accgtcaagg aggccgctgc ccagcagcag gagtcagcca ccacacagaa | 2580 |
| ggcagagaag gaggtcaccc gcatggtcat catcatggtc atcgctttcc tgatctgctg | 2640 |
| ggtgccctac gccagcgtgg cattctacat cttcacccac cagggctcca acttcggtcc | 2700 |
| catcttcatg accatcccag cgttctttgc caagagcgcc gccatctaca accctgtcat | 2760 |
| ctatatcatg atgaacaagc agttccggaa ctgcatgctc accaccatct gctgcggcaa | 2820 |
| gaacccactg ggtgacgatg aggcctctgc taccgtgtcc aagacggaga cgagccaggt | 2880 |
| ggccccggcc taaccaagaa agcttaagtt tgggactagt gcggccgct cgagcatgca | 2940 |
| tctagagggc cctattctat agtgtcacct aaatgctaga gctcgctgat cagcctcgac | 3000 |
| tgtgccttct agttgccagc catctgttgt ttgcccctcc ccgtgcctt ccttgaccct | 3060 |
| ggaaggtgcc actcccactg tcctttccta ataaaatgag gaaattgcat cgcattgtct | 3120 |
| gagtaggtgt cattctattc tggggggtgg ggtggggcag gacagcaagg gggaggattg | 3180 |
| ggaagacaat agcaggcatg ctggggagct agagtcgacc ggaccgctgc aggcatgcaa | 3240 |
| gcttggcgta atcatggtca tagctgtttc ctgtgtgaaa ttgttatccg ctcacaattc | 3300 |
| cacacaacat acgagccgga agcataaagt gtaaagcctg gggtgcctaa tgagtgagct | 3360 |
| aactcacatt aattgcgttg cgctcactgc ccgctttcca gtcgggaaac ctgtcgtgcc | 3420 |
| agctgcatta atgaatcggc caacgcgcgg ggagaggcgg tttgcgtatt gggcgctctt | 3480 |
| ccgtattagt catcgctatt accatggtga tgcggttttg gcagtacatc aatgggcgtg | 3540 |
| gatagcggtt tgactcacgg ggatttccaa gtctccaccc cattgacgtc aatgggagtt | 3600 |
| tgttttggca ccaaaatcaa cgggactttc caaaatgtcg taacaactcc gccccattga | 3660 |
| cgcaaatggg cggtaggcgt gtacggtggg aggtctatat aagcagagct ctctggctaa | 3720 |
| ctagagaacc cactgcttac tggcttatcg aaattaatac gactcactat agggagtccc | 3780 |
| aagctggcta gttaagctat caacaagttt gtacaaaaaa gcaggcttta agggaggta | 3840 |
| gtgagtcgac cagtggatcc tggaggcttg ctgaaggctg tatgctgaag gagcttacaa | 3900 |
| tctagctggg gttttggcca ctgactgacc ccagctagtg taagctcctt caggacacaa | 3960 |
| ggcctgttac tagcactcac atggaacaaa tggcccagat ctggccgcac tcgagatgct | 4020 |
| tcctcgctca ctgactcgct gcgctcggtc gttcggctgc ggcgagcggt atcagctcac | 4080 |
| tcaaaggcgg taatacggtt atccacagaa tcaggggata acgcaggaaa gaacatgtga | 4140 |
| gcaaaaggcc agcaaaaggc caggaaccgt aaaaaggccg cgttgctggc gttttttccat | 4200 |

```
aggctccgcc cccctgacga gcatcacaaa aatcgacgct caagtcagag gtggcgaaac    4260
ccgacaggac tataaagata ccaggcgttt cccctggaa gctccctcgt gcgctctcct    4320
gttccgaccc tgccgcttac cggatacctg tccgcctttc tcccttcggg aagcgtggcg    4380 cttttctcata gctcacgctg taggtatctc agttcggtgt aggtcgttcg ctccaagctg    4440
ggctgtgtgc acgaaccccc cgttcagccc gaccgctgcg ccttatccgg taactatcgt    4500
cttgagtcca acccggtaag acacgactta tcgccactgg cagcagccac tggtaacagg    4560
attagcagag cgaggtatgt aggcggtgct acagagttct tgaagtggtg gcctaactac    4620
ggctacacta aaggacagt atttggtatc tgcgctctgc tgaagccagt taccttcgga    4680
aaaagagttg gtagctcttg atccggcaaa caaaccaccg ctggtagcgg tggtttttt    4740 gtttgcaagc agcagattac gcgcagaaaa aaggatctc aagaagatcc tttgatcttt    4800
tctacggggt ctgacgctca gtggaacgaa aactcacgtt aagggatttt ggtcatgaga    4860
ttatcaaaaa ggatcttcac ctagatcctt ttaaattaaa aatgaagttt taaatcaatc    4920
taaagtatat atgagtaaac ttggtctgac agttaccaat gcttaatcag tgaggcacct    4980
atctcagcga tctgtctatt tcgttcatcc atagttgcct gactccccgt cgtgtagata    5040
actacgatac gggagggctt accatctggc cccagtgctg caatgatacc gcgagaccca    5100
cgctcaccgg ctccagattt atcagcaata aaccagccag ccggaagggc cgagcgcaga    5160
agtggtcctg caactttatc cgcctccatc cagtctatta attgttgccg ggaagctaga    5220
gtaagtagtt cgccagttaa tagtttgcgc aacgttgttg ccattgctac aggcatcgtg    5280
gtgtcacgct cgtcgtttgg tatggcttca ttcagctccg gttcccaacg atcaaggcga    5340
gttacatgat cccccatgtt gtgcaaaaaa gcggttagct ccttcggtcc tccgatcgtt    5400
gtcagaagta agttggccgc agtgttatca ctcatggtta tggcagcact gcataattct    5460
cttactgtca tgccatccgt aagatgcttt tctgtgactg gtgagtactc aaccaagtca    5520
ttctgagaat agtgtatgcg gcgaccgagt tgctcttgcc cggcgtcaat acgggataat    5580
accgcgccac atagcagaac tttaaaagtg ctcatcattg gaaaacgttc ttcggggcga    5640
aaactctcaa ggatcttacc gctgttgaga tccagttcga tgtaacccac tcgtgcaccc    5700
aactgatctt cagcatcttt tactttcacc agcgtttctg ggtgagcaaa aacaggaagg    5760
caaaatgccg caaaaaaggg aataagggcg acacggaaat gttgaatact catactcttc    5820 cttttcaat attattgaag catttatcag ggttattgtc tcatgagcgg atacatattt    5880
gaatgtattt agaaaaataa acaaataggg gttccgcgca catttcccg aaaagtgcca    5940 cctgacgtct aagaaaccat tattatcatg acattaacct ataaaaatag gcgtatcacg    6000
aggccctttc gtctcgcgcg tttcggtgat gacggtgaaa acctctgaca catgcagctc    6060
ccggagacgg tcacagcttg tctgtaagcg gatgccggga gcagacaagc ccgtcagggc    6120
gcgtcagcgg gtgttggcgg gtgtcgggc tggcttaact atgcggcatc agagcagatt    6180
gtactgagag tgcaccatat gcggtgtgaa ataccgcaca gatgcgtaag gagaaaatac    6240
cgcatcaggc gccattcgcc attcaggctg cgcaactgtt gggaagggcg atcggtgcgg    6300
gcctcttcgc tattacgcca gctggcgaaa ggggatgtg ctgcaaggcg attaagttgg    6360
gtaacgccag ggttttccca gtcacgacgt tgtaaaacga cggccagt              6408
```

<210> SEQ ID NO 13
<211> LENGTH: 155
<212> TYPE: DNA

<213> ORGANISM: Artificial Sequence
<220> FEATURE:
<223> OTHER INFORMATION: Synthetic Construct

<400> SEQUENCE: 13

| | | | | | |
|---|---|---|---|---|---|
| gatcctggag | gcttgctgaa | ggctgtatgc | tgaaggagct | tacaatctag | ctggggtttt | 60 |
| ggccactgac | tgaccccagc | tagtgtaagc | tccttcagga | cacaaggcct | gttactagca | 120 |
| ctcacatgga | acaaatggcc | cagatctggc | cgcac | | | 155 |

<210> SEQ ID NO 14
<211> LENGTH: 189
<212> TYPE: DNA
<213> ORGANISM: Homo sapiens

<400> SEQUENCE: 14

| | | | | | |
|---|---|---|---|---|---|
| aacctaaccc | ccatggttgg | cgagggactg | ctgtgtgtga | aatggtaact | gccctcaagg | 60 |
| agcttacaat | ctagctgggg | gtaaatgact | tgcacatgaa | cacaactaga | ctgtgagctt | 120 |
| ctagagggca | gggaccttac | cctagtcatc | tctcttctca | ccctgcacac | cctccctgag | 180 |
| ggatctcat | | | | | | 189 |

<210> SEQ ID NO 15
<211> LENGTH: 6172
<212> TYPE: DNA
<213> ORGANISM: Artificial Sequence
<220> FEATURE:
<223> OTHER INFORMATION: Synthetic Construct

<400> SEQUENCE: 15

| | | | | | |
|---|---|---|---|---|---|
| tatgcggtgt | gaaataccgc | acagatgcgt | aaggagaaaa | taccgcatca | ggcgccattc | 60 |
| gccattcagg | ctgcgcaact | gttgggaagg | gcgatcggtg | cgggcctctt | cgctattacg | 120 |
| ccagctggcg | aaagggggat | gtgctgcaag | gcgattaagt | tgggtaacgc | cagggttttc | 180 |
| ccagtcacga | cgttgtaaaa | cgacggccag | tgaattcgga | ccgtcgacat | tgattattgg | 240 |
| gccccagaag | cctggtggtt | gtttgtcctt | ctcagggaa | aagtgaggcg | gccccttgga | 300 |
| ggaaggggcc | gggcagaatg | atctaatcgg | attccaagca | gctcagggga | ttgtcttttt | 360 |
| ctagcacctt | cttgccactc | ctaagcgtcc | tccgtgaccc | cggctgggat | ttagcctggt | 420 |
| gctgtgtcag | ccccggtctc | ccaggggctt | cccagtggtc | cccaggaacc | ctcgacaggg | 480 |
| cccggtctct | ctcgtccagc | aagggcaggg | acgggccaca | ggccaagggc | ggagtcgctg | 540 |
| cgacgctgcc | ttcgccccgt | gccccgctcc | gccgccgcct | cgcgccgccc | gccccggctc | 600 |
| tgactgaccg | cgttactccc | acaggtgagc | gggcgggacg | gcccttctcc | tccgggctgt | 660 |
| aattagcaag | aggtaagggt | ttaagggatg | gttggttggt | ggggtattaa | tgtttaatta | 720 |
| cctgttttac | aggcctgaaa | tcacttggtt | ttaggttggg | gatccggtac | ccaattgcca | 780 |
| tgggctagca | tgcatgagct | ccctgcaggg | tttatctgca | gaattcagcc | accaccggca | 840 |
| caatgaatgg | cacagaaggc | cctaacttct | acgtgccctt | ctccaatgcg | acgggtgtgg | 900 |
| tacgcagccc | cttcgagtac | ccacagtact | acctggctga | gccatggcag | ttctccatgc | 960 |
| tggccgccta | catgtttctg | ctgatcgtgc | tgggcttccc | catcaacttc | ctcacgctct | 1020 |
| acgtcaccgt | ccagcacaag | aagctgcgca | cgcctctcaa | ctacatcctg | ctcaacctag | 1080 |
| ccgtggctga | cctcttcatg | gtcctaggtg | gcttcaccag | caccctctac | acctctctgc | 1140 |
| atggatactt | cgtcttcggg | cccacaggat | gcaatttgga | gggcttcttt | gccaccctgg | 1200 |
| gcggtgaaat | tgccctgtgg | tccttggtgg | tcctggccat | cgagcggtac | gtggtggtgt | 1260 |

-continued

```
gtaagcccat gagcaacttc cgcttcgggg agaaccatgc catcatgggc gttgccttca    1320
cctgggtcat ggcgctggcc tgcgccgcac ccccactcgc cggctggtcc aggtacatcc    1380
ccgagggcct gcagtgctcg tgtggaatcg actactacac gctcaagccg gaggtcaaca    1440
acgagtcttt tgtcatctac atgttcgtgg tccacttcac catccccatg attatcatct    1500
ttttctgcta tgggcagctc gtcttcaccg tcaaggaggc cgctgcccag cagcaggagt    1560
cagccaccac acagaaggca gagaaggagg tcacccgcat ggtcatcatc atggtcatcg    1620
cttttcctgat ctgctgggtg ccctacgcca gcgtggcatt ctacatcttc acccaccagg    1680
gctccaactt cggtcccatc ttcatgacca tcccagcgtt ctttgccaag agcgccgcca    1740
tctacaaccc tgtcatctat atcatgatga caagcagtt ccggaactgc atgctcacca    1800
ccatctgctg cggcaagaac ccactgggtg acgatgaggc ctctgctacc gtgtccaaga    1860
cggagacgag ccaggtggcc ccggcctaac caagaaagct taagtttgtg tcccggctta    1920
gggctaaatg tctaggacag aatggaacac atagtagctg attaataaat gctagctgga    1980
tgaagggagg aatgagtgac tgactgagtg gatatatgag tgaagggatt aatggaaggg    2040
aacatggatg tcctcaggtg cccaacctgg cagatccagt catgtctggc tggaatctat    2100
aagcagtttt acatacctgc cctgagcttt attgcggtag tttatcacag ttaaattgct    2160
aacgcagtca gtgcttctga cacaacagtc tcgaacttaa gctgcagtga ctctcttaag    2220
gtagccttgc agaagttggt cgtgaggcac tgggcaggta agtatcaagg ttacaagaca    2280
ggtttaagga gaccaataga aactgggctt gtcgagacag agaaaaacct aacccccatg    2340
gttggcgagg gactgctgtg tgtgaaatgg taactgccct caaggagctt acaatctagc    2400
tgggggtaaa tgacttgcac atgaaacaca ctagactgtg agcttctaga gggcagggac    2460
cttaccctag tcatctctct tctcaccctg cacaccctcc ctgagggatc tcatgactct    2520
tgcgtttctg ataggcacct attggtctta ctgacatcca cttttgccttt ctctccacag    2580
gtgtccactc ccagttcaca ccggcacaat gaatggcaca gaaggcccta acttctacgt    2640
gcccttctcc aatgcgacgg gtgtggtacg cagccccttc gagtacccac agtcagagat    2700
aaatgacagt gacagcaacg tgagctgcag cccttaggac tgagaaagca tcgagaccag    2760
gggtctccgg caaggcctag gtcctcccct cagtatggaa accttgcctc atgtctctca    2820
gcctccttgg cctgtggaga tccagccctt cctcttggct tctggataca tttgctcttc    2880
tacaccagca accaagtggc aacagttcca ggccagtatg gagttttaga agccatgcca    2940
atatgcccac cttcagggag cagctgagtc cttgatgcca cccttgttct gaagagttca    3000
gaaacacagt gcaagacatg accaggcctc atccttagga tgctcatgga tccagttctt    3060
agctcccttg ttggatatgc tgttttcctt ggcctttggt cttttcttta tcccagaggg    3120
ttttggcttt aaggccaaca ggaactatgg ggtaccagaa ttgagcagcc tcagtctgca    3180
tccctcctct atagaaccac agctgggccc tcagcaggcc caactctgca tgggacagaa    3240
ggcattaaaa gcctagagta tccctcgagg ggcccaagct tacgcgtacc cagctttctt    3300
gtacaaagtg gtccctatag tgagtcgtat tataagctag gcactggccg tcgttttaca    3360
acgtcgtgac tgggaaaact gctagcttgg gatcttgtg aaggaacctt acttctgtgg    3420
tgtgacataa ttggacaaac tacctacaga gatttaaagc tctaaggtaa atataaaatt    3480
tttaagtgta taatgtgtta aactagctgc aaaacctgtg ccttctagtt gccagccatc    3540
tgttgtttgc cctcccccg tgccttcctt gaccctggaa ggtgccactc ccactgtcct    3600
```

-continued

```
ttcctaataa aatgaggaaa ttgcatcgca ttgtctgagt aggtgtcatt ctattctggg      3660
gggtggggtg gggcaggaca gcaaggggga ggattgggaa gacaatagca ggcatgctgg      3720
ggaactagtc ggaccgctgc aggcatgcaa gcttggcgta atcatggtca tagctgtttc      3780
ctgtgtgaaa ttgttatccg ctcacaattc cacacaacat acgagccgga agcataaagt      3840
gtaaagcctg gggtgcctaa tgagtgagct aactcacatt aattgcgttg cgctcactgc      3900 ccgcttttcca gtcgggaaac ctgtcgtgcc agctgcatta tgaatcggc caacgcgcgg      3960 ggagaggcgg tttgcgtatt gggcgctctt ccgcttcctc gctcactgac tcgctgcgct      4020
cggtcgttcg gctgcggcga gcggtatcag ctcactcaaa ggcggtaata cggttatcca      4080
cagaatcagg ggataacgca ggaaagaaca tgtgagcaaa aggccagcaa aaggccagga      4140
accgtaaaaa ggccgcgttg ctggcgtttt tccataggct ccgcccccct gacgagcatc      4200
acaaaaatcg acgctcaagt cagaggtggc gaaacccgac aggactataa agataccagg      4260
cgtttccccc tggaagctcc ctcgtgcgct ctcctgttcc gaccctgccg cttaccggat      4320
acctgtccgc ctttctccct tcgggaagcg tggcgctttc tcatagctca cgctgtaggt      4380
atctcagttc ggtgtaggtc gttcgctcca agctgggctg tgtgcacgaa ccccccgttc      4440
agcccgaccg ctgcgcctta tccggtaact atcgtcttga gtccaacccg gtaagacacg      4500
acttatcgcc actggcagca gccactggta acaggattag cagagcgagg tatgtaggcg      4560
gtgctacaga gttcttgaag tggtggccta actacggcta cactagaagg acagtatttg      4620
gtatctgcgc tctgctgaag ccagttacct tcggaaaaag agttggtagc tcttgatccg      4680
gcaaacaaac caccgctggt agcggtggtt tttttgtttg caagcagcag attacgcgca      4740
gaaaaaaagg atctcaagaa gatcctttga tcttttctac ggggtctgac gctcagtgga      4800
acgaaaactc acgttaaggg attttggtca tgagattatc aaaaaggatc ttcacctaga      4860
tccttttaaa ttaaaaatga agttttaaat caatctaaag tatatatgag taaacttggt      4920
ctgacagtta ccaatgctta atcagtgagg cacctatctc agcgatctgt ctatttcgtt      4980
catccatagt tgcctgactc cccgtcgtgt agataactac gatacgggag ggcttaccat      5040
ctggccccag tgctgcaatg ataccgcgag acccacgctc accggctcca gatttatcag      5100
caataaacca gccagccgga agggccgagc gcagaagtgg tcctgcaact ttatccgcct      5160
ccatccagtc tattaattgt tgccgggaag ctagagtaag tagttcgcca gttaatagtt      5220
tgcgcaacgt tgttgccatt gctacaggca tcgtggtgtc acgctcgtcg tttggtatgg      5280
cttcattcag ctccggttcc caacgatcaa ggcgagttac atgatccccc atgttgtgca      5340
aaaaagcggt tagctccttc ggtcctccga tcgttgtcag aagtaagttg gccgcagtgt      5400
tatcactcat ggttatggca gcactgcata attctcttac tgtcatgcca tccgtaagat      5460
gcttttctgt gactggtgag tactcaacca agtcattctg agaatagtgt atgcggcgac      5520
cgagttgctc ttgcccggcg tcaatacggg ataataccgc gccacatagc agaactttaa      5580
aagtgctcat cattggaaaa cgttcttcgg ggcgaaaact ctcaaggatc ttaccgctgt      5640
tgagatccag ttcgatgtaa cccactcgtg cacccaactg atcttcagca tcttttactt      5700
tcaccagcgt ttctgggtga gcaaaaacag gaaggcaaaa tgccgcaaaa aagggaataa      5760
gggcgacacg gaaatgttga atactcatac tcttcctttt tcaatattat tgaagcattt      5820
atcagggtta ttgtctcatg agcggataca tatttgaatg tatttagaaa aataaacaaa      5880 tagggggttcc gcgcacattt ccccgaaaag tgccacctga cgtctaagaa accattatta      5940
tcatgacatt aacctataaa aataggcgta tcacgaggcc ctttcgtctc gcgcgtttcg      6000
```

```
gtgatgacgg tgaaaacctc tgacacatgc agctcccgga gacggtcaca gcttgtctgt    6060
aagcggatgc cgggagcaga caagcccgtc agggcgcgtc agcgggtgtt ggcgggtgtc    6120
ggggctggct taactatgcg gcatcagagc agattgtact gagagtgcac ca           6172

<210> SEQ ID NO 16
<211> LENGTH: 441
<212> TYPE: DNA
<213> ORGANISM: Homo sapiens

<400> SEQUENCE: 16
actagaagct ttattgcggt agtttatcac agttaaattg ctaacgcagt cagtgcttct      60
gacacaacag tctcgaactt aagctgcagt gactctctta aggtagcctt gcagaagttg     120
gtcgtgaggc actgggcagg taagtatcaa ggttacaaga caggtttaag gagaccaata    180
gaaactgggc ttgtcgagac agagaatgga tcctggaggc ttgctgaagg ctgtatgctg    240
aaggagctta caatctagct ggggttttgg ccactgactg accccagcta gtgtaagctc    300
cttcaggaca caaggcctgt tactagcact cacatggaac aaatgcccca gatctgagac    360
tcttgcgttt ctgataggca cctattggtc ttactgacat ccactttgcc tttctctcca    420
caggtgtcca ctcccagttc a                                              441

<210> SEQ ID NO 17
<211> LENGTH: 150
<212> TYPE: DNA
<213> ORGANISM: Artificial Sequence
<220> FEATURE:
<223> OTHER INFORMATION: Synthetic Construct

<400> SEQUENCE: 17
tggatcctgg aggcttgctg aaggctgtat gctgaaggag cttacaatct agctggggtt      60
ttggccactg actgacccca gctagtgtaa gctccttcag gacacaaggc ctgttactag    120
cactcacatg gaacaaatgg cccagatctg                                     150

<210> SEQ ID NO 18
<211> LENGTH: 190
<212> TYPE: DNA
<213> ORGANISM: Homo sapiens

<400> SEQUENCE: 18
aaacctaacc cccatggttg gcgagggact gctgtgtgtg aaatggtaac tgccctcaag      60
gagcttacaa tctagctggg gtaaatgac ttgcacatga acacaactag actgtgagct     120
tctagagggc agggacctta ccctagtcat ctctcttctc accctgcaca ccctccctga    180
gggatctcat                                                           190

<210> SEQ ID NO 19
<211> LENGTH: 79
<212> TYPE: RNA
<213> ORGANISM: Homo sapiens

<400> SEQUENCE: 19
cucugccugg agacuaaggc aaauugggcc auuaaaagcu cagcuccuau guuggauua       60 acgguggugg guuuuguug                                                  79

<210> SEQ ID NO 20
<211> LENGTH: 113
<212> TYPE: DNA
```

<213> ORGANISM: Artificial Sequence
<220> FEATURE:
<223> OTHER INFORMATION: Synthetic Construct

<400> SEQUENCE: 20

```
ccactccctc tctgcgcgct cgctcgctca ctgaggccgg gcgaccaaag gtcgcccgac    60
gcccgggctt tgcccgggcg gcctcagtga gcgagcgagc gcgcagagag gga           113
```

<210> SEQ ID NO 21
<211> LENGTH: 143
<212> TYPE: DNA
<213> ORGANISM: Artificial Sequence
<220> FEATURE:
<223> OTHER INFORMATION: Synthetic Construct

<400> SEQUENCE: 21

```
ggccactccc tctctgcgcg ctcgctcgct cactgaggcc gggcgaccaa aggtcgcccg    60
acgcccgggc tttgcccggg cggcctcagt gagcgagcga gcgcgcagag agggagtggc    120
caactccatc actaggggtt cct                                            143
```

<210> SEQ ID NO 22
<211> LENGTH: 795
<212> TYPE: DNA
<213> ORGANISM: Mus musculus

<400> SEQUENCE: 22

```
tgctgattca gccaggaact agttattaat agtaatcaat tacggggtca ttagttcata    60
gcccatatat ggagttccgc gttacataac ttacggtaaa tggcccgcct ggctgaccgc    120
ccaacgaccc ccgcccattg acgtcaataa tgacgtatgt tcccatagta acgccaatag    180
ggactttcca ttgacgtcaa tgggtggagt atttacggta aactgcccac ttggcagtac    240
atcaagtgta tcatatgcca gtacgcccc ctattgacgt caatgacggt aaatggcccg     300
cctggcatta tgcccagtac atgaccttat gggactttcc tacttggcag tacatctacg    360
tattagtcat cgctattacc acaaatagtt atcgagccgc tgagccgggg ggcgggggt     420
gtgagactgg aggcgatgga cggagctgac ggcacacaca gctcagatct gtcaagtgag    480
ccattgtcag ggcttgggga ctggataagt caggggtct cctgggaaga gatgggatag     540
gtgagttcag gaggagacat tgtcaactgg agccatgtgg agaagtgaat ttagggccca    600
aaggttccag tcgcagcctg aggccaccag actgacatgg ggaggaattc ccagaggact    660
ctggggcaga caagatgaga caccctttcc tttctttacc taagggcctc cacccgatgt    720
caccttggcc cctctgcaag ccaattaggc cccggtggca gcagtgggat tagcgttagt    780
atgatatctc gcgga                                                     795
```

<210> SEQ ID NO 23
<211> LENGTH: 315
<212> TYPE: DNA
<213> ORGANISM: Artificial Sequence
<220> FEATURE:
<223> OTHER INFORMATION: Synthetic Construct

<400> SEQUENCE: 23

```
ggagtcgctg cgacgctgcc ttcgccccgt gccccgctcc gccgccgcct cgcgccgccc    60
gccccggctc tgactgaccg cgttactccc acaggtgagc gggcgggacg gcccttctcc    120
tccgggctgt aattagcaag aggtaagggt ttaaggatg gttggttggt ggggtattaa     180
tgtttaatta cctgttttac aggcctgaaa tcacttggtt ttaggttggg gatccggtac    240
```

-continued

```
ccaattgcca tgggctagca tgcatgagct ccctgcaggg ttttaatgcc aactttgtac      300
aaaaaagcag gcacc                                                       315
```

<210> SEQ ID NO 24
<211> LENGTH: 2064
<212> TYPE: DNA
<213> ORGANISM: Artificial Sequence
<220> FEATURE:
<223> OTHER INFORMATION: Synthetic Construct

<400> SEQUENCE: 24

```
tgactagtta gggccccaga agcctggtgg ttgtttgtcc ttctcagggg aaaagtgagg       60
cggccccttg gaggaagggg ccgggcagaa tgatctaatc ggattccaag cagctcaggg      120
gattgtcttt ttctagcacc ttcttgccac tcctaagcgt cctccgtgac cccggctggg      180
atttagcctg gtgctgtgtc agccccggtc tcccaggggc ttcccagtgg tccccaggaa      240
ccctcgacag ggcccggtct ctctcgtcca gcagggcag  ggacgggcca caggccaagg      300
gcactagaag ctttattgcg gtagtttatc acagttaaat tgctaacgca gtcagtgctt      360
ctgacacaac agtctcgaac ttaagctgca gtgactctct taaggtagcc ttgcagaagt      420
tggtcgtgag gcactgggca ggtaagtatc aaggttacaa gacaggttta aggagaccaa      480
tagaaactgg gcttgtcgag acagagaatg gatcctggag gcttgctgaa ggctgtatgc      540
tgaaggagct tacaatctag ctggggtttt ggccactgac tgacccagc  tagtgtaagc      600 tccttcagga cacaaggcct gttactagca ctcacatgga acaaatggcc cagatctgag      660
actcttgcgt ttctgatagg cacctattgg tcttactgac atccactttg cctttctctc      720
cacaggtgtc cactcccagt tcacaccggc acaatgaatg gcacagaagg ccctaacttc      780
tacgtgccct tctccaatgc gacgggtgtg gtacgcagcc cttcgagta cccacagtac      840 tacctggctg agccatggca gttctccatg ctggccgcct acatgtttct gctgatcgtg      900
ctgggcttcc ccatcaactt cctcacgctc tacgtcaccg tccagcacaa gaagctgcgc      960
acgcctctca actacatcct gctcaaccta gccgtggctg acctcttcat ggtcctaggt     1020
ggcttcacca gcaccctcta cacctctctg catggatact tcgtcttcgg gcccacagga     1080
tgcaatttgg agggcttctt tgccaccctg ggcggtgaaa ttgccctgtg gtccttggtg     1140
gtcctggcca tcgagcggta cgtggtggtg tgtaagccca tgagcaactt ccgcttcggg     1200
gagaaccatg ccatcatggg cgttgccttc acctgggtca tggcgctggc ctgcgccgca     1260
cccccactcg ccggctggtc caggtacatc cccgagggcc tgcagtgctc gtgtggaatc     1320
gactactaca cgctcaagcc ggaggtcaac aacgagtctt ttgtcatcta catgttcgtg     1380
gtccacttca ccatccccat gattatcatc ttttctgct  atgggcagct cgtcttcacc     1440
gtcaaggagg ccgctgccca gcagcaggag tcagccacca cacagaaggc agagaaggag     1500
gtcacccgca tggtcatcat catggtcatc gctttcctga tctgctgggt gcctacgcc      1560 agcgtggcat tctacatctt cacccaccag ggctccaact tcggtcccat cttcatgacc     1620
atcccagcgt tctttgccaa gagcgccgcc atctacaacc tgtcatcta  tatcatgatg     1680 aacaagcagt tccggaactg catgctcacc accatctgct gcggcaagaa cccactgggt     1740
gacgatgagg cctctgctac cgtgtccaag acggagacga gccaggtggc cccggcctaa     1800
ccaagaaagc ttaagtttaa accgctgatc agcctcgact gtgccttcta gttgccagcc     1860
atctgttgtt tgcccctccc ccgtgccttc cttgaccctg gaaggtgcca ctcccactgt     1920
```

```
cctttcctaa taaaatgagg aaattgcatc gcattgtctg agtaggtgtc attctattct    1980
ggggggtggg gtggggcagg acagcaaggg ggaggattgg aagacaata gcaggcatgc    2040 tggggatgcg gtgggctcta tggc                                          2064
```

<210> SEQ ID NO 25
<211> LENGTH: 2093
<212> TYPE: DNA
<213> ORGANISM: Artificial Sequence
<220> FEATURE:
<223> OTHER INFORMATION: Synthetic Construct

<400> SEQUENCE: 25

```
gggccccaga agcctggtgg ttgtttgtcc ttctcagggg aaaagtgagg cggccccttg      60
gaggaagggg ccgggcagaa tgatctaatc ggattccaag cagctcaggg gattgtcttt    120
ttctagcacc ttcttgccac tcctaagcgt cctccgtgac cccggctggg atttagcctg    180
gtgctgtgtc agccccggtc tcccaggggc ttcccagtgg tccccaggaa ccctcgacag    240
ggcccggtct ctctcgtcca gcaagggcag ggacgggcca caggccaagg gcactagaag    300
ctttattgcg gtagtttatc acagttaaat tgctaacgca gtcagtgctt ctgacacaac    360
agtctcgaac ttaagctgca gtgactctct taaggtagcc ttgcagaagt tggtcgtgag    420
gcactgggca ggtaagtatc aaggttacaa gacaggttta aggagaccaa tagaaactgg    480
gcttgtcgag acagagaaaa acctaacccc catggttggc gagggactgc tgtgtgtgaa    540
atggtaactg ccctcaagga gcttacaatc tagctggggg taaatgactt gcacatgaac    600
acaactagac tgtgagcttc tagagggcag ggaccttacc ctagtcatct ctcttctcac    660
cctgcacacc ctccctgagg gatctcatga ctcttgcgtt tctgataggc acctattggt    720
cttactgaca tccactttgc cttttctctcc acaggtgtcc actcccagtt cacaccggca    780
caatgaatgg cacagaaggc cctaacttct acgtgccctt ctccaatgcg acgggtgtgg    840
tacgcagccc cttcgagtac ccacagtact acctggctga gccatggcag ttctccatgc    900
tggccgccta catgtttctg ctgatcgtgc tgggcttccc catcaacttc ctcacgctct    960
acgtcaccgt ccagcacaag aagctgcgca cgcctctcaa ctacatcctg ctcaacctag   1020
ccgtggctga cctcttcatg gtcctaggtg gcttcaccag caccctctac acctctctgc   1080
atggatactt cgtcttcggg cccacaggat gcaatttgga gggcttcttt gccaccctgg   1140
gcggtgaaat tgccctgtgg tccttggtgg tcctggccat cgagcggtac gtggtggtgt   1200
gtaagcccat gagcaacttc cgcttcgggg agaaccatgc catcatgggc gttgccttca   1260
cctgggtcat ggcgctggcc tgcgccgcac ccccactcgc cggctggtcc aggtacatcc   1320
ccgagggcct gcagtgctcg tgtggaatcg actactacac gctcaagccg gaggtcaaca   1380
acgagtcttt tgtcatctac atgttcgtgg tccacttcac catccccatg attatcatct   1440 tttctgcta tgggcagctc gtcttcaccg tcaaggaggc cgctgcccag cagcaggagt   1500
cagccaccac acagaaggca gagaaggagg tcacccgcat ggtcatcatc atggtcatcg   1560
ctttcctgat ctgctgggtg ccctacgcca gcgtggcatt ctacatcttc acccaccagg   1620
gctccaactt cggtcccatc ttcatgacca tcccagcgtt ctttgccaag agcgccgcca   1680
tctacaaccc tgtcatctat atcatgatga acaagcagtt ccggaactgc atgctcacca   1740
ccatctgctg cggcaagaac ccactgggtg acgatgaggc ctctgctacc gtgtccaaga   1800
cggagacgag ccaggtggcc ccggcctaac caagaaagct taagtttaaa ccgctgatca   1860
gcctcgactg tgccttctag ttgccagcca tctgttgttt gcccctcccc cgtgccttcc   1920
```

-continued

```
ttgaccctgg aaggtgccac tcccactgtc ctttcctaat aaaatgagga aattgcatcg    1980
cattgtctga gtaggtgtca ttctattctg gggggtgggg tggggcagga cagcaagggg    2040
gaggattggg aagacaatag caggcatgct ggggatgcgg tgggctctat ggc           2093
```

<210> SEQ ID NO 26
<211> LENGTH: 2716
<212> TYPE: DNA
<213> ORGANISM: Artificial Sequence
<220> FEATURE:
<223> OTHER INFORMATION: Synthetic Construct

<400> SEQUENCE: 26

```
acgcgttttc tgcagcgggg attaatatga ttatgaacac ccccaatctc ccagatgctg      60
attcagccag gaactagtta ttaatagtaa tcaattacgg ggtcattagt tcatagccca     120
tatatggagt tccgcgttac ataacttacg gtaaatggcc cgcctggctg accgcccaac     180
gacccccgcc cattgacgtc aataatgacg tatgttccca tagtaacgcc aatagggact     240
ttccattgac gtcaatgggt ggagtattta cggtaaactg cccacttggc agtacatcaa     300
gtgtatcata tgccaagtac gccccctatt gacgtcaatg acggtaaatg gcccgcctgg     360
cattatgccc agtacatgac cttatgggac tttcctactt ggcagtacat ctacgtatta     420
gtcatcgcta ttaccacaaa tagttatcga gccgctgagc cggggggcgg ggggtgtgag     480
actggaggcg atggacggag ctgacggcac acacagctca gatctgtcaa gtgagccatt     540
gtcagggctt ggggactgga taagtcaggg ggtctcctgg aagagatggg ataggtgag      600 ttcaggagga gacattgtca actggagcca tgtggagaag tgaatttagg gcccaaaggt     660
tccagtcgca gcctgaggcc accagactga catgggagg aattcccaga ggactctggg     720
gcagacaaga tgagacaccc tttcctttct ttacctaagg gcctccaccc gatgtcacct    780
tggcccctct gcaagccaat taggcccccgg tggcagcagt gggattagcg ttagtatgat    840
atctcgcgga tgctgaatca gcctctggct tagggagaga aggtcacttt ataagggtct     900
ggggggggtc agtgcctgga gttgcgctgt gggagccgtc agtggctgag ctcaactaga    960
agctttattg cggtagttta tcacagttaa attgctaacg cagtcagtgc ttctgacaca   1020
acagtctcga acttaagctg cagtgactct cttaaggtag ccttgcagaa gttggtcgtg   1080
aggcactggg caggtaagta tcaaggttac aagacaggtt taaggagacc aatagaaact   1140
gggcttgtcg agacagagaa tggatcctgg aggcttgctg aaggctgtat gctgaaggag   1200
cttacaatct agctggggtt ttggccactg actgacccca gctagtgtaa gctccttcag   1260
gacacaaggc ctgttactag cactcacatg aacaaatggg cccagatctg agactcttgc   1320
gtttctgata ggcacctatt ggtcttactg acatccactt tgcctttctc tccacaggtg   1380
tccactccca gttcacaccg gcacaatgaa tggcacagaa ggccctaact tctacgtgcc   1440
cttctccaat gcgacgggtg tggtacgcag cccttcgag tacccacagt actacctggc    1500
tgagccatgg cagttctcca tgctggccgc ctacatgttt ctgctgatcg tgctgggctt   1560
ccccatcaac ttcctcacgc tctacgtcac cgtccagcac aagaagctgc gcacgcctct   1620
caactacatc ctgctcaacc tagccgtggc tgacctcttc atggtcctag gtggcttcac   1680 cagcacctc tacacctctc tgcatggata cttcgtcttc gggcccacag gatgcaattt    1740
ggagggcttc tttgccaccc tgggcggtga aattgccctg tggtccttgg tggtcctggc   1800
catcgagcgg tacgtggtgg tgtgtaagcc catgagcaac ttccgcttcg gggagaacca   1860
```

| | |
|---|---|
| tgccatcatg ggcgttgcct tcacctgggt catggcgctg gcctgcgccg cacccccact | 1920 |
| cgccggctgg tccaggtaca tccccgaggg cctgcagtgc tcgtgtggaa tcgactacta | 1980 |
| cacgctcaag ccggaggtca caacgagtc ttttgtcatc tacatgttcg tggtccactt | 2040 |
| caccatcccc atgattatca tcttttctg ctatgggcag ctcgtcttca ccgtcaagga | 2100 |
| ggccgctgcc cagcagcagg agtcagccac cacacagaag gcagagaagg aggtcacccg | 2160 |
| catggtcatc atcatggtca tcgctttcct gatctgctgg gtgccctacg ccagcgtggc | 2220 |
| attctacatc ttcacccacc agggctccaa cttcggtccc atcttcatga ccatcccagc | 2280 |
| gttctttgcc aagagcgccg ccatctacaa ccctgtcatc tatatcatga tgaacaagca | 2340 |
| gttccggaac tgcatgctca ccaccatctg ctgcggcaag aacccactgg gtgacgatga | 2400 |
| ggcctctgct accgtgtcca agacggagac gagccaggtg gccccggcct aaccaagaaa | 2460 |
| gcttaagttt aaaccgctga tcagcctcga ctgtgccttc tagttgccag ccatctgttg | 2520 |
| tttgccccctc ccccgtgcct tccttgaccc tggaaggtgc cactcccact gtcctttcct | 2580 |
| aataaaatga ggaaattgca tcgcattgtc tgagtaggtg tcattctatt ctgggggtg | 2640 |
| gggtggggca ggacagcaag ggggaggatt gggaagacaa tagcaggcat gctggggatg | 2700 |
| cggtgggctc tatggc | 2716 |

<210> SEQ ID NO 27
<211> LENGTH: 2755
<212> TYPE: DNA
<213> ORGANISM: Artificial Sequence
<220> FEATURE:
<223> OTHER INFORMATION: Synthetic Construct

<400> SEQUENCE: 27

| | |
|---|---|
| acgcgttttc tgcagcgggg attaatatga ttatgaacac ccccaatctc ccagatgctg | 60 |
| attcagccag gaactagtta ttaatagtaa tcaattacgg ggtcattagt tcatagccca | 120 |
| tatatggagt tccgcgttac ataacttacg gtaaatggcc cgcctggctg accgcccaac | 180 |
| gacccccgcc cattgacgtc aataatgacg tatgttccca tagtaacgcc aatagggact | 240 |
| ttccattgac gtcaatgggt ggagtattta cggtaaactg cccacttggc agtacatcaa | 300 |
| gtgtatcata tgccaagtac gccccctatt gacgtcaatg acggtaaatg gcccgcctgg | 360 |
| cattatgccc agtacatgac cttatgggac tttcctactt ggcagtacat ctacgtatta | 420 |
| gtcatcgcta ttaccacaaa tagttatcga gccgctgagc cggggggcgg ggggtgtgag | 480 |
| actggaggcg atggacggag ctgacggcac acacagctca gatctgtcaa gtgagccatt | 540 |
| gtcagggctt ggggactgga taagtcaggg ggtctcctgg aagagatgg gataggtgag | 600 |
| ttcaggagga gacattgtca actggagcca tgtggagaag tgaatttagg gcccaaaggt | 660 |
| tccagtcgca gcctgaggcc accagactga catggggagg aattcccaga ggactctggg | 720 |
| gcagacaaga tgagcaccc tttccttct ttacctaagg gcctccaccc gatgtcacct | 780 |
| tggcccctct gcaagccaat taggcccggg tggcagcagt gggattagcg ttagtatgat | 840 |
| atctcgcgga tgctgaatca gcctctggct tagggagaga aggtcacttt ataagggtct | 900 |
| gggggggtc agtgcctgga gttgcgctgt gggagccgtc agtggctgag ctcaactaga | 960 |
| agctttattg cggtagttta tcacagttaa attgctaacg cagtcagtgc ttctgacaca | 1020 |
| acagtctcga acttaagctg cagtgactct cttaaggtag ccttgcagaa gttggtcgtg | 1080 |
| aggcactggg caggtaagta tcaaggttac aagacaggtt taaggagacc aatagaaact | 1140 |
| gggcttgtcg agacagagaa aaacctaacc cccatggttg gcgagggact gctgtgtgtg | 1200 |

-continued

```
aaatggtaac tgccctcaag gagcttacaa tctagctggg ggtaaatgac ttgcacatga    1260
acacaactag actgtgagct tctagagggc agggacctta ccctagtcat ctctcttctc    1320
accctgcaca ccctccctga gggatctcat gactcttgcg tttctgatag cacctattg     1380
gtcttactga catccacttt gcctttctct ccacaggtgt ccactcccag ttcacaccgg    1440
cacaatgaat ggcacagaag gccctaactt ctacgtgccc ttctccaatg cgacgggtgt    1500
ggtacgcagc cccttcgagt acccacagta ctacctggct gagccatggc agttctccat    1560
gctggccgcc tacatgtttc tgctgatcgt gctgggcttc cccatcaact tcctcacgct    1620
ctacgtcacc gtccagcaca agaagctgcg cacgcctctc aactacatcc tgctcaacct    1680
agccgtggct gacctcttca tggtcctagg tggcttcacc agcaccctct acacctctct    1740
gcatggatac ttcgtcttcg ggcccacagg atgcaatttg gagggcttct ttgccaccct    1800
gggcggtgaa attgccctgt ggtccttggt ggtcctggcc atcgagcggt acgtggtggt    1860
gtgtaagccc atgagcaact tccgcttcgg ggagaaccat gccatcatgg gcgttgcctt    1920
cacctgggtc atggcgctgg cctgcgccgc accccactc gccggctggt ccaggtacat    1980
ccccgagggc ctgcagtgct cgtgtggaat cgactactac acgctcaagc cggaggtcaa    2040
caacgagtct tttgtcatct acatgttcgt ggtccacttc accatcccca tgattatcat    2100
cttttttctgc tatgggcagc tcgtcttcac cgtcaaggag gccgctgccc agcagcagga    2160
gtcagccacc acacagaagg cagagaagga ggtcacccgc atggtcatca tcatggtcat    2220
cgcttttcctg atctgctggg tgccctacgc cagcgtggca ttctacatct tcacccacca    2280
gggctccaac ttcggtccca tcttcatgac catcccagcg ttctttgcca agagcgccgc    2340
catctacaac cctgtcatct atatcatgat gaacaagcag ttccggaact gcatgctcac    2400
caccatctgc tgcggcaaga acccactggg tgacgatgag gcctctgcta ccgtgtccaa    2460
gacggagacg agccaggtgg ccccggccta accaagaaag cttaagtta aaccgctgat     2520
cagcctcgac tgtgccttct agttgccagc catctgttgt ttgcccctcc ccgtgccttt    2580
ccttgacccct ggaaggtgcc actcccactg tcctttccta ataaaatgag gaaattgcat    2640
cgcattgtct gagtaggtgt cattctattc tggggggtgg ggtggggcag acagcaagg    2700
gggaggattg ggaagacaat agcaggcatg ctggggatgc ggtgggctct atggc         2755
```

<210> SEQ ID NO 28
<211> LENGTH: 145
<212> TYPE: DNA
<213> ORGANISM: Mus musculus

<400> SEQUENCE: 28

```
agaggactaa gccacaggtg aggagaaagg gggggggggg tctgctgacc cagcaacact      60
ctttccttct gaggcttaag agctattagc gtaggtgact cagtccctaa tcctccattc     120
aatgccctgt gactgcccct gcttc                                           145
```

<210> SEQ ID NO 29
<211> LENGTH: 364
<212> TYPE: DNA
<213> ORGANISM: Cytomegalovirus

<400> SEQUENCE: 29

```
actagttatt aatagtaatc aattacgggg tcattagttc atagcccata tatggagttc      60
cgcgttacat aacttacggt aaatggcccg cctggctgac cgcccaacga ccccccgccca   120
```

```
ttgacgtcaa taatgacgta tgttcccata gtaacgccaa tagggacttt ccattgacgt    180
caatgggtgg agtatttacg gtaaactgcc cacttggcag tacatcaagt gtatcatatg    240
ccaagtacgc cccctattga cgtcaatgac ggtaaatggc ccgcctggca ttatgcccag    300
tacatgacct tatgggactt tcctacttgg cagtacatct acgtattagt catcgctatt    360
acca                                                                 364

<210> SEQ ID NO 30
<211> LENGTH: 66
<212> TYPE: DNA
<213> ORGANISM: Artificial Sequence
<220> FEATURE:
<223> OTHER INFORMATION: Synthetic Construct

<400> SEQUENCE: 30
tttctgcagc ggggattaat atgattatga acacccccaa tctcccagat gctgattcag     60
ccagga                                                                66
```

GENE THERAPY FOR RETINITIS PIGMENTOSA

CROSS REFERENCE TO RELATED APPLICATIONS

This application is a divisional of U.S. patent application Ser. No. 16/503,091, filed Jul. 3, 2019, which is a divisional of U.S. patent application Ser. No. 15/127,757 (U.S. Pat. No. 10,383,953), which adopts the international filing date of Mar. 20, 2015, which is a National Phase application under 35 U.S.C. § 371 of International Application No. PCT/US2015/021896, filed Mar. 20, 2015, which claims the priority benefit of U.S. Provisional Application No. 61/969,027, filed Mar. 21, 2014, the disclosure of each of which is incorporated herein by reference in its entirety.

SEQUENCE LISTING

The content of the following submission on ASCII text file is incorporated herein by reference in its entirety: a computer readable form (CRF) of the Sequence Listing (file name: 159792010011SeqList.txt, date recorded: Jul. 13, 2021, size: 61 KB).

FIELD OF THE INVENTION

The present invention relates to AAV vectors and methods of using AAV vectors for treating retinitis pigmentosa.

BRIEF SUMMARY OF THE INVENTION

Retinitis pigmentosa (RP) is the most common cause of inherited retinal degeneration, which is clinically characterized by night blindness and the loss of peripheral vision. Mutations in the rod visual pigment rhodopsin are recognized as the most common cause of autosomal dominant RP (ADRP), and although a number of treatments for rhodopsin RP have been proposed and tested in animal models and clinical studies, the disease remains incurable (Kalloniatis, M., et al. (2004) *Clin. Exp. Optom.* 87(2):65-80). Much data supports the view that rhodopsin RP is a protein-misfolding disease in which the misfolding or misassembly of a mutant protein alters its cellular fate and induces cell death (Gregersen, N. et al. (2006) *Annu. Rev. Genomics Hum. Genet.* 7:103-24). Known RP mutations in the rhodopsin gene include missense and short, in-frame deletion mutations, with a single base substitution in codon 23 (P23H) of the rhodopsin gene accounting for ~7% of all cases of dominant Retinitis Pigmentosa in the US (Dryja, T. P., et al. (1995) *Proc. Natl. Acad. Sci. U.S.A.* 92(22):10177-81). In cultured cells, the P23H mutant protein, unlike wild type (WT) protein, is retained in the ER, leading to induction of the unfolded protein response (UPR), inhibition of the proteasome, and aggregation of the mutant protein into oligomeric, high molecular weight species that form intracellular inclusions (Saliba, R. S., et al. (2002) *J. Cell Sci.* 115:2907-18). Similarly, P23H rhodopsin mislocalizes and/or aggregates in the rod cells of animal RP models (Olsson, J. E., et al. (1992) *Neuron* 9(5):815-30), suggesting that cell culture models may be predictive of in vivo models of this disease. What is needed is a means of ameliorating the symptoms of RP.

The invention described herein provides methods for treating retinitis pigmentosa in a mammal, comprising administering to the eye of the mammal a recombinant adeno-associated virus (rAAV) viral particle comprising a vector encoding a miR-708. In some embodiments, the rAAV vector comprising nucleic acid encoding a miR-708 and rhodopsin. In some embodiments, the invention provides methods for treating retinitis pigmentosa comprising administering to the eye of the mammal a first rAAV viral particle comprising a first rAAV vector comprising nucleic acid encoding a miR-708 and a second rAAV viral particle comprising a second rAAV vector comprising nucleic acid encoding a rhodopsin. In other embodiments, the invention provides methods for treating retinitis pigmentosa comprising administering to the eye of the mammal a rAAV viral particle comprising a rAAV vector comprising nucleic acid encoding a miR-708 and rhodopsin. In some embodiments, treating retinitis pigmentosa comprises reducing or preventing symptoms associated with the retinitis pigmentosa. In some embodiments or the invention, methods of treating retinitis pigmentosa include methods of reducing a symptom associated with RP, methods of preventing retinal degeneration, methods for arresting progression of RP, methods for increasing photoreceptor function, and the like. Symptoms and/or pathology of RP include but are not limited to loss of sight, loss of night vision, loss of peripheral visual fields, loss of ERG function; loss of visual acuity and contrast sensitivity; loss of visually guided behavior, reduction in rod photoreceptor function, rod photoreceptor cell death, decreased scotopic vision, reduction in retinal cell changes (loss of photoreceptor structure or function; thinning or thickening of the outer nuclear layer (ONL); thinning or thickening of the outer plexiform layer (OPL); disorganization followed by loss of rod and cone outer segments; shortening of the rod and cone inner segments; retraction of bipolar cell dendrites; thinning or thickening of the inner retinal layers including inner nuclear layer, inner plexiform layer, ganglion cell layer and nerve fiber layer; opsin mislocalization; overexpression of neurofilaments; and the like. In some embodiments, the invention provides methods to prevent deterioration of rod cell function and rod cell death and cone cell function and cone cell death.

In some aspects, the invention provides methods for treating endoplasmic reticulum (ER) stress in a cell comprising administering to the mammal a rAAV viral particle comprising a rAAV vector comprising nucleic acid encoding a miR-708. In some embodiments, the mammal has or is at risk of having RP. In some embodiments, the mammal is a human that has or is at risk of having RP. In some embodiments, the rAAV particle is administered to an eye of the mammal. In some embodiments, the cell is an ocular cell. In further embodiments, the cell is a photoreceptor cell. In yet further embodiments, the cell is a rod photoreceptor cell. In some embodiments, the method comprises reducing one or more cellular markers of ER stress. In further embodiments, the one or more cellular marker of ER stress is spliced XBP-1, CHOP or Grp78. In some embodiments, the rAAV vector comprises nucleic acid encoding a miR-708 and rhodopsin. In other embodiments, the invention provides methods for treating endoplasmic reticulum (ER) stress in a cell comprising administering to the mammal a first rAAV vector comprising nucleic acid encoding a miR-708 and a second rAAV viral particle comprising a second rAAV vector comprising nucleic acid encoding a rhodopsin.

In some embodiments of the invention, the nucleic acid encoding miR-708 is operably linked to a promoter. In some embodiments, the promoter is capable of expressing the miR-708 in photoreceptor cells (e.g., a rod photoreceptor cell). In further embodiments, the promoter comprises a rhodopsin kinase (RK) promoter or an opsin promoter. In other embodiments of the invention, the nucleic acid encoding rhodopsin is operably linked to a promoter. In some embodiments, the promoter is capable of expressing the rhodopsin in photoreceptor cells (e.g., a rod photoreceptor cell). In further embodiments, the promoter comprises a RK promoter or an opsin promoter.

In some embodiments, the invention provides methods to treat RP and/or ER stress comprising administering to a mammal, a rAAV particle comprising a rAAV vector comprising nucleic acid encoding miR-708 and rhodopsin. In some embodiments, the nucleic acid encoding miR-708 and the nucleic acid encoding rhodopsin are operably linked to one RK promoter. In other embodiments, the nucleic acid encoding miR-708 is operably linked to a first RK promoter or a first opsin promoter and the nucleic acid encoding rhodopsin is operably linked to a second RK promoter or a second opsin promoter. In some embodiments, the first and/or second opsin promoter includes an MVM intron (e.g., an intron of SEQ ID NO:23). In some embodiments, the nucleic acid encoding miR-708 is 5' to the nucleic acid encoding rhodopsin. In other embodiments, the nucleic acid encoding miR-708 is 3' to the nucleic acid encoding rhodopsin. In some embodiments, the nucleic acid encoding miR-708 is operably linked to the chicken β-actin (CBA) promoter. In some embodiments, the nucleic acid encoding rhodopsin is operably linked to the chicken β-actin (CBA) promoter. In some embodiments, a sequence derived from a minute virus of mouse (MVM) intron is located 3' to the promoter. In some embodiments, the MMV intron comprises the nucleotide sequence of SEQ ID NO:23. In some embodiments, the promoter further comprises i) a CMV enhancer; ii) a sequence derived from a photoreceptor specific transcription factor; iii) a sequence derived from a rod photoreceptor specific transcription factor; iv) a sequence derived from a neural retinal basic zipper factor; v) a sequence derived from a cone rod homeobox-containing transcription factor sequence; vi) a CMV enhancer and at least one or more of a sequence derived from a photoreceptor specific transcription factor, a sequence derived from a rod photoreceptor specific transcription factor, a sequence derived from a neural retinal basic zipper factor; a sequence derived from a cone rod homeobox-containing transcription factor sequence; vii) a neural retinal basic leucine zipper factor, a CMV enhancer and an Opsin promoter (−500 to +17); viii) a neural retinal basic leucine zipper factor, a CMV enhancer, an Opsin promoter (−500 to +17), and an MVM intron; ix) a CMV enhancer comprising SEQ ID NO:29; x) a neural retinal basic leucine zipper factor sequence comprising SEQ ID NO:30; xi) a sequence derived from a cone rod homeobox-containing transcription factor sequence comprising SEQ ID NO:28; xii) a CMV enhancer comprising SEQ ID NO:29 and at least one or more of a sequence derived from a photoreceptor specific transcription factor, a sequence derived from a rod photoreceptor specific transcription factor, a sequence derived from a neural retinal basic zipper factor comprising SEQ ID NO:30; a sequence derived from a cone rod homeobox-containing transcription factor sequence comprising SEQ ID NO:28; xiii) a neural retinal basic leucine zipper factor comprising SEQ ID NO:30, a CMV enhancer comprising SEQ ID NO:29 and an Opsin promoter (−500 to +17) comprising SEQ ID NO:22; or xiv) a neural retinal basic leucine zipper factor comprising SEQ ID NO:28, a CMV enhancer comprising SEQ ID NO:29, an Opsin promoter (−500 to +17) comprising SEQ ID NO:22, and an MVM intron comprising SEQ ID NO:23. In some embodiments, the nucleic acid encoding miR-708 is embedded in an intron. In some embodiments, the nucleic acid encoding miR-708 comprises an endogenous miR-708 scaffold or a miR-155 scaffold.

In some embodiments, the invention provides methods to treat RP and/or ER stress comprising administering to a mammal, a rAAV particle comprising a rAAV vector comprising nucleic acid encoding miR-708. In some embodiments, the nucleic acid encoding miR-708 comprises the nucleic acid of SEQ ID NO:1. In some embodiments, the nucleic acid encoding miR-708 comprises a nucleic acid having about at least 85%, 90%, 91%, 92%, 93%, 94%, 95%, 96%, 97%, 98%, or 99% identity to SEQ ID NO:1.

In some embodiments, the invention provides methods to treat RP and/or ER stress comprising administering to a mammal, a rAAV particle comprising a rAAV vector comprising nucleic acid encoding rhodopsin. In some embodiments, the rhodopsin is mammalian rhodopsin or functional equivalent thereof. In some embodiments, the rhodopsin is human rhodopsin or functional equivalent thereof. In some embodiments, the rhodopsin lacks the 3' untranslated region (UTR) miR-708 target sequence. In some embodiments, the nucleic acid encoding rhodopsin comprises a substitution, insertion or deletion of nucleic acid in the miR-708 target sequence. In some embodiments, the substitution, insertion or deletion reduces or prevents recognition by miR-708. In some embodiments, the nucleic acid encoding rhodopsin comprises a substitution, insertion or deletion of nucleic acid in the miR-708 target sequence wherein the miR-708 target sequence is SEQ ID NO:19. In some embodiments, expression of the rhodopsin is refractory to suppression by miR-708. In some embodiments, the rhodopsin comprises the amino acid sequence of SEQ ID NO:2. In some embodiments, the rhodopsin comprises an amino acid sequence having about at least t 85%, 90%, 91%, 92%, 93%, 94%, 95%, 96%, 97%, 98%, or 99% identity to SEQ ID NO:2. In some embodiments, the nucleic acid encoding the rhodopsin comprises nucleic acid of SEQ ID NO:3. In some embodiments, the nucleic acid encoding the rhodopsin comprises a nucleic acid having about 85%, 90%, 91%, 92%, 93%, 94%, 95%, 96%, 97%, 98%, or 99% identity to SEQ ID NO:3.

In some embodiments, the invention provides methods to treat RP and/or ER stress comprising administering to a mammal, a rAAV particle comprising a polynucleotide of SEQ ID NO:5., SEQ ID NO:6, SEQ ID NO:7, SEQ ID NO:8 or SEQ ID NO:9. In some embodiments, the AAV viral particle comprises a recombinant viral genome comprises a polynucleotide having about at least t 85%, 90%, 91%, 92%, 93%, 94%, 95%, 96%, 97%, 98%, or 99% identity to SEQ ID NO:5, SEQ ID NO:6 SEQ ID NO:7, SEQ ID NO:8, SEQ ID NO:9, SEQ ID NO:24, SEQ ID NO:25, SEQ ID NO:26, or SEQ ID NO:27.

In some embodiments, the invention provides methods to treat RP and/or ER stress comprising administering to a mammal, a rAAV particle wherein the AAV viral particle comprises an AAV1, AAV2, AAV3, AAV4, AAV5, AAV6, AAV7, AAV8, AAVrh8, AAVrh8R, AAV9, AAV10, AAVrh10, AAV11, AAV12, AAV2R471A, AAV2/2-7m8, AAV DJ, AAV2 N587A, AAV2 E548A, AAV2 N708A, AAV V708K, a goat AAV, AAV1/AAV2 chimeric, bovine AAV, or mouse AAV capsid rAAV2/HBoV1 serotype capsid. In some embodiments, the rAAV viral particle comprises an AAV serotype 5 capsid. In some embodiments, the rAAV viral particle comprises an AAV serotype 5 tyrosine mutant capsid.

In some embodiments, the invention provides methods of treating RP and/or ER stress comprising administering to a mammal a first rAAV virus particle comprising nucleic acid encoding miR-708 and a second rAAV virus particle encoding rhodopsin. In some embodiments, the first rAAV particle and/or the second rAAV virus particle comprises an AAV1, AAV2, AAV3, AAV4, AAV5, AAV6, AAV7, AAV8, AAVrh8, AAVrh8R, AAV9, AAV10, AAVrh10, AAV11, AAV12, AAV2R471A, AAV2/2-7m8, AAV DJ, AAV2 N587A, AAV2 E548A, AAV2 N708A, AAV V708K, a goat AAV, AAV1/AAV2 chimeric, bovine AAV, or mouse AAV capsid rAAV2/HBoV1 serotype capsid. In some embodiments, the first rAAV viral particle and/or the second rAAV viral particle comprise an AAV serotype 5 capsid. In some embodiments, the first rAAV viral particle and/or the second rAAV viral particle comprise an AAV serotype 5 tyrosine mutant capsid.

In some embodiments, the invention provides methods to treat RP and/or ER stress comprising administering to a mammal, a rAAV particle wherein the AAV vector comprises an AAV1, AAV2, AAV3, AAV4, AAV5, AAV6, AAV7, AAV8, AAVrh8, AAVrh8R, AAV9, AAV10, AAVrh10, AAV11, AAV12, AAV2R471A, AAV DJ, a goat AAV, bovine AAV, or mouse AAV serotype ITR. In some embodiments, the invention provides methods of treating RP and/or ER stress comprising administering to a mammal a first rAAV virus particle comprising a first rAAV vector comprising nucleic acid encoding miR-708 and a second rAAV virus particle comprising a second rAAV vector encoding rhodopsin. In some embodiments, the first rAAV vector and/or the second rAAV virus vector comprises an AAV1, AAV2, AAV3, AAV4, AAV5, AAV6, AAV7, AAV8, AAVrh8, AAVrh8R, AAV9, AAV10, AAVrh10, AAV11, AAV12, AAV2R471A, AAV DJ, a goat AAV, bovine AAV, or mouse AAV serotype ITR.

In some embodiments of the invention, the rAAV vectors of the method comprise AAV serotype 2 ITRs. In some embodiments, the ITR and the capsid of the rAAV viral particle are derived from the same AAV serotype. In other embodiments, the ITR and the capsid of the rAAV viral particles are derived from different AAV serotypes. In some embodiments, the rAAV viral particle comprises an AAV-5 capsid, and wherein the vector comprises AAV2 ITRs. In some embodiments, the rAAV viral particle comprises an AAV-5 tyrosine mutant capsid, and wherein the vector comprises AAV2 ITRs.

In some embodiments, the invention provides methods to treat RP and/or ER stress in a mammal wherein the rAAV particles are injected into the subretinal space of the retina of the mammal. In some embodiments, the rAAV is administered to more than one location of the subretinal space of the retina of the mammal. In other embodiments, the rAAV particles are injected intravitreally to the mammal. In some embodiments, at least 10-30% of the photoreceptor cells (e.g., rod photoreceptor cells) are transduced by the AAV.

In some embodiments, the invention provides methods to treat RP and/or ER stress in a mammal, wherein the mammal has a mutation in the endogenous rhodopsin gene. In some embodiments, the mutation in the endogenous rhodopsin gene is an autosomal dominant mutation. In some embodiments, the retinitis pigmentosa is autosomal dominant retinitis pigmentosa. In some embodiments, the mammal is a human. In some embodiments, the human has a P23H mutation in the endogenous rhodopsin gene.

In some embodiments, the invention provides methods of treating RP and/or ER stress comprising administering to a mammal a first rAAV virus particle comprising nucleic acid encoding miR-708 and a second rAAV virus particle encoding rhodopsin wherein the first rAAV viral particle encoding the miR-708 and the second rAAV viral particle encoding the rhodopsin are administered to the mammal at the same time. In some embodiments, the first rAAV viral particle encoding the miR-708 and the rAAV viral particle encoding the rhodopsin are administered to the mammal sequentially. In some embodiments, the rAAV viral particle encoding the miR-708 is administered to the mammal first and the rAAV viral particle encoding the rhodopsin is administered to the mammal second. In some embodiments, the rAAV viral particle encoding the rhodopsin is administered to the mammal first and the rAAV viral particle encoding the miR-708 is administered to the mammal second.

In some embodiments of the invention, the rAAV viral particles are in a pharmaceutical composition. In some embodiments, the pharmaceutical composition further comprises a pharmaceutically acceptable carrier. In some embodiments, the invention provides a composition comprising a rAAV particle comprising a rAAV vector comprising nucleic acid encoding miR-708 used in the methods described herein. In some embodiments, the invention provides a rAAV particle comprising a rAAV vector comprising nucleic acid encoding a miR708 for use in treating retitinis pigmentosa or reducing ER stress according to any of the methods described herein. In some embodiments, the invention provides a first rAAV particle comprising a rAAV vector comprising nucleic acid encoding a miR708 and a second rAAV particle comprising a rAAV vector comprising nucleic acid encoding rhodopsin for use in treating retitinis pigmentosa or reducing ER stress according to any of the methods described herein. In some embodiments, the rAAV particle comprises a rAAV vector comprising nucleic acid encoding a miR708 and rhodopsin for use in treating retitinis pigmentosa or reducing ER stress according to any one of the methods described herein.

In some aspects, the invention described herein provides compositions for treating retinitis pigmentosa in a mammal, comprising a recombinant adeno-associated virus (rAAV) viral particle comprising a vector encoding a miR-708. In some embodiments, the rAAV vector comprising nucleic acid encoding a miR-708 further comprises nucleic acid encoding rhodopsin. In some embodiments, the invention provides compositions for treating retinitis pigmentosa comprising a first rAAV viral particle comprising a first rAAV vector comprising nucleic acid encoding a miR-708 and a second rAAV viral particle comprising a second rAAV vector comprising nucleic acid encoding a rhodopsin. In other embodiments, the invention provides compositions for treating retinitis pigmentosa comprising a rAAV viral particle comprising a rAAV vector comprising nucleic acid encoding a miR-708 and rhodopsin.

In some aspects, the invention provides compositions for treating endoplasmic reticulum (ER) stress in a cell comprising a rAAV viral particle comprising a rAAV vector comprising nucleic acid encoding a miR-708. In some aspects, the invention provides compositions for treating endoplasmic reticulum (ER) stress in a cell comprising a rAAV viral particle comprising a rAAV vector comprising nucleic acid encoding a miR-708 and rhodopsin. In some embodiments, the mammal with ER stress has or is at risk of having RP. In some embodiments, the mammal with ER stress is a human who has or is at risk of having RP. In some embodiments, the rAAV particle is administered to an eye of the mammal. In some embodiments, the cell is an ocular cell. In further embodiments, the cell is a photoreceptor cell. In yet further embodiments, the cell is a rod photoreceptor cell. In some embodiments, the composition reduces one or more cellular markers of ER stress. In further embodiments, the one or more cellular marker of ER stress is spliced XBP-1, CHOP or Grp78. In some embodiments, the rAAV vector comprises nucleic acid encoding a miR-708 further comprises nucleic acid encoding rhodopsin. In other embodiments, the invention provides compositions for treating endoplasmic reticulum (ER) stress in a cell comprising a first rAAV vector comprising nucleic acid encoding a miR-708 and a second rAAV viral particle comprising a second rAAV vector comprising nucleic acid encoding a rhodopsin.

In some embodiments of the invention, the nucleic acid encoding miR-708 is operably linked to a promoter. In some embodiments, the promoter is capable of expressing the miR-708 in photoreceptor cells (e.g., rod photoreceptor cells). In further embodiments, the promoter comprises a rhodopsin kinase (RK) promoter or an opsin promoter. In other embodiments of the invention, the nucleic acid encoding rhodopsin is operably linked to a promoter. In some embodiments, the promoter is capable of expressing the rhodopsin in photoreceptor cells (e.g., rod photoreceptor cells). In further embodiments, the promoter comprises a RK promoter or an opsin promoter.

In some embodiments, the invention provides compositions to treat RP and/or ER stress comprising a rAAV particle comprising a rAAV vector comprising nucleic acid encoding miR-708 and rhodopsin. In some embodiments, the nucleic acid encoding miR-708 and the nucleic acid encoding rhodopsin are operably linked to one RK promoter. In other embodiments, the nucleic acid encoding miR-708 is operably linked to a first RK promoter or a first opsin promoter and the nucleic acid encoding rhodopsin is operably linked to a second RK promoter or a second opsin promoter. In some embodiments, the first and/or second opsin promoter includes an MVM intron (e.g., an intron of SEQ ID NO:23). In some embodiments, the nucleic acid encoding miR-708 is 5' to the nucleic acid encoding rhodopsin. In other embodiments, the nucleic acid encoding miR-708 is 3' to the nucleic acid encoding rhodopsin. In some embodiments, the nucleic acid encoding miR-708 is operably linked to the chicken β-actin (CBA) promoter. In some embodiments, the nucleic acid encoding rhodopsin is operably linked to the chicken β-actin (CBA) promoter. In some embodiments, the first and/or second opsin promoter includes an MVM intron (e.g., an intron of SEQ ID NO:23). In some embodiments, the nucleic acid encoding miR-708 is 5' to the nucleic acid encoding rhodopsin. In other embodiments, the nucleic acid encoding miR-708 is 3' to the nucleic acid encoding rhodopsin. In some embodiments, the nucleic acid encoding miR-708 is operably linked to the chicken β-actin (CBA) promoter. In some embodiments, the nucleic acid encoding rhodopsin is operably linked to the chicken β-actin (CBA) promoter. In some embodiments, a sequence derived from a minute virus of mouse (MVM) intron is located 3' to the promoter. In some embodiments, the MMV intron comprises the nucleotide sequence of SEQ ID NO:23. In some embodiments, the promoter further comprises i) a CMV enhancer; ii) a sequence derived from a photoreceptor specific transcription factor; iii) a sequence derived from a rod photoreceptor specific transcription factor; iv) a sequence derived from a neural retinal basic zipper factor; v) a sequence derived from a cone rod homeobox-containing transcription factor sequence; vi) a CMV enhancer and at least one or more of a sequence derived from a photoreceptor specific transcription factor, a sequence derived from a rod photoreceptor specific transcription factor, a sequence derived from a neural retinal basic zipper factor; a sequence derived from a cone rod homeobox-containing transcription factor sequence; vii) a neural retinal basic leucine zipper factor, a CMV enhancer and an Opsin promoter (−500 to +17); viii) a neural retinal basic leucine zipper factor, a CMV enhancer, an Opsin promoter (−500 to +17), and an MVM intron; ix) a CMV enhancer comprising SEQ ID NO:29; x) a neural retinal basic leucine zipper factor sequence comprising SEQ ID NO:30; xi) a sequence derived from a cone rod homeobox-containing transcription factor sequence comprising SEQ ID NO:28; xii) a CMV enhancer comprising SEQ ID NO:29 and at least one or more of a sequence derived from a photoreceptor specific transcription factor, a sequence derived from a rod photoreceptor specific transcription factor, a sequence derived from a neural retinal basic zipper factor comprising SEQ ID NO:30; a sequence derived from a cone rod homeobox-containing transcription factor sequence comprising SEQ ID NO:28; xiii) a neural retinal basic leucine zipper factor comprising SEQ ID NO:30, a CMV enhancer comprising SEQ ID NO:29 and an Opsin promoter (−500 to +17) comprising SEQ ID NO:22; or xiv) a neural retinal basic leucine zipper factor comprising SEQ ID NO:28, a CMV enhancer comprising SEQ ID NO:29, an Opsin promoter (−500 to +17) comprising SEQ ID NO:22, and an MVM intron comprising SEQ ID NO:23. In some embodiments, the nucleic acid encoding miR-708 is embedded in an intron. In some embodiments, the nucleic acid encoding miR-708 comprises an endogenous miR-708 scaffold or a miR-155 scaffold.

In some embodiments, the invention provides compositions to treat RP and/or ER stress comprising a rAAV particle comprising a rAAV vector comprising nucleic acid encoding miR-708. In some embodiments, the nucleic acid encoding miR-708 comprises the nucleic acid of SEQ ID NO:1. In some embodiments, the nucleic acid encoding miR-708 comprises a nucleic acid having about at least 85%, 90%, 91%, 92%, 93%, 94%, 95%, 96%, 97%, 98%, or 99% identity to SEQ ID NO:1.

In some embodiments, the invention provides compositions to treat RP and/or ER stress comprising a rAAV particle comprising a rAAV vector comprising nucleic acid encoding rhodopsin. In some embodiments, the rhodopsin is mammalian rhodopsin or functional equivalent thereof. In some embodiments, the rhodopsin is human rhodopsin or functional equivalent thereof. In some embodiments, the rhodopsin lacks the 3' untranslated region (UTR) miR-708 target sequence. In some embodiments, the nucleic acid encoding rhodopsin comprises a substitution, insertion or deletion of nucleic acid in the miR-708 target sequence. In some embodiments, the substitution, insertion or deletion reduces or prevents recognition by miR-708. In some embodiments, the nucleic acid encoding rhodopsin comprises a substitution, insertion or deletion of nucleic acid in the miR-708 target sequence wherein the miR-708 target sequence is SEQ ID NO:19. In some embodiments, expression of the rhodopsin is refractory to suppression by miR-708. In some embodiments, the rhodopsin comprises the amino acid sequence of SEQ ID NO:2. In some embodiments, the rhodopsin comprises an amino acid sequence having about at least 85%, 90%, 91%, 92%, 93%, 94%, 95%, 96%, 97%, 98%, or 99% identity to SEQ ID NO:2. In some embodiments, the nucleic acid encoding the rhodopsin comprises nucleic acid of SEQ ID NO:3. In some embodiments, the nucleic acid encoding the rhodopsin comprises a nucleic acid having about 85%, 90%, 91%, 92%, 93%, 94%, 95%, 96%, 97%, 98%, or 99% identity to SEQ ID NO:3.

In some embodiments, the invention provides compositions to treat RP and/or ER stress comprising a rAAV particle comprising a polynucleotide of SEQ ID NO:5, SEQ ID NO:6, SEQ ID NO:7, SEQ ID NO:8 or SEQ ID NO:9.

In some embodiments, the AAV viral particle comprises a recombinant viral genome comprises a polynucleotide having about at least t 85%, 90%, 91%, 92%, 93%, 94%, 95%, 96%, 97%, 98%, or 99% identity to SEQ ID NO:5, SEQ ID NO:6, SEQ ID NO:7, SEQ ID NO:8 SEQ ID NO:9, SEQ ID NO:24, SEQ ID NO:25, SEQ ID NO:26, or SEQ ID NO:27.

In some embodiments, the invention provides compositions to treat RP and/or ER stress comprising a rAAV particle wherein the AAV viral particle comprises an AAV1, AAV2, AAV3, AAV4, AAV5, AAV6, AAV7, AAV8, AAVrh8, AAVrh8R, AAV9, AAV10, AAVrh10, AAV11, AAV12, AAV2R471A, AAV2/2-7m8, AAV DJ, AAV2 N587A, AAV2 E548A, AAV2 N708A, AAV V708K, a goat AAV, AAV1/AAV2 chimeric, bovine AAV, or mouse AAV capsid rAAV2/HBoV1 serotype capsid. In some embodiments, the rAAV viral particle comprises an AAV serotype 5 capsid. In some embodiments, the rAAV viral particle comprises an AAV serotype 5 tyrosine mutant capsid.

In some embodiments, the invention provides compositions for treating RP and/or ER stress comprising a first rAAV virus particle comprising nucleic acid encoding miR-708 and a second rAAV virus particle encoding rhodopsin. In some embodiments, the first rAAV particle and/or the second rAAV virus particle comprises an AAV1, AAV2, AAV3, AAV4, AAV5, AAV6, AAV7, AAV8, AAVrh8, AAVrh8R, AAV9, AAV10, AAVrh10, AAV11, AAV12, AAV2R471A, AAV2/2-7m8, AAV DJ, AAV2 N587A, AAV2 E548A, AAV2 N708A, AAV V708K, a goat AAV, AAV1/AAV2 chimeric, bovine AAV, or mouse AAV capsid rAAV2/HBoV1 serotype capsid. In some embodiments, the first rAAV viral particle and/or the second rAAV viral particle comprise an AAV serotype 5 capsid. In some embodiments, the first rAAV viral particle and/or the second rAAV viral particle comprise an AAV serotype 5 tyrosine mutant capsid.

In some embodiments, the invention provides compositions to treat RP and/or ER stress comprising a rAAV particle wherein the AAV vector comprises an AAV1, AAV2, AAV3, AAV4, AAV5, AAV6, AAV7, AAV8, AAVrh8, AAVrh8R, AAV9, AAV10, AAVrh10, AAV11, AAV12, AAV2R471A, AAV DJ, a goat AAV, bovine AAV, or mouse AAV serotype ITR. In some embodiments, the invention provides compositions for treating RP and/or ER stress comprising a first rAAV virus particle comprising a first rAAV vector comprising nucleic acid encoding miR-708 and a second rAAV virus particle comprising a second rAAV vector encoding rhodopsin. In some embodiments, the first rAAV vector and/or the second rAAV virus vector comprises an AAV1, AAV2, AAV3, AAV4, AAV5, AAV6, AAV7, AAV8, AAVrh8, AAVrh8R, AAV9, AAV10, AAVrh10, AAV11, AAV12, AAV2R471A, AAV DJ, a goat AAV, bovine AAV, or mouse AAV serotype ITR.

In some embodiments of the invention, the rAAV vectors of the composition comprise AAV serotype 2 ITRs. In some embodiments, the ITR and the capsid of the rAAV viral particle are derived from the same AAV serotype. In other embodiments, the ITR and the capsid of the rAAV viral particles are derived from different AAV serotypes. In some embodiments, the rAAV viral particle comprises an AAV-5 capsid, and wherein the vector comprises AAV2 ITRs. In some embodiments, the rAAV viral particle comprises an AAV-5 tyrosine mutant capsid, and wherein the vector comprises AAV2 ITRs.

In some embodiments, the invention provides compositions to treat RP and/or ER stress in a mammal, wherein the mammal has a mutation in the endogenous rhodopsin gene. In some embodiments, the mutation in the endogenous rhodopsin gene is an autosomal dominant mutation. In some embodiments, the retinitis pigmentosa is autosomal dominant retinitis pigmentosa. In some embodiments, the mammal is a human. In some embodiments, the human has a P23H mutation in the endogenous rhodopsin gene.

In some embodiments, the invention provides kits to treat RP or to reduce ER stress in a mammal comprising an effective amount of rAAV particles according to the methods described herein. In some embodiments, the kits comprise an effective amount of a composition as described herein. In some embodiments, the kit comprises an effective amount of rAAV particles comprising a rAAV vector comprising nucleic acid encoding miR-708. In some embodiments, the kit comprises an effective amount of rAAV particles comprising a rAAV vector comprising nucleic acid encoding miR-708 and rhodopsin. In some embodiments, the kit comprises an effective amount of first rAAV particles comprising a rAAV vector comprising nucleic acid encoding miR-708 and an effective amount of second rAAV particles comprising a second rAAV vector comprising nucleic acid encoding rhodopsin. In further embodiments, the kit comprising instructions for use of the rAAV particles in the treatment of retinitis pigmentosa and/or reduction of ER stress. In further embodiments, the kit comprising instructions for use in any one of the methods described herein.

In some aspects, the invention provides an article of manufacture comprising an effective amount of rAAV particles according to the methods described herein. In some embodiments, the article of manufacture comprises an effective amount of any of the compositions described herein. In some embodiments, the article of manufacture comprises an effective amount of rAAV particles comprising a rAAV vector comprising nucleic acid encoding miR-708. In some embodiments, the article of manufacture comprises an effective amount of rAAV particles comprising a rAAV vector comprising nucleic acid encoding miR-708 and rhodopsin. In some embodiments, the article of manufacture comprises an effective amount of first rAAV particles comprising a rAAV vector comprising nucleic acid encoding miR-708 and an effective amount of second rAAV particles comprising a second rAAV vector comprising nucleic acid encoding rhodopsin.

Is some aspects, the invention provides a nucleic acid comprising an intron derived from an MVM. In some embodiments, the MVM intron comprises SEQ ID NO:23. In some embodiments, the nucleic acid further comprises a promoter. In some embodiments, the nucleic acid further comprises an enhancer. In some embodiments, the promoter is located 5' to the MVM intron. In some embodiments, the invention provides an expression construct comprising the nucleic acid. In some embodiments, the invention provides a vector comprising the nucleic acid or the expression construct. In some embodiments, the invention provides a cell comprising the nucleic acid, the expression construct, or the vector.

BRIEF DESCRIPTION OF THE DRAWINGS

(FIG. 2A) Western blot of detergent soluble extracts from cells expressing wild-type ("wt") or P23H mutant rhodopsin. (FIG. 2B) Western blot of detergent soluble extracts from cells expressing wild-type ("wt") or P23H mutant rhodopsin. Extracts were treated with Endoglycosidase H ("Endo-H") or left untreated.

(FIG. 3A) Relative expression of C/EBP homologous protein (CHOP; a.k.a. Ddit3), binding immunoglobulin protein (BiP; a.k.a. Hspa5), and rhodopsin genes in cells expressing wild-type ("wt") or P23H mutant rhodopsin. The relative expression of each gene was compared to beta-glucoronidase expression using the $\Delta\Delta C_t$ method. (FIG. 3B) Percentage of apoptotic cells in cells expressing control (pcDNA), wild-type rhodopsin, or P23H mutant rhodopsin, as measured by TUNEL staining.

(FIG. 9A) Expression of miR-708 in WERI or RPE cells upon transfection of a vector encoding miR-708 driven by the RK promoter or a control miRNA ("Scramble"). Expression is depicted relative to expression of miR-16. (FIG. 9B) Expression of P23H rhodopsin mRNA in WERI cells transfected with a pRK-miR-708 plasmid, relative to cells transfected with a control plasmid.

FIGS. 10A-10C show that subretinal delivery of an AAV5 miR-708 vector results in knockdown of mouse rhodopsin. (FIG. 10A) Expression of mRhodopsin in mouse retinas injected with AAV5 miR-708 or AAV5 miR-Control. (FIG. 10B) Expression of RdCVF in mouse retinas injected with AAV5 miR-708 or AAV5 miR-Control. (FIG. 10C) Expression of miR-708 in mouse retinas injected with AAV5 miR-708 or AAV5 miR-Control.

(FIG. 11A) Three representative electroretinograms representing scoptopic responses in eyes receiving AAV5 miR-708 or AAV5 miR-Control ("Scram"). (FIG. 11B) Three representative electroretinograms representing photopic responses in the same eyes as in (FIG. 11A) receiving AAV5 miR-708 or AAV5 miR-Control ("Scram").

DETAILED DESCRIPTION

Figure 1B:
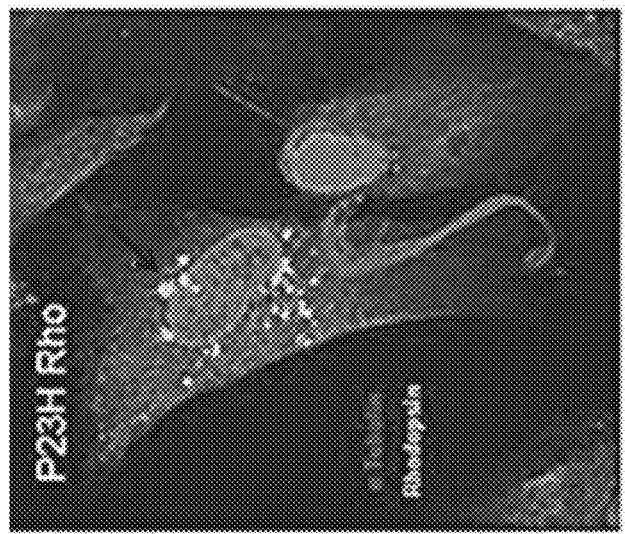
FIGS. 1A & 1B show the localization of wild-type (FIG. 1A) and P23H mutant (FIG. 1B) rhodopsin in human retinal pigmented epithelial cells. Cells are stained for rhodopsin (green), α-tubulin (red), and DNA (blue). The staining pattern of wild-type rhodopsin is characteristic of membrane localization (solid arrow), whereas the staining pattern of P23H mutant rhodopsin is characteristic of perinuclear/reticular localization (dashed arrow).

The present invention provides methods for treating retinitis pigmentosa (RP) in a mammal, comprising administering to the eye of the mammal a recombinant adeno-associated virus (rAAV) viral particle comprising a vector encoding a miR-708. The miR-708 targets a region in the 3' untranslated region of the rhodopsin gene and as such, may suppress activity of a mutant rhodopsin associated with RP. In some aspects, the invention provides methods for treating retinitis pigmentosa in a mammal, comprising administering to the eye of the mammal a recombinant adeno-associated virus (rAAV) viral particle comprising a vector encoding a miR-708 and a wild-type rhodopsin nucleic acid. As such, the vector may suppress the activity of a mutant rhodopsin associated with RP while concurrently replacing the mutant rhodopsin with a wild-type rhodopsin. In some embodiments, the nucleic acid encoding the wild-type rhodopsin does not include the 3' UTR target of miR-708 such that the miR-708 will only target expression of mutant rhodopsin. The invention also provides compositions comprising rAAV particles encoding miR-708 and rAAV particles encoding rhodopsin. In some embodiments, the invention provides compositions comprising rAAV particles encoding both miR-708 and rhodopsin.

I. General Techniques

The techniques and procedures described or referenced herein are generally well understood and commonly employed using conventional methodology by those skilled in the art, such as, for example, the widely utilized methodologies described in *Molecular Cloning: A Laboratory Manual* (Sambrook et al., 4*th* ed., Cold Spring Harbor Laboratory Press, Cold Spring Harbor, N.Y., 2012); *Current Protocols in Molecular Biology* (F. M. Ausubel, et al. eds., 2003); the series *Methods in Enzymology* (Academic Press, Inc.); *PCR 2: A Practical Approach* (M. J. MacPherson, B. D. Hames and G. R. Taylor eds., 1995); *Antibodies, A Laboratory Manual* (Harlow and Lane, eds., 1988); *Culture of Animal Cells: A Manual of Basic Technique and Specialized Applications* (R. I. Freshney, 6*th* ed., J. Wiley and Sons, 2010); *Oligonucleotide Synthesis* (M. J. Gait, ed., 1984); *Methods in Molecular Biology*, Humana Press; *Cell Biology: A Laboratory Notebook* (J. E. Cellis, ed., Academic Press, 1998); *Introduction to Cell and Tissue Culture* (J. P. Mather and P. E. Roberts, Plenum Press, 1998); *Cell and Tissue Culture: Laboratory Procedures* (A. Doyle, J. B. Griffiths, and D. G. Newell, eds., J. Wiley and Sons, 1993-8); *Handbook of Experimental Immunology* (D. M. Weir and C. C. Blackwell, eds., 1996); *Gene Transfer Vectors for Mammalian Cells* (J. M. Miller and M. P. Calos, eds., 1987); *PCR: The Polymerase Chain Reaction*, (Mullis et al., eds., 1994); *Current Protocols in Immunology* (J. E. Coligan et al., eds., 1991); *Short Protocols in Molecular Biology* (Ausubel et al., eds., J. Wiley and Sons, 2002); *Immunobiology* (C. A. Janeway et al., 2004); *Antibodies* (P. Finch, 1997); *Antibodies: A Practical Approach* (D. Catty., ed., IRL Press, 1988-1989); *Monoclonal Antibodies: A Practical Approach* (P. Shepherd and C. Dean, eds., Oxford University Press, 2000); *Using Antibodies: A Laboratory Manual* (E. Harlow and D. Lane, Cold Spring Harbor Laboratory Press, 1999); *The Antibodies* (M. Zanetti and J. D. Capra, eds., Harwood Academic Publishers, 1995); and *Cancer: Principles and Practice of Oncology* (V. T. DeVita et al., eds., J. B. Lippincott Company, 2011).

II. Definitions

A "vector," as used herein, refers to a recombinant plasmid or virus that comprises a nucleic acid to be delivered into a host cell, either in vitro or in vivo.

The term "polynucleotide" or "nucleic acid" as used herein refers to a polymeric form of nucleotides of any length, either ribonucleotides or deoxyribonucleotides. Thus, this term includes, but is not limited to, single-, double- or multi-stranded DNA or RNA, genomic DNA, cDNA, DNA-RNA hybrids, or a polymer comprising purine and pyrimidine bases, or other natural, chemically or biochemically modified, non-natural, or derivatized nucleotide bases. The backbone of the polynucleotide can comprise sugars and phosphate groups (as may typically be found in RNA or DNA), or modified or substituted sugar or phosphate groups. Alternatively, the backbone of the polynucleotide can comprise a polymer of synthetic subunits such as phosphoramidates and thus can be an oligodeoxynucleoside phosphoramidate ($P-NH_2$) or a mixed phosphoramidate-phosphodiester oligomer. In addition, a double-stranded polynucleotide can be obtained from the single stranded polynucleotide product of chemical synthesis either by synthesizing the complementary strand and annealing the strands under appropriate conditions, or by synthesizing the complementary strand de novo using a DNA polymerase with an appropriate primer.

The terms "polypeptide" and "protein" are used interchangeably to refer to a polymer of amino acid residues, and are not limited to a minimum length. Such polymers of amino acid residues may contain natural or non-natural amino acid residues, and include, but are not limited to, peptides, oligopeptides, dimers, trimers, and multimers of amino acid residues. Both full-length proteins and fragments thereof are encompassed by the definition. The terms also include post-expression modifications of the polypeptide, for example, glycosylation, sialylation, acetylation, phosphorylation, and the like. Furthermore, for purposes of the present invention, a "polypeptide" refers to a protein which includes modifications, such as deletions, additions, and substitutions (generally conservative in nature), to the native sequence, as long as the protein maintains the desired activity. These modifications may be deliberate, as through site-directed mutagenesis, or may be accidental, such as through mutations of hosts which produce the proteins or errors due to PCR amplification.

A "recombinant viral vector" refers to a recombinant polynucleotide vector comprising one or more heterologous sequences (i.e., nucleic acid sequence not of viral origin). In the case of recombinant AAV vectors, the recombinant nucleic acid is flanked by at least one, preferably two, inverted terminal repeat sequences (ITRs).

A "recombinant AAV vector (rAAV vector)" refers to a polynucleotide vector comprising one or more heterologous sequences (i.e., nucleic acid sequence not of AAV origin) that are flanked by at least one, preferably two, AAV inverted terminal repeat sequences (ITRs). Such rAAV vectors can be replicated and packaged into infectious viral particles when present in a host cell that has been infected with a suitable helper virus (or that is expressing suitable helper functions) and that is expressing AAV rep and cap gene products (i.e. AAV Rep and Cap proteins). When a rAAV vector is incorporated into a larger polynucleotide (e.g., in a chromosome or in another vector such as a plasmid used for cloning or transfection), then the rAAV vector may be referred to as a "pro-vector" which can be "rescued" by replication and encapsidation in the presence of AAV packaging functions and suitable helper functions. An rAAV vector can be in any of a number of forms, including, but not limited to, plasmids, linear artificial chromosomes, complexed with lipids, encapsulated within liposomes, and, most preferable, encapsidated in a viral particle, particularly an AAV particle. A rAAV vector can be packaged into an AAV virus capsid to generate a "recombinant adeno-associated viral particle (rAAV particle)".

"Heterologous" means derived from a genotypically distinct entity from that of the rest of the entity to which it is compared or into which it is introduced or incorporated. For example, a polynucleotide introduced by genetic engineering techniques into a different cell type is a heterologous polynucleotide (and, when expressed, can encode a heterologous polypeptide). Similarly, a cellular sequence (e.g., a gene or portion thereof) that is incorporated into a viral vector is a heterologous nucleotide sequence with respect to the vector.

The term "transgene" refers to a polynucleotide that is introduced into a cell and is capable of being transcribed into RNA and optionally, translated and/or expressed under appropriate conditions. In aspects, it confers a desired property to a cell into which it was introduced, or otherwise leads to a desired therapeutic or diagnostic outcome. In another aspect, it may be transcribed into a molecule that mediates RNA interference, such as siRNA.

The terms "genome particles (gp)," "genome equivalents," or "genome copies" as used in reference to a viral titer, refer to the number of virions containing the recombinant AAV DNA genome, regardless of infectivity or functionality. The number of genome particles in a particular vector preparation can be measured by procedures such as described in the Examples herein, or for example, in Clark et al. (1999) *Hum. Gene Ther.*, 10:1031-1039; Veldwijk et al. (2002) *Mol. Ther.*, 6:272-278.

The terms "infection unit (iu)," "infectious particle," or "replication unit," as used in reference to a viral titer, refer to the number of infectious and replication-competent recombinant AAV vector particles as measured by the infectious center assay, also known as replication center assay, as described, for example, in McLaughlin et al. (1988) *J. Virol.*, 62:1963-1973.

The term "transducing unit (tu)" as used in reference to a viral titer, refers to the number of infectious recombinant AAV vector particles that result in the production of a functional transgene product as measured in functional assays such as described in Examples herein, or for example, in Xiao et al. (1997) *Exp. Neurobiol.*, 144:113-124; or in Fisher et al. (1996) *J. Virol.*, 70:520-532 (LFU assay).

An "inverted terminal repeat" or "ITR" sequence is a term well understood in the art and refers to relatively short sequences found at the termini of viral genomes which are in opposite orientation.

An "AAV inverted terminal repeat (ITR)" sequence, a term well-understood in the art, is an approximately 145-nucleotide sequence that is present at both termini of the native single-stranded AAV genome. The outermost 125 nucleotides of the ITR can be present in either of two alternative orientations, leading to heterogeneity between different AAV genomes and between the two ends of a single AAV genome. The outermost 125 nucleotides also contains several shorter regions of self-complementarity (designated A, A', B, B', C, C' and D regions), allowing intrastrand base-pairing to occur within this portion of the ITR.

A "terminal resolution sequence" or "trs" is a sequence in the D region of the AAV ITR that is cleaved by AAV rep proteins during viral DNA replication. A mutant terminal resolution sequence is refractory to cleavage by AAV rep proteins.

A "helper virus" for AAV refers to a virus that allows AAV (which is a defective parvovirus) to be replicated and packaged by a host cell. A number of such helper viruses have been identified, including adenoviruses, herpesviruses and poxviruses such as vaccinia. The adenoviruses encompass a number of different subgroups, although Adenovirus type 5 of subgroup C (Ad5) is most commonly used. Numerous adenoviruses of human, non-human mammalian and avian origin are known and are available from depositories such as the ATCC. Viruses of the herpes family, which are also available from depositories such as ATCC, include, for example, herpes simplex viruses (HSV), Epstein-Barr viruses (EBV), cytomegaloviruses (CMV) and pseudorabies viruses (PRV).

"Percent (%) sequence identity" with respect to a reference polypeptide or nucleic acid sequence is defined as the percentage of amino acid residues or nucleotides in a candidate sequence that are identical with the amino acid residues or nucleotides in the reference polypeptide or nucleic acid sequence, after aligning the sequences and introducing gaps, if necessary, to achieve the maximum percent sequence identity, and not considering any conservative substitutions as part of the sequence identity. Alignment for purposes of determining percent amino acid or nucleic acid sequence identity can be achieved in various ways that are within the skill in the art, for instance, using publicly available computer software programs, for example, those described in Current Protocols in Molecular Biology (Ausubel et al., eds., 1987), Supp. 30, section 7.7.18, Table 7.7.1, and including BLAST, BLAST-2, ALIGN or Megalign (DNASTAR) software. A preferred alignment program is ALIGN Plus (Scientific and Educational Software, Pa.). Those skilled in the art can determine appropriate parameters for measuring alignment, including any algorithms needed to achieve maximal alignment over the full length of the sequences being compared. For purposes herein, the % amino acid sequence identity of a given amino acid sequence A to, with, or against a given amino acid sequence B (which can alternatively be phrased as a given amino acid sequence A that has or comprises a certain % amino acid sequence identity to, with, or against a given amino acid sequence B) is calculated as follows: 100 times the fraction X/Y, where X is the number of amino acid residues scored as identical matches by the sequence alignment program in that program's alignment of A and B, and where Y is the total number of amino acid residues in B. It will be appreciated that where the length of amino acid sequence A is not equal to the length of amino acid sequence B, the % amino acid sequence identity of A to B will not equal the % amino acid sequence identity of B to A. For purposes herein, the % nucleic acid sequence identity of a given nucleic acid sequence C to, with, or against a given nucleic acid sequence D (which can alternatively be phrased as a given nucleic acid sequence C that has or comprises a certain % nucleic acid sequence identity to, with, or against a given nucleic acid sequence D) is calculated as follows: 100 times the fraction W/Z, where W is the number of nucleotides scored as identical matches by the sequence alignment program in that program's alignment of C and D, and where Z is the total number of nucleotides in D. It will be appreciated that where the length of nucleic acid sequence C is not equal to the length of nucleic acid sequence D, the % nucleic acid sequence identity of C to D will not equal the % nucleic acid sequence identity of D to C.

An "isolated" molecule (e.g., nucleic acid or protein) or cell means it has been identified and separated and/or recovered from a component of its natural environment.

An "effective amount" is an amount sufficient to effect beneficial or desired results, including clinical results (e.g., amelioration of symptoms, achievement of clinical endpoints, and the like). An effective amount can be administered in one or more administrations. In terms of a disease state, an effective amount is an amount sufficient to ameliorate, stabilize, or delay development of a disease.

An "individual" or "subject" is a mammal. Mammals include, but are not limited to, domesticated animals (e.g., cows, sheep, cats, dogs, and horses), primates (e.g., humans and non-human primates such as monkeys), rabbits, and rodents (e.g., mice and rats). In certain embodiments, the individual or subject is a human.

As used herein, "treatment" is an approach for obtaining beneficial or desired clinical results. For purposes of this invention, beneficial or desired clinical results include, but are not limited to, alleviation of symptoms, diminishment of extent of disease, stabilized (e.g., not worsening) state of disease, preventing spread (e.g., metastasis) of disease, delay or slowing of disease progression, amelioration or palliation of the disease state, and remission (whether partial or total), whether detectable or undetectable. "Treatment" can also mean prolonging survival as compared to expected survival if not receiving treatment.

"Retinitis pigmentosa (RP)" refers to a heterogeneous group of diseases characterized by progressive loss of sight. Symptoms generally stem from degeneration or abnormalities of the retina, which may include the loss of photoreceptor cell function.

"Rhodopsin" refers to a member of the G-protein-coupled receptor family that functions in light perception in the rod photoreceptor cells of the retina. A visual pigment, rhodopsin contains a polypeptide opsin reversibly bound to its cofactor retinal. Light causes isomerization of retinal from an 11-cis to an all-trans form. This in turn causes a conformational change in the polypeptide that leads to G-protein activation. By converting the presence of light into a biochemical response, rhodopsin enables visual perception. Its function is required for scotopic vision (i.e., noncolor vision in dim light), and it is also thought to be required for photoreceptor cell viability.

As used herein, "rhodopsin" may refer to the full visual pigment including retinal or simply the amino acid component or sequence of the molecule. Rhodopsin may also be known as OPN2, Opsin-2, or RP4. Examples of rhodopsin proteins may include without limitation human, mouse, dog, and cat rhodopsin, e.g., NCBI Reference Sequences NP 000530, NP_663358, NP_001008277, and NP_001009242. Examples of rhodopsin genes may include without limitation human, mouse, dog, and cat rhodopsin genes, e.g., GenBank Entrez Gene ID 6010 (RHO, a.k.a. RP4, OPN2, and CSNBAD1), GenBank Entrez Gene ID 212541 (Rho, a.k.a. Ops, RP4, Opn2, and Noerg1), GenBank Entrez Gene ID 493763, and GenBank Entrez Gene ID 493762. The term rhodopsin as used herein also includes functional equivalents of rhodopsin (e.g., rhodopsin variants) including mutations, truncations, deletions, and/or insertions, provided that the functional equivalent maintains at least a portion of the activity of wild-type rhodopsin to ameliorate symptoms of retinitis pigmentosa.

As used herein "refractory" refers to resistance to modulation. For example, a rhodopsin gene that is refractory to suppression by miR-708 is substantially or totally resistant to suppression by miR-708.

"Opsin promoter" refers to a polynucleotide sequence derived from an opsin gene (e.g., mouse opsin) that drives expression specifically in rod photoreceptor cells (e.g., rod photoreceptor cells). As used herein, "opsin promoter" may refer to an entire promoter sequence or a fragment of the promoter sequence sufficient to drive rod-specific expression, such as the sequences described in Quiambao, A. B., et al. (1997) *Vis. Neurosci.* 14(4):617-25 and Le, Y. Z., et al. (2006) *Mol. Vis.* 12:389-98. In some embodiments, the opsin promoter contains a 676 bp fragment encoding a 400 bp CMV enhancer upstream of a portion of the opsin promoter sequence (−500 bp-+15 bp). In addition 65 bp NRL sequence is included; this encodes a neural retinal basic zipper factor (a Rod photoreceptor specific transcription factor).

"Rhodopsin kinase (RK) promoter" refers to a polynucleotide sequence derived from a rhodopsin kinase gene (e.g., human RK, represented by GenBank Entrez Gene ID 6011) that drives expression specifically in rod and cone photoreceptor cells, as well as retinal cell lines such as WERI Rb-1. As used herein, "rhodopsin kinase promoter" may refer to an entire promoter sequence or a fragment of the promoter sequence sufficient to drive photoreceptor-specific expression, such as the sequences described in Khani, S. C., et al. (2007) *Invest. Ophthalmol. Vis. Sci.* 48(9):3954-61 and Young, J. E., et al. (2003) *Invest. Ophthalmol. Vis. Sci.* 44(9):4076-85. In some embodiments, the RK promoter spans from −112 to +180 relative to the transcription start site.

Figure 4:
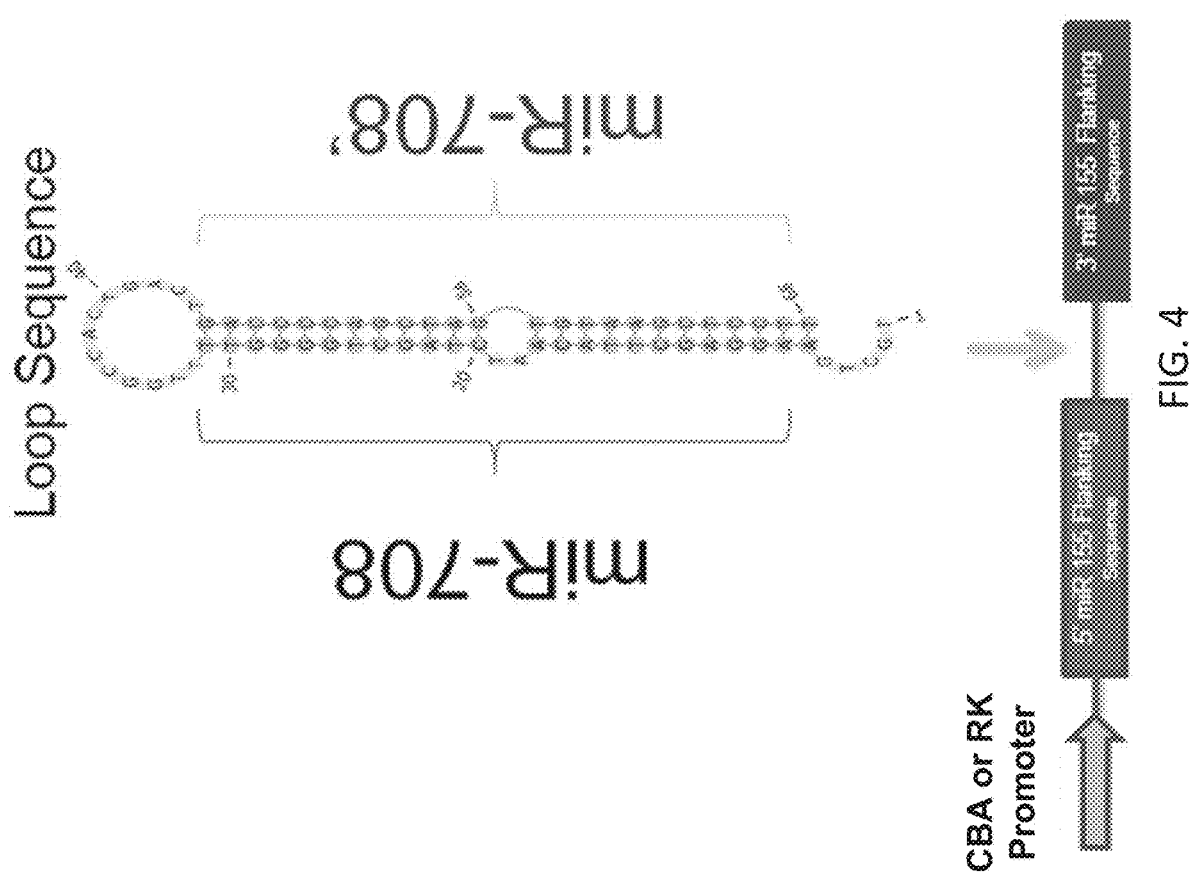
FIG. 4 shows a diagram of the construction of an expression vector for expressing miR-708 under the control of a ubiquitous promoter (chicken β-actin, CBA) or a photoreceptor-specific promoter (rhodopsin kinase, RK). DNA encoding the miR-708 stem and loop sequences was synthesized and cloned between 5' and 3' miR-155 scaffold sequence. This scaffold sequence contains the target sites required for Drosha to process pri-miR-708 into pre-miR-708 in the nucleus, allowing subsequent processing of pre-miR-708 by Dicer in the cytoplasm.

"miR-708" refers to a micro-RNA (miRNA) polynucleotide sequence comprising the stem and loop sequences as shown in FIG. 4. Examples of miR-708 polynucleotides may include without limitation human, mouse, dog, and cat miR-708, e.g., as represented by GenBank Entrez Gene IDs 100126333, 735284, and 100885899. miRNAs are small, non-coding RNA molecules that regulate the expression of genes (e.g., by downregulation of the gene transcript) containing a target site recognized by the miRNA (Bartel, D. P. (2004) *Cell* 116(2):281-97). miR-708 is known to be induced by CHOP and may be involved in the regulating rhodopsin expression (Behrman, S., et al. (2011) *J. Cell Biol.* 192(6):919-27). As used herein, "miR-708" may refer to the processed miR-708 polynucleotide or any intermediate in the processing pathway, e.g., pri-miRNA or pre-miRNA. As used herein, "miR-708" may refer to a DNA sequence that is transcribed to yield miR-708 RNA, or the RNA sequence itself.

Reference to "about" a value or parameter herein includes (and describes) embodiments that are directed to that value or parameter per se. For example, description referring to "about X" includes description of "X."

As used herein, the singular form of the articles "a," "an," and "the" includes plural references unless indicated otherwise.

It is understood that aspects and embodiments of the invention described herein include "comprising," "consisting," and/or "consisting essentially of" aspects and embodiments.

III. Retinitis Pigmentosa and Experimental Models Thereof

As described above, retinitis pigmentosa (RP) refers to a group of degenerative eye diseases that can cause progressive loss of sight, including loss of night vision, loss of peripheral visual fields, and total blindness. In America, the incidence of RP is thought to be approximately 1 in 4,000 people. RP is often inherited, and autosomal dominant, autosomal recessive, and X-linked RP disorders have been described. Mutations in more than 50 different genes have been associated with RP, including components involved in the phototransduction cascade, the retinal cycle, and splicing factors, as well as over 100 distinct mutations in rhodopsin itself. In many cases, mutations associated with RP lead to loss of rod photoreceptor function and/or cell death. This loss results in decreased scotopic vision and may manifest as night blindness or decreased peripheral vision. Rod cell death has also been associated with subsequent cone cell death, causing loss of high acuity vision and, combined with rod cell death, blindness.

A variety of cell- and animal-based models have been established for examining the cellular basis of RP and for testing experimental treatments. One cell-based model for RP is cultured human retinal pigmented epithelial (RPE) cells (Adamowicz, M., et al. (2012) *Adv. Exp. Med. Biol.* 723:573-9). This model may be used to express mutant proteins implicated in RP and test the effect of these mutations on protein function, or the effect of mutant proteins on cellular function and/or viability. For example, human wild-type and mutant rhodopsin may be expressed, using any appropriate promoter (e.g., CMV). Without wishing to be bound to theory, it is thought that misfolding of opsin polypeptides results in ER retention and stress, induction of the unfolded protein response (UPR), and increased cell death. This model may be used to examine the effect of any RP-associated mutation, for example a rhodopsin mutation such as P23H.

Animal-based RP models may include mice harboring mutations known or suspected to cause RP in mice, or mutations orthologous to those found in humans. In some embodiments, mouse models may include mice engineered to express a rhodopsin, for example a mutated human or mouse form, in photoreceptor cells. Examples of mouse models include the rhodopsin P347S mouse (Li, T., et al. (1996) *Proc. Natl. Acad. Sci.* 93(24):14176-81), the Rho$^{-/-}$ mouse (Humphries, M. M., et al. (1997) *Nat. Genet.* 15(2): 216-9), and a mouse expressing P23H mutant rhodopsin ("P23H mouse") (Olsson, J. E., et al. (1992) *Neuron* 9(5): 815-30). In the P23H mouse, mutant human rhodopsin may be inserted into the mouse germline. Any promoter known in the art to express in photoreceptor cells may be used (e.g., the mouse opsin or human RK promoter). In some embodiments, rhodopsin may be expressed using an AAV vector.

Other animal models for RP may also be used. In addition to mouse models, rat, dog, pig, frog (Tam, B. M. and Moritz, O. L. (2006) *Invest. Ophthalmol. Vis. Sci.* 47(8):3234-41), and non-human primate models may also be used.

IV. Methods to Treat Retinitis Pigmentosa

In some aspects, the invention provides methods and compositions for treating retinitis pigmentosa in a mammal comprising administering to the mammal (e.g., to the retina) an effective amount of rAAV viral particles comprising a vector encoding a miR-708. The methods can be used for treating a human with RP, to improve the pathologies and vision impairment associated with RP. In some embodiments, the invention includes administering an effective amount of rAAV viral particles comprising a vector comprising nucleic acid encoding rhodopsin (e.g., a normal or wild-type rhodopsin). In some embodiments, the miR-708 serves to suppress activity of a mutated rhodopsin associated with RP. In some embodiments, the normal or wild-type rhodopsin serves to supplement the eye with a functional rhodopsin. In some embodiments, the viral particle comprises an AAV serotype 5 capsid (AAV5 capsid) and either AAV 2 or AAV 5 inverted terminal repeats. In some embodiments, the viral particle comprises an AAV serotype 5 tyrosine mutant capsid and either AAV 2 or AAV 5 inverted terminal repeats.

In some aspects, the invention provides methods and compositions for ameliorating a symptom of RP, comprising administration to the eye of a mammal an effective amount of rAAV viral particles comprising a vector encoding a miR-708. In other aspects, the invention provides methods and compositions for ameliorating a symptom of RP, comprising administration to the eye of a mammal an effective amount of rAAV viral particles comprising a vector encoding a miR-708 and a rhodopsin. In some embodiments the symptoms of RP include, but is not limited to, blindness, night blindness, decreased peripheral vision, and loss of high acuity vision. In some embodiments, treating retinitis pigmentosa comprises reducing or preventing symptoms associated with the retinitis pigmentosa including but not limited to methods of preventing retinal degeneration, methods for arresting progression of RP, methods for increasing photoreceptor function, and the like. Symptoms and/or pathology of RP include but are not limited to loss of sight, loss of night vision, loss of peripheral visual fields, loss of ERG function; loss of visual acuity and contrast sensitivity; loss of visually guided behavior, reduction in rod photoreceptor function, rod photoreceptor cell death, decreased scotopic vision, reduction in retinal cell changes (loss of photoreceptor structure or function; thinning or thickening of the outer nuclear layer (ONL); thinning or thickening of the outer plexiform layer (OPL); disorganization followed by loss of rod and cone outer segments; shortening of the rod and cone inner segments; retraction of bipolar cell dendrites; thinning or thickening of the inner retinal layers including inner nuclear layer, inner plexiform layer, ganglion cell layer and nerve fiber layer; opsin mislocalization; overexpression of neurofilaments; and the like. In some embodiments, the invention provides methods to prevent deterioration of rod cell function and rod cell death and cone cell function and cone cell death.

In some aspects, the invention provides methods to prevent or delay progression of RP. Autosomal dominant RP is a genetic disease that can be genotyped. Onset and progression of RP may be determined by Optical Coherence Tomography (OCT) which allows examination of outer plexiform layer (OPL) abnormalities.

Means for determining amelioration of the symptoms of RP are known in the art. For example, measurement of visual fields (e.g., Goldmann visual fields), determination of electroretinogram (ERG), fundus photographs, optical coherence tomography, and fluorescein angiography. Improvements in visually-evoked behavior can also be used to determine amelioration of the symptoms of RP; for example, statements such as "I can find things that drop," "I can see faces during a candle-lit dinner," "I can see stripes on my shirt," "I can see stars at night," "I can read regular books and sit in the front of the classroom," "now I can play soccer and don't need someone next to me to help me find the ball," "I can ride my bicycle around my neighborhood by myself," "I achieved my dream: I saw my daughter hit a homerun," and "when can I have my other eye injected?"

In some aspects of the invention, the methods and compositions are used for the treatment of humans with RP. RP can be inherited in an autosomal dominant, autosomal recessive, or X-linked manner. X-linked RP can be either recessive, affecting primarily only males, or dominant, affecting both males and females. RP may be caused by mutations in the rho gene that encodes the rhodopsin protein. In some embodiments of the invention, the methods are used to treat humans with a mutation in the rho gene and/or in the rhodopsin protein. In some embodiments of the invention, the mutation in the rhodopsin protein is a P23H mutation (substitution of histidine for proline at amino acid residue 23 of the rhodopsin protein). In other embodiments, the mutation in the rhodopsin protein is a T58R, P347L, or P347S, or a deletion of residue 1255. Mutations associated with retinitis pigmentosa are provided by McWilliam, P, et al., (1989) *Genomics* 5:619-622; Dryja, T P et al., (1990) *Nature* 343:364-266; Farrar, G J et al., (1990) *Genomics* 8:35-40; Farrar, G J et al., (2002) *EMBO J.* 21:857-864; all incorporated herein by reference.

miR-708 is a CHOP regulated micro RNA that regulated rhodopsin expression (Behrman, S., et al. (2011) *J. Cell Biol.* 192(6):919-27). miR-708 is an intronic micro RNA residing within the CHOP inducible gene Odz4 (Tenurin-4). CHOP regulates miR-708 expression during ER stress. There is a putative miR-708 sequence in the 3' UTR of the rhodopsin gene that is highly conserved (see FIG. 4 of Behrman et al., ibid)

In some embodiments, the invention provides methods for treating a human with RP. In some embodiments, the invention provides methods for treating a human with autosomal dominant RP. In some embodiments, the invention provides methods for treating a human with RP associated with a mutation in the rhodopsin gene. In some embodiments, the invention provides a method for treating a human with RP by administering an effective amount of an AAV vector encoding miR-708 to suppress the activity of a mutated rhodopsin. In some embodiments, the invention provides methods for treating a mammal (e.g., a dog or a cat) with RP. In some embodiments, the miR-708 nucleic acid may include without limitation nucleic acid represented by GenBank Entrez Gene IDs 100126333, 735284, or 100885899.

In some embodiments of the invention, the suppression of a mutant rhodopsin is supplemented by the delivery of an effective amount of AAV vector encoding a wild-type rhodopsin or a rhodopsin with activity essentially the same as a wild-type rhodopsin. In some embodiments, the rhodopsin is a human rhodopsin. In some embodiments, the invention provides a method for treating a human with RP by administering an effective amount of an AAV vector encoding miR-708 to suppress the activity of a mutated rhodopsin and an effective amount of an AAV vector encoding a human rhodopsin with wild-type activity. In some embodiments, the AAV vector encoding miR-708 and the AAV vector encoding the human rhodopsin are the same AAV vector. In some embodiments, the AAV vector encoding miR-708 and the AAV vector encoding the human rhodopsin are the different AAV vectors. In some embodiments, nucleic acid encoding rhodopsin may include without limitation nucleic acid provided by identified by NCBI Reference Sequences NP_000530, NP_663358, NP_001008277, and NP_001009242.

In some aspects, the invention provides methods for treating endoplasmic reticulum (ER) stress in a cell comprising administering to the mammal a rAAV viral particle comprising a rAAV vector comprising nucleic acid encoding a miR-708. In some embodiments, the cell is an ocular cell. In further embodiments, the cell is a photoreceptor cell. In yet further embodiments, the cell is a rod photoreceptor cell. In some embodiments, the method comprises reducing one or more cellular markers of ER stress. In further embodiments, the one or more cellular marker of ER stress is spliced XBP-1, CHOP or Grp78. In some embodiments, the rAAV vector comprises nucleic acid encoding a miR-708 further comprises nucleic acid encoding rhodopsin. In other embodiments, the invention provides methods for treating endoplasmic reticulum (ER) stress in a cell comprising administering to the mammal a first rAAV vector comprising nucleic acid encoding a miR-708 and a second rAAV viral particle comprising a second rAAV vector comprising nucleic acid encoding a rhodopsin.

In some aspects, the invention provides methods to deliver miR-708 or miR-708 and rhodopsin to a mammal with RP, the method comprising administering to the retina of the mammal, an effective amount of rAAV viral particles comprising vector encoding the miR-708 and/or rhodopsin. The administration delivers the transgene product to the photoreceptor cells, where the miR-708 and/or rhodopsin mediates a beneficial effect on the photoreceptor cell and surrounding photoreceptor cells. In some embodiments, delivery of AAV viral particles to the retina is by injection of viral particles to the sub-retinal space of the retina. In some embodiments, the delivery of AAV particles to the retina is by intravitreal delivery provided the AAV particle is capable of penetrating to the back of the eye and transduces photoreceptor cells. In some embodiments, the AAV particles are administered in one or more locations in the sub-retinal space of the retina.

In some embodiments, the administration to the retina of an effective amount of rAAV viral particles comprising a vector encoding miR-708 and/or rhodopsin transduces photoreceptor cells at or near the site of administration. In some embodiments, more than about any of 5%, 10%, 15%, 20%, 25%, 30%, 35%, 40%, 45%, 50%, 55%, 60%, 65%, 70%, 75% or 100% of photoreceptor cells are transduced. In some embodiments, about 5% to about 100%, about 10% to about 50%, about 10% to about 30%, about 25% to about 75%, about 25% to about 50%, or about 30% to about 50% of the photoreceptor cells are transduced. Methods to identify photoreceptor cells transduced by AAV expressing miR-708 and/or rhodopsin are known in the art; for example, immunohistochemistry or the use of a marker such as enhanced green fluorescent protein can be used to detect expression of miR-708 and/or rhodopsin.

In some embodiments of the invention, the methods comprise administration to the retina (e.g., the subretinal space) of a mammal an effective amount of AAV viral particles comprising a vector encoding a miR708 and/or rhodopsin for treating a mammal, e.g., a human, with RP. In some embodiments, the composition is injected to one or more subretinal spaces to allow expression of miR-708 and/or rhodopsin in photoreceptor cells. In some embodiments, the composition is injected into any one of one, two, three, four, five, six, seven, eight, nine, ten or more than ten locations in the subretinal space of the retina.

In some embodiments the rAAV viral particles are administered to more than one location simultaneously or sequentially. In some embodiment, multiple injections of rAAV viral particles are no more than one hour, two hours, three hours, four hours, five hours, six hours, nine hours, twelve hours or 24 hours apart.

In some embodiments, first rAAV viral particles encoding miR-708 and second rAAV viral particles encoding rhodopsin are administered to one or more locations simultaneously or sequentially. In some embodiment, multiple injections of rAAV viral particles are no more than one hour, two hours, three hours, four hours, five hours, six hours, nine hours, twelve hours or 24 hours apart. In some embodiments the first rAAV viral particles encoding miR-708 are administered before the second rAAV viral particles encoding rhodopsin are administered. In some embodiments the first rAAV viral particles encoding miR-708 are administered after the second rAAV viral particles encoding rhodopsin are administered.

In some embodiments, the invention provides a method for treating a human with RP by administering an effective amount of a pharmaceutical composition comprising an AAV vector encoding miR-708 to suppress the activity of a mutated rhodopsin. In some embodiments, the invention provides a method for treating a human with RP by administering an effective amount of a pharmaceutical composition comprising an AAV vector encoding miR-708 to suppress the activity of a mutated rhodopsin and an effective amount of a pharmaceutical composition comprising an AAV vector encoding rhodopsin to supplement photoreceptors with wild-type rhodopsin activity. In some embodiments, the pharmaceutical composition comprising an AAV vector encoding miR-708 and the pharmaceutical composition comprising an AAV vector encoding the human rhodopsin are the same pharmaceutical composition. In some embodiments, the pharmaceutical composition comprising an AAV vector encoding miR-708 and the pharmaceutical composition comprising an AAV vector encoding the human rhodopsin are the different pharmaceutical composition. In some embodiments, the pharmaceutical composition comprises one or more pharmaceutically acceptable excipients.

In some embodiments of the invention, the volume of the composition injected to the subretinal space of the retina or intravitreally is more than about any one of 1 µl, 2 µl, 3 µl, 4 µl, 5 µl, 6 µl, 7 µl, 8 µl, 9 µl, 10 µl, 15 µl, 20 µl, 25 µl, 50 µl, 75 µl, 100 µl, 200 µl, 300 µl, 400 µl, 500 µl, 600 µl, 700 µl, 800 µl, 900 µl, or 1 mL, or any amount therebetween.

Compositions of the invention (e.g., AAV viral particles comprising a vector encoding miR-708 and/or rhodopsin) can be used either alone or in combination with one or more additional therapeutic agents for treating RP. The interval between sequential administration can be in terms of at least (or, alternatively, less than) minutes, hours, or days.

V. Expression Constructs

In some embodiments, the transgene (e.g., miRNA 708 and/or rhodopsin) is operably linked to a promoter. Exemplary promoters include, but are not limited to, the cytomegalovirus (CMV) immediate early promoter, the RSV LTR, the MoMLV LTR, the phosphoglycerate kinase-1 (PGK) promoter, a simian virus 40 (SV40) promoter and a CK6 promoter, a transthyretin promoter (TTR), a TK promoter, a tetracycline responsive promoter (TRE), an HBV promoter, an hAAT promoter, a LSP promoter, chimeric liver-specific promoters (LSPs), the E2F promoter, the telomerase (hTERT) promoter; the cytomegalovirus enhancer/chicken beta-actin/Rabbit β-globin promoter (CAG promoter; Niwa et al., *Gene*, 1991, 108(2):193-9) and the elongation factor 1-alpha promoter (EF1-alpha) promoter (Kim et al., *Gene*, 1990, 91(2):217-23 and Guo et al., *Gene Ther.*, 1996, 3(9):802-10). In some embodiments, the promoter comprises a human β-glucuronidase promoter or a cytomegalovirus enhancer linked to a chicken β-actin (CBA) promoter. The promoter can be a constitutive, inducible or repressible promoter. In some embodiments, the invention provides an AAV vector comprising nucleic acid encoding miR-708 operably linked to a CBA promoter. In some embodiments, the invention provides an AAV vector comprising nucleic acid encoding rhodopsin (e.g., human rhodopsin) operably linked to a CBA promoter. In some embodiments, the invention provides an AAV vector comprising nucleic acid encoding miR-708 and nucleic acid encoding rhodopsin (e.g., human rhodopsin) operably linked to a CBA promoter.

In some embodiments, the promoter is capable of expressing the transgene in photoreceptor cells. In embodiments, the promoter is a rhodopsin kinase (RK) promoter; e.g., a human RK promoter. In some embodiments, the promoter is an opsin promoter; e.g., a human opsin promoter or a mouse opsin promoter.

In some embodiments, the invention provides an AAV vector comprising nucleic acid encoding miR-708 operably linked to an RK promoter. In some embodiments, the invention provides an AAV vector comprising nucleic acid encoding rhodopsin (e.g., human rhodopsin) operably linked to an RK promoter. In some embodiments, the invention provides an AAV vector comprising nucleic acid encoding miR-708 and rhodopsin (e.g., human rhodopsin) operably linked to an RK promoter. In some embodiments, the nucleic acid encoding miR-708 is 5' to nucleic acid encoding rhodopsin. In other embodiments, the nucleic acid encoding miR-708 is 3' to nucleic acid encoding rhodopsin. In some embodiments, the invention provides an AAV vector comprising nucleic acid encoding miR-708 operably linked to a first RK promoter and nucleic acid encoding rhodopsin operably linked to a second RK promoter. In some embodiments, the nucleic acid encoding miR-708 operably linked to a first RK promoter is 5' to nucleic acid encoding rhodopsin operably linked to a second RK promoter. In other embodiments, the nucleic acid encoding miR-708 operably linked to a first RK promoter is 3' to nucleic acid encoding rhodopsin operably linked to a second RK promoter. In some embodiments, the miR-708 comprises the sequence of SEQ ID NO:1. In some embodiments, the miR-708 comprises a nucleotide sequence that is at least about 80%, 85%, 90%, 91%, 92%, 93%, 94%, 95%, 96%, 97%, 98%, or 99% identical to the sequence of SEQ ID NO:1. In some embodiments, the rhodopsin comprises the amino acid sequence of SEQ ID NO:2. In some embodiments, the rhodopsin comprises an amino acid sequence that is at least about 80%, 85%, 90%, 91%, 92%, 93%, 94%, 95%, 96%, 97%, 98%, or 99% identical to the amino acid sequence of SEQ ID NO:2. In some embodiments, the rhodopsin is a functional equivalent of wild-type rhodopsin. In some embodiments, expression of rhodopsin from the AAV vector is refractory to suppression by miR-708. In some embodiments, nucleic acid encoding rhodopsin lacks the miR-708 target site in the 3' UTR of the rhodopsin gene. In some embodiments, nucleic acid encoding rhodopsin comprises a mutation (e.g., a deletion, a substitution, an insertion, etc.) in the miR-708 target site in the 3' UTR of the rhodopsin gene such that it is refractory to suppression by miR-708.

In some embodiments, the invention provides an AAV vector comprising nucleic acid encoding miR-708 operably linked to an opsin promoter. In some embodiments, the invention provides an AAV vector comprising nucleic acid encoding rhodopsin (e.g., human rhodopsin) operably linked to an opsin promoter. In some embodiments, the invention provides an AAV vector comprising nucleic acid encoding miR-708 and nucleic acid encoding rhodopsin (e.g., human rhodopsin) operably linked to an opsin promoter. In some embodiments, the nucleic acid encoding miR-708 is 5' to nucleic acid encoding rhodopsin. In other embodiments, the nucleic acid encoding miR-708 is 3' to nucleic acid encoding rhodopsin. In some embodiments, the invention provides an AAV vector comprising nucleic acid encoding miR-708 operably linked to a first opsin promoter and nucleic acid encoding rhodopsin operably linked to a second opsin promoter. In some embodiments, the nucleic acid encoding miR-708 operably linked to a first opsin promoter is 5' to nucleic acid encoding rhodopsin operably linked to a second opsin promoter. In other embodiments, the nucleic acid encoding miR-708 operably linked to a first opsin promoter is 3' to nucleic acid encoding rhodopsin operably linked to a second opsin promoter. In some embodiments, the miR-708 comprises the sequence of SEQ ID NO:1. In some embodiments, the miR-708 comprises the sequence of SEQ ID NO:1. In some embodiments, the miR-708 comprises a nucleotide sequence that is at least about 80%, 85%, 90%, 91%, 92%, 93%, 94%, 95%, 96%, 97%, 98%, or 99% identical to the sequence of SEQ ID NO:1. In some embodiments, the rhodopsin comprises the amino acid sequence of SEQ ID NO:2. In some embodiments, the rhodopsin comprises an amino acid sequence that is at least about 80%, 85%, 90%, 91%, 92%, 93%, 94%, 95%, 96%, 97%, 98%, or 99% identical to the amino acid sequence of SEQ ID NO:2. In some embodiments, the rhodopsin is a functional equivalent of wild-type rhodopsin. In some embodiments, expression of rhodopsin from the AAV vector is refractory to suppression by miR-708. In some embodiments, nucleic acid encoding rhodopsin lacks the miR-708 target site in the 3' UTR of the rhodopsin gene. In some embodiments, nucleic acid encoding rhodopsin comprises a mutation (e.g., a deletion, a substitution, an insertion, etc.) in the miR-708 target site in the 3' UTR of the rhodopsin gene such that it is refractory to suppression by miR-708.

In some embodiments, the invention provides an AAV vector comprising nucleic acid encoding miR-708 operably linked to an RK promoter and nucleic acid encoding rhodopsin operably linked to an opsin promoter. In some embodiments, the nucleic acid encoding miR-708 operably linked to the RK promoter is 5' to nucleic acid encoding rhodopsin operably linked to an opsin promoter. In some embodiments, the nucleic acid encoding miR-708 operably linked to the RK promoter is 3' to nucleic acid encoding rhodopsin operably linked to an opsin promoter. In some embodiments, the invention provides an AAV vector comprising nucleic acid encoding miR-708 operably linked to an opsin promoter and nucleic acid encoding rhodopsin operably linked to an RK promoter. In some embodiments, the nucleic acid encoding miR-708 operably linked to the opsin promoter is 5' to nucleic acid encoding rhodopsin operably linked to an RK promoter. In some embodiments, the nucleic acid encoding miR-708 operably linked to the opsin promoter is 3' to nucleic acid encoding rhodopsin operably linked to an RK promoter. In some embodiments, the miR-708 comprises the sequence of SEQ ID NO:1. In some embodiments, the miR-708 comprises the sequence of SEQ ID NO:1. In some embodiments, the miR-708 comprises a nucleotide sequence that is at least about 80%, 85%, 90%, 91%, 92%, 93%, 94%, 95%, 96%, 97%, 98%, or 99% identical to the sequence of SEQ ID NO:1. In some embodiments, the rhodopsin comprises the amino acid sequence of SEQ ID NO:2. In some embodiments, the rhodopsin comprises an amino acid sequence that is at least about 80%, 85%, 90%, 91%, 92%, 93%, 94%, 95%, 96%, 97%, 98%, or 99% identical to the amino acid sequence of SEQ ID NO:2. In some embodiments, the rhodopsin is a functional equivalent of wild-type rhodopsin. In some embodiments, expression of rhodopsin from the AAV vector is refractory to suppression by miR-708. In some embodiments, nucleic acid encoding rhodopsin lacks the miR-708 target site in the 3' UTR of the rhodopsin gene. In some embodiments, nucleic acid encoding rhodopsin comprises a mutation (e.g., a deletion, a substitution, an insertion, etc.) in the miR-708 target site in the 3' UTR of the rhodopsin gene such that it is refractory to suppression by miR-708.

In some embodiments, the invention provides an AAV vector comprising nucleic acid encoding miR-708 operably linked to a CBA promoter and nucleic acid encoding rhodopsin operably linked to an RK promoter. In some embodiments, the nucleic acid encoding miR-708 operably linked to the CBA promoter is 5' to nucleic acid encoding rhodopsin operably linked to an RK promoter. In some embodiments, the nucleic acid encoding miR-708 operably linked to the CBA promoter is 3' to nucleic acid encoding rhodopsin operably linked to an RK promoter. In some embodiments, the invention provides an AAV vector comprising nucleic acid encoding miR-708 operably linked to an RK promoter and nucleic acid encoding rhodopsin operably linked to a CBA promoter. In some embodiments, the nucleic acid encoding miR-708 operably linked to the RK promoter is 5' to nucleic acid encoding rhodopsin operably linked to a CBA promoter. In some embodiments, the nucleic acid encoding miR-708 operably linked to the RK promoter is 3' to nucleic acid encoding rhodopsin operably linked to a CBA promoter. In some embodiments, the miR-708 comprises the sequence of SEQ ID NO:1. In some embodiments, the miR-708 comprises the sequence of SEQ ID NO:1. In some embodiments, the miR-708 comprises a nucleotide sequence that is at least about 80%, 85%, 90%, or 95% identical to the sequence of SEQ ID NO:1. In some embodiments, the rhodopsin comprises the amino acid sequence of SEQ ID NO:2. In some embodiments, the rhodopsin comprises an amino acid sequence that is at least about 80%, 85%, 90%, 91%, 92%, 93%, 94%, 95%, 96%, 97%, 98% identical to the amino acid sequence of SEQ ID NO:2. In some embodiments, the rhodopsin is a functional equivalent of wild-type rhodopsin. In some embodiments, expression of rhodopsin from the AAV vector is refractory to suppression by miR-708. In some embodiments, nucleic acid encoding rhodopsin lacks the miR-708 target site in the 3' UTR of the rhodopsin gene. In some embodiments, nucleic acid encoding rhodopsin comprises a mutation (e.g., a deletion, a substitution, an insertion, etc.) in the miR-708 target site in the 3' UTR of the rhodopsin gene such that it is refractory to suppression by miR-708.

In some embodiments, nucleic acid encoding miR-708 comprises an endogenous miR-708 scaffold. In some embodiments, the miR-708 scaffold is provided by SEQ ID NO:14. In some embodiments, nucleic acid encoding miR- 708 comprises a heterologous miRNA scaffold. In some embodiments, use of a heterologous miRNA scaffold is used to modulate miRNA expression; for example, to increase miRNA expression or to decrease miRNA expression. In some embodiments, nucleic acid encoding miR-708 comprises an endogenous miR-155 scaffold. In some embodiments, the miR-155 scaffold is provided by SEQ ID NO:14.

Recombinant Viral Vector

The present invention contemplates the use of a recombinant viral genome for introduction of one or more nucleic acid sequences encoding for a miR-708 miRNA and/or a rhodopsin protein described herein for packaging into an AAV viral particle. The recombinant viral genome may include any element to establish the expression of a miR-708 miRNA and/or a rhodopsin protein, for example, a promoter, a miR-708 miRNA and/or a rhodopsin transgene, an ITR, a ribosome binding element, terminator, enhancer, selection marker, intron, polyA signal, and/or origin of replication.

VI. Viral Particles and Methods of Producing Viral Particles rAAV Viral Particles The invention provides methods of using rAAV particles to treat retinitis pigmentosa and provides compositions comprising rAAV particles. In some embodiments, the viral particle is a recombinant AAV particle comprising a nucleic acid comprising a sequence encoding miR-708 miRNA and/or a rhodopsin protein described herein flanked by one or two ITRs. The nucleic acid is encapsidated in the AAV particle. The AAV particle also comprises capsid proteins. In some embodiments, the nucleic acid comprises the coding sequence(s) of interest (e.g., nucleic acid encoding miR-708 miRNA and/or a rhodopsin protein) operatively linked components in the direction of transcription, control sequences including transcription initiation and termination sequences, thereby forming an expression cassette. In some embodiments, nucleic acid encoding the miR-708 is embedded in an intron. The expression cassette is flanked on the 5' and 3' end by at least one functional AAV ITR sequences. By "functional AAV ITR sequences" it is meant that the ITR sequences function as intended for the rescue, replication and packaging of the AAV virion. See Davidson et al., PNAS, 2000, 97(7)3428-32; Passini et al., *J. Virol.*, 2003, 77(12):7034-40; and Pechan et al., *Gene Ther.*, 2009, 16:10-16, all of which are incorporated herein in their entirety by reference. For practicing some aspects of the invention, the recombinant vectors comprise at least all of the sequences of AAV essential for encapsidation and the physical structures for infection by the rAAV. AAV ITRs for use in the vectors of the invention need not have a wild-type nucleotide sequence (e.g., as described in Kotin, *Hum. Gene Ther.*, 1994, 5:793-801), and may be altered by the insertion, deletion or substitution of nucleotides or the AAV ITRs may be derived from any of several AAV serotypes. More than 40 serotypes of AAV are currently known, and new serotypes and variants of existing serotypes continue to be identified. See Gao et al., *PNAS*, 2002, 99(18): 11854-6; Gao et al., *PNAS*, 2003, 100(10):6081-6; and Bossis et al., *J. Virol.*, 2003, 77(12):6799-810. Use of any AAV serotype is considered within the scope of the present invention. In some embodiments, a rAAV vector is a vector derived from an AAV serotype, including without limitation, AAV1, AAV2, AAV3, AAV4, AAV5, AAV6, AAV7, AAV8, AAVrh8, AAVrh8R, AAV9, AAV10, AAVrh10, AAV11, AAV12, AAV2R471A, AAV DJ, a goat AAV, bovine AAV, or mouse AAV capsid serotype ITRs or the like. In some embodiments, the nucleic acid in the AAV comprises an ITR of AAV1, AAV2, AAV3, AAV4, AAV5, AAV6, AAV7, AAV8, AAVrh8, AAVrh8R, AAV9, AAV10, AAVrh10, AAV11, AAV12, AAV2R471A, AAV DJ, a goat AAV, bovine AAV, or mouse AAV capsid serotype ITRs or the like. In some embodiments, the nucleic acid in the AAV further encodes miR-708, rhodopsin, or miR-708 and rhodopsin as described herein. For example, the nucleic acid in the AAV can comprise at least one ITR of any AAV serotype contemplated herein and can further encode a miR-708 comprising the nucleic acid of SEQ ID NO:1 and/or nucleic acid encoding a human rhodopsin comprising the amino acid sequence of SEQ ID NO:2. In some embodiments, the nucleic acid in the AAV comprises 5' to 3' nucleic acid encoding the following: an AAV ITR, a stuffer fragment (e.g., SEQ ID NO:11), a chimeric intron (e.g., SEQ ID NO:10), a miR-708, a bovine growth hormone polyadenylation sequence, a stuffer fragment, and an AAV ITR. In some embodiments, the nucleic acid in the AAV comprises 5' to 3' nucleic acid encoding the following: an AAV ITR, an RK promoter, a β globin intron, a miR-708 imbedded in the β globin intron, a human rhodopsin, a bovine growth hormone polyadenylation sequence, and an AAV ITR. In some embodiments, the nucleic acid in the AAV comprises 5' to 3' nucleic acid encoding the following: an AAV ITR, a stuffer fragment (e.g., SEQ ID NO:11), an RK promoter, a chimeric intron (e.g., SEQ ID NO:10), a human rhodopsin, a β-globin intron, a miR-708 embedded in a β-globin intron, a bovine growth hormone polyadenylation sequence, a stuffer fragment, and an AAV ITR. In some embodiments, the nucleic acid in the AAV comprises 5' to 3' nucleic acid encoding the following: an AAV ITR, a stuffer fragment (e.g., SEQ ID NO:11), an RK promoter, a chimeric intron (e.g., SEQ ID NO:10), a miR-708, a mouse opsin promoter, a human rhodopsin, a bovine growth hormone polyadenylation sequence, and an AAV ITR. In some embodiments, the nucleic acid in the AAV comprises the nucleic acid of SEQ ID NO:5. In some embodiments, the nucleic acid in the AAV comprises a nucleic acid that is at least about 80%, 85%, 90%, 91%, 92%, 93%, 94%, 95%, 96%, 97%, 98%, or 99% identical to SEQ ID NO:5. In some embodiments, the nucleic acid in the AAV the nucleic acid of SEQ ID NO:6. In some embodiments, the nucleic acid in the AAV comprises a nucleic acid that is at least about 80%, 85%, 90%, 91%, 92%, 93%, 94%, 95%, 96%, 97%, 98%, or 99% identical to SEQ ID NO:6. In some embodiments, the nucleic acid in the AAV comprises the nucleic acid of SEQ ID NO:7. In some embodiments, the nucleic acid in the AAV comprises a nucleic acid that is at least about 80%, 85%, 90%, 91%, 92%, 93%, 94%, 95%, 96%, 97%, 98%, or 99% identical to SEQ ID NO:7. In some embodiments, the nucleic acid in the AAV comprises the nucleic acid of SEQ ID NO:8. In some embodiments, the nucleic acid in the AAV comprises a nucleic acid that is at least about 80%, 85%, 90%, 91%, 92%, 93%, 94%, 95%, 96%, 97%, 98%, or 99% identical to SEQ ID NO:8. In some embodiments, the nucleic acid in the AAV comprises the nucleic acid of SEQ ID NO:9. In some embodiments, the nucleic acid in the AAV comprises a nucleic acid that is at least about 80%, 85%, 90%, 91%, 92%, 93%, 94%, 95%, 96%, 97%, 98%, or 99% identical to SEQ ID NO:9. In some embodiments, the nucleic acid in the AAV comprises the nucleic acid of SEQ ID NO:24. In some embodiments, the nucleic acid in the AAV comprises a nucleic acid that is at least about 80%, 85%, 90%, 91%, 92%, 93%, 94%, 95%, 96%, 97%, 98%, or 99% identical to SEQ ID NO:24. In some embodiments, the nucleic acid in the AAV comprises the nucleic acid of SEQ ID NO:25. In some embodiments, the nucleic acid in the AAV comprises a nucleic acid that is at least about 80%, 85%, 90%, 91%, 92%, 93%, 94%, 95%, 96%, 97%, 98%, or 99% identical to SEQ ID NO:25. In some embodiments, the nucleic acid in the AAV comprises the nucleic acid of SEQ ID NO:26. In some embodiments, the nucleic acid in the AAV comprises a nucleic acid that is at least about 80%, 85%, 90%, 91%, 92%, 93%, 94%, 95%, 96%, 97%, 98%, or 99% identical to SEQ ID NO:26. In some embodiments, the nucleic acid in the AAV comprises the nucleic acid of SEQ ID NO:27. In some embodiments, the nucleic acid in the AAV comprises a nucleic acid that is at least about 80%, 85%, 90%, 91%, 92%, 93%, 94%, 95%, 96%, 97%, 98%, or 99% identical to SEQ ID NO:27. In further embodiments, the rAAV particle comprises capsid proteins of AAV1, AAV2, AAV3, AAV4, AAV5, AAV6, AAV7, AAV8, AAVrh8, AAVrh8R, AAV9, AAV10, AAVrh10, AAV11, AAV12, AAV2R471A, AAV2/2-7m8, AAV DJ, AAV2 N587A, AAV2 E548A, AAV2 N708A, AAV V708K, a goat AAV, AAV1/AAV2 chimeric, bovine AAV, mouse AAV capsid rAAV2/HBoV1 serotype capsid, or mutants of these capsid proteins. In some embodiments, a mutant capsid protein maintains the ability to form an AAV capsid. In some embodiments, the rAAV particle comprises AAV5 tyrosine mutant capsid (Zhong L. et al., (2008) *Proc Natl Acad Sci USA* 105(22):7827-7832. In further embodiments, the rAAV particle comprises capsid proteins of an AAV serotype from Clades A-F (Gao, et al., *J. Virol.* 2004, 78(12):6381). In some embodiments, the nucleic acid in the AAV comprises the nucleic acid sequence selected from the group consisting of SEQ ID NOs:5-8, and is flanked by at least one AAV2 ITR. In some embodiments, the nucleic acid in the AAV comprises the nucleic acid sequence that is at least about 80%, 85%, 90%, 91%, 92%, 93%, 94%, 95%, 96%, 97%, 98%, or 99% identical to the nucleic acid selected from the group consisting of SEQ ID NOs:5-9, and is flanked by at least one AAV2 ITR.

Different AAV serotypes are used to optimize transduction of particular target cells or to target specific cell types within a particular target tissue (e.g., a diseased tissue). A rAAV particle can comprise viral proteins and viral nucleic acids of the same serotype or a mixed serotype. For example, in some embodiments a rAAV particle can comprise AAV5 capsid proteins and at least one AAV2 ITR or it can comprise AAV2 capsid proteins and at least one AAV5 ITR. In other embodiments a rAAV particle can comprise AAV5 tyrosine mutant capsid proteins and at least one AAV2 ITR. In yet another example, a rAAV particle can comprise capsid proteins from both AAV5 and AAV2, and further comprise at least one AAV2 ITR. Any combination of AAV serotypes for production of a rAAV particle is provided herein as if each combination had been expressly stated herein. In some embodiments, the invention provides rAAV particles comprising AAV5 capsid proteins and a nucleic acid encoding miR-708 RNA and/or a rhodopsin transgene, flanked by at least one AAV2 ITR.

Self-Complementary AAV Viral Genomes

In some aspects, the invention provides viral particles comprising a recombinant self-complementing genome. AAV viral particles with self-complementing genomes and methods of use of self-complementing AAV genomes are described in U.S. Pat. Nos. 6,596,535; 7,125,717; 7,765,583; 7,785,888; 7,790,154; 7,846,729; 8,093,054; and 8,361,457; and Wang Z., et al., (2003) *Gene Ther* 10:2105-2111, each of which are incorporated herein by reference in its entirety. A rAAV comprising a self-complementing genome will quickly form a double stranded DNA molecule by virtue of its partially complementing sequences (e.g., complementing coding and non-coding strands of a transgene). In some embodiments, the invention provides an AAV viral particle comprising an AAV genome, wherein the rAAV genome comprises a first heterologous polynucleotide sequence (e.g., miR-708 and/or a rhodopsin coding strand) and a second heterologous polynucleotide sequence (e.g., antisense strand of miR-708 and/or a rhodopsin noncoding or antisense strand) wherein the first heterologous polynucleotide sequence can form intrastrand base pairs with the second polynucleotide sequence along most or all of its length. In some embodiments, the first heterologous polynucleotide sequence and a second heterologous polynucleotide sequence are linked by a sequence that facilitates intrastrand basepairing; e.g., a hairpin DNA structure. Hairpin structures are known in the art, for example in siRNA molecules. In some embodiments, the first heterologous polynucleotide sequence and a second heterologous polynucleotide sequence are linked by a mutated ITR (e.g., the right ITR). In some embodiments, the ITR comprises the polynucleotide sequence 5'-CACTCCCTCTCTGCGCGCTCGCTCGCTCACT-GAGGCCGGGCGACCAAAGGTCGCCC ACGCCGGGCTTTGCCCGGGCG-3' (SEQ ID NO:20). The mutated ITR comprises a deletion of the D region comprising the terminal resolution sequence. As a result, on replicating an AAV viral genome, the rep proteins will not cleave the viral genome at the mutated ITR and as such, a recombinant viral genome comprising the following in 5' to 3' order will be packaged in a viral capsid: an AAV ITR, the first heterologous polynucleotide sequence including regulatory sequences, the mutated AAV ITR, the second heterologous polynucleotide in reverse orientation to the first heterologous polynucleotide and a third AAV ITR. In some embodiments, the invention provides AAV viral particles comprising a recombinant viral genome comprising a functional AAV2 ITR, a first polynucleotide sequence encoding miR-708 RNA and/or a rhodopsin transgene, a mutated AAV2 ITR comprising a deletion of the D region and lacking a functional terminal resolution sequence, a second polynucleotide sequence comprising the complementary sequence to the sequence encoding miR-708 RNA and/or a rhodopsin, of the first polynucleotide sequence and a functional AAV2 ITR.

Production of AAV Particles

The rAAV particles can be produced using methods know in the art. See, e.g., U.S. Pat. Nos. 6,566,118; 6,989,264; and 6,995,006. In practicing the invention, host cells for producing rAAV particles include mammalian cells, insect cells, plant cells, microorganisms and yeast. Host cells can also be packaging cells in which the AAV rep and cap genes are stably maintained in the host cell or producer cells in which the AAV vector genome is stably maintained. Exemplary packaging and producer cells are derived from 293, A549 or HeLa cells. AAV vectors are purified and formulated using standard techniques known in the art.

In some aspects, a method is provided for producing any rAAV particle as disclosed herein comprising (a) culturing a host cell under a condition that rAAV particles are produced, wherein the host cell comprises (i) one or more AAV package genes, wherein each said AAV packaging gene encodes an AAV replication and/or encapsidation protein; (ii) an rAAV pro-vector comprising a nucleic acid encoding miR-708 RNA and/or any rhodopsin transgene as described herein flanked by at least one AAV ITR, and (iii) an AAV helper function; and (b) recovering the rAAV particles produced by the host cell. In some embodiments, a nucleic acid encodes miR-708 RNA of SEQ ID NO:1 and/or a transgene encoding a rhodopsin; e.g., a rhodopsin with the amino acid of SEQ ID NO:2. In some embodiments, said at least one AAV ITR is selected from the group consisting of AAV1, AAV2, AAV3, AAV4, AAV5, AAV6, AAV7, AAV8, AAVrh8, AAVrh8R, AAV9, AAV10, AAVrh10, AAV11, AAV12, AAV2R471A, AAV DJ, a goat AAV, bovine AAV, or mouse AAV serotype ITR or the like. In some embodiments, said encapsidation protein is selected from the group consisting of AAV1, AAV2, AAV3, AAV4, AAV5, AAV6 (e.g., a wild-type AAV6 capsid, or a variant AAV6 capsid such as ShH10, as described in U.S. PG Pub. 2012/0164106), AAV7, AAV8, AAVrh8, AAVrh8R, AAV9 (e.g., a wild-type AAV9 capsid, or a modified AAV9 capsid as described in U.S. PG Pub. 2013/0323226), AAV10, AAVrh10, AAV11, AAV12, a tyrosine capsid mutant, a heparin binding capsid mutant, an AAV2R471A capsid, an AAVAAV2/2-7m8 capsid, an AAV DJ capsid (e.g., an AAV-DJ/8 capsid, an AAV-DJ/9 capsid, or any other of the capsids described in U.S. PG Pub. 2012/0066783), AAV2 N587A capsid, AAV2 E548A capsid, AAV2 N708A capsid, AAV V708K capsid, goat AAV capsid, AAV1/AAV2 chimeric capsid, bovine AAV capsid, mouse AAV capsid, rAAV2/HBoV1 capsid, an AAV capsid described in U.S. Pat. No. 8,283,151 or International Publication No. WO/2003/042397, or mutants thereof. In some embodiments, the encapsidation protein is an AAV5 tyrosine mutant capsid protein. In further embodiments, the rAAV particle comprises capsid proteins of an AAV serotype from Clades A-F. In some embodiments, the rAAV particles comprise an AAV5 capsid and a recombinant genome comprising AAV2 ITRs, a mutant AAV2 ITR and nucleic acid encoding miR-708 and/or rhodopsin. In some embodiments, the rAAV particles comprise an AAV5 tyrosine mutant capsid and a recombinant genome comprising AAV2 ITRs, a mutant AAV2 ITR and nucleic acid encoding miR-708 and/or rhodopsin. In a further embodiment, the rAAV particles are purified. The term "purified" as used herein includes a preparation of rAAV particles devoid of at least some of the other components that may also be present where the rAAV particles naturally occur or are initially prepared from. Thus, for example, isolated rAAV particles may be prepared using a purification technique to enrich it from a source mixture, such as a culture lysate or production culture supernatant. Enrichment can be measured in a variety of ways, such as, for example, by the proportion of DNase-resistant particles (DRPs) or genome copies (gc) present in a solution, or by infectivity, or it can be measured in relation to a second, potentially interfering substance present in the source mixture, such as contaminants, including production culture contaminants or in-process contaminants, including helper virus, media components, and the like.

Also provided herein are pharmaceutical compositions comprising a rAAV particle comprising a transgene encoding miR-708 and/or a rhodopsin transgene of the invention and a pharmaceutically acceptable carrier. In some embodiments, the composition comprises rAAV particles comprising a transgene encoding miR-708 and rAAV particles comprising a rhodopsin transgene. In some embodiments, the composition comprises rAAV particles comprising a transgene encoding miR-708 and a rhodopsin transgene. The pharmaceutical compositions may be suitable for any mode of administration described herein. A pharmaceutical composition of a rAAV comprising a nucleic acid encoding miR-708 RNA and/or a rhodopsin transgene, described herein can be introduced to the eye; for example, by subretinal administration or intravitreal administration.

In some embodiments, the pharmaceutical compositions comprising a rAAV described herein and a pharmaceutically acceptable carrier is suitable for administration to human. Such carriers are well known in the art (see, e.g., Remington's Pharmaceutical Sciences, 15th Edition, pp. 1035-1038 and 1570-1580). In some embodiments, the pharmaceutical compositions comprising a rAAV described herein and a pharmaceutically acceptable carrier is suitable for ocular injection. Such pharmaceutically acceptable carriers can be sterile liquids, such as water and oil, including those of petroleum, animal, vegetable or synthetic origin, such as peanut oil, soybean oil, mineral oil, and the like. Saline solutions and aqueous dextrose, polyethylene glycol (PEG) and glycerol solutions can also be employed as liquid carriers, particularly for injectable solutions. The pharmaceutical composition may further comprise additional ingredients, for example preservatives, buffers, tonicity agents, antioxidants and stabilizers, nonionic wetting or clarifying agents, viscosity-increasing agents, and the like. The pharmaceutical compositions described herein can be packaged in single unit dosages or in multidosage forms. The compositions are generally formulated as sterile and substantially isotonic solution.

VII. Articles of Manufacture and Kits

Also provided are kits or articles of manufacture for use in the methods described herein. In aspects, the kits comprise the compositions described herein (e.g., rAAV particles comprising nucleic acid encoding miR-708 RNA and/or a rhodopsin transgene) in suitable packaging. Suitable packaging for compositions (such as ocular compositions) described herein are known in the art, and include, for example, vials (such as sealed vials), vessels, ampules, bottles, jars, flexible packaging (e.g., sealed Mylar or plastic bags), and the like. These articles of manufacture may further be sterilized and/or sealed.

The present invention also provides kits comprising compositions described herein and may further comprise instruction(s) on methods of using the composition, such as uses described herein. The kits described herein may further include other materials desirable from a commercial and user standpoint, including other buffers, diluents, filters, needles, syringes, and package inserts with instructions for performing any methods described herein. For example, in some embodiments, the kit comprises an rAAV comprising a transgene encoding miR-708 RNA and/or a rhodopsin transgene for intraocular delivery of at least $1 \times 10^9$ genome copies to a primate as described herein, a pharmaceutically acceptable carrier suitable for intraocular injection, and one or more of: a buffer, a diluent, a filter, a needle, a syringe, and a package insert with instructions for performing ocular injections. In some embodiments, the kit comprising instructions for treating retinitis pigmentosa with the rAAV particles described herein. In some embodiments, the kit comprising instructions for reducing ER stress in a cell with the rAAV particles described herein. In some embodiments, the kit comprising instructions for using the rAAV particles described herein according to any one of the methods described herein.

EXAMPLES

The invention will be more fully understood by reference to the following examples. They should not, however, be construed as limiting the scope of the invention. It is understood that the examples and embodiments described herein are for illustrative purposes only and that various modifications or changes in light thereof will be suggested to persons skilled in the art and are to be included within the spirit and purview of this application and scope of the appended claims.

Example 1: Development of a Cellular Model of Retinitis Pigmentosa

A therapeutic strategy for RHO-associated autosomal dominant RP would be to knock down both mutant and wild-type rhodopsin and alleviate ER stress. This could be achieved by co-delivering a micro-RNA (miR) that would inhibit the rhodopsin alleles and optionally co-delivering a wild-type rhodopsin sequence refractory to knockdown by the exogenously delivered miR. A CHOP-regulated miR, miR-708, regulates rhodopsin expression (Behrman, S., et al. (2011) *J. Cell Biol.* 192(6):919-27). miR-708 is an intronic miR residing within the CHOP-inducible gene Odz4 (Tenurin-4). CHOP regulates miR-708 expression during ER stress, and there is a putative miR-708 sequence in the 3' UTR of rhodopsin.

Described herein are methods for using an AAV vector to deliver exogenous miR-708 targeting both wild type and mutant rhodopsin through the 3' UTR miR-708 target sequence present in both alleles. In embodiments, a wild-type rhodopsin replacement sequence is also co-delivered. This replacement rhodopsin sequence may be engineered to have decreased binding to miR-708 (e.g., nucleotide substitution, deletion or addition to the 3' UTR) and thus will be refractory to knockdown by the exogenous miR-708. In embodiments, the replacement rhodopsin sequence lacks a 3' UTR miR-708 target sequence. In short, these AAV vectors would knock down expression of the rhodopsin that causes ER stress (and therefore photoreceptor cell death) and optionally supplementing expression of a wild-type, or codon-optimized, rhodopsin gene that is refractory to miR-708-induced knockdown, thereby restoring normal expression and function of rhodopsin.

Methods

Cell Culture

HEK-293 cells were engineered to express human or mouse Rhodopsin P23H using the T-Rex Tetracycline Inducible system from Invitrogen. Confluent cells in 6 well plates were transfected with 4 μg miR-708 (pcDNA) vector or a control miRNA vector using Lipofectamine 2000 (Invitrogen) per the manufacturer's instructions. 48 hours post-transfection the medium was replaced with medium containing 2 μM Tetracycline. The cells were incubated an additional 24 hours and the medium was removed from each well.

Western Blotting

Cells were lysed in 400 μL RIPA buffer (Thermo Scientific) containing 1 mM PMSF, and passed through a 25 g syringe several times. The lysate was centrifuged at 14,000 rpm for 10 min. Cells were kept at 4° C. throughout the process. 30 μL of supernatant was loaded onto a 4-12% Bis/Tris Gel and SDS-PAGE was performed in MOPS buffer (Invitrogen). Proteins were then transferred to a Nitrocellulose membrane using the I-Blot system from Invitrogen. The membrane was blocked for an hour at room temperature in PBS containing 0.05% Tween-20 (PBS-T) and 0.1% I-Block (Invitrogen). The membrane was incubated overnight at 4° C. in PBS-T containing 1 μg/mL anti Rhodopsin mAb 1D4 (Abcam). After washing in PBS-T several times the membrane was incubated in secondary antibody solution containing a 1:1000 dilution of anti-mouse IgG HRP conjugated Ab (R&D Systems) for an hour at room temperature. The membrane was washed in PBS-T several times and developed using ECL Reagent (Thermo Scientific). mRhodopsin protein levels were quantified using the Image-J software. The membrane was stripped of proteins in PBS containing 0.1M Glycine pH 2 and then rinsed several times in PBS-T. The membrane was then probed for hGAPDH in PBS-T containing a 1:20,000 dilution of anti GAPDH pAb (Sigma) for 2 hours at Room Temperature. After washing several times in PBS-T, secondary antibody (Anti-Rabbit IgG-HRP, R&D Systems) was diluted 1:1000 in PBS-T and incubated for 1 hour at room temperature. The membrane was washed several times and developed using ECL reagent (Thermo Scientific). mRhodopsin protein levels were then normalized to hGAPDH protein levels using Image J software.

Endogenous miR-708 Knockdown in HEK-293 Cells

HEK-293 cells expressing mouse or human rhodopsin (described above) were transfected with 100 pmol pre-miR-708, anti-miR-708, or control miRNA (Ambion) using the Lipofectamine 2000 protocol for transfection with siRNA molecules (Invitrogen). At 48 hours post-transfection, the medium was replaced with medium containing 2 uM Tetracycline to induce Rhodopsin expression. 24 hours later each well was split into 2 samples. One was probed for mRhodopsin and hGAPDH using the western blot protocol above, and RNA was extracted from the other for TaqMan® (Life Technologies) analysis of Rhodopsin and miR-708 RNA expression. Total RNA (including small RNAs) was extracted from the cells using the miRNeasy kit from Qiagen, according to the manufacturer's instructions, including DNAse treatment of the samples. cDNA was synthesized from total RNA using the Quantitect Reverse Transcription system from Qiagen. cDNA was added to mRhodopsin, hCHOP (Ddit3), hBiP (Hspa5) or hGAPDH TaqMan® gene expression assays (Life Technologies). Gene expression was normalized relative to hGAPDH using the $\Delta\Delta C_t$ method. miR-708 expression was quantified using the miR-708 TaqMan® expression assay (Life Technologies). miR-708 expression was displayed relative to endogenous miR-16 expression using the $\Delta\Delta C_t$ method.

Rhodopsin Kinase Promoter-Driven Expression of miR-708 in WERI Rb-1 Cells miR-708 sequence was subcloned downstream of the Rhodopsin Kinase (RK) promoter after excision from pcDNA 6.2 GW vector (Block-iT system, Invitrogen) into vector pRK-MVM, which contains the native hRK promoter and MVM intron sequences. WERI Rb-1 cells (ATCC) were transfected with 2 μg pRK-miR-708 or pRK-miR-Control vector using Fugene-HD (Promega), according to the manufacturer's instructions. At 48 hours post-transfection, the cells were collected, and total RNA (including small RNAs) was extracted using the miRNeasy kit protocol (Qiagen). miR-708 was quantified in each sample using the miR-708 TaqMan® gene expression assay as described earlier (Life Technologies). To quantify mRhodopsin knockdown in miR-708 expressing WERI Rb-1 cells, cells were co-transfected with 2 μg each of pRK-miR-708 (or control) and pSport6 mRhodopsin P23H using Fugene-HD according to the manufacturer's instructions (Promega). RNA was extracted as described and mRhodopsin RNA levels were quantified as described above using the $\Delta\Delta Ct$ method relative to hGAPDH RNA levels.

Extraction of RNA from Mouse Retinas Injected with AAV Vectors

RNA was extracted from mouse retinas using the miRNeasy kit according to the manufacturer's instructions (Qiagen). Individual mouse retinas were homogenized in Qiazol Lysis Buffer using 1 mm Zirconia/Silica beads (Biospec) for 10 min. After homogenization RNA was extracted according to the manufacturer's instructions. miR-708 levels in each retina were quantified using the qStar microRNA quantification system (Origene). cDNA was synthesized using the first strand cDNA synthesis kit (Origene), followed by miR-708 specific amplification and quantification using miR-708 specific primers and a miR-708 copy standard (Origene). For quantification of Rhodopsin levels in injected mouse eyes, mRhodopsin was amplified using specific primers (Life Technologies) and quantified against a Rhodopsin cDNA standard. RdCVF levels were qualitatively analyzed against GAPDH expression using the ΔΔCt method.

Rhodopsin Suppression/Replacement Vector hRhodopsin cDNA (with no flanking UTR sequences) was cloned into the pRK vector by excision from the pcDNA vector and performing a blunt ended ligation into pRK-MCS. cDNA was synthesized (Biobasic) containing the hRhodopsin Kinase promoter sequence and the hβ-globin Intron with a hmiR-708 sequence insertion (sequence taken from Genbank/NCBI) located between the intron's splice acceptor/donor sites. This sequence was subcloned from pUC57 vector, ligated into pcDNA hRhodopsin vector, and renamed pRK-miR-708 hRho/wt. miRNA-708 and hRhodopsin protein levels were assayed as described above in transfected WERI Rb-1 cells.

Quantification of XBP-1 Splicing in P23H mRhodopsin-Transfected WERI Rb-1 Cells hWERI Rb-1 cells were co-transfected with pcDNA vector encoding a non-glycosylated P23H mutated mRhodopsin and pRK-miR-708 vector. This P23H Rhodopsin cDNA was mutated using site-directed PCR mutagenesis (Agilent Technologies) to change two Asparagine codons (at positions 2 and 5) to Alanine. The cells were transfected as described with 2 μg of each vector and incubated for 72 hrs. Total RNA was collected from the cells as described previously. cDNA was synthesized using the High Capacity cDNA synthesis kit (Invitrogen). XBP-1 spicing was assessed using primers specific for XBP-1 and High Fidelity PCR MasterMix (Roche). Amplified sequences were analyzed on a 2% agarose gel and the relative amounts of spliced (~280 nt) vs. unspliced (~300 nt) XBP-1 transcript was quantified using Image-J software.

Additional Methods

Methods for immunofluorescence, Western blotting with and without Endo-glycosidase H treatment, UPR marker expression, and TUNEL staining of cells expressing wild-type or P23H mutant rhodopsin were performed as described in Adamowicz, M., et al. (2012) *Adv. Exp. Med. Biol.* 723:573-9.

Results

Figure 1A:
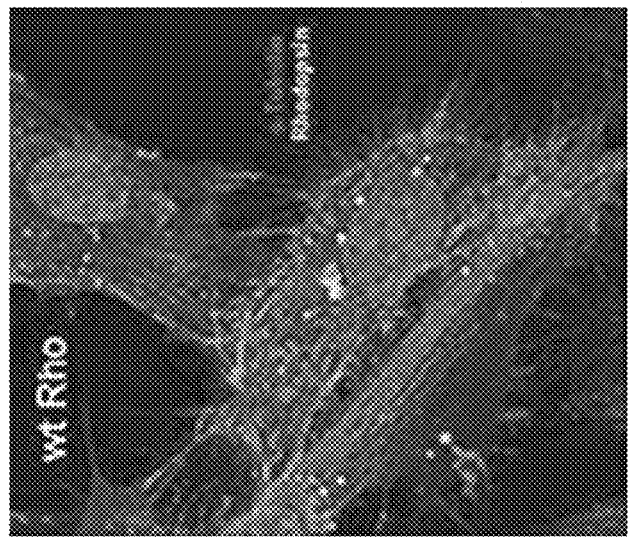

Human retinal pigmented epithelial (RPE) cells were transiently transfected with a gene encoding either human wild-type (WT) or human P23H mutant rhodopsin (a mutation linked to RP). The localization of rhodopsin was investigated by confocal immunofluorescence microscopy using anti-rhodopsin antibody. In the case of the wild type protein, the majority of the protein was processed to the plasma membrane (FIG. 1A), indicating normal biogenesis. By contrast, the mutant P23H showed a perinuclear/reticular distribution characteristic of endoplasmic reticulum (ER) retention, with almost no expression at the cell surface (FIG. 1B). These results demonstrate that P23H mutant rhodopsin fails to be trafficked properly to the plasma membrane and is instead retained in the ER.

Figure 2B:
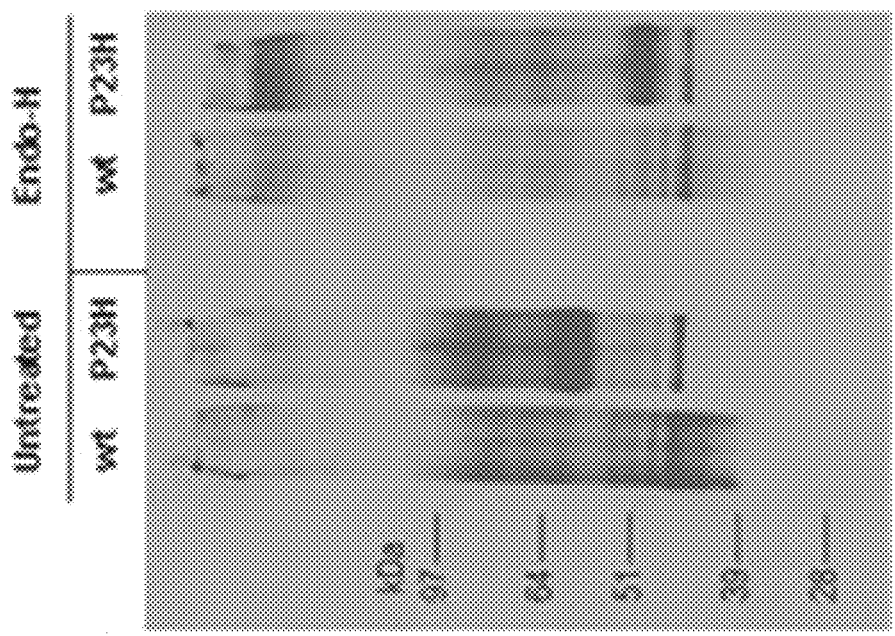
FIGS. 2A & 2B show that P23H mutant rhodopsin forms non-native oligomers and retains ER-specific oligosaccharides.
Figure 2A:
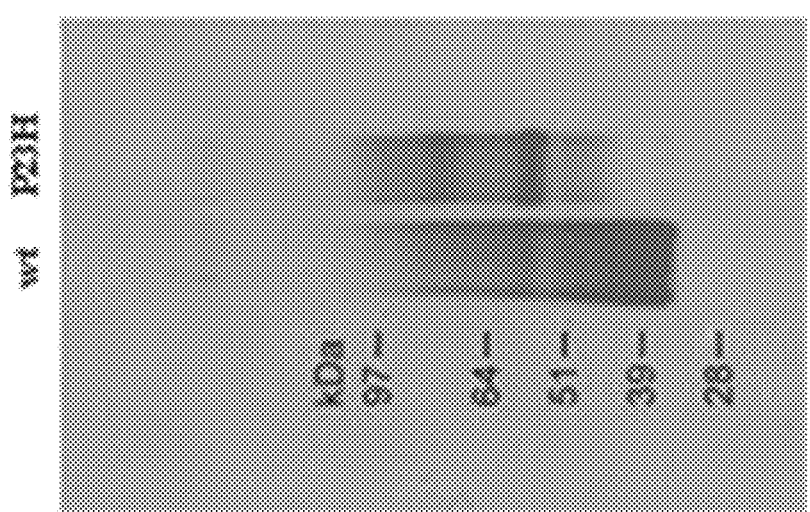

Aggregation of rhodopsin was assessed by SDS-PAGE immunoblot analysis of detergent soluble extracts from RPE cells transiently expressing wild type or P23H mutant protein (FIG. 2A). Wild-type rhodopsin migrated predominantly as a diffuse band at a molecular mass of ~40 kDa. This species corresponds to monomeric, mature rhodopsin containing N-linked glycans. The mobility of P23H mutant rhodopsin differed markedly from wild-type rhodopsin, with the majority of P23H migrating as higher-weight dimers and oligomers (FIG. 2A). P23H was also sensitive to Endoglycosidase H—note that treatment with Endoglycosidase H affects the migration of P23H rhodopsin, but not wild-type, as shown in FIG. 2B. Endoglycosidase H is specific for core glycosylated, high mannose N-linked oligosaccharide structures typical of proteins that have not matured beyond the ER.

Together, these data suggest that in RPE cells wild type rhodopsin is able to fold and mature beyond the ER, whereas the P23H mutant is more prone to forming non-native oligomers and is retained within the ER, perhaps due to an inability to fold productively.

Figures 3A, 3B:
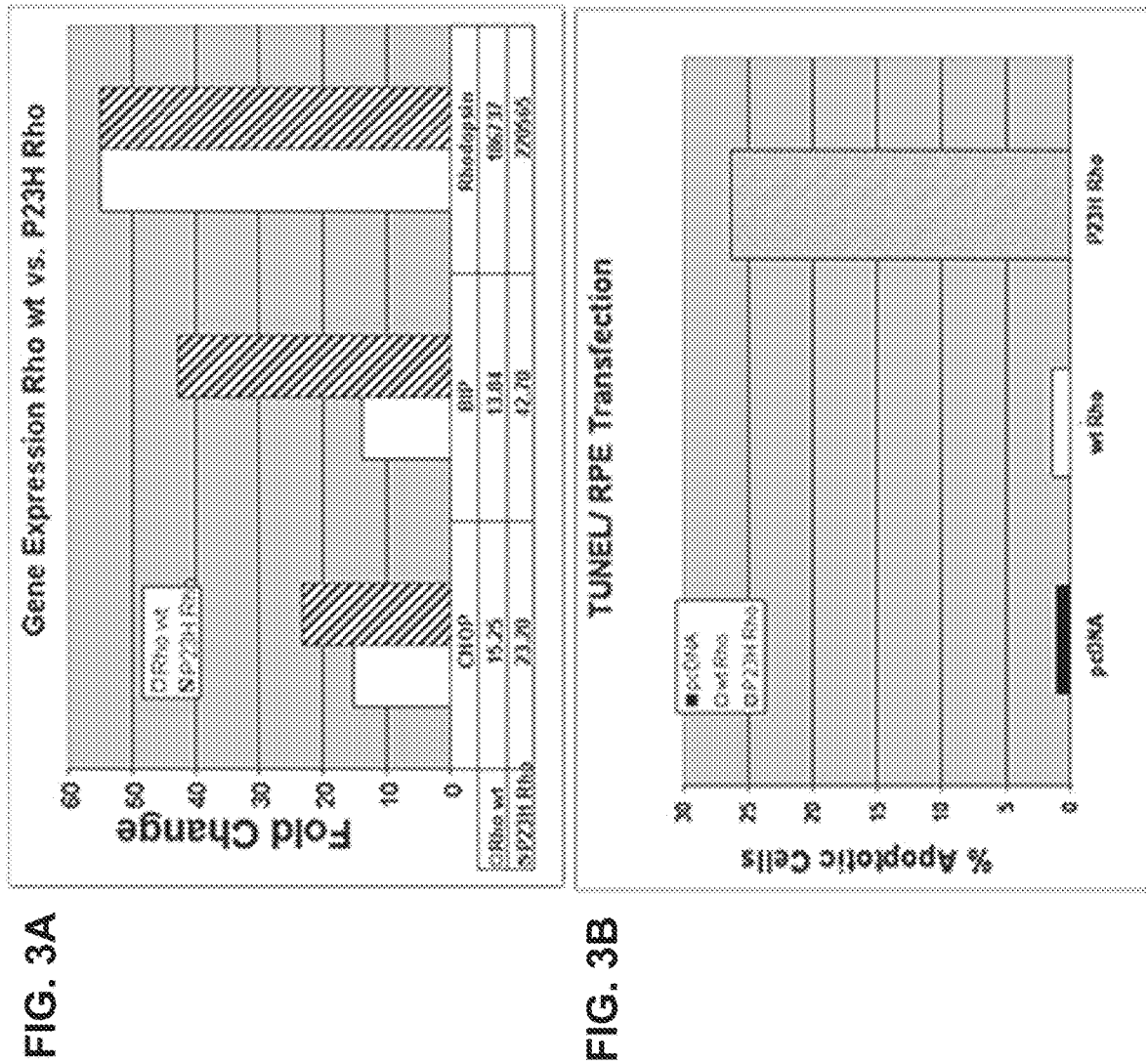
FIGS. 3A & 3B show that cells expressing P23H rhodopsin have higher expression of UPR markers and a higher propensity toward apoptosis.

Next, P23H rhodopsin's ability to induce ER stress in transfected RPE cells was assessed by measuring the levels of two markers of the UPR, BiP and CHOP. Increased BiP mRNA levels were detected in cells transiently expressing both WT and P23H rhodopsin (FIG. 3A), suggesting that increasing the folding load of the ER per se induced the UPR. However, BiP mRNA expression was significantly higher in cells expressing P23H rhodopsin (43-fold over untransfected cells) as compared with cells expressing WT rhodopsin (14-fold over untransfected cells) (FIG. 3A). The rhodopsin mRNA levels were identical in cells expressing WT or mutant forms of the protein (FIG. 3A). Thus, P23H rhodopsin is a more potent inducer of BiP than WT rhodopsin. Without wishing to be bound to theory, this discrepancy may be due to the folding defect of the mutant protein.

CHOP expression was examined next. Cells expressing the WT rhodopsin protein showed a 15-fold induction of CHOP compared to untransfected cells, while cells expressing P23H mutant showed an even greater 23-fold induction (FIG. 3A). As CHOP is a UPR-induced transcription factor that mediates apoptosis (Lee, E. S., et al. (2007) *FEBS Lett.* 581(22):4325-32), the relative levels of apoptosis between WT and P23H mutant expressing cells was measured. In agreement with the mRNA levels of CHOP, TUNEL assay results further suggested that RPE cells transiently expressing the P23H mutant are more prone to apoptosis than those expressing the wild type rhodopsin (FIG. 3B).

Example 2: Modulation of miR-708 Levels Regulates Rhodopsin Expression and the UPR in HEK-293 Cells A consensus sequence corresponding to a putative miR-708 target site has been found in the 3' UTR of several mammalian rhodopsin genes (Behrman, S., et al. (2011) *J. Cell Biol.* 192(6):919-27). This Example demonstrates that miR-708 regulation of rhodopsin may be used as a tool to modulate rhodopsin expression in cultured cells.

Figure 5:
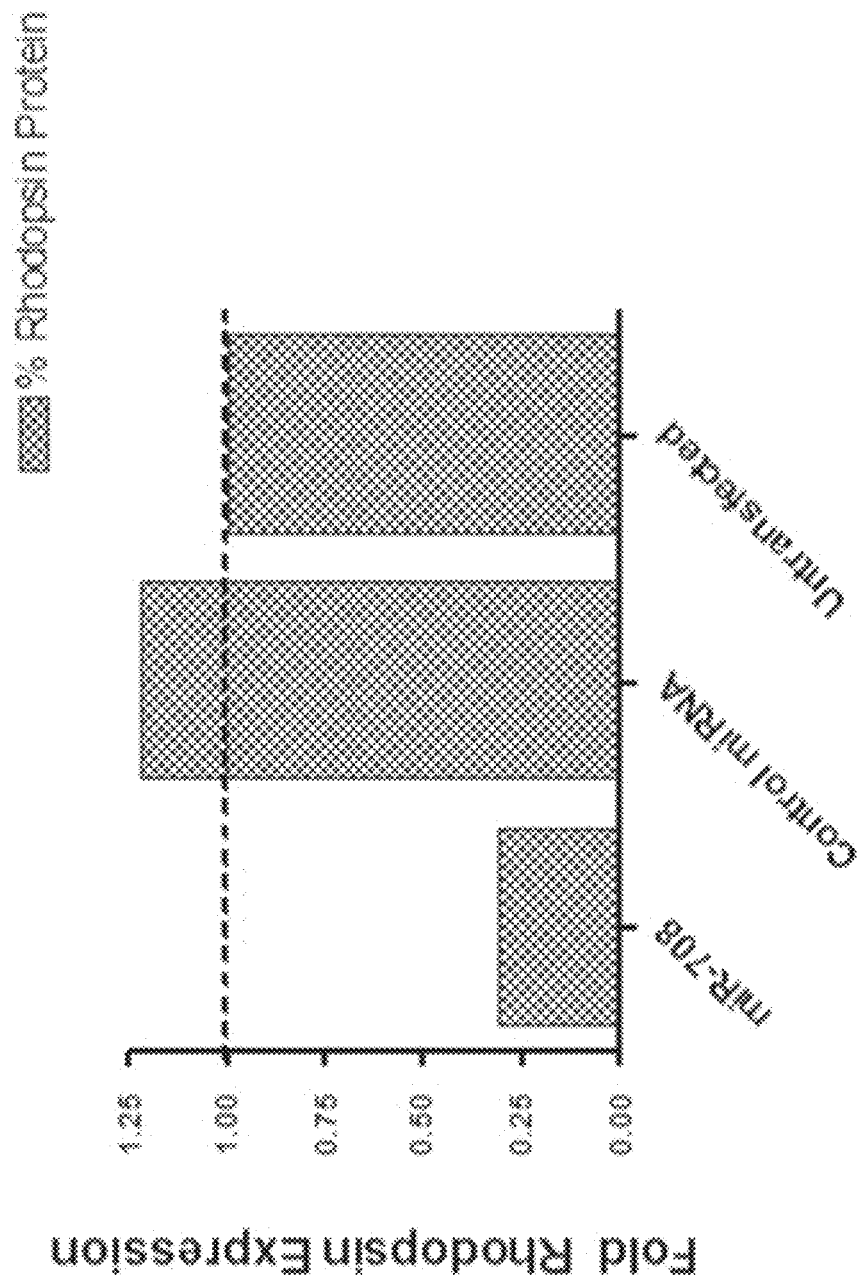
FIG. 5 shows the expression of rhodopsin protein in cells expressing miR-708 or a control miRNA, relative to untransfected cells. All cells are HEK-293 cells expressing mP23H rhodopsin which has a 3'UTR miR708 target sequence. Rhodopsin protein expression is normalized to hGAPDH expression. Rhodopsin protein levels are decreased in the presence of miR708 compared to control miR.

HEK-293 cells expressing a P23H mutant mRhodopsin gene encoding a 3'UTR miR-708 target sequence were transfected with a plasmid expressing miR-708 or miR-Control as depicted in FIG. 4. After 72 hrs, the cells were collected, and mP23H Rhodopsin protein expression was analyzed using a Western blot (FIG. 5). P23H mRhodopsin protein expression was reduced to ~30% in cells transfected with CBA-miR-708, compared to cells transfected with a CBA-miR-Control vector.

Figure 6:
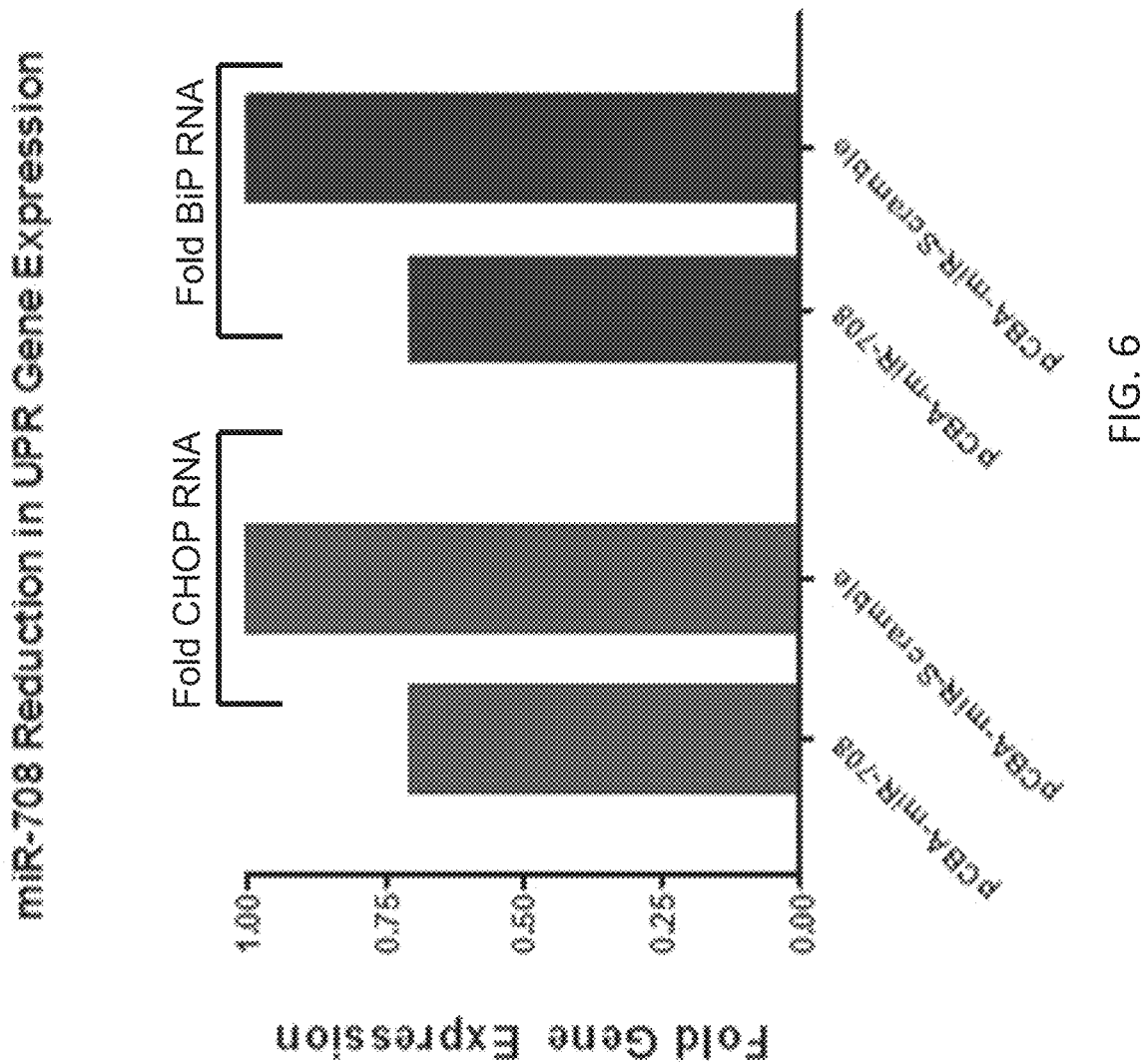
FIG. 6 shows that HEK-293 cells expressing mP23H rhodopsin have reduced RNA levels of the UPR marker genes CHOP and BiP upon expression of miR-708, compared to cells expressing a control miRNA ("Scramble").

Expression of UPR target genes (CHOP/BIP) was also analyzed by TaqMan® gene expression analysis. HEK-293 cells expressing miR-708 also showed reduced expression of CHOP and BiP RNA compared to control cells (FIG. 6). These results suggest that reducing the level of misfolded P23H mRhodopsin results in a concomitant reduction in expression of UPR genes BiP and CHOP.

Figures 7A, 7B:
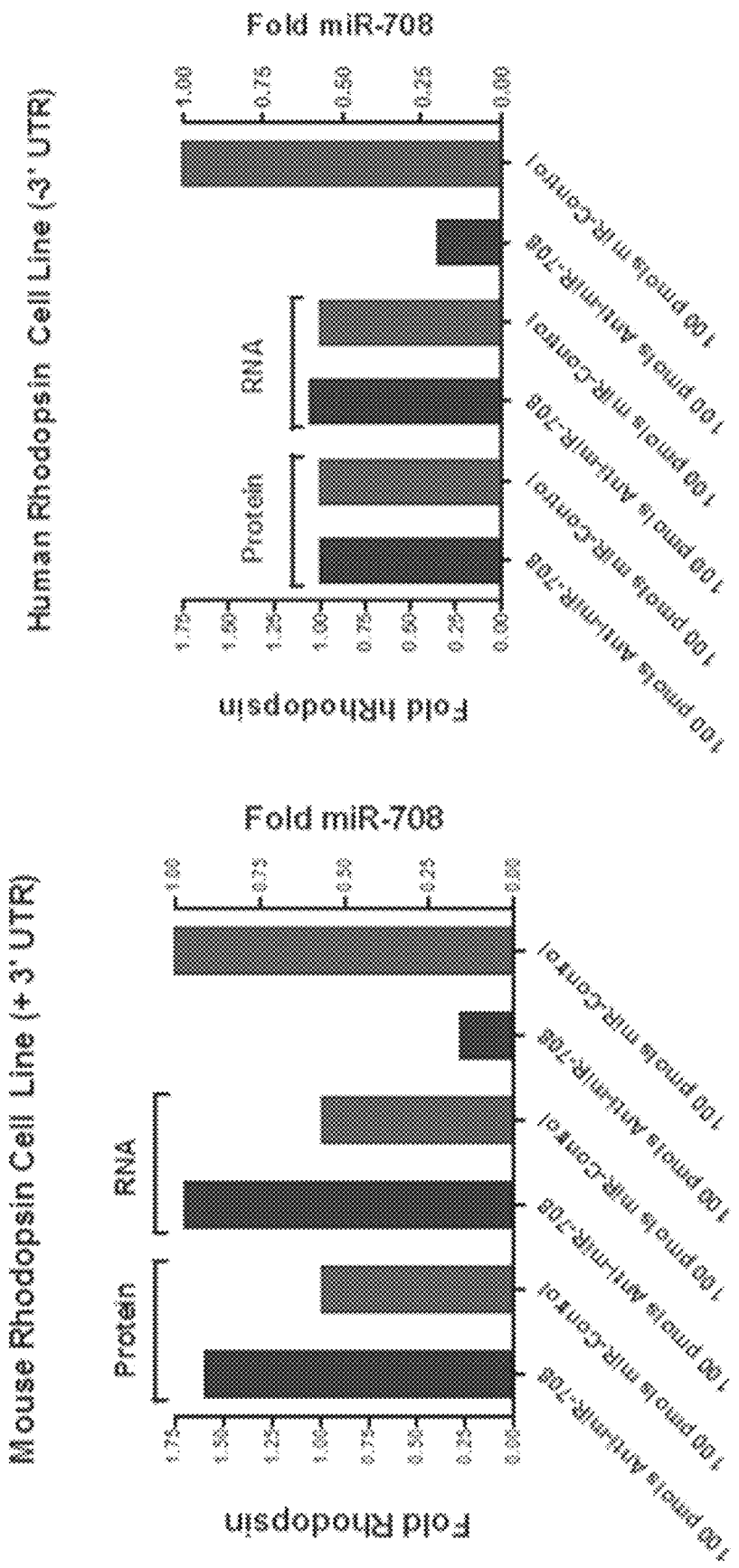
FIGS. 7A & 7B show that down-regulation of rhodopsin by endogenous miR-708 is dependent upon the presence of a miR-708 target sequence in the rhodopsin 3' UTR. HEK-293 cells were transfected with a mouse P23H rhodopsin gene containing the miR-708 target sequence (FIG. 7A), or with a human P23H rhodopsin gene lacking the miR-708 target sequence (FIG. 7B). Cells were also transfected with a control pre-miRNA or an anti-miR-708 pre-miRNA to inhibit endogenous miR-708. Rhodopsin protein was measured relative to hGAPDH protein, and rhodopsin mRNA was measured relative to hGAPDH mRNA. Levels of endogenous miR-708 are also shown (right axis and rightmost two columns in FIGS. 7A & 7B).

In the converse experiment, HEK-293 cells expressing either mouse P23H Rhodopsin (including a 3' UTR miR-708 target sequence) or human P23H Rhodopsin (lacking the 3' UTR miR-708 target sequence) were transfected with anti-miR-708 pre-miRNA or negative control pre-miRNA (FIG. 7). In this experiment, exogenous anti-miR-708 was used to inhibit endogenous HEK293 miR-708. If endogenous miR-708 regulated rhodopsin expression through the putative miR-708 target sequence, then changes in levels of the P23H rhodopsin would be observed only if there was a miR-708 target sequence in the 3' UTR of the rhodopsin gene. Cells were transfected with 100 pmol of each RNA. Cell lysates were generated, and rhodopsin protein was quantified on a Western blot while mRNA levels were analyzed by TaqMan® analysis (FIG. 7). Inhibition of endogenous miR-708 resulted in an increase of both mouse Rhodopsin mRNA and protein (FIG. 7A), whereas the levels of both human rhodopsin mRNA and protein remained unaffected (FIG. 7B), despite lower levels of endogenous miR-708. These results demonstrate that the regulation of rhodopsin by miR-708 requires the miR-708 target sequence in the rhodopsin 3' UTR.

Together, these results show that rhodopsin is a functional target of miR-708, and that modulation of miR-708 activity may be used as a tool to affect rhodopsin expression.

Example 3: Design of an AAV ITR Plasmid Expressing miR-708 Under the Control of the Photoreceptor-Specific Rhodopsin Kinase Promoter It is thought that buildup of mutant rhodopsin protein in the ER contributes to the ER stress underlying photoreceptor cell death in RP. The previous Example demonstrates that miR-708 expression is able to regulate overall rhodopsin levels. An adeno-associated virus (AAV)-based vector was constructed for specific expression of miR-708 in the photoreceptor cells of the retina to determine if lowering total rhodopsin levels (including wild-type and mutant forms) may alleviate ER stress independent of the rhodopsin mutation.

Figure 8:
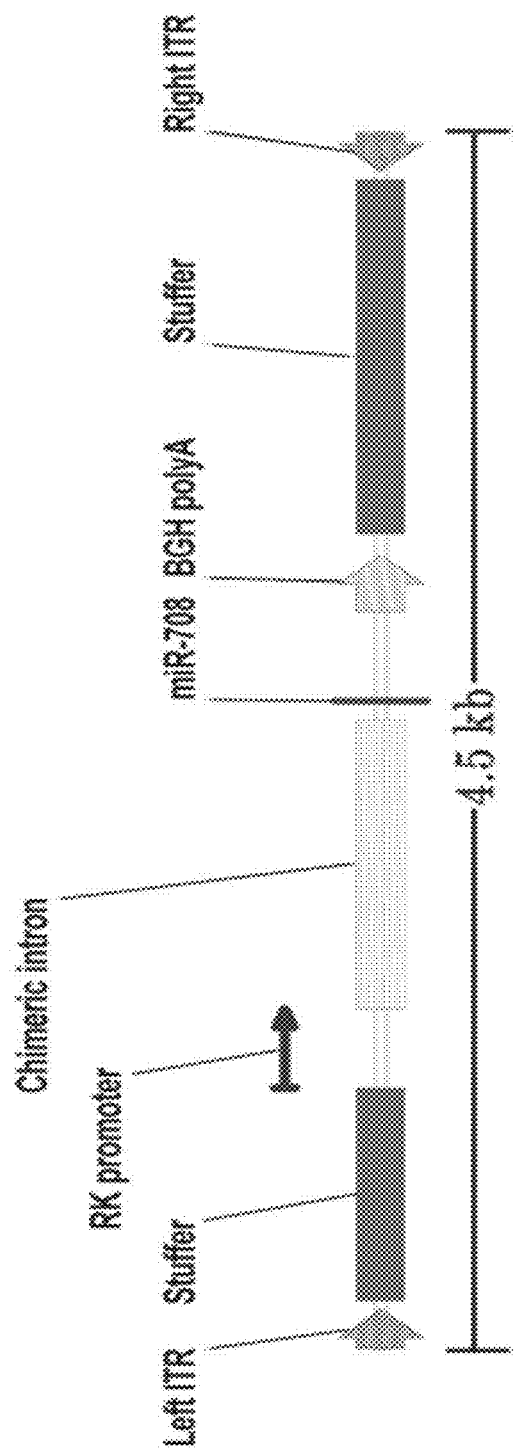
FIG. 8 depicts a diagram of an AAV vector for expressing miR-708 in rod photoreceptors. Relevant vector features are labeled.

FIG. 8 depicts an AAV inverted terminal repeat (ITR) plasmid designed to express miR-708 specifically in retinal photoreceptor cells. miR-708 expression was driven by the rhodopsin kinase promoter (pRK), which is specifically expressed in rod photoreceptor cells. In this vector, miR-708 was expressed from the miR-155 scaffold shown in FIG. 4.

Figure 9A:
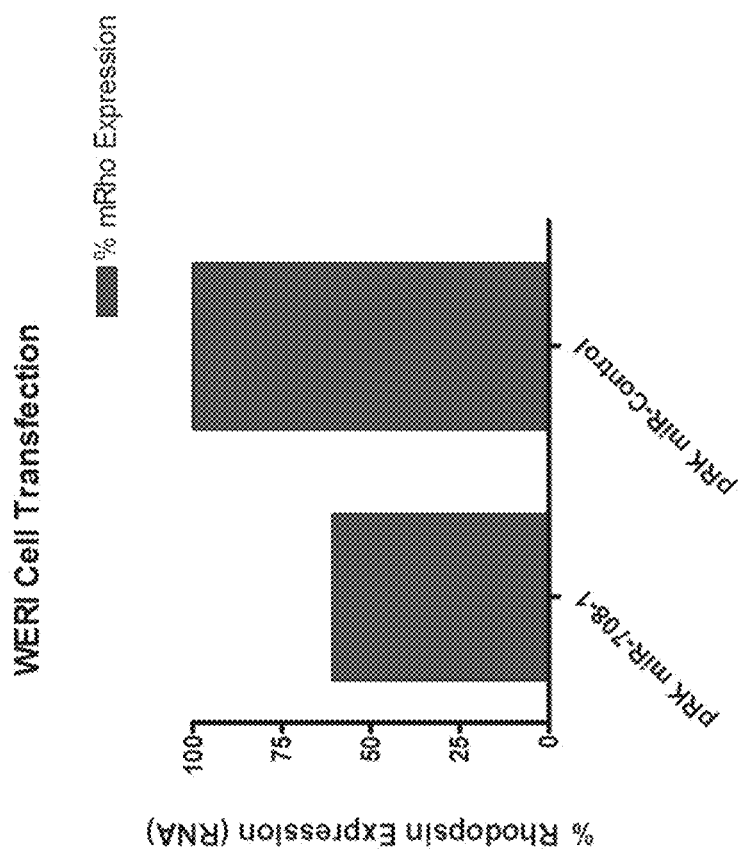
FIGS. 9A & 9B show that expression of miR-708 using an AAV vector down-regulates P23H mutant rhodopsin.

Next, this AAV ITR plasmid was validated in cultured cells. WERI or RPE cells were transfected with the pre-viral plasmid described in FIG. 8, and the levels of miR-708 were quantitated by TaqMan® analysis. FIG. 9A shows that WERI cells transfected with the pRK-driven miR-708 plasmid had over a 2000-fold increase in miR-708 levels compared to WERI cells transfected with a plasmid expressing miR-Scramble (control). In contrast, RPE cells, in which the RK promoter is not significantly expressed, did not show a significant increase in miR-708 levels (FIG. 9A).

Figure 9B:
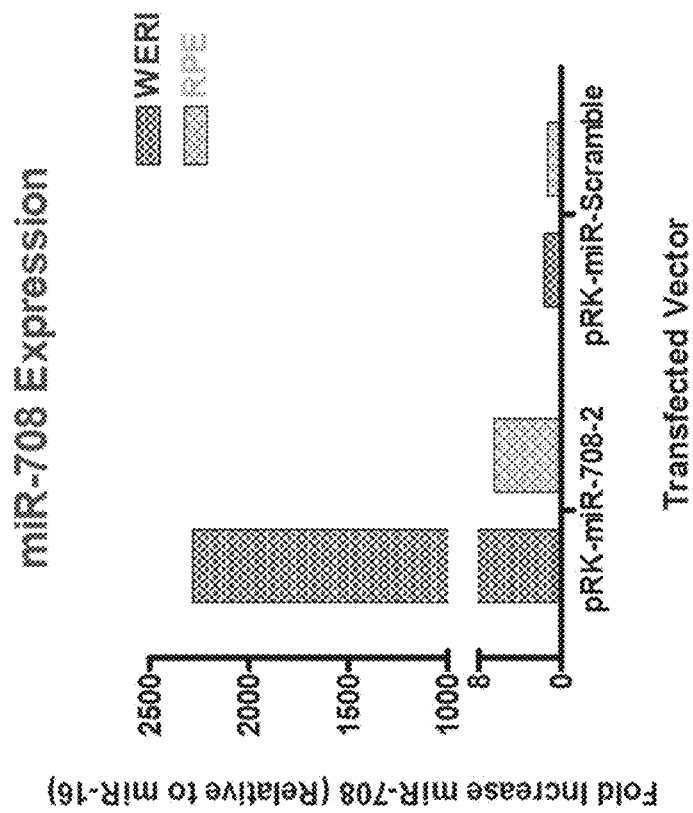

The function of miR-708 in regulating rhodopsin expression was confirmed by co-transfecting the pRK-miR-708 plasmid (or a miR-Control plasmid) and a plasmid with the P23H mouse rhodopsin gene harboring a 3'miR708 target sequence into WERI cells. FIG. 9B shows that the P23H mRhodopsin mRNA was reduced in the presence of the miR-708, compared to a miR-Control. These results demonstrate that expression of miR-708 using an AAV ITR vector is effective in reducing the expression of rhodopsin in photoreceptor cells.

Example 4: Knockdown of Rhodopsin in Mouse Retinas Using a miR-708 AAV5 Vector

To test whether an AAV vector could be used to reduce rhodopsin expression in the retina in vivo, the pRK-miR-708 plasmid described in FIG. 8 was packaged into an AAV5 capsid to generate AAV5-RK miR-708. In addition, an AAV5 miR-Control vector was generated. Wild-type C57bl mice received a subretinal injection of $1 \times 10^8$ vgs of AAV5-RK miR-708 or AAV5 miR-Control in the contralateral eye. At 1 month post-injection, the mice were euthanized, and the neuro retina was extracted and flash-frozen for qPCR analysis of gene expression.

FIG. 10A shows that mouse eyes that had been injected with an AAV5 vector expressing miR-708 had reduced rhodopsin expression, compared to mouse eyes injected with an AAV5 miR-Control vector. In contrast, the expression of another rod-specific gene, Rod Derived Cone Viability Factor (RdCVF), was not affected (FIG. 10B). FIG. 10C confirms that eyes injected with AAV5miR708 vector showed a significant increase in miR-708 copy number, compared to eyes that received AAV5miR control. These results suggest that AAV-based vectors expressing miR-708 in rod photoreceptors are effective in reducing endogenous rhodopsin expression in vivo.

Figure 11A:
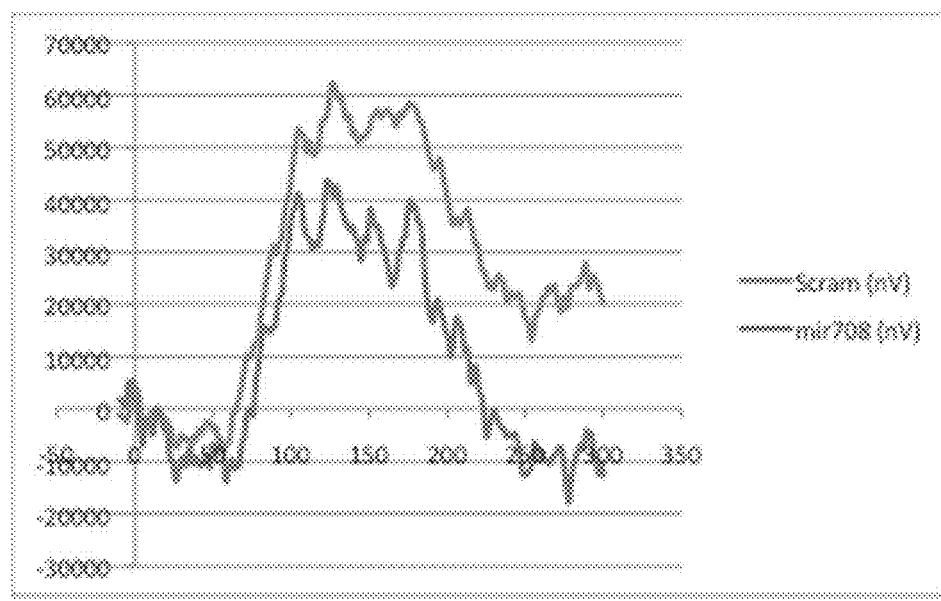
FIGS. 11A & 11B show that treatment of eyes with AAV5 miR-708 reduces rod-mediated, but not cone-mediated, responses.
Figure 11A:
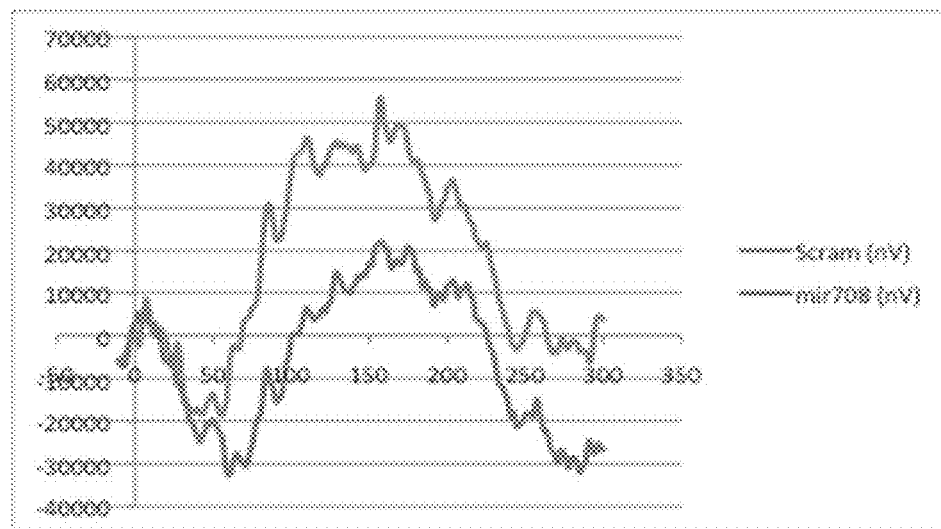
Figure 11A:
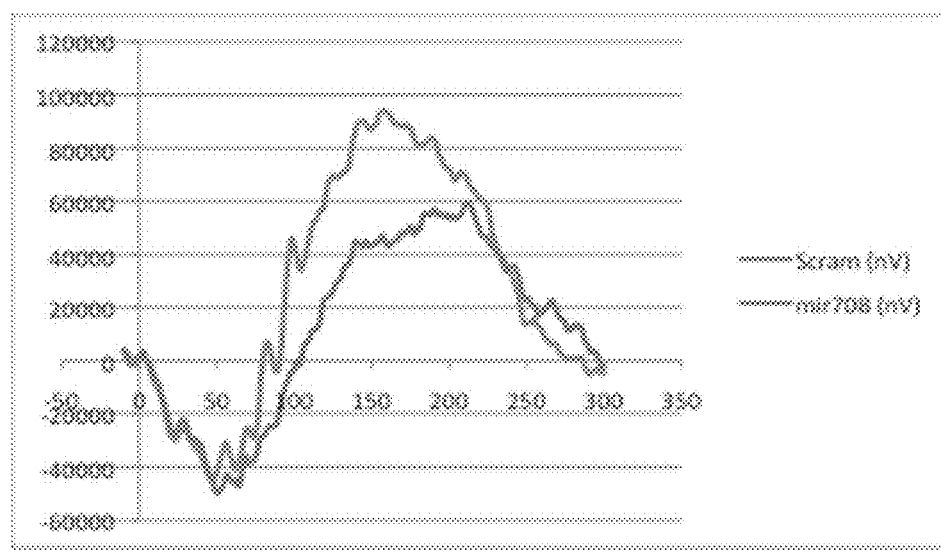
Figure 11B:
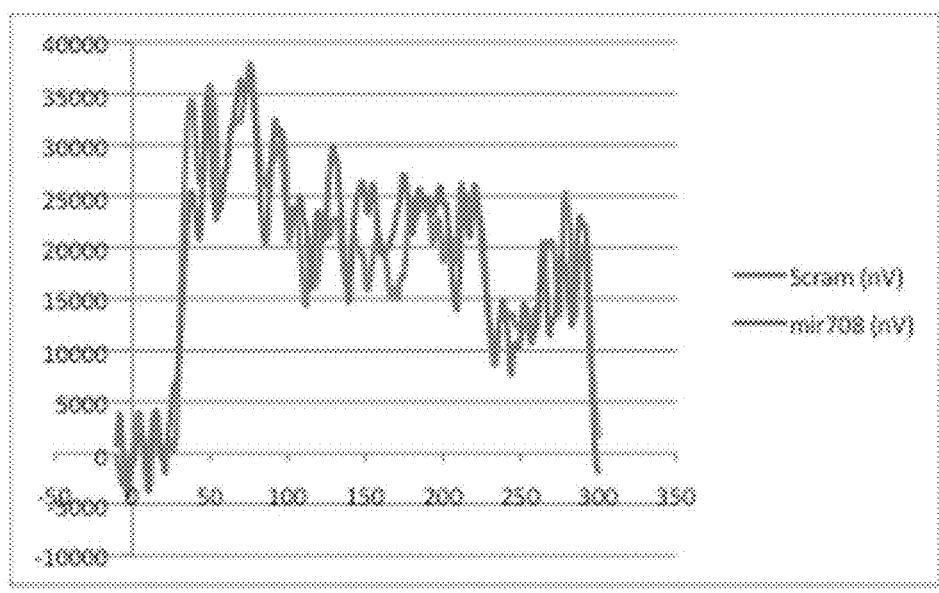
Figure 11B:
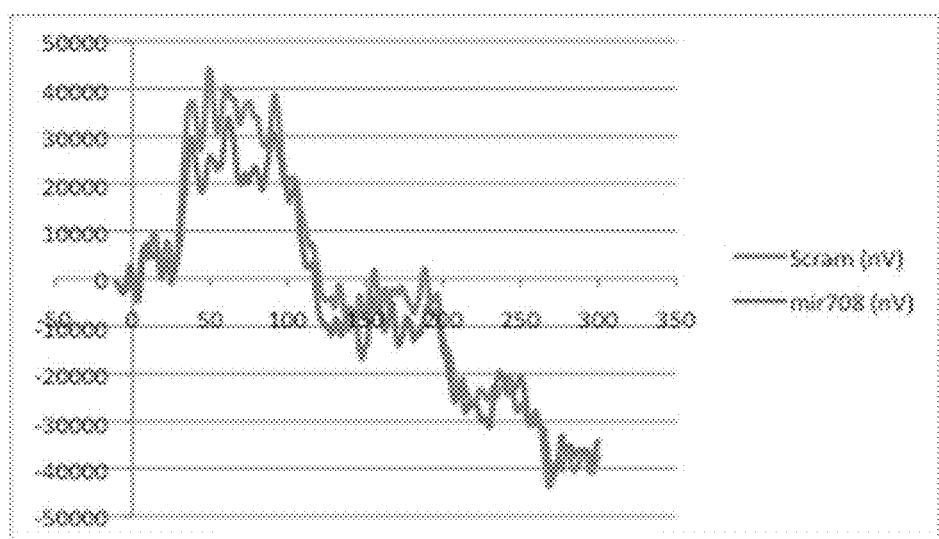
Figure 11B:
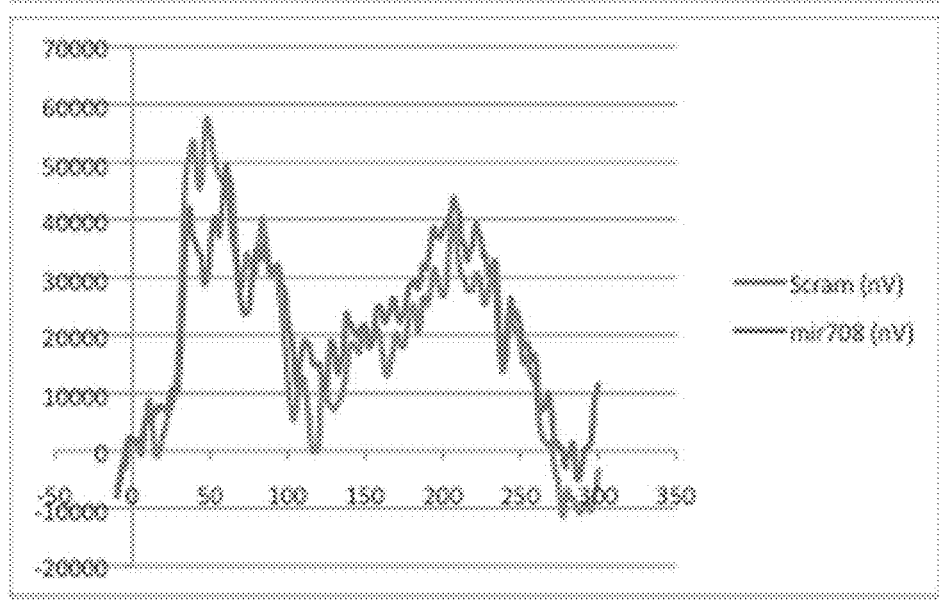

To demonstrate the functional relevance of rhodopsin knockdown, mouse eyes treated with AAV5 miR-708 or AAV5 miR-Control were analyzed by electroretinogram (ERG) to assess retinal function. Eyes that received the AAV5 miR-708 vector showed a decreased scotopic response, as expected if levels of rhodopsin are reduced (FIG. 11A). Scotopic ERG responses are an assessment of rod function, and this measurement can be correlated to rhodopsin levels. However, cone function in the same animals, as assessed by photopic ERG, was unchanged following AAV5 miR-708 delivery (FIG. 11B), confirming that miR-708 had a biological effect on rod photoreceptor cells while sparing the cone cells. These data demonstrate that AAV5 miR-708 delivery results in a biological effect that is restricted to the rod target cell.

Example 5: Construction of a hRhodopsin Suppression/Replacement Vector with an Intron-Embedded miR-708 Expression Cassette miR-708 is normally expressed in vivo from the first intron in the ODZ4 gene. Therefore, a novel construct was designed based on the sequence of miR-708 and its endogenous scaffold/flanking sequence. The miR-708 sequence was embedded into a synthetic intron and cloned downstream of the photoreceptor specific promoter Rhodopsin Kinase (RK), but upstream of the hRhodopsin cDNA. The endogenous miR-708 sequence including its flanking regulatory and processing sequences were cloned into the β-globin intron sequence upstream of the hRhodopsin cDNA sequence but downstream of the RK promoter. As such, the miR-708 sequence is 5' relative to the rhodopsin coding sequence.

Figure 12:
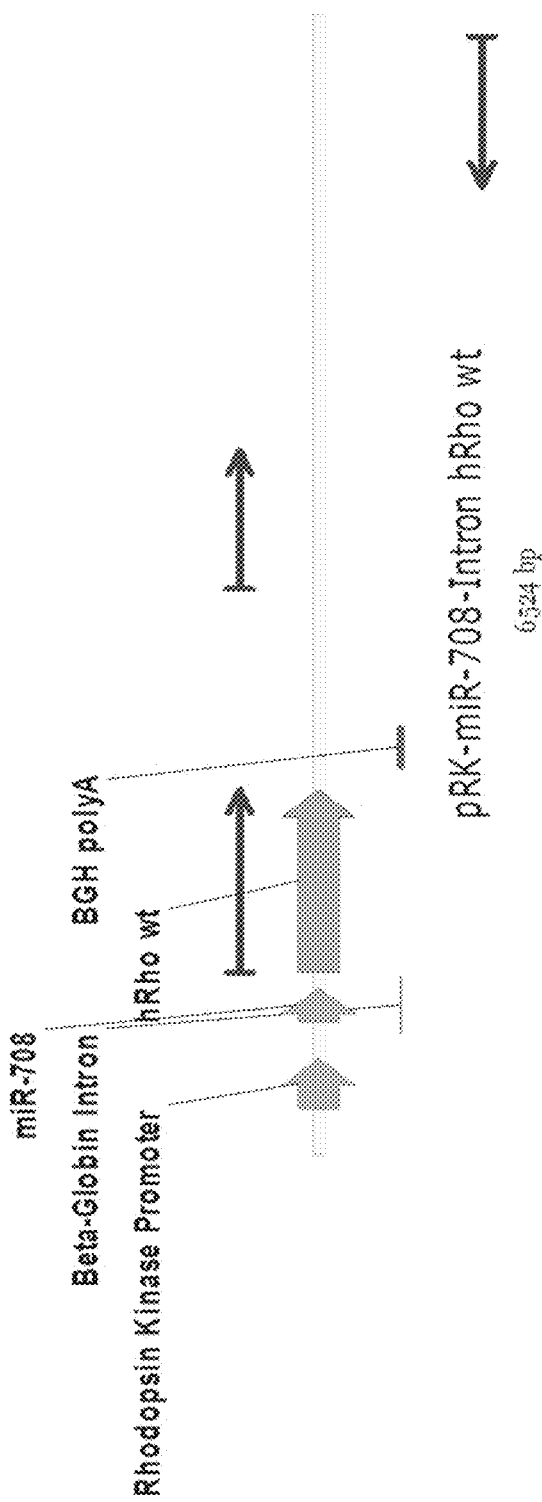
FIG. 12 provides a diagram of the miR-708 intron-embedded hRhodopsin suppression/replacement vector.

FIG. 12 provides a diagram of this 5' suppression/replacement vector. hRhodopsin (lacking a 3' UTR mir708 target sequence) was controlled by the RK promoter. The endogenous miR-708 sequence including endogenous scaffold (e.g., including any Drosha/Dicer recognition motifs) was embedded within the β-globin intron. hRhodopsin cDNA (with no 3' miR-708 UTR target sequence) was included downstream of the splice junction site. miR-708 was embedded within the β-globin, which is located downstream of the RK promoter, and therefore the miR-708 was processed after splicing of the β-globin intronic sequence. In addition vector with a similar structure harboring a control miR was generated.

The vector described in FIG. 12, or a vector with a control miRNA, was used to transfect WERI cells. WERI cells were used because they express little, if any, endogenous miR-708, and they are permissive to the RK promoter. WERI cells were co-transfected with a cDNA encoding P23H mRhodopsin (with a 3'UTR miR-708 sequence). Both rhodopsin knockdown (RNA levels) and levels of the UPR genes CHOP and BIP were examined in transfected cells.

Figure 13:
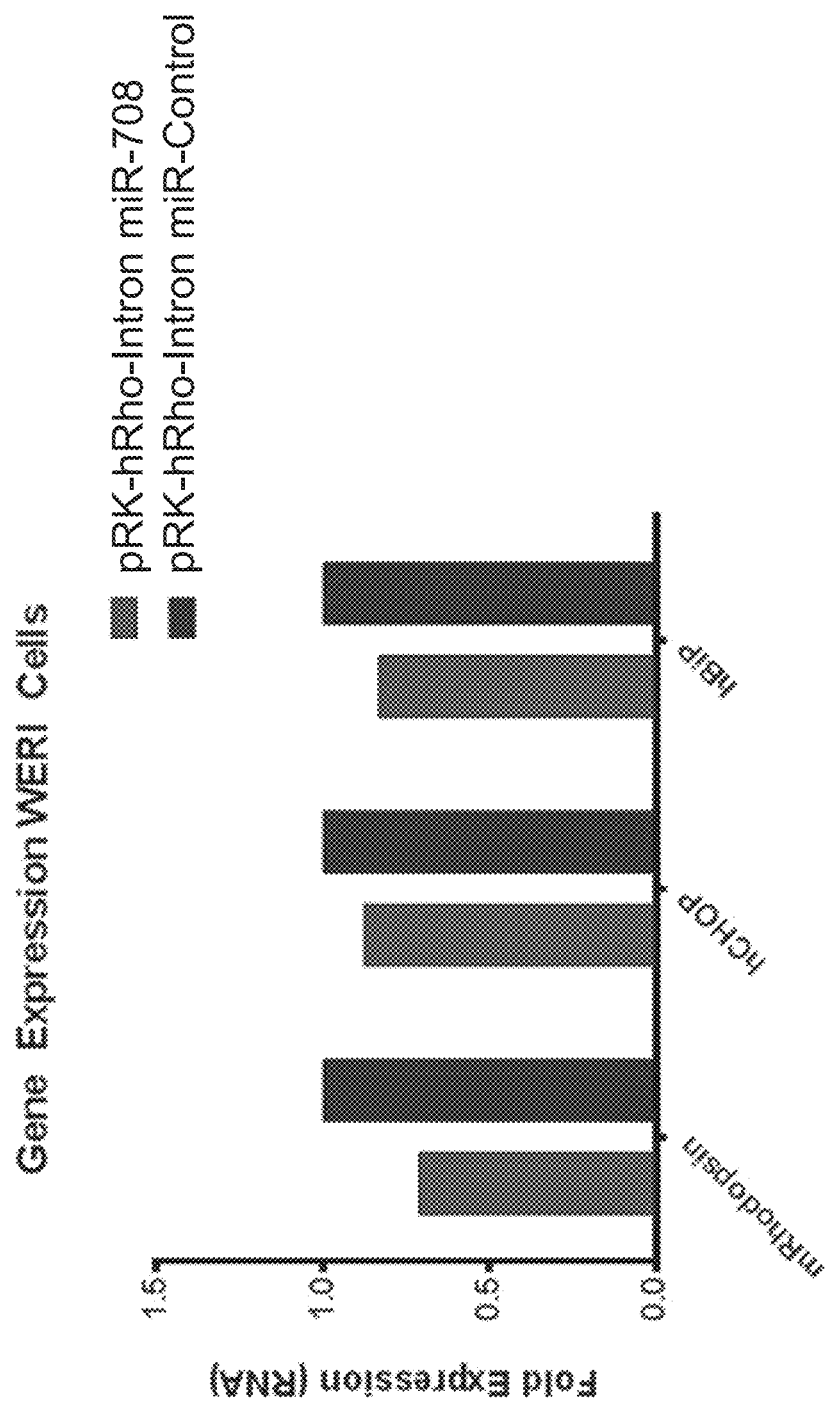
FIG. 13 shows that an intron-embedded miR-708 vector reduces expression of mRhodopsin, hCHOP, and hBiP in WERI cells transfected with P23H mRhodopsin, as compared to a miR-Control vector.

FIG. 13 shows that cells co-transfected with mRhodopsin (P23H) and the miR-708 vector had reduced mRhodopsin levels compared to cells co-transfected with mRhodopsin and control miRNA vector. Additionally, the UPR genes CHOP and BiP were also down regulated in the miR-708 transfected cells compared to control. This data suggests that using the endogenous miR708 scaffold with intronic expression of miR708 provides an alternative scaffold that supports miR708 processing and expression.

Example 6: Comparison of Different miR-708 Scaffolds

Lower levels of miR-708 expression may be beneficial in reducing any potential off-target effects of the miRNA in a clinical setting. Therefore, different miR scaffolds were tested for strength of expression in the WERI human retinoblastoma cell line.

Figure 14:
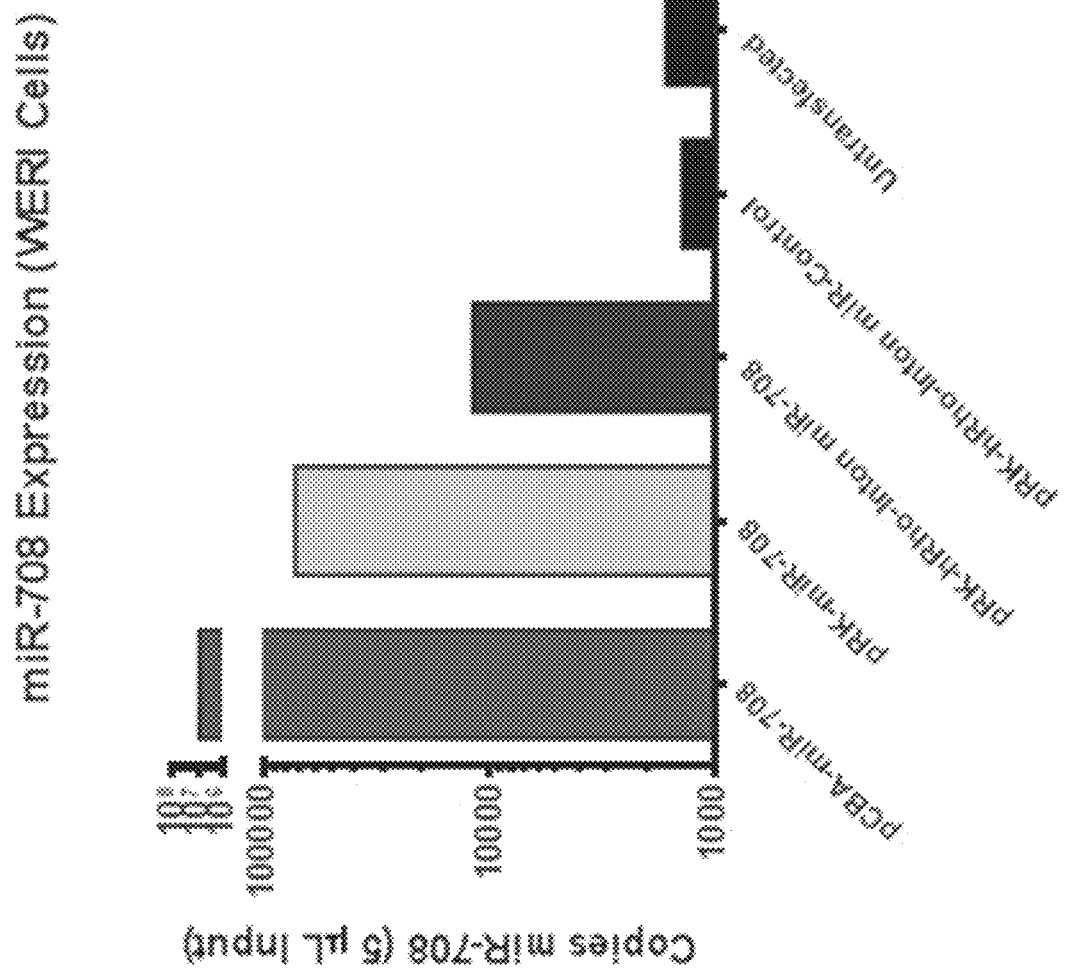
FIG. 14 shows that miR-708 expression from the intron-embedded vector has reduced expression compared to the non-embedded vector in WERI cells, the caveat being that the intron-embedded vector pRK-hRHO-intron miR-708 also co-expresses hRhodopsin. All vectors driving miR-708 expression using the RK promoter had orders of magnitude lower expression than a vector using the CBA promoter.

FIG. 14 depicts quantified miR-708 levels in WERI cells transfected with CBA-driven miR-708, RK-driven miR708 using the miR-155 scaffold shown in FIG. 4, or the RK intron-embedded miR-708 hRhodopsin vector shown in FIG. 12. miR-708 expression in the RK intronic system was not as robust as the CBA driven system. However, miR-708 expression was still well above background and about 5 fold lower than pRKmiR708 using the miR-155 scaffold. Note that hRhodopsin was co-expressed from the intron-embedded vectors, but not in the CBA or RK miR-155 scaffold vectors.

Figure 15:
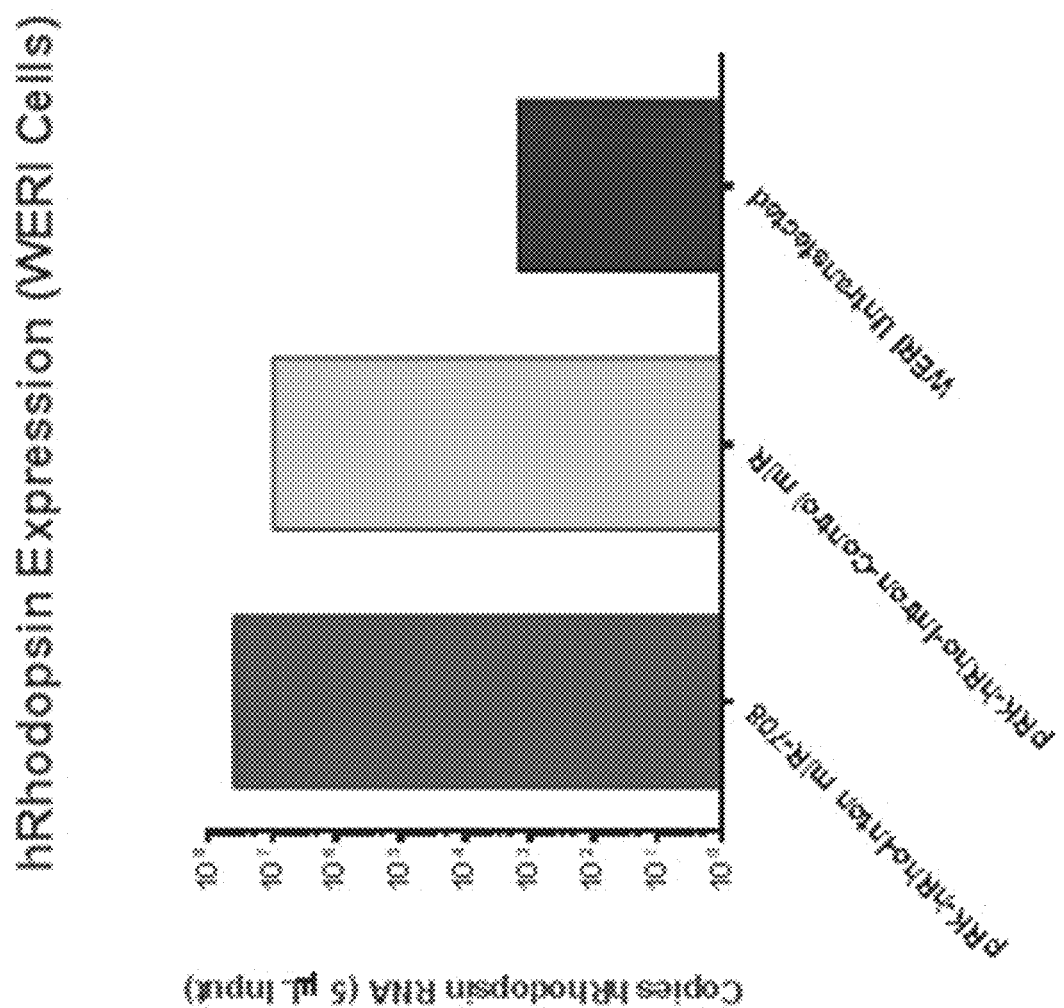
FIG. 15 shows that hRhodopsin expression from the intron-embedded suppression/replacement vector is refractory to knockdown by co-expressed miR-708. The levels of hRhodopsin RNA are the same in cells transfected with vectors expressing miR-708 or miR-Control.

Next, the levels of hRhodopsin mRNA were compared in WERI cells expressing the miR-708 intron-embedded, suppression/replacement vector or a miR-Control vector. FIG. 15 shows that WERI cells transfected with the miR-708 intron-embedded, suppression/replacement vector had a similar level of hRhodopsin compared to cells transfected with the control vector. These results indicate that hRhodopsin expression from the suppression/replacement vector, which lacks the 3' UTR miR-708 target sequence, is refractory to inhibition by miR-708 expression. Both cells showed higher hRhodopsin expression than untransfected WERI cells.

Example 7: Knockdown of Mutant Rhodopsin by the miR-708 Suppression/Replacement Vector Reduces a Marker of ER Stress The ability of the miR-708 suppression/replacement vector to reduce ER stress in cells expressing mutant rhodopsin was examined. WERI cells expressing a non-glycosylated, P23H mutant rhodopsin (N2K/N15K/P23H), with or without a 3'UTR miR708 target sequence, were transfected with the suppression replacement vector described in FIG. 12. Cells were harvested and RNA extracted to measure X-box binding protein 1 (XBP-1) splicing. XBP-1 is a transcription factor important in regulating ER stress genes. Its splicing is a known marker of cellular ER stress/UPR; cells undergoing UPR show increased levels of spliced XBP-1.

Figure 16:
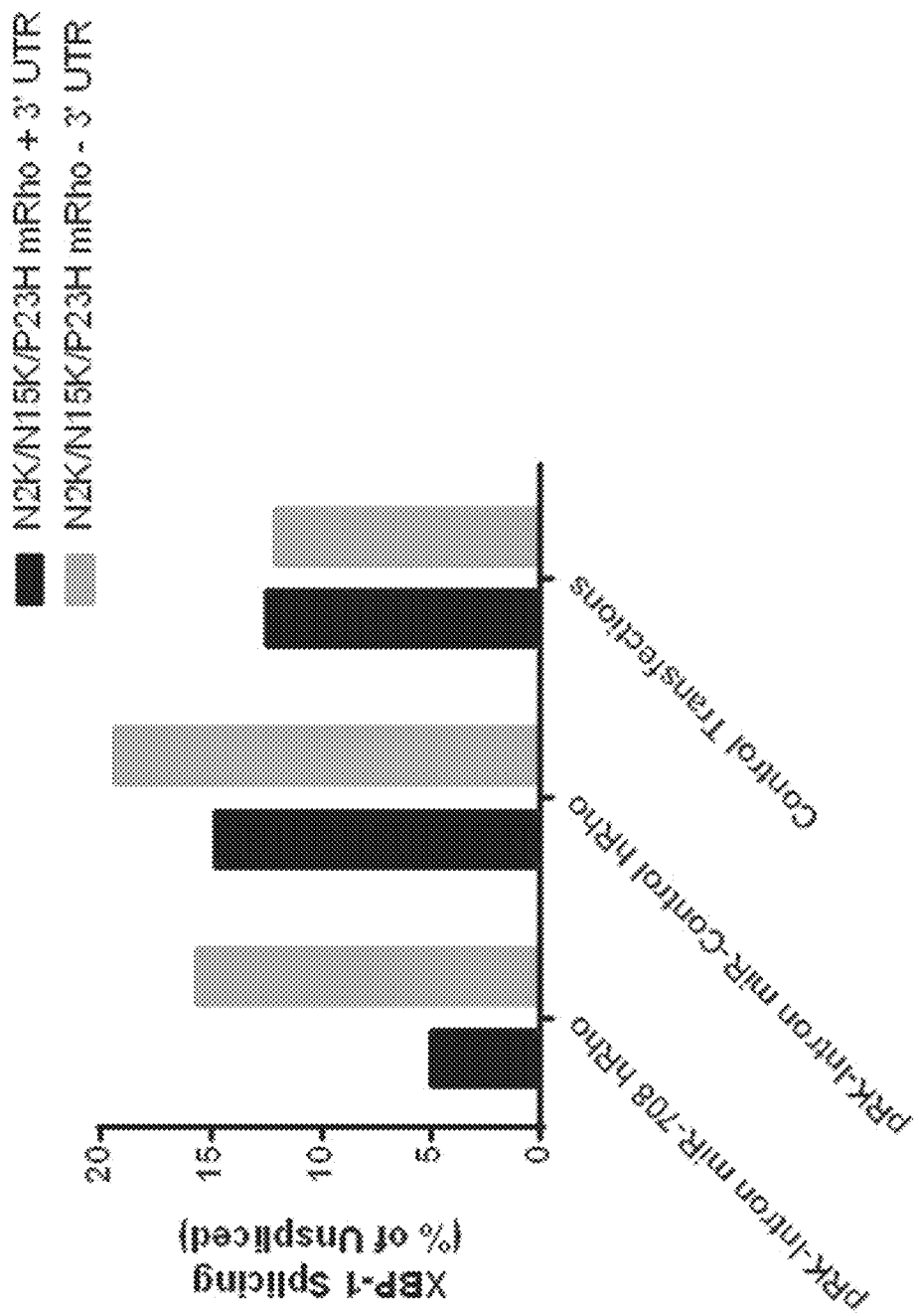
FIG. 16 shows that the miR-708 suppression/replacement vector reduces XBP-1 splicing, a marker of ER stress, in WERI cells expressing mutant rhodopsin. This reduction is observed only if the 3'UTR miR-708 target sequence is present in the rhodopsin transcript.

As shown in FIG. 16, cells expressing mutant Rhodopsin with a 3' UTR target sequence had decreased XBP-1 splicing when transfected with the miR-708 suppression/replacement vector. In contrast, cells expressing the mutant P23H Rhodopsin lacking the 3'UTR miR-708 target sequence had equivalent levels of XBP-1 splicing compared to cells transfected with the miR-Control sequence. These results demonstrate that knockdown of mutant rhodopsin using the miR-708 suppression/replacement vector is effective in reducing ER stress.

Example 8: Expression of miR-708 in the β-Globin Intron Scaffold Placed in the Rhodopsin 3' UTR Increases the Expression of Rhodopsin and miR-708

Figure 17:
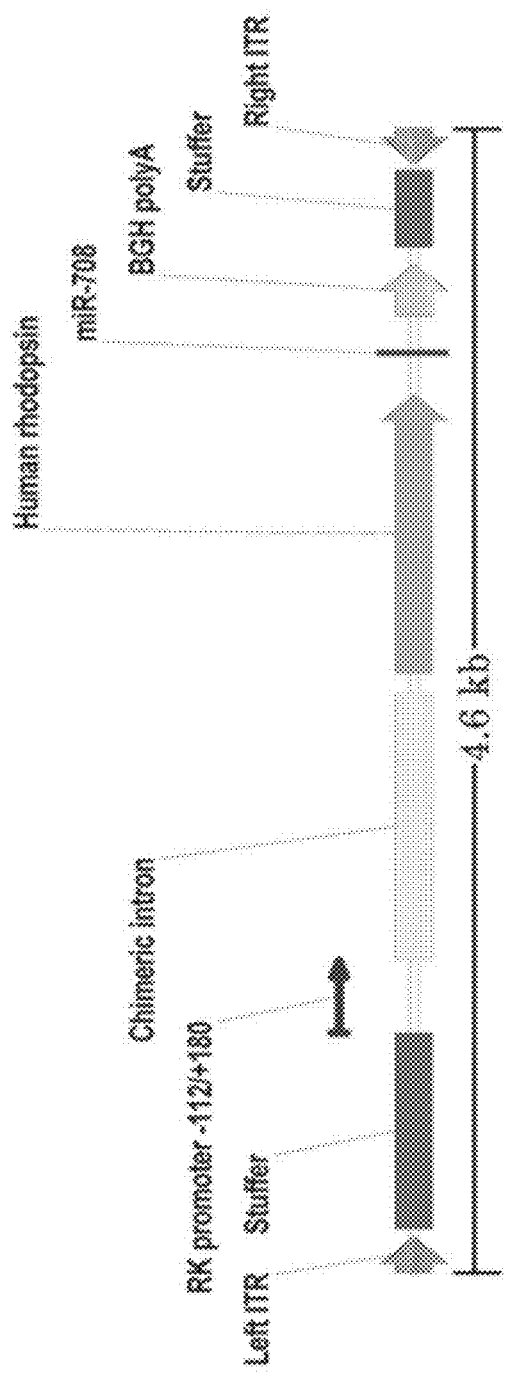
FIG. 17 shows a diagram of a vector with the miR-708 human β-globin intron scaffold in the 3' UTR of the rhodopsin cDNA.

In order to test whether the position of the miR-708 scaffold affects its expression, a vector was constructed where the miR-708 sequence (including its flanking regulatory/processing sequences) was cloned into the β-globin intron sequence downstream of the Rhodopsin cDNA, i.e., within the 3' UTR. FIG. 17 shows a diagram of this 3' suppression/replacement vector, which is similar to that shown in FIG. 12, except that the miR-708 human β-globin intron scaffold is in the 3' UTR of the rhodopsin cDNA, rather than the 5' UTR.

Figure 18:
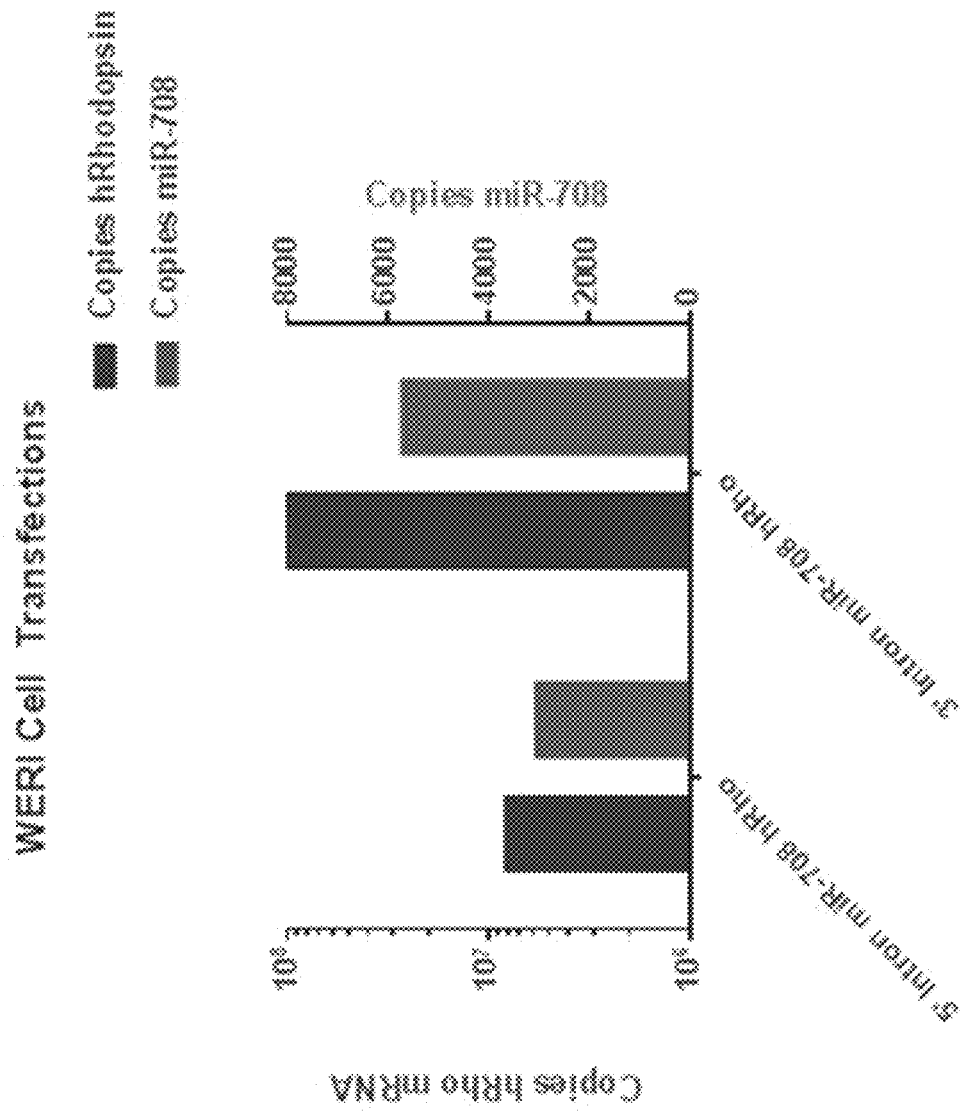
FIG. 18 shows that a vector with the miR-708 human β-globin intron scaffold in the 3' UTR of the rhodopsin cDNA produces higher hRhodopsin and miR-708 expression than a vector with the scaffold in the 5' UTR.

To determine if the position of the miR-708 human β-globin intron scaffold in the vector affected miR-708 or hRhodopsin expression from the vector, WERI cells were transfected with the 5' UTR vector of FIG. 12 or the 3' UTR vector of FIG. 17. FIG. 18 shows the expression of hRhodopsin and miR-708 in these cells. The vector with the miR-708 scaffold in the 3' UTR was found to produce higher levels of both hRhodopsin and miR-708 RNA than the vector using the 5' UTR configuration.

Example 9: Evaluation of the Suppression/Replacement Vector in a P23H Mouse Model of Retinal Degeneration Suppression/replacement constructs are evaluated in a P23H mouse model of retinal degeneration. In this model, the mutant P23H protein expressed in rod photoreceptor cells induces ER stress/UPR, causing apoptosis and ultimate rod cell death (Lee, E. S., et al. (2007) *FEBS Lett.* 581(22): 4325-32). Following rod cell death there is a non-cell-autonomous death of cone cells.

The P23H mouse is treated with a suppression/replacement AAV vector expressing miR-708 and a human rhodopsin gene refractory to knockdown by miR708 (because it lacks a miR-708 target sequence). The suppression/replacement vector results in knockdown of both WT and P23H mouse rhodopsin, but the replacement rhodopsin gene compensates for the reduction in WT levels of rhodopsin. Therefore, the vector provides the necessary rod rhodopsin to maintain rod cell function and integrity.

Figure 19:
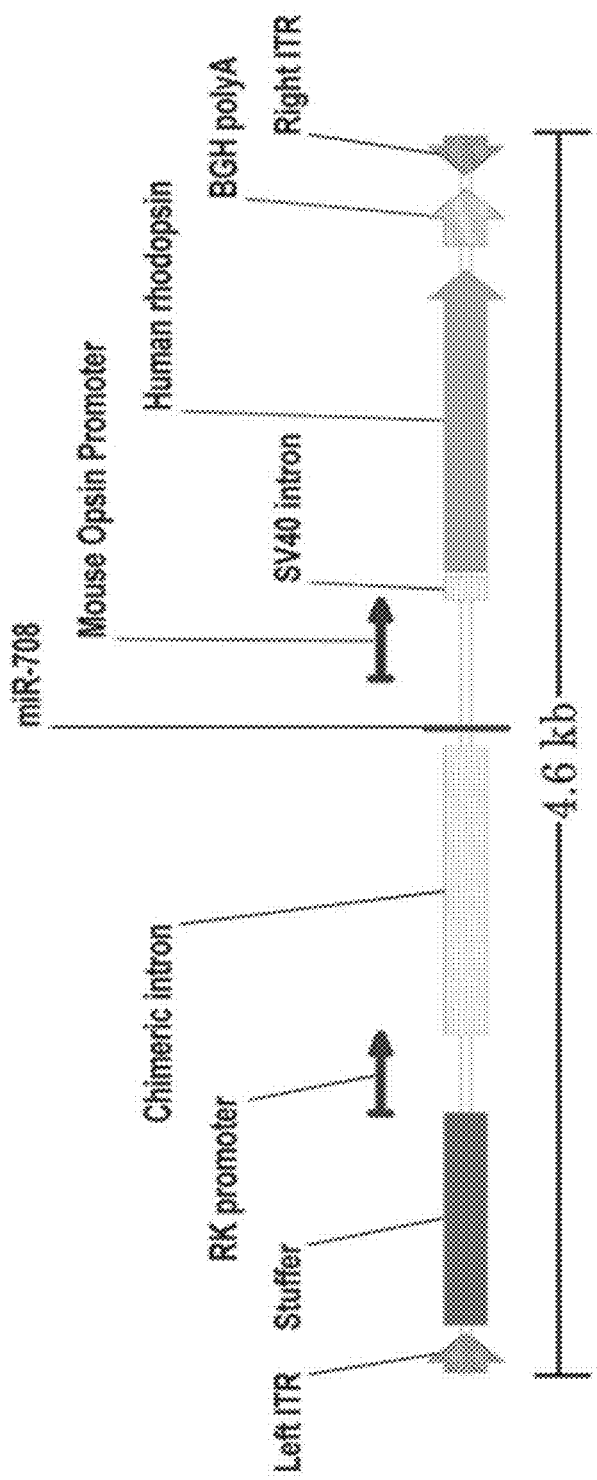
FIG. 19 shows a diagram of an alternate vector design using separate promoters to drive expression of miR-708 (RK promoter) and hRhodopsin (mouse opsin promoter).

An alternate suppression/replacement construct design is also tested. As shown in FIG. 19, this alternate vector drives expression of miR-708 from the RK promoter and co-express hRhodopsin (refractory to miR-708 knockdown) using the mouse opsin promoter.

These suppression/replacement vectors are also tested as described above in a P23H mouse model in which the endogenous mRhodopsin gene harbors a single copy loss-of-function allele (e.g., the mouse is heterozygous with respect to a mRhodopsin knockout allele). This heterozygous mouse model may be constructed using standard mouse genetic techniques from a mRho$^{-/-}$ mouse and the P23H model described above. Without wishing to be bound to theory, it is thought that this mRho$^{+/-}$ P23H mouse model, which contains one copy of the mutant hRhodopsin P23H allele and one copy of the wild-type mouse gene, may resemble a human ADRP genotype in which patients have equal copies of the mutant and wild-type rhodopsin alleles.

Example 10: Evaluation of Additional Suppression/Replacement Vectors

Several vectors were cloned that express both miR-708 (or a control miRNA sequence) and hRhodopsin from a single vector. The vectors differ from each other in that the flanking sequences of the miRNA sequence are derived from either miR-155 (taken from Invitrogen "Block-It" system) or endogenous miR-708 5' and 3' flanking sequences. The miRNA sequences are embedded in the hβ-globin intron downstream of the Rhodopsin Kinase promoter and upstream of the hRhodopsin ORF. The goal was to test if expression and miRNA processing are similar from each construct. An additional pair of vectors contained the miRNA sequences (control or miR-708) downstream of the hRhodopsin ORF, also embedded in the β-globin intron. Only the vectors containing the miR-708 endogenous flanking 5' and 3' sequences located downstream of the hRhodopsin ORF were tested in this experiment, both endogenous miR-708 and miR-155 flanking sequences were tested in the vectors where the β-globin intron is located upstream of the hRhodopsin ORF. WERI cells were transfected with each construct and both miR-708 expression and hRhodopsin expression were determined.

Figure 20:
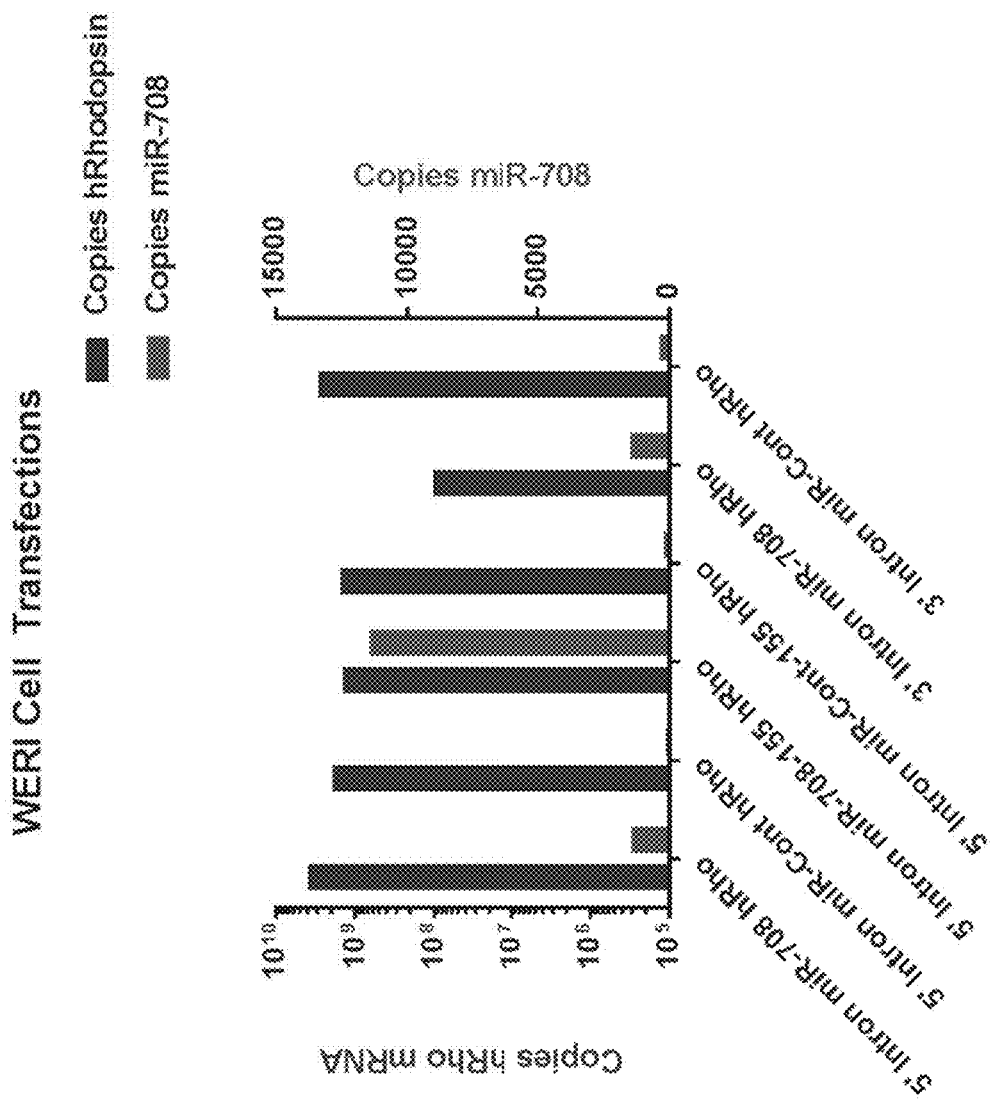
FIG. 20 shows hRhodopsin (left) and miR-708 (right) expression in WERI cells transfected with the specified vector. Expression is expressed as copy number calculated against a DNA standard.

The results in FIG. 20 indicate that the miR-155 flanking sequences generate better expression (or miRNA processing) of miR-708 compared to endogenous miR-708 flanking sequences. miR-708 expression was about 10 fold higher in those cells transfected with vectors containing the miR-155 flanking sequences compared to miR-708 flanking sequences. The vectors containing miR-708 flanking sequences had lower expression of miR-708 regardless of whether the sequences were upstream or downstream relative to the hRhodopsin ORF. hRhodopsin expression was unaffected by miR-708 overexpression, as its expression levels are approximately equal regardless of the miRNA sequence co-expressed in the vector. miR-708 expression was not detected in vectors containing control miRNA sequences, as expected.

Example 11: Evaluation of Additional Suppression/Replacement Vectors with a Mutated miR-708 Target Sequence As described above, a consensus sequence corresponding to a putative miR-708 target site has been found in the 3' UTR of several mammalian rhodopsin genes (Behrman, S., et al. (2011) *J. Cell Biol.* 192(6):919-27). This Example demonstrates that a rhodopsin with a mutated miR-708 target sequence can be used in a suppression/replacement vector.

An rAAV vector is constructed comprising nucleic acid encoding miR-708 and a human rhodopsin gene. The human rhodopsin gene is mutated in the miR-708 target sequence (SEQ ID NO:19) by nucleotide substitution, deletion or insertion to reduce or prevent recognition by miR-708. In some examples, the entire miR-708 target sequence is deleted. In some examples, reduction or prevention by miR-708 is measured in reference to miR-708 recognition of a wild-type rhodopsin 3'UTR comprising the miR-708 target sequence.

To test for suppression of autosomal dominant rhodopsin by miR-708 with concomitant expression of wild-type rhodopsin, HEK-293 cells expressing a P23H mutant mRhodopsin gene encoding a 3'UTR miR-708 target sequence are transfected with a plasmid expressing miR-708 and human rhodopsin with (CBA-miR-708-hRho-3'UTR$^-$) or without (CBA-miR-708-hRho-3'UTR$^+$) a mutated miR-708 target sequence. A miR-Control as described in Example 2 is also used. After 72 hrs, the cells are collected, and mP23H Rhodopsin and human rhodopsin protein expression are analyzed using a Western blot. Reduction of P23H mRhodopsin protein expression in cells transfected with the CBA-miR-708-hRho-3'UTR$^-$ or CBA-miR-708-hRho-3'UTR$^+$ compared to cells transfected with a CBA-miR-Control vector indicates miR-708 activity. Expression of human rhodopsin in cells transfected with CBA-miR-708-hRho-3'UTR$^-$ but not CBA-miR-708-hRho-3'UTR$^+$ indicates that the rhodopsin encoded by CBA-miR-708-hRho-3'UTR$^-$ is refractory to suppression by miR-708.

Example 12: AAV-Mediated Suppression of Endogenous Rhodopsin and Expression of Human Rhodopsin in the Mouse Retina Based on the experiments described above, further experiments were performed to test the rhodopsin suppression/replacement strategy in an intact eye. This Example demonstrates the efficacy of a suppression/replacement AAV vector built using a miR-708 scaffold in the mouse retina.

An AAV5 capsid with a vector bearing the rod-specific opsin promoter, the miR-708 scaffold (e.g., the miR-708 endogenous scaffold/flanking sequences), and a human rhodopsin replacement gene was constructed. In one version of this vector, the miR-708 sequence (e.g., the miR-708 sequence that binds the miR-708 target sequence) was inserted to drive expression of miR-708 in the context of the miR708 scaffold and the human rhodopsin replacement gene (AAV5OPSmiR708$_{708}$hRHO). In another version of this vector, a control vector was generated that harbored a miR control sequence (AAV5OPSmiRcontrol$_{708}$hRHO). In both vectors, the replacement human rhodopsin gene was refractory to miR-708 knockdown because it lacks a miR-708 target sequence. Both vectors were injected subretinally into the retinas of wild type mice. For each mouse, the contralateral naïve eye was uninjected, and expression in each injected retina was normalized as fold expression compared to the contralateral uninjected retina. Three weeks post injection, the retinas were harvested and assayed for miR-708 levels (FIG. 21A), mouse rhodopsin mRNA levels (FIG. 21B), and human rhodopsin (FIG. 21C).

Figure 21A:
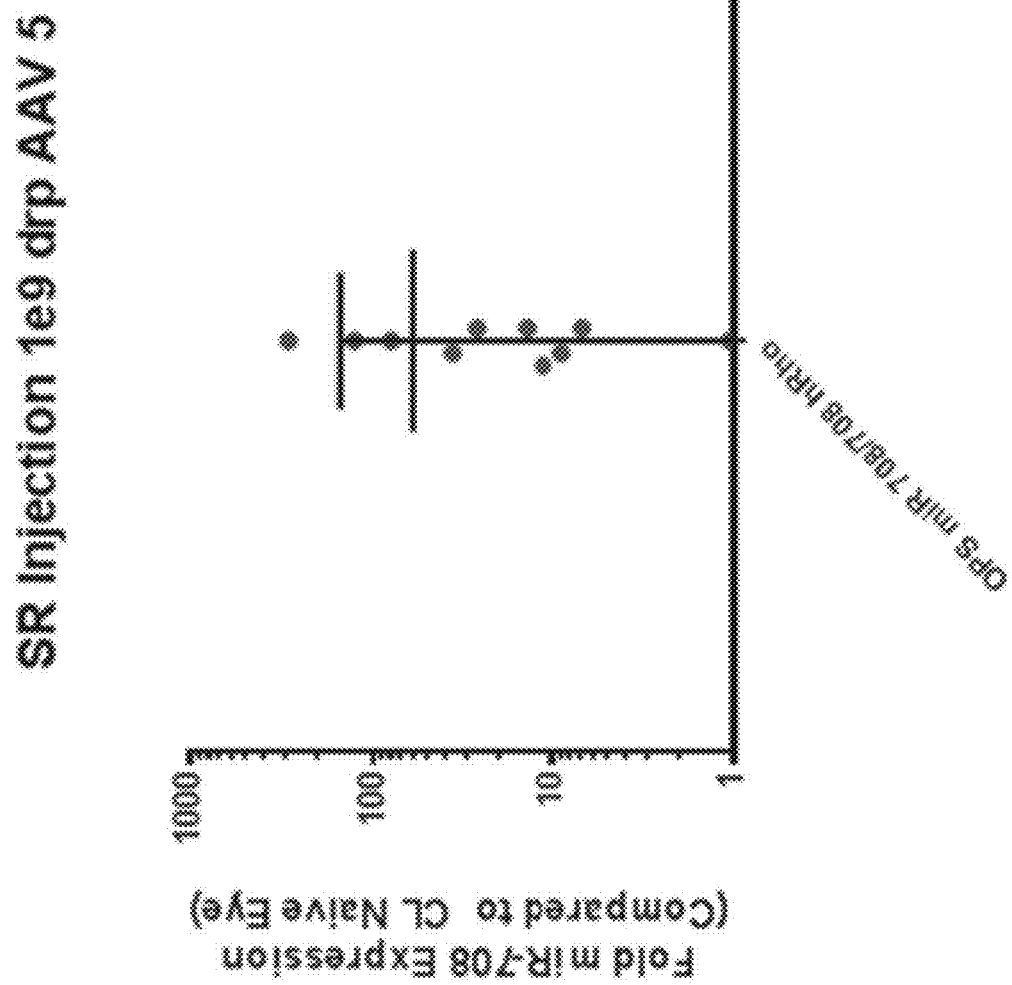
FIGS. 21A-C show the levels of miR-708 (FIG. 21A), mouse rhodopsin (FIG. 21B), and human rhodopsin (FIG. 21C) in mouse retinas three weeks after subretinal injection with an AAV5 capsid vector driving expression of human rhodopsin and miR-708 (miR 708/708), or human rhodopsin and control miRNA (miR-Cont), in a miR-708 scaffold using the opsin promoter. For each experiment, expression is shown as fold expression, as compared to the contralateral, uninjected eye.
Figure 21B:
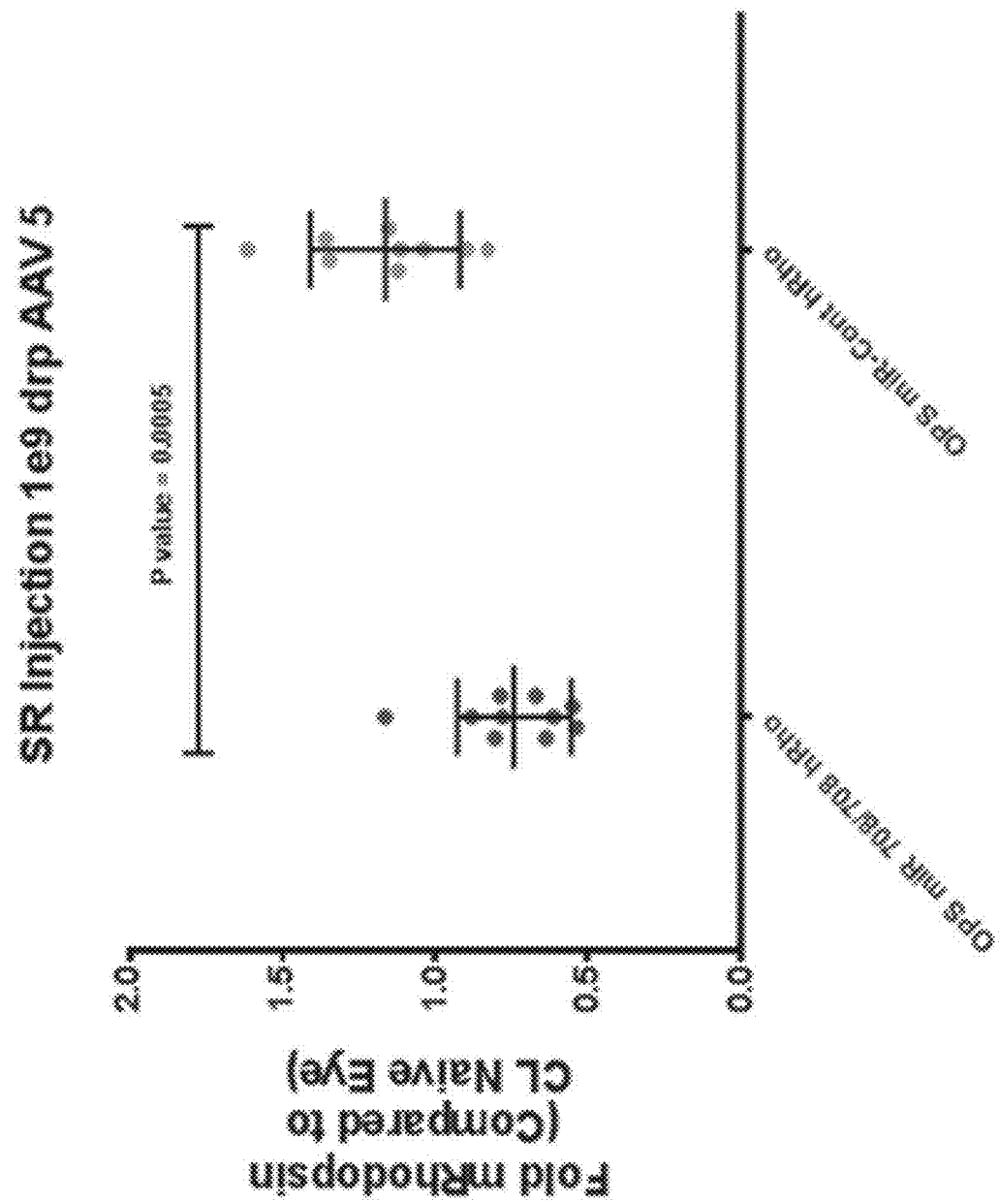
Figure 21C:
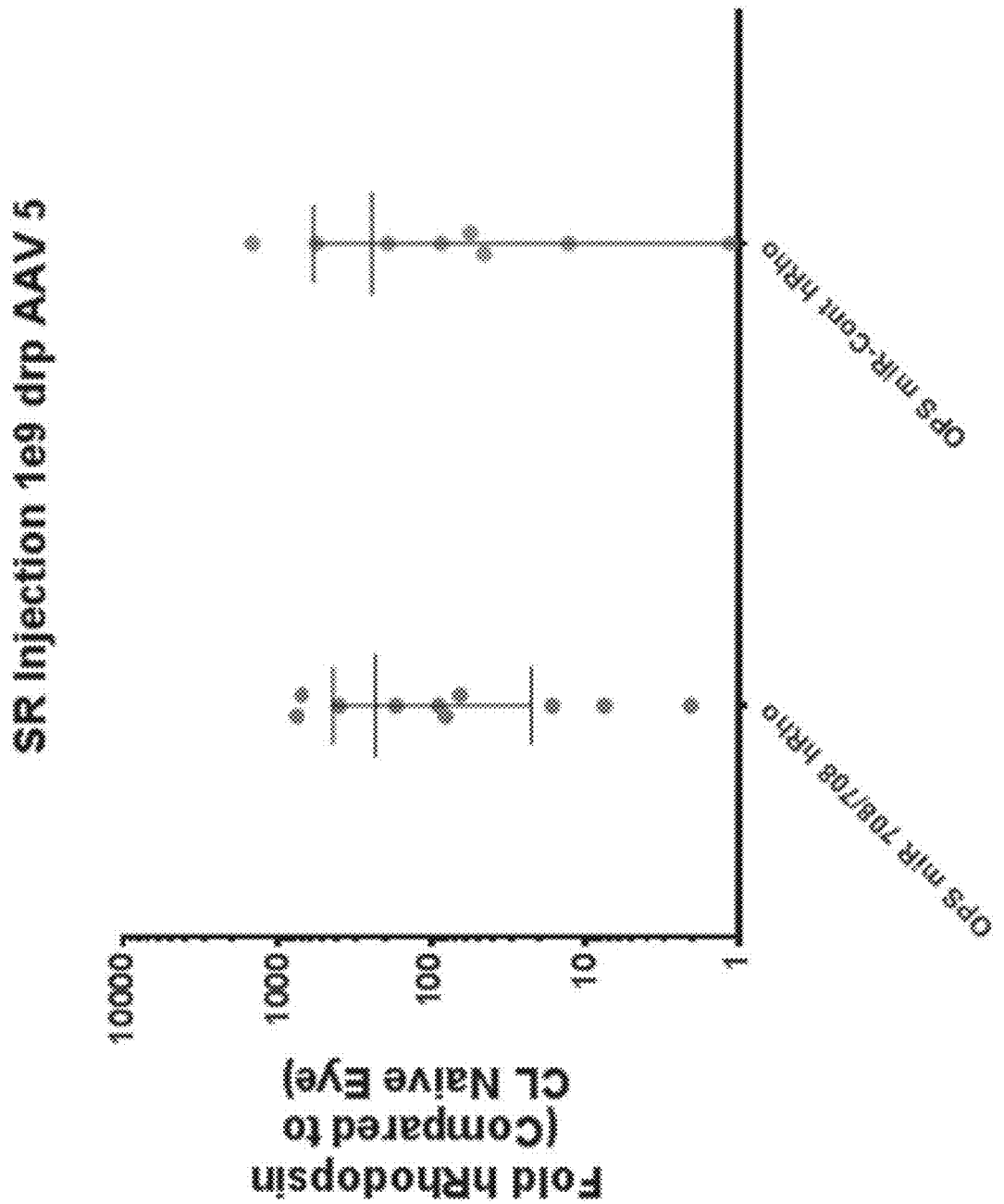

FIG. 21A shows an increase in miR-708 levels in the mouse retina following injection with the AAV5OPSmiR708$_{708}$hRHO vector, as compared to the contralateral naive eye. A significant reduction in mouse rhodopsin was measured in the eye that received AAV5OPSmiR708₇₀₈hRHO, and no reduction in mouse rhodopsin was measured in eyes that received the control vector, AAV5OPSmiRcontrol₇₀₈hRHO (FIG. 21B). In addition, human rhodopsin levels were increased up to 100 fold by both vectors, compared to the contralateral uninjected naïve eye (FIG. 21C). These data demonstrate that the AAV5OPSmiR708₇₀₈hRHO vector was efficacious in vivo.

In summary, the optimized suppression/replacement vector AAV5OPSmiR708₇₀₈hRHO achieved knockdown of mouse rhodopsin by miR-708 (endogenous mouse rhodopsin has a 3'UTR target sequence) with concomitant expression of the replacement human rhodopsin, which was refractory to miR708 knockdown (the human rhodopsin replacement gene lacks a 3'UTR miR708 target sequence). These results show the efficacy of the suppression/replacement strategy in the intact mammalian eye.

Example 13: Validation of Candidate Vectors in Human Cells

Candidate AAV5-based vectors were next assayed for the ability to promote miR-708 and human rhodopsin expression in human cells (HeLa).

Figure 22:
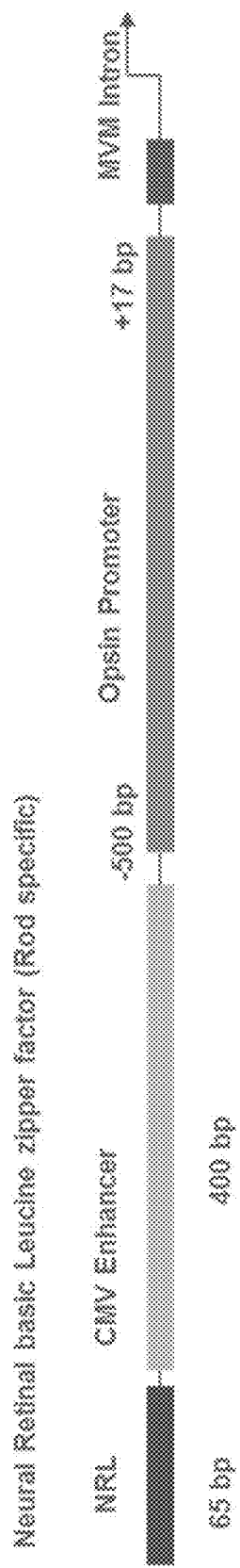
FIG. 22 shows a schematic of the opsin promoter construct, including the neural retinal basic zipper factor sequence (NRL), the CMV enhancer, the opsin promoter, and the MVM intron sequence, which includes a hybrid intron sequence from CBA exon 1 and an intron from the minute virus of mice (MVM).

Two different promoters were tested: rhodopsin kinase (GRK1) and the opsin promoter. The rhodopsin kinase promoter is described above. The opsin promoter (shown in SEQ ID NO:22) contains a 676 bp fragment encoding a 400 bp CMV enhancer upstream of the opsin promoter sequence (~500 bp-+15 bp). In addition 65 bp NRL sequence is included; this encodes a neural retinal basic zipper factor (a Rod photoreceptor specific transcription factor). Downstream of the promoter construct is a hybrid intron sequence from CBA exon1 and minute virus of mouse (MVM)—called MVM intron sequence (shown in SEQ ID NO:23). A diagram of this promoter construct is depicted in FIG. 22.

Figure 23A:
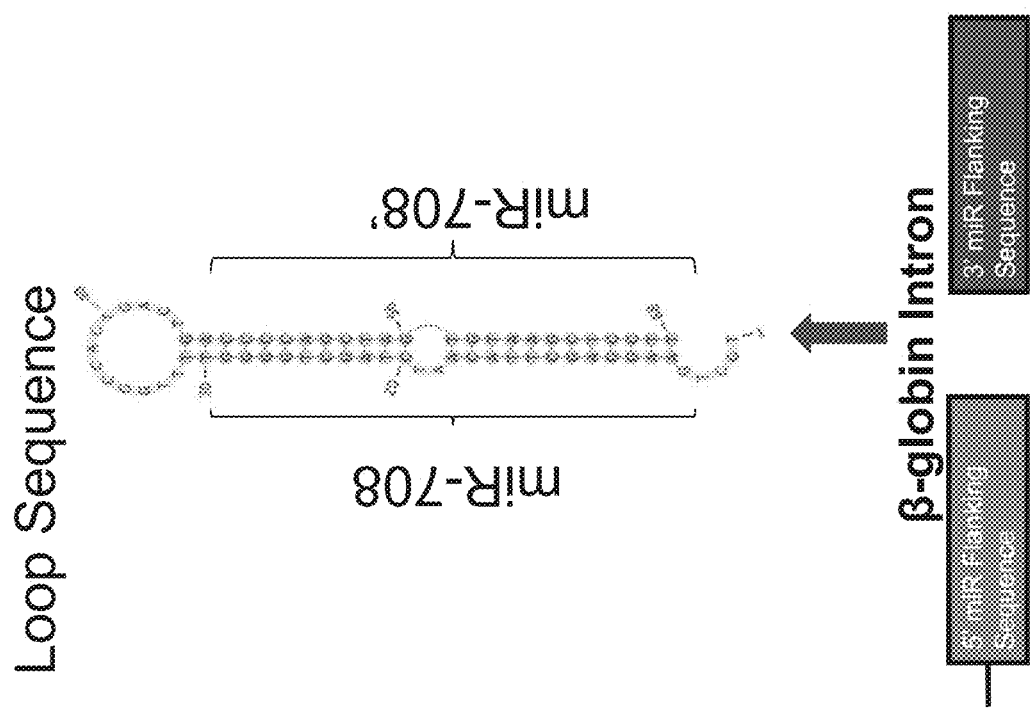
FIG. 23A shows a schematic of the miR-708 sequence embedded in a beta-globin intron.
Figure 23C:
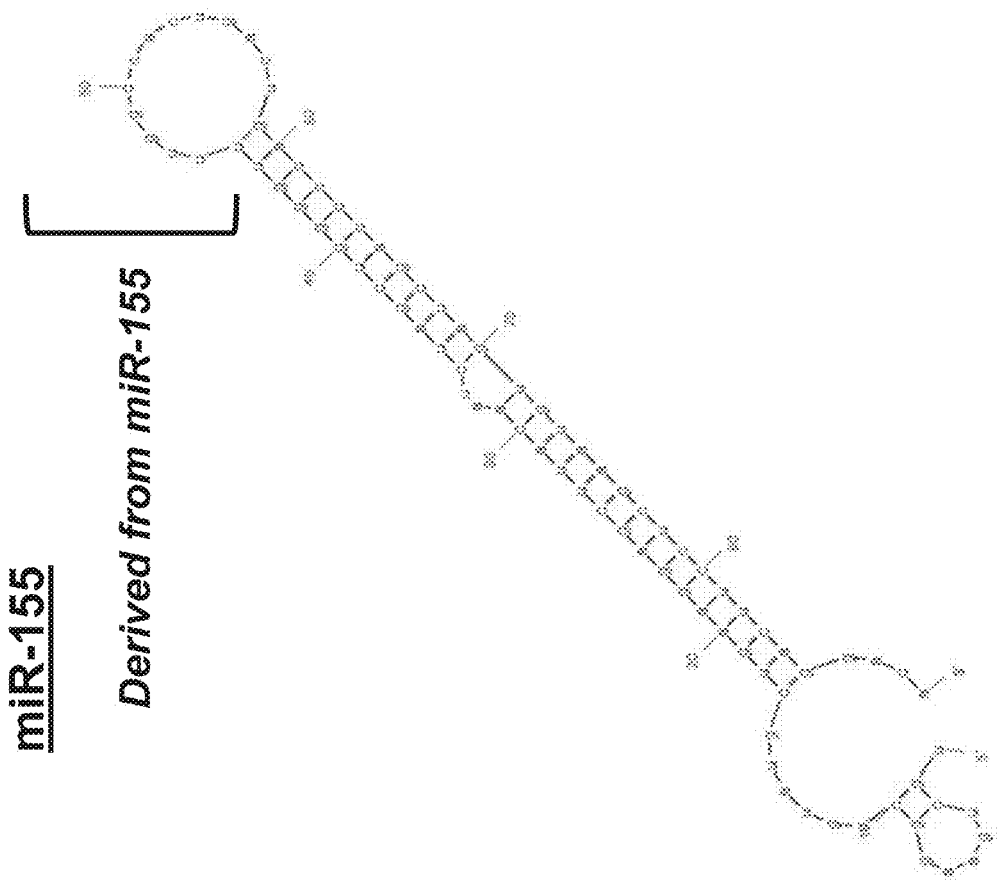
FIGS. 23B & 23C show schematics of the miR-708 sequence in the context of either the miR-708 endogenous scaffold (FIG. 23B) or the miR-155 scaffold (FIG. 23C), embedded in a beta globin intron. The miR-155 "loop sequence" between the 5' and 3' miR flanking sequences is labeled in FIG. 23C.
Figure 23B:
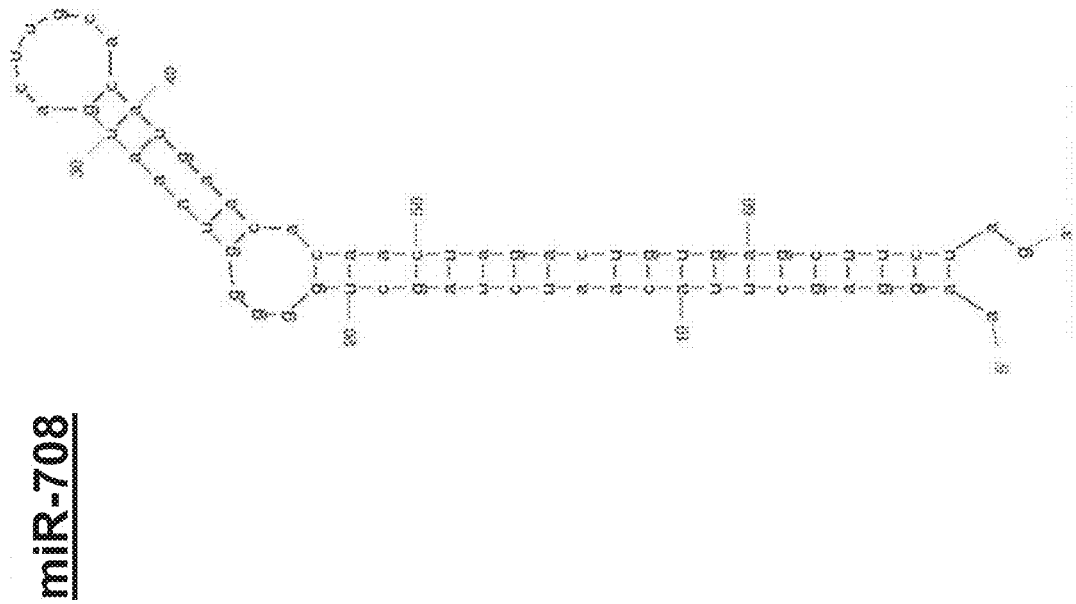

Two different scaffolds were used: the miR-155 scaffold or the miR-708 scaffold. Both were embedded in a beta globin intron. In total, 4 candidate vectors were tested: AAV5GRK1miR708_155hRho (AAV5 vector with rhodopsin kinase promoter driving expression of miR-708 in a miR-155 scaffold and human rhodopsin minus the miR-708 target sequence; SEQ ID NO:24), AAV5GRK1miR708 708hRho (AAV5 vector with rhodopsin kinase promoter driving expression of miR-708 in a miR-708 scaffold and human rhodopsin minus the miR-708 target sequence; SEQ ID NO:25), AAV5OPSmiR708 155hRho (AAV5 vector with opsin promoter driving expression of miR-708 in a miR-155 scaffold and human rhodopsin minus the miR-708 target sequence; SEQ ID NO:26), and AAV5OPSmiR708_708hRho (AAV5 vector with opsin promoter driving expression of miR-708 in a miR-708 scaffold and human rhodopsin minus the miR-708 target sequence; SEQ ID NO:27). FIG. 23A shows the miR-708 sequence embedded in the beta globin intron. The miR-708 and miR-155 scaffolds are shown in FIGS. 23B and 23C, respectively.

Figure 24:
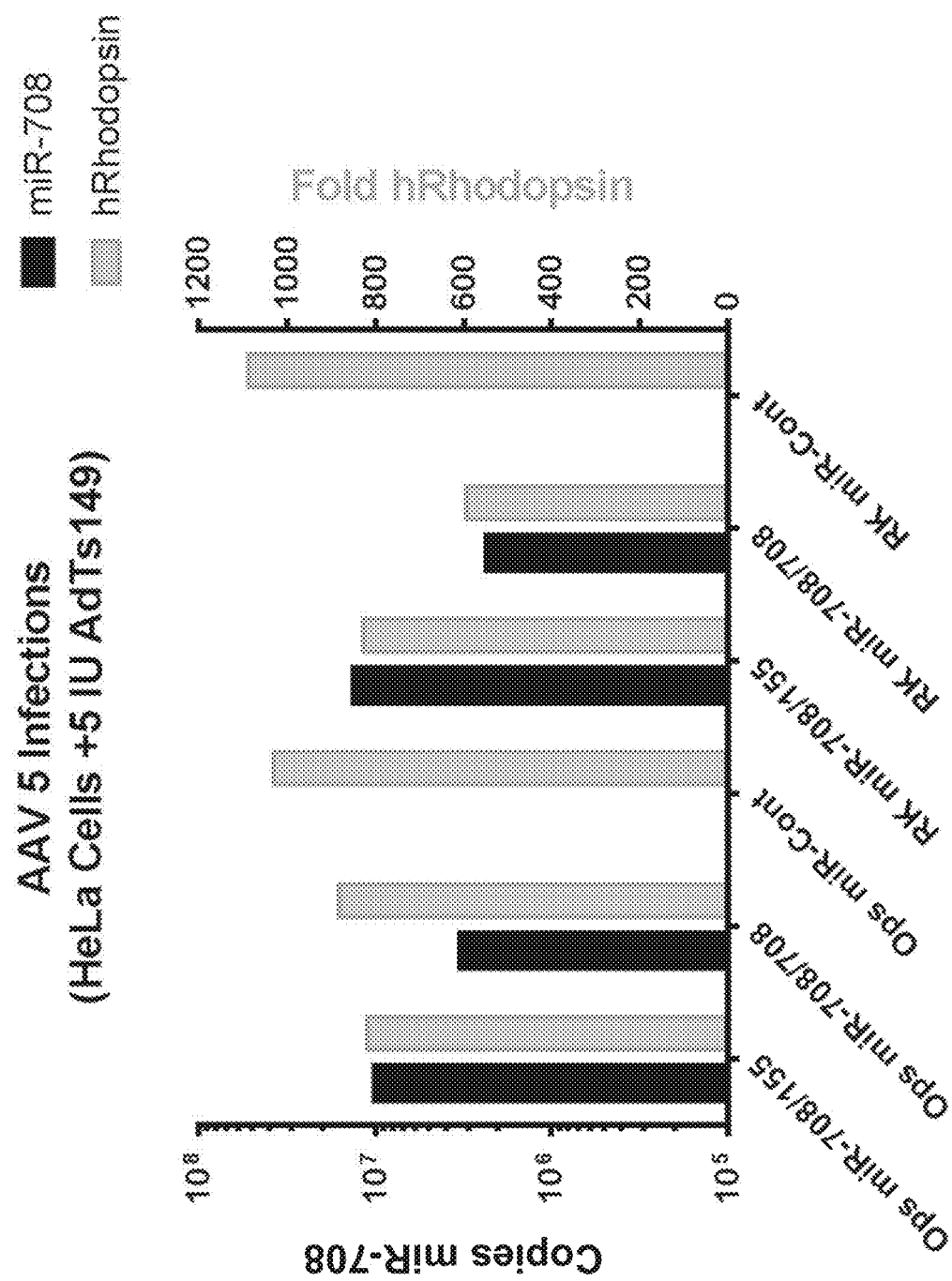
FIG. 24 shows the evaluation of candidate vectors harboring the miR-708 sequence, either in the miR-155 or the miR-708 scaffold (embedded in the beta-globin intron), and the human rhodopsin coding sequence (hRhodopsin; also lacking a 3'UTR miR-708 target sequence) driven by either the rhodopsin kinase (GRK1) promoter or the opsin (Ops) promoter. All four combinations were tested for effects on miR-708 and hRhodopsin expression, as shown.

Each of the 4 candidate AAV5 vectors was used to infect HeLa cells (using the AdTs149 helper virus), and levels of miR-708 and hRhodopsin were measured. As shown in FIG. 24, all four vectors resulted in miR-708 and hRhodopsin expression in human cells in vivo, as compared to vectors driving expression of a control miR from either the opsin or the rhodopsin kinase promoter (Ops miR-Cont and RK miR-Cont, respectively). These results demonstrate the successful validation of several vectors that may be used for suppression/replacement strategies (such as those described above) in human cells.

```
miR-708 nucleotide sequence
                                       (SEQ ID NO: 1)
AACTGCCCTCAAGGAGCTTACAATCTAGCTGGGGGTAAATGACTTGCACA

TGAACACAACTAGACTGTGAGCTTCTAGAGGGCAGGGA

Human rhodopsin amino acid sequence
                                       (SEQ ID NO: 2)
MNGTEGPNFYVPFSNATGVVRSPFEYPQYYLAEPWQFSMLAAYMFLLIVL

GFPINFLTLYVTVQHKKLRTPLNYILLNLAVADLFMVLGGFTSTLYTSLH

GYFVFGPTGCNLEGFFATLGGEIALWSLVVLAIERYVVVCKPMSNFRFGE

NHAIMGVAFTWVMALACAAPPLAGWSRYIPEGLQCSCGIDYYTLKPEVNN

ESFVIYMFVVHFTIPMIIIFFCYGQLVFTVKEAAAQQQESATTQKAEKEV

TRMVIIMVIAFLICWVPYASVAFYIFTHQGSNFGPIEMTIPAFFAKSAAI

YNPVIYIMMNKQFRNCMLTTICCGKNPLGDDEASATVSKTETSQVAPA

Human rhodopsin cDNA-UTR deleted
                                       (SEQ ID NO: 3)
ATGAATGGCACAGAAGGCCCTAACTTCTACGTGCCCTTCTCCAATGCGACGGGTGTGGTACGCAGCCCC

TTCGAGTACCCACAGTACTACCTGGCTGAGCCATGGCAGTTCTCCATGCTGGCCGCCTACATGTTTCTG

CTGATCGTGCTGGGCTTCCCCATCAACTTCCTCACGCTCTACGTCACCGTCCAGCACAAGAAGCTGCGC

ACGCCTCTCAACTACATCCTGCTCAACCTAGCCGTGGCTGACCTCTTCATGGTCCTAGGTGGCTTCACC

AGCACCCTCTACACCTCTCTGCATGGATACTTCGTCTTCGGGCCCACAGGATGCAATTTGGAGGGCTTC

TTTGCCACCCTGGGCGGTGAAATTGCCCTGTGGTCCTTGGTGGTCCTGGCCATCGAGCGGTACGTGGTG

GTGTGTAAGCCCATGAGCAACTTCCGCTTCGGGGAGAACCATGCCATCATGGGCGTTGCCTTCACCTGG

GTCATGGCGCTGGCCTGCGCCGCACCCCCACTCGCCGGCTGGTCCAGGTACATCCCCGAGGGCCTGCAG

TGCTCGTGTGGAATCGACTACTACACGCTCAAGCCGGAGGTCAACAACGAGTCTTTTGTCATCTACATG

TTCGTGGTCCACTTCACCATCCCCATGATTATCATCTTTTTCTGCTATGGGCAGCTCGTCTTCACCGTC

AAGGAGGCCGCTGCCCAGCAGCAGGAGTCAGCCACCACACAGAAGGCAGAGAAGGAGGTCACCCGCATG
```

-continued

GTCATCATCATGGTCATCGCTTTCCTGATCTGCTGGGTGCCCTACGCCAGCGTGGCATTCTACATCTTC

ACCCACCAGGGCTCCAACTTCGGTCCCATCTTCATGACCATCCCAGCGTTCTTTGCCAAGAGCGCCGCC

ATCTACAACCCTGTCATCTATATCATGATGAACAAGCAGTTCCGGAACTGCATGCTCACCACCATCTGC

TGCGGCAAGAACCCACTGGGTGACGATGAGGCCTCTGCTACCGTGTCCAAGACGGAGACGAGCCAGGTG

GCCCCGGCC

Human rhodopsin cDNA-includes 3'UTR
(SEQ ID NO: 4)
AGAGTCATCCAGCTGGAGCCCTGAGTGGCTGAGCTCAGGCCTTCGCAGCATTCTTGGGTGGGAGCAGCC

ACGGGTCAGCCACAAGGGCCACAGCCATGAATGGCACAGAAGGCCCTAACTTCTACGTGCCCTTCTCCA

ATGCGACGGGTGTGGTACGCAGCCCCTTCGAGTACCCACAGTACTACCTGGCTGAGCCATGGCAGTTCT

CCATGCTGGCCGCCTACATGTTTCTGCTGATCGTGCTGGGCTTCCCCATCAACTTCCTCACGCTCTACG

TCACCGTCCAGCACAAGAAGCTGCGCACGCCTCTCAACTACATCCTGCTCAACCTAGCCGTGGCTGACC

TCTTCATGGTCCTAGGTGGCTTCACCAGCACCCTCTACACCTCTCTGCATGGATACTTCGTCTTCGGGC

CCACAGGATGCAATTTGGAGGGCTTCTTTGCCACCCTGGGCGGTGAAATTGCCCTGTGGTCCTTGGTGG

TCCTGGCCATCGAGCGGTACGTGGTGGTGTGTAAGCCCATGAGCAACTTCCGCTTCGGGGAGAACCATG

CCATCATGGGCGTTGCCTTCACCTGGGTCATGGCGCTGGCCTGCGCCGCACCCCCACTCGCCGGCTGGT

CCAGGTACATCCCCGAGGGCCTGCAGTGCTCGTGTGGAATCGACTACTACACGCTCAAGCCGGAGGTCA

ACAACGAGTCTTTTGTCATCTACATGTTCGTGGTCCACTTCACCATCCCCATGATTATCATCTTTTTCT

GCTATGGGCAGCTCGTCTTCACCGTCAAGGAGGCCGCTGCCCAGCAGCAGGAGTCAGCCACCACACAGA

AGGCAGAGAAGGAGGTCACCCGCATGGTCATCATCATGGTCATCGCTTTCCTGATCTGCTGGGTGCCCT

ACGCCAGCGTGGCATTCTACATCTTCACCCACCAGGGCTCCAACTTCGGTCCCATCTTCATGACCATCC

CAGCGTTCTTTGCCAAGAGCGCCGCCATCTACAACCCTGTCATCTATATCATGATGAACAAGCAGTTCC

GGAACTGCATGCTCACCACCATCTGCTGCGGCAAGAACCCACTGGGTGACGATGAGGCCTCTGCTACCG

TGTCCAAGACGGAGACGAGCCAGGTGGCCCCGGCCTAAGACCTGCCTAGGACTCTGTGGCCGACTATAG

GCGTCTCCCATCCCCTACACCTTCCCCCAGCCACAGCCATCCCACCAGGAGCAGCGCCTGTGCAGAATG

AACGAAGTCACATAGGCTCCTTAATTTTTTTTTTTTTTAAGAAATAATTAATGAGGCTCCTCACTCA

CCTGGGACAGCCTGAGAAGGGACATCCACCAAGACCTACTGATCTGGAGTCCCACGTTCCCAAGGCCA

GCGGGATGTGTGCCCCTCCTCCTCCCAACTCATCTTTCAGGAACACGAGGATTCTTGCTTTCTGGAAAA

GTGTCCCAGCTTAGGGATAAGTGTCTAGCACAGAATGGGCACACAGTAGGTGCTTAATAAATGCTGGA

TGGATGCAGGAAGGAATGGAGGAATGAATGGGAAGGGAGAACATATCTATCCTCTCAGACCCTCGCAGC

AGCAGCAACTCATACTTGGCTAATGATATGGAGCAGTTGTTTTTCCCTCCCTGGGCCTCACTTTCTTCT

CCTATAAAATGGAAATCCCAGATCCCTGGTCCTGCCGACACGCAGCTACTGAGAAGACCAAAAGAGGTG

TGTGTGTGTCTATGTGTGTGTTTCAGCACTTTGTAAATAGCAAGAAGCTGTACAGATTCAGTTAATGT

TGTGAATAACATCAATTAATGTAACTAGTTAATTACTATGATTATCACCTCCTGATAGTGAACATTTTG

AGATTGGGCATTCAGATGATGGGGTTTCACCCAACCTTGGGGCAGGTTTTTAAAAATTAGCTAGGCATC

AAGGCCAGACCAGGGCTGGGGGTTGGGCTGTAGGCAGGGACAGTCACAGGAATGCAGAATGCAGTCATC

AGACCTGAAAAACAACACTGGGGAGGGGGACGGTGAAGGCCAAGTTCCCAATGAGGGTGAGATTGGG

CCTGGGGTCTCACCCCTAGTGTGGGGCCCCAGGTCCCGTGCCTCCCCTTCCCAATGTGGCCTATGGAGA

GACAGGCCTTTCTCTCAGCCTCTGGAAGCCACCTGCTCTTTTGCTCTAGCACCTGGGTCCCAGCATCTA

GAGCATGGAGCCTCTAGAAGCCATGCTCACCCGCCCACATTTAATTAACAGCTGAGTCCCTGATGTCAT

-continued

CCTTATCTCGAAGAGCTTAGAAACAAAGAGTGGGAAATTCCACTGGGCCTACCTTCCTTGGGGATGTTC

ATGGGCCCCAGTTTCCAGTTTCCCTTGCCAGACAAGCCCATCTTCAGCAGTTGCTAGTCCATTCTCCAT

TCTGGAGAATCTGCTCCAAAAAGCTGGCCACATCTCTGAGGTGTCAGAATTAAGCTGCCTCAGTAACTG

CTCCCCCTTCTCCATATAAGCAAAGCCAGAAGCTCTAGCTTTACCCAGCTCTGCCTGGAGACTAAGGCA

AATTGGGCCATTAAAAGCTCAGCTCCTATGTTGGTATTAACGGTGGTGGGTTTTGTTGCTTTCACACTC

TATCCACAGGATAGATTGAAACTGCCAGCTTCCACCTGATCCCTGACCCTGGGATGGCTGGATTGAGCA

ATGAGCAGAGCCAAGCAGCACAGAGTCCCCTGGGGCTAG

AGGTGGAGGAGGCAGTCCTGGGAATGGGAAAAACCCCA

RK-miR708 only
(SEQ ID NO: 5)
GGCCCCAGAAGCCTGGTGGTTGTTTGTCCTTCTCAGGGGAAAAGTGAGGCGGCCCCTTGGAGGAAGGGG

CCGGGCAGAATGATCTAATCGGATTCCAAGCAGCTCAGGGGATTGTCTTTTTCTAGCACCTTCTTGCCA

CTCCTAAGCGTCCTCCGTGACCCCGGCTGGGATTTAGCCTGGTGCTGTGTCAGCCCCGGTCTCCCAGGG

GCTTCCCAGTGGTCCCCAGGAACCCTCGACAGGGCCCGGTCTCTCTCGTCCAGCAAGGGCAGGGACGGG

CCACAGGCCAAGGGCGGAGTCGCTGCGACGCTGCCTTCGCCCCGTGCCCCGCTCCGCCGCCGCCTCGCG

CCGCCCGCCCCGGCTCTGACTGACCGCGTTACTCCCACAGGTGAGCGGGCGGGACGGCCCTTCTCCTCC

GGGCTGTAATTAGCGCTTGGTTTAATGACGGCTTGTTTCTTTTCTGTGGCTGCGTGAAAGCCTTGAGGG

GCTCCGGGAGGGCCCTTTGTGCGGGGGAGCGGCTCGGGGGGTGCGTGCGTGTGTGTGCGTGGGGAG

CGCCGCGTGCGGCTCCGCGCTGCCCGGCGGCTGTGAGCGCTGCGGGCGCGGCGCGGGGCTTTGTGCGCT

CCGCAGTGTGCGCGAGGGGAGCGCGGCCGGGGCGGTGCCCCGCGGTGCGGGGGGGGCTGCGAGGGGAA

CAAAGGCTGCGTGCGGGGTGTGTGCGTGGGGGGGTGAGCAGGGGGTGTGGGCGCGTCGGTCGGGCTGCA

ACCCCCCTGCACCCCCCTCCCCGAGTTGCTGAGCACGGCCCGGCTTCGGGTGCGGGGCTCCGTACGGG

GCGTGGCGCGGGGCTCGCCGTGCCGGGCGGGGGGTGGCGGCAGGTGGGGGTGCCGGGCGGGGCGGGGCC

GCCTCGGGCCGGGGAGGGCTCGGGGGAGGGGCGCGGCGGCCCCCGGAGCGCCGGCGGCTGTCGAGGCGC

GGCGAGCCGCAGCCATTGCCTTTTATGGTAATCGTGCGAGAGGGCGCAGGGACTTCCTTTGTCCCAAAT

CTGTGCGGAGCCGAAATCTGGGAGGCGCCGCCGCACCCCCTCTAGCGGGCGCGGGGCGAAGCGGTGCGG

CGCCGGCAGGAAGGAAATGGGCGGGAGGGCCTTCGTGCGTCGCCGCGCCGCCGTCCCCTTCTCCCTCT

CCAGCCTCGGGGCTGTCCGCGGGGGGACGGCTGCCTTCGGGGGGGACGGGGCAGGGCGGGGTTCGGCTT

CTGGCGTGTGACCGGCGGCTCTAGAGCCTCTGCTAACCATGTTCATGCCTTCTTCTTTTTCCTACAGCT

CCTGGGCAACGTGCTGGTTATTGTGCTGTCTCATCATTTTGGCAAAGAATTCTTCGAAAGATCCTGGAG

GCTTGCTGAAGGCTGTATGCTGAAGGAGCTTACAATCTAGCTGGGGTTTTGGCCACTGACTGACCCCAG

CTAGTGTAAGCTCCTTCAGGACACAAGGCCTGTTACTAGCACTCACATGGAACAAATGGCCCA

RK-miR-708-op-rhodopsin
(SEQ ID NO: 6)
CAATCTCCCAGATGCTGATTCAGCCAGGAACTAGTTATTAATAGTAATCAATTACGGGGTCATTAGTTC

ATAGCCCATATATGGAGTTCCGCGTTACATAACTTACGGTAAATGGCCCGCCTGGCTGACCGCCCAACG

ACCCCCGCCCATTGACGTCAATAATGACGTATGTTCCCATAGTAACGCCAATAGGGACTTTCCATTGAC

GTCAATGGGTGGAGTATTTACGGTAAACTGCCCACTTGGCAGTACATCAAGTGTATCATATGCCAAGTA

CGCCCCCTATTGACGTCAATGACGGTAAATGGCCCGCCTGGCATTATGCCCAGTACATGACCTTATGGG

-continued

```
ACTTTCCTACTTGGCAGTACATCTACGTATTAGTCATCGCTATTACCACAAATAGTTATCGAGCCGCTG

AGCCGGGGGGGGGGGGTGTGAGACTGGAGGCGATGGACGGAGCTGACGGCACACACAGCTCAGATCTG

TCAAGTGAGCCATTGTCAGGGCTTGGGGACTGGATAAGTCAGGGGGTCTCCTGGGAAGAGATGGGATAG

GTGAGTTCAGGAGGAGACATTGTCAACTGGAGCCATGTGGAGAAGTGAATTTAGGGCCCAAAGGTTCCA

GTCGCAGCCTGAGGCCACCAGACTGACATGGGAGGAATTCCCAGAGGACTCTGGGGCAGACAAGATGA

GACACCCTTTCCTTTCTTTACCTAAGGGCCTCCACCCGATGTCACCTTGGCCCCTCTGCAAGCCAATTA

GGCCCCGGTGGCAGCAGTGGGATTAGCGTTAGTATGATATCTCGCGGATGCTGAATCAGCCTCTGGCTT

AGGGAGAGAAGGTCACTTTATAAGGGTCTGGGGGGGGTCAGTGCCTGGAGTTGCGCTGTGGGAGCCGTC

AGTGGCTGAGCTCAAGAGGTAAGGGTTTAAGGGATGGTTGGTTGGTGGGTATTAATGTTTAATTACCT

GTTTTACAGGCCTGAAATCACTTGGTTTTAGGTTGGTACATCTGCAGAATTCAGCCACCACCGGCACAA

TGAATGGCACAGAAGGCCCTAACTTCTACGTGCCCTTCTCCAATGCGACGGGTGTGGTACGCAGCCCCT

TCGAGTACCCACAGTACTACCTGGCTGAGCCATGGCAGTTCTCCATGCTGGCCGCCTACATGTTTCTGC

TGATCGTGCTGGGCTTCCCCATCAACTTCCTCACGCTCTACGTCACCGTCCAGCACAAGAAGCTGCGCA

CGCCTCTCAACTACATCCTGCTCAACCTAGCCGTGGCTGACCTCTTCATGGTCCTAGGTGGCTTCACCA

GCACCCTCTACACCTCTCTGCATGGATACTTCGTCTTCGGGCCCACAGGATGCAATTTGGAGGGCTTCT

TTGCCACCCTGGGCGGTGAAATTGCCCTGTGGTCCTTGGTGGTCCTGGCCATCGAGCGGTACGTGGTGG

TGTGTAAGCCCATGAGCAACTTCCGCTTCGGGGAGAACCATGCCATCATGGGCGTTGCCTTCACCTGGG

TCATGGCGCTGGCCTGCGCCGCACCCCCACTCGCCGGCTGGTCCAGGTACATCCCCGAGGGCCTGCAGT

GCTCGTGTGGAATCGACTACTACACGCTCAAGCCGGAGGTCAACAACGAGTCTTTTGTCATCTACATGT

TCGTGGTCCACTTCACCATCCCCATGATTATCATCTTTTTCTGCTATGGGCAGCTCGTCTTCACCGTCA

AGGAGGCCGCTGCCCAGCAGCAGGAGTCAGCCACCACACAGAAGGCAGAGAAGGAGGTCACCCGCATGG

TCATCATCATGGTCATCGCTTTCCTGATCTGCTGGGTGCCCTACGCCAGCGTGGCATTCTACATCTTCA

CCCACCAGGGCTCCAACTTCGGTCCCATCTTCATGACCATCCCAGCGTTCTTTGCCAAGAGCGCCGCCA

TCTACAACCCTGTCATCTATATCATGATGAACAAGCAGTTCCGGAACTGCATGCTCACCACCATCTGCT

GCGGCAAGAACCCACTGGGTGACGATGAGGCCTCTGCTACCGTGTCCAAGACGGAGACGAGCCAGGTGG

CCCCGGCCTAACCAAGAAAGCTTAAGTTTGTGTCCCGGCTTAGGGCTAAATGTCTAGGACAGAATGGAA

CACATAGTAGCTGATTAATAAATGCTAGCTGGATGAAGGGAGGAATGAGTGACTGACTGAGTGGATATA

TGAGTGAAGGGATTAATGGAAGGGAACATGGATGTCCTCAGGTGCCCAACCTGGCAGATCCAGTCATGT

CTGGCTGGAATCTATAAGCAGTTTTACATACCTGCCCTGAGCTTTATTGCGGTAGTTTATCACAGTTAA

ATTGCTAACGCAGTCAGTGCTTCTGACACAACAGTCTCGAACTTAAGCTGCAGTGACTCTCTTAAGGTA

GCCTTGCAGAAGTTGGTCGTGAGGCACTGGGCAGGTAAGTATCAAGGTTACAAGACAGGTTTAAGGAGA

CCAATAGAAACTGGGCTTGTCGAGACAGAGAAAAACCTAACCCCCATGGTTGGCGAGGGACTGCTGTGT

GTGAAATGGTAACTGCCCTCAAGGAGCTTACAATCTAGCTGGGGTAAATGACTTGCACATGAACACAA

CTAGACTGTGAGCTTCTAGAGGGCAGGGACCTTACCCTAGTCATCTCTCTTCTCACCCTGCACACCCTC

CCTGAGGGATCTCATGACTCTTGCGTTTCTGATAGGCACCTATTGGTCTTACTGACATCCACTTTGCCT

TTCTCTCCACAGGTGTCCACTCCCAGTTCACACCGGCACAATGAATGGCACAGAAGGCCCTAACTTCTA

CGTGCCCTTCTCCAATGCGACGGGTGTGGTACGCAGCCCCTTCGAGTACCCACAGTCAGAGATAAATGA

CAGTGACAGCAACGTGAGCTGCAGCCCTTAGGACTGAGAAAGCATCGAGACCAGGGGTCTCCGGCAAGG

CCTAGGTCCTCCCTTCAGTATGGAAACCTTGCCTCATGTCTCTCAGCCTCCTTGGCCTGTGGAGATCCA

GCCCTTCCTCTTGGCTTCTGGATACATTTGCTCTTCTACACCAGCAACCAAGTGGCAACAGTTCCAGGC

CAGTATGGAGTTTTAGAAGCCATGCCAATATGCCCACCTTCAGGGAGCAGCTGAGTCCTTGATGCCACC
```

-continued

CTTGTTCTGAAGAGTTCAGAAACACAGTGCAAGACATGACCAGGCCTCATCCTTAGGATGCTCATGGAT

CCAGTTCTTAGCTCCCTTGTTGGATATGCTGTTTTCCTTGGCCTTTGGTCTTTTCTTTATCCCAGAGGG

TTTTGGCTTTAAGGCCAACAGGAACTATGGGGTACCAGAATTGAGCAGCCTCAGTCTGCATCCCTCCTC

TATAGAACCACAGCTGGGCCCTCAGCAGGCCCAACTCTGCATGGGACAGAGGCATTAAAAGC

RK-intron-rhodopsin-miR-708.

(SEQ ID NO: 7)

GGGCCCCAGAAGCCTGGTGGTTGTTTGTCCTTCTCAGGGGAAAAGTGAGGCGGCCCCTTGGAGGAAGGGGCCGGGC

AGAATGATCTAATCGGATTCCAAGCAGCTCAGGGGATTGTCTTTTTCTAGCACCTTCTTGCCACTCCTAAGCGTCC

TCCGTGACCCCGGCTGGGATTTAGCCTGGTGCTGTGTCAGCCCCGGTCTCCCAGGGGCTTCCCAGTGGTCCCCAGG

AACCCTCGACAGGGCCCGGTCTCTCTCGTCCAGCAAGGGCAGGGACGGGCCACAGGCCAAGGGCGGAGTCGCTGCG

ACGCTGCCTTCGCCCCGTGCCCCGCTCCGCCGCCGCCTCGCGCCGCCCGCCCCGGCTCTGACTGACCGCGTTACTC

CCACAGGTGAGCGGGCGGGACGGCCCTTCTCCTCCGGGCTGTAATTAGCAAGAGGTAAGGGTTTAAGGGATGGTTG

GTTGGTGGGGTATTAATGTTTAATTACCTGTTTTACAGGCCTGAAATCACTTGGTTTTAGGTTGGGGATCCGGTAC

CCAATTGCCATGGGCTAGCATGCATGAGCTCCCTGCAGGGTTTATCTGCAGAATTCAGCCACCACCGGCACAATGA

ATGGCACAGAAGGCCCTAACTTCTACGTGCCCTTCTCCAATGCGACGGGTGTGGTACGCAGCCCCTTCGAGTACCC

ACAGTACTACCTGGCTGAGCCATGGCAGTTCTCCATGCTGGCCGCCTACATGTTTCTGCTGATCGTGCTGGGCTTC

CCCATCAACTTCCTCACGCTCTACGTCACCGTCCAGCACAAGAAGCTGCGCACGCCTCTCAACTACATCCTGCTCA

ACCTAGCCGTGGCTGACCTCTTCATGGTCCTAGGTGGCTTCACCAGCACCCTCTACACCTCTCTGCATGGATACTT

CGTCTTCGGGCCCACAGGATGCAATTTGGAGGGCTTCTTTGCCACCCTGGGCGGTGAAATTGCCCTGTGGTCCTTG

GTGGTCCTGGCCATCGAGCGGTACGTGGTGGTGTGTAAGCCCATGAGCAACTTCCGCTTCGGGGAGAACCATGCCA

TCATGGGCGTTGCCTTCACCTGGGTCATGGCGCTGGCCTGCGCCGCACCCCCACTCGCCGGCTGGTCCAGGTACAT

CCCCGAGGGCCTGCAGTGCTCGTGTGGAATCGACTACTACACGCTCAAGCCGGAGGTCAACAACGAGTCTTTTGTC

ATCTACATGTTCGTGGTCCACTTCACCATCCCCATGATTATCATCTTTTTCTGCTATGGGCAGCTCGTCTTCACCG

TCAAGGAGGCCGCTGCCCAGCAGCAGGAGTCAGCCACCACACAGAAGGCAGAGAAGGAGGTCACCCGCATGGTCAT

CATCATGGTCATCGCTTTCCTGATCTGCTGGGTGCCCTACGCCAGCGTGGCATTCTACATCTTCACCCACCAGGGC

TCCAACTTCGGTCCCATCTTCATGACCATCCCAGCGTTCTTTGCCAAGAGCGCCGCCATCTACAACCCTGTCATCT

ATATCATGATGAACAAGCAGTTCCGGAACTGCATGCTCACCACCATCTGCTGCGGCAAGAACCCACTGGGTGACGA

TGAGGCCTCTGCTACCGTGTCCAAGACGGAGACGAGCCAGGTGGCCCCGGCCTAACCAAGAAAGCTTAAGTTTGTG

TCCCGGCTTAGGGCTAAATGTCTAGGACAGAATGGAACACATAGTAGCTGATTAATAAATGCTAGCTGGATGAAGG

GAGGAATGAGTGACTGACTGAGTGGATATATGAGTGAAGGGATTAATGGAAGGGAACATGGATGTCCTCAGGTGCC

CAACCTGGCAGATCCAGTCATGTCTGGCTGGAATCTATAAGCAGTTTTACATACCTGCCCTGAGCTTTATTGCGGT

AGTTTATCACAGTTAAATTGCTAACGCAGTCAGTGCTTCTGACACAACAGTCTCGAACTTAAGCTGCAGTGACTCT

CTTAAGGTAGCCTTGCAGAAGTTGGTCGTGAGGCACTGGGCAGGTAAGTATCAAGGTTACAAGACAGGTTTAAGGA

GACCAATAGAAACTGGGCTTGTCGAGACAGAGAAAAACCTAACCCCCATGGTTGGCGAGGGACTGCTGTGTGTGAA

ATGGTAACTGCCCTCAAGGAGCTTACAATCTAGCTGGGGGTAAATGACTTGCACATGAACACAACTAGACTGTGAG

CTTCTAGAGGGCAGGGACCTTACCCTAGTCATCTCTCTTCTCACCCTGCACACCCTCCCTGAGGGATCTCATGACT

CTTGCGTTTCTGATAGGCACCTATTGGTCTTACTGACATCCACTTTGCCTTTCTCTCCACAGGTGTCCACTCCCAG

TTCACACCGGCACAATGAATGGCACAGAAGGCCCTAACTTCTACGTGCCCTTCTCCAATGCGACGGGTGTGGTACG

CAGCCCCTTCGAGTACCCACAGTCAGAGATAAATGACAGTGACAGCAACGTGAGCTGCAGCCCTTAGGACTGAGAA

AGCATCGAGACCAGGGGTCTCCGGCAAGGCCTAGGTCCTCCCTTCAGTATGGAAACCTTGCCTCATGTCTCTCAGC

-continued

CTCCTTGGCCTGTGGAGATCCAGCCCTTCCTCTTGGCTTCTGGATACATTTGCTCTTCTACACCAGCAACCAAGTG

GCAACAGTTCCAGGCCAGTATGGAGTTTTAGAAGCCATGCCAATATGCCCACCTTCAGGGAGCAGCTGAGTCCTTG

ATGCCACCCTTGTTCTGAAGAGTTCAGAAACACAGTGCAAGACATGACCAGGCCTCATCCTTAGGATGCTCATGGA

TCCAGTTCTTAGCTCCCTTGTTGGATATGCTGTTTTCCTTGGCCTTTGGTCTTTTCTTTATCCCAGAGGGTTTTGG

CTTTAAGGCCAACAGGAACTATGGGGTACCAGAATTGAGCAGCCTCAGTCTGCATCCCTCCTCTATAGAACCACAG

CTGGGCCCTCAGCAGGCCCAACTCTGCATGGGGACAGAGGCATTAAAAGC

RK-miR-708-intron hRho wt
(SEQ ID NO: 8)
GGGCCCCAGAAGCCTGGTGGTTGTTTGTCCTTCTCAGGGGAAAAGTGAGGCGGCCCCTTGGAGGAAGGG

GCCGGGCAGAATGATCTAATCGGATTCCAAGCAGCTCAGGGGATTGTCTTTTTCTAGCACCTTCTTGCC

ACTCCTAAGCGTCCTCCGTGACCCCGGCTGGGATTTAGCCTGGTGCTGTGTCAGCCCCGGTCTCCCAGG

GGCTTCCCAGTGGTCCCCAGGAACCCTCGACAGGGCCCGGTCTCTCTCGTCCAGCAAGGGCAGGGACGG

GCCACAGGCCAAGGGCACTAGAAGCTTTATTGCGGTAGTTTATCACAGTTAAATTGCTAACGCAGTCAG

TGCTTCTGACACAACAGTCTCGAACTTAAGCTGCAGTGACTCTCTTAAGGTAGCCTTGCAGAAGTTGGT

CGTGAGGCACTGGGCAGGTAAGTATCAAGGTTACAAGACAGGTTTAAGGAGACCAATAGAAACTGGGCT

TGTCGAGACAGAGAAAAACCTAACCCCCATGGTTGGCGAGGGACTGCTGTGTGTGAAATGGTAACTGCC

CTCAAGGAGCTTACAATCTAGCTGGGGGTAAATGACTTGCACATGAACACAACTAGACTGTGAGCTTCT

AGAGGGCAGGGACCTTACCCTAGTCATCTCTCTTCTCACCCTGCACACCCTCCCTGAGGGATCTCATGA

CTCTTGCGTTTCTGATAGGCACCTATTGGTCTTACTGACATCCACTTTGCCTTTCTCTCCACAGGTGTC

CACTCCCAGTTCACACCGGCACAATGAATGGCACAGAAGGCCCTAACTTCTACGTGCCCTTCTCCAATG

CGACGGGTGTGGTACGCAGCCCCTTCGAGTACCCACAGTACTACCTGGCTGAGCCATGGCAGTTCTCCA

TGCTGGCCGCCTACATGTTTCTGCTGATCGTGCTGGGCTTCCCCATCAACTTCCTCACGCTCTACGTCA

CCGTCCAGCACAAGAAGCTGCGCACGCCTCTCAACTACATCCTGCTCAACCTAGCCGTGGCTGACCTCT

TCATGGTCCTAGGTGGCTTCACCAGCACCCTCTACACCTCTCTGCATGGATACTTCGTCTTCGGGCCCA

CAGGATGCAATTTGGAGGGCTTCTTTGCCACCCTGGGCGGTGAAATTGCCCTGTGGTCCTTGGTGGTCC

TGGCCATCGAGCGGTACGTGGTGGTGTGTAAGCCCATGAGCAACTTCCGCTTCGGGGAGAACCATGCCA

TCATGGGCGTTGCCTTCACCTGGGTCATGGCGCTGGCCTGCGCCGCACCCCCACTCGCCGGCTGGTCCA

GGTACATCCCCGAGGGCCTGCAGTGCTCGTGTGGAATCGACTACTACACGCTCAAGCCGGAGGTCAACA

ACGAGTCTTTTGTCATCTACATGTTCGTGGTCCACTTCACCATCCCCATGATTATCATCTTTTTCTGCT

ATGGGCAGCTCGTCTTCACCGTCAAGGAGGCCGCTGCCCAGCAGCAGGAGTCAGCCACCACACAGAAGG

CAGAGAAGGAGGTCACCCGCATGGTCATCATCATGGTCATCGCTTTCCTGATCTGCTGGGTGCCCTACG

CCAGCGTGGCATTCTACATCTTCACCCACCAGGGCTCCAACTTCGGTCCCATCTTCATGACCATCCCAG

CGTTCTTTGCCAAGAGCGCCGCCATCTACAACCCTGTCATCTATATCATGATGAACAAGCAGTTCCGGA

ACTGCATGCTCACCACCATCTGCTGCGGCAAGAACCCACTGGGTGACGATGAGGCCTCTGCTACCGTGT

CCAAGACGGAGACGAGCCAGGTGGCCCCGGCC

RK-intron-miR-708-op-hRho wt
(SEQ ID NO: 9)
CAATCTCCCAGATGCTGATTCAGCCAGGAACTAGTTATTAATAGTAATCAATTACGGGGTCATTAGTTC

ATAGCCCATATATGGAGTTCCGCGTTACATAACTTACGGTAAATGGCCCGCCTGGCTGACCGCCCAACG

ACCCCCGCCCATTGACGTCAATAATGACGTATGTTCCCATAGTAACGCCAATAGGGACTTTCCATTGAC

-continued

```
GTCAATGGGTGGAGTATTTACGGTAAACTGCCCACTTGGCAGTACATCAAGTGTATCATATGCCAAGTA

CGCCCCCTATTGACGTCAATGACGGTAAATGGCCCGCCTGGCATTATGCCCAGTACATGACCTTATGGG

ACTTTCCTACTTGGCAGTACATCTACGTATTAGTCATCGCTATTACCACAAATAGTTATCGAGCCGCTG

AGCCGGGGGCGGGGGGTGTGAGACTGGAGGCGATGGACGGAGCTGACGGCACACACAGCTCAGATCTG

TCAAGTGAGCCATTGTCAGGGCTTGGGGACTGGATAAGTCAGGGGGTCTCCTGGGAAGAGATGGGATAG

GTGAGTTCAGGAGGAGACATTGTCAACTGGAGCCATGTGGAGAAGTGAATTTAGGGCCCAAAGGTTCCA

GTCGCAGCCTGAGGCCACCAGACTGACATGGGGAGGAATTCCCAGAGGACTCTGGGCAGACAAGATGA

GACACCCTTTCCTTTCTTTACCTAAGGGCCTCCACCCGATGTCACCTTGGCCCCTCTGCAAGCCAATTA

GGCCCCGGTGGCAGCAGTGGGATTAGCGTTAGTATGATATCTCGCGGATGCTGAATCAGCCTCTGGCTT

AGGGAGAGAAGGTCACTTTATAAGGGTCTGGGGGGGTCAGTGCCTGGAGTTGCGCTGTGGGAGCCGTC

AGTGGCTGAGCTCAAGAGGTAAGGGTTTAAGGGATGGTTGGTTGTGGGTATTAATGTTTAATTACCT

GTTTTACAGGCCTGAAATCACTTGGTTTTAGGTTGGTACATCTGCAGAATTCAGCCACCACCGGCACAA

TGAATGGCACAGAAGGCCCTAACTTCTACGTGCCCTTCTCCAATGCGACGGGTGTGGTACGCAGCCCCT

TCGAGTACCCACAGTACTACCTGGCTGAGCCATGGCAGTTCTCCATGCTGGCCGCCTACATGTTTCTGC

TGATCGTGCTGGGCTTCCCCATCAACTTCCTCACGCTCTACGTCACCGTCCAGCACAAGAAGCTGCGCA

CGCCTCTCAACTACATCCTGCTCAACCTAGCCGTGGCTGACCTCTTCATGGTCCTAGGTGGCTTCACCA

GCACCCTCTACACCTCTCTGCATGGATACTTCGTCTTCGGGCCCACAGGATGCAATTTGGAGGGCTTCT

TTGCCACCCTGGGCGGTGAAATTGCCCTGTGGTCCTTGGTGGTCCTGGCCATCGAGCGGTACGTGGTGG

TGTGTAAGCCCATGAGCAACTTCCGCTTCGGGGAGAACCATGCCATCATGGGCGTTGCCTTCACCTGGG

TCATGGCGCTGGCCTGCGCCGCACCCCCACTCGCCGGCTGGTCCAGGTACATCCCCGAGGGCCTGCAGT

GCTCGTGTGGAATCGACTACTACACGCTCAAGCCGGAGGTCAACAACGAGTCTTTTGTCATCTACATGT

TCGTGGTCCACTTCACCATCCCCATGATTATCATCTTTTTCTGCTATGGGCAGCTCGTCTTCACCGTCA

AGGAGGCCGCTGCCCAGCAGCAGGAGTCAGCCACCACACAGAAGGCAGAGAAGGAGGTCACCCGCATGG

TCATCATCATGGTCATCGCTTTCCTGATCTGCTGGGTGCCCTACGCCAGCGTGGCATTCTACATCTTCA

CCCACCAGGGCTCCAACTTCGGTCCCATCTTCATGACCATCCCAGCGTTCTTTGCCAAGAGCGCCGCCA

TCTACAACCCTGTCATCTATATCATGATGAACAAGCAGTTCCGGAACTGCATGCTCACCACCATCTGCT

GCGGCAAGAACCCACTGGGTGACGATGAGGCCTCTGCTACCGTGTCCAAGACGGAGACGAGCCAGGTGG

CCCCGGCCTAACCAAGAAAGCTTAAGTTTGTGTCCCGGCTTAGGGCTAAATGTCTAGGACAGAATGGAA

CACATAGTAGCTGATTAATAAATGCTAGCTGGATGAAGGGAGGAATGAGTGACTGACTGAGTGGATATA

TGAGTGAAGGGATTAATGGAAGGGAACATGGATGTCCTCAGGTGCCCAACCTGGCAGATCCAGTCATGT

CTGGCTGGAATCTATAAGCAGTTTTACATACCTGCCCTGAGCTTTATTGCGGTAGTTTATCACAGTTAA

ATTGCTAACGCAGTCAGTGCTTCTGACACAACAGTCTCGAACTTAAGCTGCAGTGACTCTCTTAAGGTA

GCCTTGCAGAAGTTGGTCGTGAGGCACTGGGCAGGTAAGTATCAAGGTTACAAGACAGGTTTAAGGAGA

CCAATAGAAACTGGGCTTGTCGAGACAGAGAAAAACCTAACCCCCATGGTTGGCGAGGGACTGCTGTGT

GTGAAATGGTAACTGCCCTCAAGGAGCTTACAATCTAGCTGGGGTAAATGACTTGCACATGAACACAA

CTAGACTGTGAGCTTCTAGAGGGCAGGGACCTTACCCTAGTCATCTCTCTTCTCACCCTGCACACCCTC

CCTGAGGGATCTCATGACTCTTGCGTTTCTGATAGGCACCTATTGGTCTTACTGACATCCACTTTGCCT

TTCTCTCCACAGGTGTCCACTCCCAGTTCACACCGGCACAATGAATGGCACAGAAGGCCCTAACTTCTA

CGTGCCCTTCTCCAATGCGACGGGTGTGGTACGCAGCCCCTTCGAGTACCCACAGTCAGAGATAAATGA

CAGTGACAGCAACGTGAGCTGCAGCCCTTAGGACTGAGAAAGCATCGAGACCAGGGGTCTCCGGCAAGG
```

-continued

CCTAGGTCCTCCCTTCAGTATGGAAACCTTGCCTCATGTCTCTCAGCCTCCTTGGCCTGTGGAGATCCA

GCCCTTCCTCTTGGCTTCTGGATACATTTGCTCTTCTACACCAGCAACCAAGTGGCAACAGTTCCAGGC

CAGTATGGAGTTTTAGAAGCCATGCCAATATGCCCACCTTCAGGGAGCAGCTGAGTCCTTGATGCCACC

CTTGTTCTGAAGAGTTCAGAAACACAGTGCAAGACATGACCAGGCCTCATCCTTAGGATGCTCATGGAT

CCAGTTCTTAGCTCCCTTGTTGGATATGCTGTTTTCCTTGGCCTTTGGTCTTTTCTTTATCCCAGAGGG

TTTTGGCTTTAAGGCCAACAGGAACTATGGGGTACCAGAATTGAGCAGCCTCAGTCTGCATCCCTCCTC

TATAGAACCACAGCTGGGCCCTCAGCAGGCCCAACTCTGCATGGGGACAGAGGCATTAAAAGC

Chimeric Intron
(SEQ ID NO: 10)
GGAGTCGCTGCGACGCTGCCTTCGCCCCGTGCCCCGCTCCGCCGCCGCCTCGCGCCGCCCGCCCCGGCT

CTGACTGACCGCGTTACTCCCACAGGTGAGCGGGCGGGACGGCCCTTCTCCTCCGGGCTGTAATTAGCG

CTTGGTTTAATGACGGCTTGTTTCTTTTCTGTGGCTGCGTGAAAGCCTTGAGGGGCTCCGGGAGGGCCC

TTTGTGCGGGGGGAGCGGCTCGGGGGTGCGTGCGTGTGTGTGCGTGGGGAGCGCCGCGTGCGGCTC

CGCGCTGCCCGGCGGCTGTGAGCGCTGCGGGCGCGGCGCGGGGCTTTGTGCGCTCCGCAGTGTGCGCGA

GGGGAGCGCGGCCGGGGGCGGTGCCCCGCGGTGCGGGGGGGGCTGCGAGGGGAACAAAGGCTGCGTGCG

GGGTGTGTGCGTGGGGGGGTGAGCAGGGGGTGTGGGCGCGTCGGTCGGGCTGCAACCCCCCCTGCACCC

CCCTCCCCGAGTTGCTGAGCACGGCCCGGCTTCGGGTGCGGGGCTCCGTACGGGGCGTGGCGCGGGGCT

CGCCGTGCCGGGCGGGGGGTGGCGGCAGGTGGGGGTGCCGGGCGGGGGGGGCCGCCTCGGGCCGGGGA

GGGCTCGGGGGAGGGGCGCGGCGGCCCCCGGAGCGCCGGCGGCTGTCGAGGCGCGGCGAGCCGCAGCCA

TTGCCTTTTATGGTAATCGTGCGAGAGGGCGCAGGGACTTCCTTTGTCCCAAATCTGTGCGGAGCCGAA

ATCTGGGAGGCGCCGCCGCACCCCCTCTAGCGGGCGCGGGGCGAAGCGGTGCGGCGCCGGCAGGAAGGA

AATGGGCGGGGAGGGCCTTCGTGCGTCGCCGCGCCGCCGTCCCCTTCTCCCTCTCCAGCCTCGGGGCTG

TCCGCGGGGGACGGCTGCCTTCGGGGGGGACGGGGCAGGGCGGGGTTCGGCTTCTGGCGTGTGACCGG

CGGCTCTAGAGCCTCTGCTAACCATGTTCATGCCTTCTTCTTTTTCCTACA

Stuffer sequence
(SEQ ID NO: 11)
AAGCTTGAAATGCCACCTCCTCTGATATTCTAGGTGTCCTGGAAGCCTGTCTCATCTTGCCCTGTAGTG

TTGGGTCACCTGGCCCCCAGCCTGTAACATCCCCAGGGCCCTACACCCAGAGAAACACGGGGCTGGTGG

CAGTGCCCAGTGACAACCGTTTAGTGGATAAGAGAAGAGTGACCACACCAGGCTGAGTGCTCCTCTCTG

GTTTTCCATGGGGAGACAATGCCACCCTGAGCAGGGTCTGGTGTGAGCGGCAGCTGGCTCTGGGCTCTC

TGATCCGTTACCCTCTCAGCCTCTTTGTTCTTTCTCAACCCCTGGAGCAGAGACCTCAGGAGGTGCTGG

CATGGAACAGAGAAATTCCAGCCTCGATTCCTATTATGAACCCGACACCTTTTGTATTTTCATCTTGGT

TTTACAGTGTACAAAACGAACTAGATCAGCAGGGCATGGGCATAATCACGAATGCACACACATACACTA

ATGTGTGGCTCATGTTTAAGTATCACTTACTACAGGACACCCAATCTAACAGCACCGATAAAGTGACAG

AGAAACGCAAGCCTTCTGCGAACATGGCCTGGCTGTTCCAATTCCGAACCTTGCTTTTCTGGGCCTTGC

CACACAGGCTCTTCCCCCGTCCCCCAGGGACATTCTACCCTTGAACTCCACACTCCACTGCTGCCTTT

GCCAGGAAGCCCATCTGTTCCTTTTTGGTTCTGCCAGAACGTGTGGTGGTGCTGCTGTCCCTGCCTTGG

GCACTGGATATTGGAAGGGACAGTGTCCACACTGGAGTGGGAAGTTCCAGGGACGAGACCTTTACCT

CCTCACCCTGGGTACTGTTCTCCTCATGGAGCATGGACGGCGCTGCCTGAACTCAGTGGTGGCCTCATT

-continued

CTGGAAGCCAAGTTTATACAGAGTAGCAGTGACCCAGGGATGTGGGGTTCACCCTCCTCAGCCCTCTGG

CCAGTCCTGATGGGCCTCAGTCCCAACATGGCTAAGAGGTGTGGGCAGCTTCTTGGTCACCCTCAGGTT

GGGGAATCACCTTCTGTCTTCATTTTCCAGGAACTTGGTGATGATATCGTGGGTGAGTTCATTTACCAG

GTGCTGTAGTTTCCCCTCATCAGGCAGGAAGAAGATGGCGGTGGCATTGCCCAGGTATTTCATCAGCAG

CACCCAGCTGGACAGCTTCTTACAGTGCTGGATGTTAAACATGCCTAAACGCTTCATCATAGGCACCTT

CACGGTGGTCACCTGGTCCACGTGGAAGTCCTCTTCCTCGGTGTCCTTGACTTCAAAGGGTCTCTCCCA

TTTGCCTGGAGAGAGGGGAAGGTGGGCATCACCAGGGGTGAGTGAAGGTTTGGAAGAGTGTAGCAGAAT

AAGAAACCATGAGTCCCCTCCCTGAGAAGCCCTGAGCCCCCTTGACGACACACATCCCTCGAGGCTCAG

CTTCATCATCTGTAAAAGGTGCTGAAACTGACCATCCAAGCTGCCGAAAAAGATTGTGTGGGGATAATT

CAAAACTAGAGGAAGATGCAGAATTTCTACATCGTGGCGATGTCAGGCTAAGAGATGCCATCGTGGCTG

TGCATTTTTATTGGAATCATATGTTTATTTGAGGGTGTCTTGGATATTACAAATAAAATGTTGGAGCAT

CAGGCATATTTGGTACCTTCTGTCTAAGGCTCCCTGCCCCTTGTTAATTGGCAGCTCAGTTATTCATCC

AGGGCAAACATTCTGCTTACTATTCCTGAGAGCTTTCCTCATCCTCTAGATTGGCAGGGAAATGCAGA

TGCCTGAGCAGCCTCCCCTCTGCCATACCAACAGAGCTTCACCATCGAGGCATGCAGAGTGGACAGGGG

CCTCAGGGACCCCTGATCCCAGCTTTCTCATTGGACAGAAGGAGGAGACTGGGGCTGGAGAGGGACCTG

GGCCCCCACTAAGGCCACAGCAGAGCCAGGACTTTAGCTGTGCTGACTGCAGCCTGGCTTGCCTCCACT

GCCCTCCTTTGCCTCAAGAGCAAGGGAGCCTCAGAGTGGAGGAAGCAGCCCCTGGCCTTGCCTCCCACC

TCCCCTCCCCTATGCTGTTTTCCTGGGACAGTGGGAGCTGGCTTAGAATGCCCTGGGGCCCCCAGGACC

CTGGCATTTTAACCCCTCAGGGGCAGGAAGGCAGCCTGAGATACAGAAGAGTCCATCACCTGCTGTATG

CCACACACCATCCCCACAGTTACGTACTAGT pCBA-hRhodopsin-miR708 (miR-155 scaffold)
(SEQ ID NO: 12)
GAATTCGGACCGTCGACATTGATTATTGACTAGTTATTAATAGTAATCAATTACGGGGTCATTAGTTCA

TAGCCCATATATGGAGTTCCGCGTTACATAACTTACGGTAAATGGCCCGCCTGGCTGACCGCCCAACGA

CCCCCGCCCATTGACGTCAATAATGACGTATGTTCCCATAGTAACGCCAATAGGGACTTTCCATTGACG

TCAATGGGTGGAGTATTTACGGTAAACTGCCCACTTGGCAGTACATCAAGTGTATCATATGCCAAGTAC

GCCCCCTATTGACGTCAATGACGGTAAATGGCCCGCCTGGCATTATGCCCAGTACATGACCTTATGGGA

CTTTCCTACTTGGCAGTACATCTACGTATTAGTCATCGCTATTACCATGGTCGAGGTGAGCCCCACGTT

CTGCTTCACTCTCCCCATCTCCCCCCCCTCCCCACCCCCAATTTTGTATTTATTTATTTTTTAATTATT

TTGTGCAGCGATGGGGGCGGGGGGGGGGGGGGCGCGCGCCAGGCGGGGGGGGCGGGGCGAGGGGCG

GGGCGGGGCGAGGCGGAGAGGTGCGGCGGCAGCCAATCAGAGCGGCGCGCTCCGAAAGTTTCCTTTTAT

GGCGAGGCGGCGGCGGCGGCGGCCCTATAAAAAGCGAAGCGCGCGGCGGGCGGGGAGTCGCTGCGACGC

TGCCTTCGCCCCGTGCCCCGCTCCGCCGCCGCCTCGCGCCGCCCGCCCCGGCTCTGACTGACCGCGTTA

CTCCCACAGGTGAGCGGGCGGGACGGCCCTTCTCCTCCGGGCTGTAATTAGCGCTTGGTTTAATGACGG

CTTGTTTCTTTTCTGTGGCTGCGTGAAAGCCTTGAGGGGCTCCGGGAGGGCCCTTTGTGCGGGGGGAGC

GGCTCGGGGGTGCGTGCGTGTGTGTGCGTGGGGAGCGCCGCGTGCGGCTCCGCGCTGCCCGGCGGC

TGTGAGCGCTGCGGGCGCGGCGCGGGGCTTTGTGCGCTCCGCAGTGTGCGCGAGGGGAGCGCGGCCGGG

GGCGGTGCCCCGCGGTGCGGGGGGGCTGCGAGGGGAACAAAGGCTGCGTGCGGGGTGTGTGCGTGGGG

GGGTGAGCAGGGGGTGTGGGCGCGTCGGTCGGGCTGCAACCCCCCCTGCACCCCCCTCCCCGAGTTGCT

GAGCACGGCCCGGCTTCGGGTGCGGGGCTCCGTACGGGGCGTGGCGCGGGGCTCGCCGTGCCGGGCGGG

-continued

```
GGGTGGCGGCAGGTGGGGGTGCCGGGCGGGGCGGGGCCGCCTCGGGCCGGGGAGGGCTCGGGGGAGGGG

CGCGGCGGCCCCCGGAGCGCCGGCGGCTGTCGAGGCGCGGCGAGCCGCAGCCATTGCCTTTTATGGTAA

TCGTGCGAGAGGGCGCAGGGACTTCCTTTGTCCCAAATCTGTGCGGAGCCGAAATCTGGGAGGCGCCGC

CGCACCCCCTCTAGCGGGCGCGGGGCGAAGCGGTGCGGCGCCGGCAGGAAGGAAATGGGCGGGGAGGGC

CTTCGTGCGTCGCCGCGCCGCCGTCCCCTTCTCCCTCTCCAGCCTCGGGGCTGTCCGCGGGGGACGGC

TGCCTTCGGGGGGGACGGGGCAGGGCGGGGTTCGGCTTCTGGCGTGTGACCGGCGGCTCTAGAGCCTCT

GCTAACCATGTTCATGCCTTCTTCTTTTTCCTACAGCTCCTGGGCAACGTGCTGGTTATTGTGCTGTCT

CATCATTTTGGCAAAGAATTCTTCGAAAGATCTGCTAGCTTAATTAACCCAAACGGGCCCTCTAGACTC

GAGCGGCCGCCACTGTGCTGGATATCTGCAGAATTCAGCCACCACCGGCACAATGAATGGCACAGAAGG

CCCTAACTTCTACGTGCCCTTCTCCAATGCGACGGGTGTGGTACGCAGCCCCTTCGAGTACCCACAGTA

CTACCTGGCTGAGCCATGGCAGTTCTCCATGCTGGCCGCCTACATGTTTCTGCTGATCGTGCTGGGCTT

CCCCATCAACTTCCTCACGCTCTACGTCACCGTCCAGCACAAGAAGCTGCGCACGCCTCTCAACTACAT

CCTGCTCAACCTAGCCGTGGCTGACCTCTTCATGGTCCTAGGTGGCTTCACCAGCACCCTCTACACCTC

TCTGCATGGATACTTCGTCTTCGGGCCCACAGGATGCAATTTGGAGGGCTTCTTTGCCACCCTGGGCGG

TGAAATTGCCCTGTGGTCCTTGGTGGTCCTGGCCATCGAGCGGTACGTGGTGGTGTAAGCCCATGAG

CAACTTCCGCTTCGGGGAGAACCATGCCATCATGGGCGTTGCCTTCACCTGGGTCATGGCGCTGGCCTG

CGCCGCACCCCCACTCGCCGGCTGGTCCAGGTACATCCCCGAGGGCCTGCAGTGCTCGTGTGGAATCGA

CTACTACACGCTCAAGCCGGAGGTCAACAACGAGTCTTTTGTCATCTACATGTTCGTGGTCCACTTCAC

CATCCCCATGATTATCATCTTTTTCTGCTATGGGCAGCTCGTCTTCACCGTCAAGGAGGCCGCTGCCCA

GCAGCAGGAGTCAGCCACCACACAGAAGGCAGAGAAGGAGGTCACCCGCATGGTCATCATCATGGTCAT

CGCTTTCCTGATCTGCTGGGTGCCCTACGCCAGCGTGGCATTCTACATCTTCACCCACCAGGGCTCCAA

CTTCGGTCCCATCTTCATGACCATCCCAGCGTTCTTTGCCAAGAGCGCCGCCATCTACAACCCTGTCAT

CTATATCATGATGAACAAGCAGTTCCGGAACTGCATGCTCACCACCATCTGCTGCGGCAAGAACCCACT

GGGTGACGATGAGGCCTCTGCTACCGTGTCCAAGACGGAGACGAGCCAGGTGGCCCCGGCCTAACCAAG

AAAGCTTAAGTTTGGGACTAGTGGCGGCCGCTCGAGCATGCATCTAGAGGGCCCTATTCTATAGTGTCA

CCTAAATGCTAGAGCTCGCTGATCAGCCTCGACTGTGCCTTCTAGTTGCCAGCCATCTGTTGTTTGCCC

CTCCCCCGTGCCTTCCTTGACCCTGGAAGGTGCCACTCCCACTGTCCTTTCCTAATAAAATGAGGAAAT

TGCATCGCATTGTCTGAGTAGGTGTCATTCTATTCTGGGGGGTGGGGTGGGGCAGGACAGCAAGGGGGA

GGATTGGGAAGACAATAGCAGGCATGCTGGGGAGCTAGAGTCGACCGGACCGCTGCAGGCATGCAAGCT

TGGCGTAATCATGGTCATAGCTGTTTCCTGTGTGAAATTGTTATCCGCTCACAATTCCACACAACATAC

GAGCCGGAAGCATAAAGTGTAAAGCCTGGGGTGCCTAATGAGTGAGCTAACTCACATTAATTGCGTTGC

GCTCACTGCCCGCTTTCCAGTCGGGAAACCTGTCGTGCCAGCTGCATTAATGAATCGGCCAACGCGCGG

GGAGAGGCGGTTTGCGTATTGGGCGCTCTTCCGCTTAGTCATCGCTATTACCATGGTGATGCGGTTTT

GGCAGTACATCAATGGGCGTGGATAGCGGTTTGACTCACGGGGATTTCCAAGTCTCCACCCCATTGACG

TCAATGGGAGTTTGTTTTGGCACCAAAATCAACGGGACTTTCCAAAATGTCGTAACAACTCCGCCCCAT

TGACGCAAATGGGCGGTAGGCGTGTACGGTGGGAGGTCTATATAAGCAGAGCTCTCTGGCTAACTAGAG

AACCCACTGCTTACTGGCTTATCGAAATTAATACGACTCACTATAGGGAGTCCCAAGCTGGCTAGTTAA

GCTATCAACAAGTTTGTACAAAAAAGCAGGCTTTAAAGGGAGGTAGTGAGTCGACCAGTGGATCCTGGA

GGCTTGCTGAAGGCTGTATGCTGAAGGAGCTTACAATCTAGCTGGGGTTTTGGCCACTGACTGACCCCA

GCTAGTGTAAGCTCCTTCAGGACACAAGGCCTGTTACTAGCACTCACATGGAACAAATGCCCAGATCT

GGCCGCACTCGAGATGCTTCCTCGCTCACTGACTCGCTGCGCTCGGTCGTTCGGCTGCGGCGAGCGGTA
```

-continued

```
TCAGCTCACTCAAAGGCGGTAATACGGTTATCCACAGAATCAGGGGATAACGCAGGAAAGAACATGTGA
GCAAAAGGCCAGCAAAAGGCCAGGAACCGTAAAAAGGCCGCGTTGCTGGCGTTTTTCCATAGGCTCCGC
CCCCCTGACGAGCATCACAAAAATCGACGCTCAAGTCAGAGGTGGCGAAACCCGACAGGACTATAAAGA
TACCAGGCGTTTCCCCCTGGAAGCTCCCTCGTGCGCTCTCCTGTTCCGACCCTGCCGCTTACCGGATAC
CTGTCCGCCTTTCTCCCTTCGGGAAGCGTGGCGCTTTCTCATAGCTCACGCTGTAGGTATCTCAGTTCG
GTGTAGGTCGTTCGCTCCAAGCTGGGCTGTGTGCACGAACCCCCCGTTCAGCCCGACCGCTGCGCCTTA
TCCGGTAACTATCGTCTTGAGTCCAACCCGGTAAGACACGACTTATCGCCACTGGCAGCAGCCACTGGT
AACAGGATTAGCAGAGCGAGGTATGTAGGCGGTGCTACAGAGTTCTTGAAGTGGTGGCCTAACTACGGC
TACACTAGAAGGACAGTATTTGGTATCTGCGCTCTGCTGAAGCCAGTTACCTTCGGAAAAAGAGTTGGT
AGCTCTTGATCCGGCAAACAAACCACCGCTGGTAGCGGTGGTTTTTTTGTTTGCAAGCAGCAGATTACG
CGCAGAAAAAAAGGATCTCAAGAAGATCCTTTGATCTTTTCTACGGGGTCTGACGCTCAGTGGAACGAA
AACTCACGTTAAGGGATTTTGGTCATGAGATTATCAAAAAGGATCTTCACCTAGATCCTTTTAAATTAA
AAATGAAGTTTTAAATCAATCTAAAGTATATATGAGTAAACTTGGTCTGACAGTTACCAATGCTTAATC
AGTGAGGCACCTATCTCAGCGATCTGTCTATTTCGTTCATCCATAGTTGCCTGACTCCCCGTCGTGTAG
ATAACTACGATACGGGAGGGCTTACCATCTGGCCCCAGTGCTGCAATGATACCGCGAGACCCACGCTCA
CCGGCTCCAGATTTATCAGCAATAAACCAGCCAGCCGGAAGGGCCGAGCGCAGAAGTGGTCCTGCAACT
TTATCCGCCTCCATCCAGTCTATTAATTGTTGCCGGGAAGCTAGAGTAAGTAGTTCGCCAGTTAATAGT
TTGCGCAACGTTGTTGCCATTGCTACAGGCATCGTGGTGTCACGCTCGTCGTTTGGTATGGCTTCATTC
AGCTCCGGTTCCCAACGATCAAGGCGAGTTACATGATCCCCCATGTTGTGCAAAAAAGCGGTTAGCTCC
TTCGGTCCTCCGATCGTTGTCAGAAGTAAGTTGGCCGCAGTGTTATCACTCATGGTTATGGCAGCACTG
CATAATTCTCTTACTGTCATGCCATCCGTAAGATGCTTTTCTGTGACTGGTGAGTACTCAACCAAGTCA
TTCTGAGAATAGTGTATGCGGCGACCGAGTTGCTCTTGCCCGGCGTCAATACGGGATAATACCGCGCCA
CATAGCAGAACTTTAAAAGTGCTCATCATTGGAAAACGTTCTTCGGGGCGAAAACTCTCAAGGATCTTA
CCGCTGTTGAGATCCAGTTCGATGTAACCCACTCGTGCACCCAACTGATCTTCAGCATCTTTTACTTTC
ACCAGCGTTTCTGGGTGAGCAAAAACAGGAAGGCAAAATGCCGCAAAAAAGGGAATAAGGGCGACACGG
AAATGTTGAATACTCATACTCTTCCTTTTTCAATATTATTGAAGCATTTATCAGGGTTATTGTCTCATG
AGCGGATACATATTTGAATGTATTTAGAAAAATAAACAAATAGGGGTTCCGCGCACATTTCCCCGAAAA
GTGCCACCTGACGTCTAAGAAACCATTATTATCATGACATTAACCTATAAAAATAGGCGTATCACGAGG
CCCTTTCGTCTCGCGCGTTTCGGTGATGACGGTGAAAACCTCTGACACATGCAGCTCCCGGAGACGGTC
ACAGCTTGTCTGTAAGCGGATGCCGGGAGCAGACAAGCCCGTCAGGGCGCGTCAGCGGGTGTTGGCGGG
TGTCGGGGCTGGCTTAACTATGCGGCATCAGAGCAGATTGTACTGAGAGTGCACCATATGCGGTGTGAA
ATACCGCACAGATGCGTAAGGAGAAAATACCGCATCAGGCGCCATTCGCCATTCAGGCTGCGCAACTGT
TGGGAAGGGCGATCGGTGCGGGCCTCTTCGCTATTACGCCAGCTGGCGAAAGGGGGATGTGCTGCAAGG
CGATTAAGTTGGGTAACGCCAGGGTTTTCCCAGTCACGACGTTGTAAAACGACGGCCAGT
```

MIR155 scaffold
(SEQ ID NO: 13)
```
GATCCTGGAGGCTTGCTGAAGGCTGTATGCTGAAGGAGCTTACAATCTAG
CTGGGGTTTTGGCCACTGACTGACCCCAGCTAGTGTAAGCTCCTTCAGGA
CACAAGGCCTGTTACTAGCACTCACATGGAACAAATGGCCCAGATCTGGC
CGCAC
```

Endogenous MIR708 scaffold
(SEQ ID NO: 14)
```
AACCTAACCCCCATGGTTGGCGAGGGACTGCTGTGTGTGAAATGGTAACT
GCCCTCAAGGAGCTTACAATCTAGCTGGGGGTAAATGACTTGCACATGAA
CACAACTAGACTGTGAGCTTCTAGAGGGCAGGGACCTTACCCTAGTCATC
TCTCTTCTCACCCTGCACACCCTCCCTGAGGGATCTCAT
``` pRK-hRhodopsin-miR-708 (mir708 in the miR708 endogenous scaffold, located in the 3'UTR of hRhodopsin)

(SEQ ID NO: 15)

TATGCGGTGTGAAATACCGCACAGATGCGTAAGGAGAAAATACCGCATCAGGCGCCATTCGCCATTCAG

GCTGCGCAACTGTTGGGAAGGGCGATCGGTGCGGGCCTCTTCGCTATTACGCCAGCTGGCGAAAGGGGG

ATGTGCTGCAAGGCGATTAAGTTGGGTAACGCCAGGGTTTTCCCAGTCACGACGTTGTAAAACGACGGC

CAGTGAATTCGGACCGTCGACATTGATTATTGGGCCCCAGAAGCCTGGTGGTTGTTTGTCCTTCTCAGG

GGAAAAGTGAGGCGGCCCCTTGGAGGAAGGGGCCGGGCAGAATGATCTAATCGGATTCCAAGCAGCTCA

GGGGATTGTCTTTTTCTAGCACCTTCTTGCCACTCCTAAGCGTCCTCCGTGACCCCGGCTGGGATTTAG

CCTGGTGCTGTGTCAGCCCCGGTCTCCCAGGGGCTTCCCAGTGGTCCCCAGGAACCCTCGACAGGGCCC

GGTCTCTCTCGTCCAGCAAGGGCAGGGACGGGCCACAGGCCAAGGGCGGAGTCGCTGCGACGCTGCCTT

CGCCCCGTGCCCCGCTCCGCCGCCGCCTCGCGCCGCCCGCCCCGGCTCTGACTGACCGCGTTACTCCCA

CAGGTGAGCGGGCGGGACGGCCCTTCTCCTCCGGGCTGTAATTAGCAAGAGGTAAGGGTTTAAGGGATG

GTTGGTTGGTGGGGTATTAATGTTTAATTACCTGTTTTACAGGCCTGAAATCACTTGGTTTTAGGTTGG

GGATCCGGTACCCAATTGCCATGGGCTAGCATGCATGAGCTCCCTGCAGGGTTTATCTGCAGAATTCAG

CCACCACCGGCACAATGAATGGCACAGAAGGCCCTAACTTCTACGTGCCCTTCTCCAATGCGACGGGTG

TGGTACGCAGCCCCTTCGAGTACCCACAGTACTACCTGGCTGAGCCATGGCAGTTCTCCATGCTGGCCG

CCTACATGTTTCTGCTGATCGTGCTGGGCTTCCCCATCAACTTCCTCACGCTCTACGTCACCGTCCAGC

ACAAGAAGCTGCGCACGCCTCTCAACTACATCCTGCTCAACCTAGCCGTGGCTGACCTCTTCATGGTCC

TAGGTGGCTTCACCAGCACCCTCTACACCTCTCTGCATGGATACTTCGTCTTCGGGCCCACAGGATGCA

ATTTGGAGGGCTTCTTTGCCACCCTGGGCGGTGAAATTGCCCTGTGGTCCTTGGTGGTCCTGGCCATCG

AGCGGTACGTGGTGGTGTGTAAGCCCATGAGCAACTTCCGCTTCGGGGAGAACCATGCCATCATGGGCG

TTGCCTTCACCTGGGTCATGGCGCTGGCCTGCGCCGCACCCCCACTCGCCGGCTGGTCCAGGTACATCC

CCGAGGGCCTGCAGTGCTCGTGTGGAATCGACTACTACACGCTCAAGCCGGAGGTCAACAACGAGTCTT

TTGTCATCTACATGTTCGTGGTCCACTTCACCATCCCCATGATTATCATCTTTTTCTGCTATGGGCAGC

TCGTCTTCACCGTCAAGGAGGCCGCTGCCCAGCAGCAGGAGTCAGCCACCACACAGAAGGCAGAGAAGG

AGGTCACCCGCATGGTCATCATCATGGTCATCGCTTTCCTGATCTGCTGGGTGCCCTACGCCAGCGTGG

CATTCTACATCTTCACCCACCAGGGCTCCAACTTCGGTCCCATCTTCATGACCATCCCAGCGTTCTTTG

CCAAGAGCGCCGCCATCTACAACCCTGTCATCTATATCATGATGAACAAGCAGTTCCGGAACTGCATGC

TCACCACCATCTGCTGCGGCAAGAACCCACTGGGTGACGATGAGGCCTCTGCTACCGTGTCCAAGACGG

AGACGAGCCAGGTGGCCCCGGCCTAACCAAGAAAGCTTAAGTTTGTGTCCCGGCTTAGGGCTAAATGTC

TAGGACAGAATGGAACACATAGTAGCTGATTAATAAATGCTAGCTGGATGAAGGGAGGAATGAGTGACT

GACTGAGTGGATATATGAGTGAAGGGATTAATGGAAGGGAACATGGATGTCCTCAGGTGCCCAACCTGG

CAGATCCAGTCATGTCTGGCTGGAATCTATAAGCAGTTTTACATACCTGCCCTGAGCTTTATTGCGGTA

GTTTATCACAGTTAAATTGCTAACGCAGTCAGTGCTTCTGACACAACAGTCTCGAACTTAAGCTGCAGT

GACTCTCTTAAGGTAGCCTTGCAGAAGTTGGTCGTGAGGCACTGGGCAGGTAAGTATCAAGGTTACAAG

ACAGGTTTAAGGAGACCAATAGAAACTGGGCTTGTCGAGACAGAGAAAAACCTAACCCCCATGGTTGGC

GAGGGACTGCTGTGTGTGAAATGGTAACTGCCCTCAAGGAGCTTACAATCTAGCTGGGGTAAATGACT

TGCACATGAACACAACTAGACTGTGAGCTTCTAGAGGGCAGGGACCTTACCCTAGTCATCTCTCTTCTC

ACCCTGCACACCCTCCCTGAGGGATCTCATGACTCTTGCGTTTCTGATAGGCACCTATTGGTCTTACTG

ACATCCACTTTGCCTTTCTCTCCACAGGTGTCCACTCCCAGTTCACACCGGCACAATGAATGGCACAGA

AGGCCCTAACTTCTACGTGCCCTTCTCCAATGCGACGGGTGTGGTACGCAGCCCCTTCGAGTACCCACA

-continued

```
GTCAGAGATAAATGACAGTGACAGCAACGTGAGCTGCAGCCCTTAGGACTGAGAAAGCATCGAGACCAG

GGGTCTCCGGCAAGGCCTAGGTCCTCCCTTCAGTATGGAAACCTTGCCTCATGTCTCTCAGCCTCCTTG

GCCTGTGGAGATCCAGCCCTTCCTCTTGGCTTCTGGATACATTTGCTCTTCTACACCAGCAACCAAGTG

GCAACAGTTCCAGGCCAGTATGGAGTTTTAGAAGCCATGCCAATATGCCCACCTTCAGGGAGCAGCTGA

GTCCTTGATGCCACCCTTGTTCTGAAGAGTTCAGAAACACAGTGCAAGACATGACCAGGCCTCATCCTT

AGGATGCTCATGGATCCAGTTCTTAGCTCCCTTGTTGGATATGCTGTTTTCCTTGGCCTTTGGTCTTTT

CTTTATCCCAGAGGGTTTTGGCTTTAAGGCCAACAGGAACTATGGGGTACCAGAATTGAGCAGCCTCAG

TCTGCATCCCTCCTCTATAGAACCACAGCTGGGCCCTCAGCAGGCCCAACTCTGCATGGGGACAGAGGC

ATTAAAAGCCTAGAGTATCCCTCGAGGGGCCCAAGCTTACGCGTACCCAGCTTTCTTGTACAAAGTGGT

CCCTATAGTGAGTCGTATTATAAGCTAGGCACTGGCCGTCGTTTTACAACGTCGTGACTGGGAAAACTG

CTAGCTTGGGATCTTTGTGAAGGAACCTTACTTCTGTGGTGTGACATAATTGGACAAACTACCTACAGA

GATTTAAAGCTCTAAGGTAAATATAAAATTTTTAAGTGTATAATGTGTTAAACTAGCTGCAAAACCTGT

GCCTTCTAGTTGCCAGCCATCTGTTGTTTGCCCCTCCCCCGTGCCTTCCTTGACCCTGGAAGGTGCCAC

TCCCACTGTCCTTTCCTAATAAAATGAGGAAATTGCATCGCATTGTCTGAGTAGGTGTCATTCTATTCT

GGGGGGTGGGGTGGGGCAGGACAGCAAGGGGGAGGATTGGGAAGACAATAGCAGGCATGCTGGGGAACT

AGTCGGACCGCTGCAGGCATGCAAGCTTGGCGTAATCATGGTCATAGCTGTTTCCTGTGTGAAATTGTT

ATCCGCTCACAATTCCACACAACATACGAGCCGGAAGCATAAAGTGTAAAGCCTGGGGTGCCTAATGAG

TGAGCTAACTCACATTAATTGCGTTGCGCTCACTGCCCGCTTTCCAGTCGGGAAACCTGTCGTGCCAGC

TGCATTAATGAATCGGCCAACGCGCGGGGAGAGGCGGTTTGCGTATTGGGCGCTCTTCCGCTTCCTCGC

TCACTGACTCGCTGCGCTCGGTCGTTCGGCTGCGGCGAGCGGTATCAGCTCACTCAAAGGCGGTAATAC

GGTTATCCACAGAATCAGGGGATAACGCAGGAAAGAACATGTGAGCAAAAGGCCAGCAAAAGGCCAGGA

ACCGTAAAAAGGCCGCGTTGCTGGCGTTTTTCCATAGGCTCCGCCCCCCTGACGAGCATCACAAAAATC

GACGCTCAAGTCAGAGGTGGCGAAACCCGACAGGACTATAAAGATACCAGGCGTTTCCCCCTGGAAGCT

CCCTCGTGCGCTCTCCTGTTCCGACCCTGCCGCTTACCGGATACCTGTCCGCCTTTCTCCCTTCGGGAA

GCGTGGCGCTTTCTCATAGCTCACGCTGTAGGTATCTCAGTTCGGTGTAGGTCGTTCGCTCCAAGCTGG

GCTGTGTGCACGAACCCCCCGTTCAGCCCGACCGCTGCGCCTTATCCGGTAACTATCGTCTTGAGTCCA

ACCCGGTAAGACACGACTTATCGCCACTGGCAGCAGCCACTGGTAACAGGATTAGCAGAGCGAGGTATG

TAGGCGGTGCTACAGAGTTCTTGAAGTGGTGGCCTAACTACGGCTACACTAGAAGGACAGTATTTGGTA

TCTGCGCTCTGCTGAAGCCAGTTACCTTCGGAAAAAGAGTTGGTAGCTCTTGATCCGGCAAACAAACCA

CCGCTGGTAGCGGTGGTTTTTTTGTTTGCAAGCAGCAGATTACGCGCAGAAAAAAAGGATCTCAAGAAG

ATCCTTTGATCTTTTCTACGGGGTCTGACGCTCAGTGGAACGAAAACTCACGTTAAGGGATTTTGGTCA

TGAGATTATCAAAAAGGATCTTCACCTAGATCCTTTTAAATTAAAAATGAAGTTTTAAATCAATCTAAA

GTATATATGAGTAAACTTGGTCTGACAGTTACCAATGCTTAATCAGTGAGGCACCTATCTCAGCGATCT

GTCTATTTCGTTCATCCATAGTTGCCTGACTCCCCGTCGTGTAGATAACTACGATACGGGAGGGCTTAC

CATCTGGCCCCAGTGCTGCAATGATACCGCGAGACCCACGCTCACCGGCTCCAGATTTATCAGCAATAA

ACCAGCCAGCCGGAAGGGCCGAGCGCAGAAGTGGTCCTGCAACTTTATCCGCCTCCATCCAGTCTATTA

ATTGTTGCCGGGAAGCTAGAGTAAGTAGTTCGCCAGTTAATAGTTTGCGCAACGTTGTTGCCATTGCTA

CAGGCATCGTGGTGTCACGCTCGTCGTTTGGTATGGCTTCATTCAGCTCCGGTTCCCAACGATCAAGGC

GAGTTACATGATCCCCCATGTTGTGCAAAAAAGCGGTTAGCTCCTTCGGTCCTCCGATCGTTGTCAGAA

GTAAGTTGGCCGCAGTGTTATCACTCATGGTTATGGCAGCACTGCATAATTCTCTTACTGTCATGCCAT

CCGTAAGATGCTTTTCTGTGACTGGTGAGTACTCAACCAAGTCATTCTGAGAATAGTGTATGCGGCGAC
```

CGAGTTGCTCTTGCCCGGCGTCAATACGGGATAATACCGCGCCACATAGCAGAACTTTAAAAGTGCTCA
TCATTGGAAAACGTTCTTCGGGGCGAAAACTCTCAAGGATCTTACCGCTGTTGAGATCCAGTTCGATGT
AACCCACTCGTGCACCCAACTGATCTTCAGCATCTTTTACTTTCACCAGCGTTTCTGGGTGAGCAAAAA
CAGGAAGGCAAAATGCCGCAAAAAAGGGAATAAGGGCGACACGGAAATGTTGAATACTCATACTCTTCC
TTTTTCAATATTATTGAAGCATTTATCAGGGTTATTGTCTCATGAGCGGATACATATTTGAATGTATTT
AGAAAAATAAACAAATAGGGGTTCCGCGCACATTTCCCCGAAAAGTGCCACCTGACGTCAAGAAACCA
TTATTATCATGACATTAACCTATAAAAATAGGCGTATCACGAGGCCCTTTCGTCTCGCGCGTTTCGGTG
ATGACGGTGAAAACCTCTGACACATGCAGCTCCCGGAGACGGTCACAGCTTGTCTGTAAGCGGATGCCG
GGAGCAGACAAGCCCGTCAGGGCGCGTCAGCGGGTGTTGGCGGGTGTCGGGGCTGGCTTAACTATGCGG
CATCAGAGCAGATTGTACTGAGAGTGCACCA

β-globin intron sequence
(SEQ ID NO: 16)
ACTAGAAGCTTTATTGCGGTAGTTTATCACAGTTAAATTGCTAACGCAG
TCAGTGCTTCTGACACAACAGTCTCGAACTTAAGCTGCAGTGACTCTCT
TAAGGTAGCCTTGCAGAAGTTGGTCGTGAGGCACTGGGCAGGTAAGTAT
CAAGGTTACAAGACAGGTTTAAGGAGACCAATAGAAACTGGGCTTGTCG
AGACAGAGAATGGATCCTGGAGGCTTGCTGAAGGCTGTATGCTGAAGGA
GCTTACAATCTAGCTGGGGTTTTGGCCACTGACTGACCCCAGCTAGTGT
AAGCTCCTTCAGGACACAAGGCCTGTTACTAGCACTCACATGGAACAAA
TGGCCCAGATCTGAGACTCTTGCGTTTCTGATAGGCACCTATTGGTCTT
ACTGACATCCACTTTGCCTTTCTCTCCACAGGTGTCCACTCCCAGTTCA MIR708 sequence in a MIR155 scaffold
(SEQ ID NO: 17)
TGGATCCTGGAGGCTTGCTGAAGGCTGTATGCTGAAGGAGCTTACAATC
TAGCTGGGGTTTTGGCCACTGACTGACCCCAGCTAGTGTAAGCTCCTTC
AGGACACAAGGCCTGTTACTAGCACTCACATGGAACAAATGGCCCAGAT
CTG MIR708 sequence in a native scaffold
(SEQ ID NO: 18)
AAACCTAACCCCCATGGTTGGCGAGGGACTGCTGTGTGTGAAATGGTAA
CTGCCCTCAAGGAGCTTACAATCTAGCTGGGGGTAAATGACTTGCACAT
GAACACAACTAGACTGTGAGCTTCTAGAGGGCAGGGACCTTACCCTAGT
CATCTCTCTTCTCACCCTGCACACCCTCCCTGAGGGATCTCAT Human rhodopsin miR-708 target from 3'UTR
(SEQ ID NO: 19)
CUCUGCCUGGAGACUAAGGCAAAUUGGGCCAUUAAAAGCUCAGCUCCUA
UGUUGGUAUUAACGGUGGUGGGUUUUGUUG Mutated AAV ITR
(SEQ ID NO: 20)
CCACTCCCTCTCTGCGCGCTCGCTCGCTCACTGAGGCCGGGCGACCAAA
GGTCGCCCGACGCCCGGGCTTTGCCCGGGCGGCCTCAGTGAGCGAGCGA
GCGCGCAGAGAGGGA Wild Type ITR sequence
(SEQ ID NO: 21)
GGCCACTCCCTCTCTGCGCGCTCGCTCGCTCACTGAGGCCGGGCGACCA
AAGGTCGCCCGACGCCCGGGCTTTGCCCGGGCGGCCTCAGTGAGCGAGC
GAGCGCGCAGAGAGGGAGTGGCCAACTCCATCACTAGGGGTTCCT Opsin promoter
(SEQ ID NO: 22)
TGCTGATTCAGCCAGGAACTAGTTATTAATAGTAATCAATTACGGGGTC
ATTAGTTCATAGCCCATATATGGAGTTCCGCGTTACATAACTTACGGTA
AATGGCCCGCCTGGCTGACCGCCCAACGACCCCCGCCCATTGACGTCAA
TAATGACGTATGTTCCCATAGTAACGCCAATAGGGACTTTCCATTGACG
TCAATGGGTGGAGTATTTACGGTAAACTGCCCACTTGGCAGTACATCAA
GTGTATCATATGCCAAGTACGCCCCCTATTGACGTCAATGACGGTAAAT
GGCCCGCCTGGCATTATGCCCAGTACATGACCTTATGGGACTTTCCTAC
TTGGCAGTACATCTACGTATTAGTCATCGCTATTACCACAAATAGTTAT
CGAGCCGCTGAGCCGGGGGCGGGGGGTGTGAGACTGGAGGCGATGGAC
GGAGCTGACGGCACACACAGCTCAGATCTGTCAAGTGAGCCATTGTCAG
GGCTTGGGGACTGGATAAGTCAGGGGGTCTCCTGGGAAGAGATGGGATA
GGTGAGTTCAGGAGGAGACATTGTCAACTGGAGCCATGTGGAGAAGTGA
ATTTAGGGCCCAAAGGTTCCAGTCGCAGCCTGAGGCCACCAGACTGACA
TGGGGAGGAATTCCCAGAGGACTCTGGGGCAGACAAGATGAGACACCCT
TTCCTTTCTTTACCTAAGGGCCTCCACCCGATGTCACCTTGGCCCCTCT
GCAAGCCAATTAGGCCCCGGTGGCAGCAGTGGGATTAGCGTTAGTATGA
TATCTCGCGGA MVM intron (SEQ ID NO: 23)
GGAGTCGCTGCGACGCTGCCTTCGCCCCGTGCCCCGCTCCGCCGCCGCC
TCGCGCCGCCCGCCCCGGCTCTGACTGACCGCGTTACTCCCACAGGTGA
GCGGGCGGGACGGCCCTTCTCCTCCGGGCTGTAATTAGCAAGAGGTAAG
GGTTTAAGGGATGGTTGGTTGGTGGGGTATTAATGTTTAATTACCTGTT
TTACAGGCCTGAAATCACTTGGTTTTAGGTTGGGGATCCGGTACCCAAT
TGCCATGGGCTAGCATGCATGAGCTCCCTGCAGGGTTTTAATGCCAACT
TTGTACAAAAAAGCAGGCACC AAV5GRK1miR708_155hRho (AAV5 vector with rhodopsin kinase promoter driving
expression of miR-708 in a miR-155 scaffold and human rhodopsin minus the
miR-708 target sequence)

(SEQ ID NO: 24)
TGACTAGTTAGGGCCCCAGAAGCCTGGTGGTTGTTTGTCCTTCTCAGGGGAAAAGTGAGGCGGCCCCTTG
GAGGAAGGGGCCGGGCAGAATGATCTAATCGGATTCCAAGCAGCTCAGGGGATTGTCTTTTTCTAGCACC
TTCTTGCCACTCCTAAGCGTCCTCCGTGACCCCGGCTGGGATTTAGCCTGGTGCTGTGTCAGCCCCGGTC
TCCCAGGGGCTTCCCAGTGGTCCCCAGGAACCCTCGACAGGGCCCGGTCTCTCTCGTCCAGCAAGGGCAG
GGACGGGCCACAGGCCAAGGGCACTAGAAGCTTTATTGCGGTAGTTTATCACAGTTAAATTGCTAACGCA
GTCAGTGCTTCTGACACAACAGTCTCGAACTTAAGCTGCAGTGACTCTCTTAAGGTAGCCTTGCAGAAGT
TGGTCGTGAGGCACTGGGCAGGTAAGTATCAAGGTTACAAGACAGGTTTAAGGAGACCAATAGAAACTGG
GCTTGTCGAGACAGAGAATGGATCCTGGAGGCTTGCTGAAGGCTGTATGCTGAAGGAGCTTACAATCTAG
CTGGGGTTTTGGCCACTGACTGACCCCAGCTAGTGTAAGCTCCTTCAGGACACAAGGCCTGTTACTAGCA
CTCACATGGAACAAATGGCCCAGATCTGAGACTCTTGCGTTTCTGATAGGCACCTATTGGTCTTACTGAC
ATCCACTTTGCCTTTCTCTCCACAGGTGTCCACTCCCAGTTCACACCGGCACAATGAATGGCACAGAAGG
CCCTAACTTCTACGTGCCCTTCTCCAATGCGACGGGTGTGGTACGCAGCCCCTTCGAGTACCCACAGTAC
TACCTGGCTGAGCCATGGCAGTTCTCCATGCTGGCCGCCTACATGTTTCTGCTGATCGTGCTGGGCTTCC
CCATCAACTTCCTCACGCTCTACGTCACCGTCCAGCACAAGAAGCTGCGCACGCCTCTCAACTACATCCT
GCTCAACCTAGCCGTGGCTGACCTCTTCATGGTCCTAGGTGGCTTCACCAGCACCCTCTACACCTCTCTG
CATGGATACTTCGTCTTCGGGCCCACAGGATGCAATTTGGAGGGCTTCTTTGCCACCCTGGGCGGTGAAA
TTGCCCTGTGGTCCTTGGTGGTCCTGGCCATCGAGCGGTACGTGGTGGTGTGTAAGCCCATGAGCAACTT
CCGCTTCGGGGAGAACCATGCCATCATGGGCGTTGCCTTCACCTGGGTCATGGCGCTGGCCTGCGCCGCA
CCCCCACTCGCCGGCTGGTCCAGGTACATCCCCGAGGGCCTGCAGTGCTCGTGTGGAATCGACTACTACA
CGCTCAAGCCGGAGGTCAACAACGAGTCTTTTGTCATCTACATGTTCGTGGTCCACTTCACCATCCCCAT
GATTATCATCTTTTTCTGCTATGGGCAGCTCGTCTTCACCGTCAAGGAGGCCGCTGCCCAGCAGCAGGAG
TCAGCCACCACACAGAAGGCAGAGAAGGAGGTCACCCGCATGGTCATCATCATGGTCATCGCTTTCCTGA
TCTGCTGGGTGCCCTACGCCAGCGTGGCATTCTACATCTTCACCCACCAGGGCTCCAACTTCGGTCCCAT
CTTCATGACCATCCCAGCGTTCTTTGCCAAGAGCGCCGCCATCTACAACCCTGTCATCTATATCATGATG
AACAAGCAGTTCCGGAACTGCATGCTCACCACCATCTGCTGCGGCAAGAACCCACTGGGTGACGATGAGG
CCTCTGCTACCGTGTCCAAGACGGAGACGAGCCAGGTGGCCCCGGCCTAACCAAGAAAGCTTAAGTTTAA
ACCGCTGATCAGCCTCGACTGTGCCTTCTAGTTGCCAGCCATCTGTTGTTTGCCCCTCCCCCGTGCCTTC
CTTGACCCTGGAAGGTGCCACTCCCACTGTCCTTTCCTAATAAAATGAGGAAATTGCATCGCATTGTCTG
AGTAGGTGTCATTCTATTCTGGGGGGTGGGGTGGGCAGGACAGCAAGGGGGAGGATTGGGAAGACAATA
GCAGGCATGCTGGGGATGCGGTGGGCTCTATGGC

AAV5GRK1miR708_708hRho (AAV5 vector with rhodopsin kinase promoter driving
expression of miR-708 in a miR-708 scaffold and human rhodopsin minus the
miR-708 target sequence)

(SEQ ID NO: 25)

GGGCCCCAGAAGCCTGGTGGTTGTTTGTCCTTCTCAGGGGAAAAGTGAGGCGGCCCCTTGGAGGAAGGGG

CCGGGCAGAATGATCTAATCGGATTCCAAGCAGCTCAGGGGATTGTCTTTTTCTAGCACCTTCTTGCCAC

TCCTAAGCGTCCTCCGTGACCCCGGCTGGGATTTAGCCTGGTGCTGTGTCAGCCCCGGTCTCCCAGGGGC

TTCCCAGTGGTCCCCAGGAACCCTCGACAGGGCCCGGTCTCTCTCGTCCAGCAAGGGCAGGGACGGGCCA

CAGGCCAAGGGCACTAGAAGCTTTATTGCGGTAGTTTATCACAGTTAAATTGCTAACGCAGTCAGTGCTT

CTGACACAACAGTCTCGAACTTAAGCTGCAGTGACTCTCTTAAGGTAGCCTTGCAGAAGTTGGTCGTGAG

GCACTGGGCAGGTAAGTATCAAGGTTACAAGACAGGTTTAAGGAGACCAATAGAAACTGGGCTTGTCGAG

ACAGAGAAAAACCTAACCCCCATGGTTGGCGAGGGACTGCTGTGTGTGAAATGGTAACTGCCCTCAAGGA

GCTTACAATCTAGCTGGGGGTAAATGACTTGCACATGAACACAACTAGACTGTGAGCTTCTAGAGGGCAG

GGACCTTACCCTAGTCATCTCTCTTCTCACCCTGCACACCCTCCCTGAGGGATCTCATGACTCTTGCGTT

TCTGATAGGCACCTATTGGTCTTACTGACATCCACTTTGCCTTTCTCTCCACAGGTGTCCACTCCCAGTT

CACACCGGCACAATGAATGGCACAGAAGGCCCTAACTTCTACGTGCCCTTCTCCAATGCGACGGGTGTGG

TACGCAGCCCCTTCGAGTACCCACAGTACTACCTGGCTGAGCCATGGCAGTTCTCCATGCTGGCCGCCTA

CATGTTTCTGCTGATCGTGCTGGGCTTCCCCATCAACTTCCTCACGCTCTACGTCACCGTCCAGCACAAG

AAGCTGCGCACGCCTCTCAACTACATCCTGCTCAACCTAGCCGTGGCTGACCTCTTCATGGTCCTAGGTG

GCTTCACCAGCACCCTCTACACCTCTCTGCATGGATACTTCGTCTTCGGGCCCACAGGATGCAATTTGGA

GGGCTTCTTTGCCACCCTGGGCGGTGAAATTGCCCTGTGGTCCTTGGTGGTCCTGGCCATCGAGCGGTAC

GTGGTGGTGTGTAAGCCCATGAGCAACTTCCGCTTCGGGGAGAACCATGCCATCATGGGCGTTGCCTTCA

CCTGGGTCATGGCGCTGGCCTGCGCCGCACCCCCACTCGCCGGCTGGTCCAGGTACATCCCCGAGGGCCT

GCAGTGCTCGTGTGGAATCGACTACTACACGCTCAAGCCGGAGGTCAACAACGAGTCTTTTGTCATCTAC

ATGTTCGTGGTCCACTTCACCATCCCCATGATTATCATCTTTTTCTGCTATGGGCAGCTCGTCTTCACCG

TCAAGGAGGCCGCTGCCCAGCAGCAGGAGTCAGCCACCACACAGAAGGCAGAGAAGGAGGTCACCCGCAT

GGTCATCATCATGGTCATCGCTTTCCTGATCTGCTGGGTGCCCTACGCCAGCGTGGCATTCTACATCTTC

ACCCACCAGGGCTCCAACTTCGGTCCCATCTTCATGACCATCCCAGCGTTCTTTGCCAAGAGCGCCGCCA

TCTACAACCCTGTCATCTATATCATGATGAACAAGCAGTTCCGGAACTGCATGCTCACCACCATCTGCTG

CGGCAAGAACCCACTGGGTGACGATGAGGCCTCTGCTACCGTGTCCAAGACGGAGACGAGCCAGGTGGCC

CCGGCCTAACCAAGAAAGCTTAAGTTTAAACCGCTGATCAGCCTCGACTGTGCCTTCTAGTTGCCAGCCA

TCTGTTGTTTGCCCCTCCCCCGTGCCTTCCTTGACCCTGGAAGGTGCCACTCCCACTGTCCTTTCCTAAT

AAAATGAGGAAATTGCATCGCATTGTCTGAGTAGGTGTCATTCTATTCTGGGGGGTGGGGTGGGGCAGGA

CAGCAAGGGGGAGGATTGGGAAGACAATAGCAGGCATGCTGGGGATGCGGTGGGCTCTATGGC

AAV5OPSmiR708_155hRho (AAV5 vector with opsin promoter driving expression
of miR-708 in a miR-155 scaffold and human rhodopsin minus the miR-708
target sequence)

(SEQ ID NO: 26)

ACGCGTTTTCTGCAGCGGGGATTAATATGATTATGAACACCCCCAATCTCCCAGATGCTGATTCAGCCAG

GAACTAGTTATTAATAGTAATCAATTACGGGGTCATTAGTTCATAGCCCATATATGGAGTTCCGCGTTAC

ATAACTTACGGTAAATGGCCCGCCTGGCTGACCGCCCAACGACCCCCGCCCATTGACGTCAATAATGACG

TATGTTCCCATAGTAACGCCAATAGGGACTTTCCATTGACGTCAATGGGTGGAGTATTTACGGTAAACTG

CCCACTTGGCAGTACATCAAGTGTATCATATGCCAAGTACGCCCCCTATTGACGTCAATGACGGTAAATG

-continued

```
GCCCGCCTGGCATTATGCCCAGTACATGACCTTATGGGACTTTCCTACTTGGCAGTACATCTACGTATTA

GTCATCGCTATTACCACAAATAGTTATCGAGCCGCTGAGCCGGGGGCGGGGGGTGTGAGACTGGAGGCG

ATGGACGGAGCTGACGGCACACACAGCTCAGATCTGTCAAGTGAGCCATTGTCAGGGCTTGGGGACTGGA

TAAGTCAGGGGGTCTCCTGGGAAGAGATGGGATAGGTGAGTTCAGGAGGAGACATTGTCAACTGGAGCCA

TGTGGAGAAGTGAATTTAGGGCCCAAAGGTTCCAGTCGCAGCCTGAGGCCACCAGACTGACATGGGGAGG

AATTCCCAGAGGACTCTGGGGCAGACAAGATGAGACACCCTTTCCTTTCTTTACCTAAGGGCCTCCACCC

GATGTCACCTTGGCCCCTCTGCAAGCCAATTAGGCCCCGGTGGCAGCAGTGGGATTAGCGTTAGTATGAT

ATCTCGCGGATGCTGAATCAGCCTCTGGCTTAGGGAGAGAAGGTCACTTTATAAGGGTCTGGGGGGGTC

AGTGCCTGGAGTTGCGCTGTGGGAGCCGTCAGTGGCTGAGCTCAACTAGAAGCTTTATTGCGGTAGTTTA

TCACAGTTAAATTGCTAACGCAGTCAGTGCTTCTGACACAACAGTCTCGAACTTAAGCTGCAGTGACTCT

CTTAAGGTAGCCTTGCAGAAGTTGGTCGTGAGGCACTGGGCAGGTAAGTATCAAGGTTACAAGACAGGTT

TAAGGAGACCAATAGAAACTGGGCTTGTCGAGACAGAGAATGGATCCTGGAGGCTTGCTGAAGGCTGTAT

GCTGAAGGAGCTTACAATCTAGCTGGGGTTTTGGCCACTGACTGACCCCAGCTAGTGTAAGCTCCTTCAG

GACACAAGGCCTGTTACTAGCACTCACATGGAACAAATGGCCCAGATCTGAGACTCTTGCGTTTCTGATA

GGCACCTATTGGTCTTACTGACATCCACTTTGCCTTTCTCTCCACAGGTGTCCACTCCCAGTTCACACCG

GCACAATGAATGGCACAGAAGGCCCTAACTTCTACGTGCCCTTCTCCAATGCGACGGGTGTGGTACGCAG

CCCCTTCGAGTACCCACAGTACTACCTGGCTGAGCCATGGCAGTTCTCCATGCTGGCCGCCTACATGTTT

CTGCTGATCGTGCTGGGCTTCCCCATCAACTTCCTCACGCTCTACGTCACCGTCCAGCACAAGAAGCTGC

GCACGCCTCTCAACTACATCCTGCTCAACCTAGCCGTGGCTGACCTCTTCATGGTCCTAGGTGGCTTCAC

CAGCACCCTCTACACCTCTCTGCATGGATACTTCGTCTTCGGGCCCACAGGATGCAATTTGGAGGGCTTC

TTTGCCACCCTGGGCGGTGAAATTGCCCTGTGGTCCTTGGTGGTCCTGGCCATCGAGCGGTACGTGGTGG

TGTGTAAGCCCATGAGCAACTTCCGCTTCGGGGAGAACCATGCCATCATGGGCGTTGCCTTCACCTGGGT

CATGGCGCTGGCCTGCGCCGCACCCCCACTCGCCGGCTGGTCCAGGTACATCCCCGAGGGCCTGCAGTGC

TCGTGTGGAATCGACTACTACACGCTCAAGCCGGAGGTCAACAACGAGTCTTTTGTCATCTACATGTTCG

TGGTCCACTTCACCATCCCCATGATTATCATCTTTTTCTGCTATGGGCAGCTCGTCTTCACCGTCAAGGA

GGCCGCTGCCCAGCAGCAGGAGTCAGCCACCACACAGAAGGCAGAGAAGGAGGTCACCCGCATGGTCATC

ATCATGGTCATCGCTTTCCTGATCTGCTGGGTGCCCTACGCCAGCGTGGCATTCTACATCTTCACCCACC

AGGGCTCCAACTTCGGTCCCATCTTCATGACCATCCCAGCGTTCTTTGCCAAGAGCGCCGCCATCTACAA

CCCTGTCATCTATATCATGATGAACAAGCAGTTCCGGAACTGCATGCTCACCACCATCTGCTGCGGCAAG

AACCCACTGGGTGACGATGAGGCCTCTGCTACCGTGTCCAAGACGGAGACGAGCCAGGTGGCCCCGGCCT

AACCAAGAAAGCTTAAGTTTAAACCGCTGATCAGCCTCGACTGTGCCTTCTAGTTGCCAGCCATCTGTTG

TTTGCCCCTCCCCCGTGCCTTCCTTGACCCTGGAAGGTGCCACTCCCACTGTCCTTTCCTAATAAAATGA

GGAAATTGCATCGCATTGTCTGAGTAGGTGTCATTCTATTCTGGGGGTGGGTGGGCAGGACAGCAAG

GGGGAGGATTGGGAAGACAATAGCAGGCATGCTGGGGATGCGGTGGGCTCTATGGC
```

AAV5OPSmiR708_708hRho (AAV5 vector with opsin promoter driving expression of miR-708 in a miR-708 scaffold and human rhodopsin minus the miR-708 target sequence)

(SEQ ID NO: 27)

```
ACGCGTTTTCTGCAGCGGGGATTAATATGATTATGAACACCCCCAATCTCCCAGATGCTGATTCAGCCAG

GAACTAGTTATTAATAGTAATCAATTACGGGGTCATTAGTTCATAGCCCATATATGGAGTTCCGCGTTAC

ATAACTTACGGTAAATGGCCCGCCTGGCTGACCGCCCAACGACCCCCGCCCATTGACGTCAATAATGACG
```

-continued

```
TATGTTCCCATAGTAACGCCAATAGGGACTTTCCATTGACGTCAATGGGTGGAGTATTTACGGTAAACTG
CCCACTTGGCAGTACATCAAGTGTATCATATGCCAAGTACGCCCCCTATTGACGTCAATGACGGTAAATG
GCCCGCCTGGCATTATGCCCAGTACATGACCTTATGGGACTTTCCTACTTGGCAGTACATCTACGTATTA
GTCATCGCTATTACCACAAATAGTTATCGAGCCGCTGAGCCGGGGGCGGGGGGTGTGAGACTGGAGGCG
ATGGACGGAGCTGACGGCACACACAGCTCAGATCTGTCAAGTGAGCCATTGTCAGGGCTTGGGGACTGGA
TAAGTCAGGGGGTCTCCTGGGAAGAGATGGGATAGGTGAGTTCAGGAGGAGACATTGTCAACTGGAGCCA
TGTGGAGAAGTGAATTTAGGGCCCAAAGGTTCCAGTCGCAGCCTGAGGCCACCAGACTGACATGGGGAGG
AATTCCCAGAGGACTCTGGGGCAGACAAGATGAGACACCCTTTCCTTTCTTTACCTAAGGGCCTCCACCC
GATGTCACCTTGGCCCCTCTGCAAGCCAATTAGGCCCCGGTGGCAGCAGTGGGATTAGCGTTAGTATGAT
ATCTCGCGGATGCTGAATCAGCCTCTGGCTTAGGGAGAGAAGGTCACTTTATAAGGGTCTGGGGGGGTC
AGTGCCTGGAGTTGCGCTGTGGGAGCCGTCAGTGGCTGAGCTCAACTAGAAGCTTTATTGCGGTAGTTTA
TCACAGTTAAATTGCTAACGCAGTCAGTGCTTCTGACACAACAGTCTCGAACTTAAGCTGCAGTGACTCT
CTTAAGGTAGCCTTGCAGAAGTTGGTCGTGAGGCACTGGGCAGGTAAGTATCAAGGTTACAAGACAGGTT
TAAGGAGACCAATAGAAACTGGGCTTGTCGAGACAGAGAAAAACCTAACCCCCATGGTTGGCGAGGGACT
GCTGTGTGTGAAATGGTAACTGCCCTCAAGGAGCTTACAATCTAGCTGGGGGTAAATGACTTGCACATGA
ACACAACTAGACTGTGAGCTTCTAGAGGGCAGGGACCTTACCCTAGTCATCTCTCTTCTCACCCTGCACA
CCCTCCCTGAGGGATCTCATGACTCTTGCGTTTCTGATAGGCACCTATTGGTCTTACTGACATCCACTTT
GCCTTTCTCTCCACAGGTGTCCACTCCCAGTTCACACCGGCACAATGAATGGCACAGAAGGCCCTAACTT
CTACGTGCCCTTCTCCAATGCGACGGGTGTGGTACGCAGCCCCTTCGAGTACCCACAGTACTACCTGGCT
GAGCCATGGCAGTTCTCCATGCTGGCCGCCTACATGTTTCTGCTGATCGTGCTGGGCTTCCCCATCAACT
TCCTCACGCTCTACGTCACCGTCCAGCACAAGAAGCTGCGCACGCCTCTCAACTACATCCTGCTCAACCT
AGCCGTGGCTGACCTCTTCATGGTCCTAGGTGGCTTCACCAGCACCCTCTACACCTCTCTGCATGGATAC
TTCGTCTTCGGGCCCACAGGATGCAATTTGGAGGGCTTCTTTGCCACCCTGGGCGGTGAAATTGCCCTGT
GGTCCTTGGTGGTCCTGGCCATCGAGCGGTACGTGGTGGTGTGTAAGCCCATGAGCAACTTCCGCTTCGG
GGAGAACCATGCCATCATGGGCGTTGCCTTCACCTGGGTCATGGCGCTGGCCTGCGCCGCACCCCCACTC
GCCGGCTGGTCCAGGTACATCCCCGAGGGCCTGCAGTGCTCGTGTGGAATCGACTACTACACGCTCAAGC
CGGAGGTCAACAACGAGTCTTTTGTCATCTACATGTTCGTGGTCCACTTCACCATCCCCATGATTATCAT
CTTTTTCTGCTATGGGCAGCTCGTCTTCACCGTCAPGGAGGCCGCTGCCCAGCAGCAGGAGTCAGCCACC
ACACAGAAGGCAGAGAAGGAGGTCACCCGCATGGTCATCATCATGGTCATCGCTTTCCTGATCTGCTGGG
TGCCCTACGCCAGCGTGGCATTCTACATCTTCACCCACCAGGGCTCCAACTTCGGTCCCATCTTCATGAC
CATCCCAGCGTTCTTTGCCAAGAGCGCCGCCATCTACAACCCTGTCATCTATATCATGATGAACAAGCAG
TTCCGGAACTGCATGCTCACCACCATCTGCTGCGGCAAGAACCCACTGGGTGACGATGAGGCCTCTGCTA
CCGTGTCCAAGACGGAGACGAGCCAGGTGGCCCCGGCCTAACCAAGAAAGCTTAAGTTTAAACCGCTGAT
CAGCCTCGACTGTGCCTTCTAGTTGCCAGCCATCTGTTGTTTGCCCCTCCCCCGTGCCTTCCTTGACCCT
GGAAGGTGCCACTCCCACTGTCCTTTCCTAATAAAATGAGGAAATTGCATCGCATTGTCTGAGTAGGTGT
CATTCTATTCTGGGGGGTGGGGTGGGGCAGGACAGCAAGGGGGAGGATTGGGAAGACAATAGCAGGCATG
CTGGGGATGCGGTGGGCTCTATGGC
```

Cone Rod Homeobox Containing Transcription Factor
(SEQ ID NO: 28)

```
AGAGGACTAAGCCACAGGTGAGGAGAAAGGGGGGGGGGGTCTGCTGAC
CCAGCAACACTCTTTCCTTCTGAGGCTTAAGAGCTATTAGCGTAGGTGA
CTCAGTCCCTAATCCTCCATTCAATGCCCTGTGACTGCCCCTGCTTC
```

CMV Enhancer
(SEQ ID NO: 29)
ACTAGTTATTAATAGTAATCAATTACGGGGTCATTAGTTCATAGCCCAT

ATATGGAGTTCCGCGTTACATAACTTACGGTAAATGGCCCGCCTGGCTG

ACCGCCCAACGACCCCCGCCCATTGACGTCAATAATGACGTATGTTCCC

ATAGTAACGCCAATAGGGACTTTCCATTGACGTCAATGGGTGGAGTATT

TACGGTAAACTGCCCACTTGGCAGTACATCAAGTGTATCATATGCCAAG

TACGCCCCCTATTGACGTCAATGACGGTAAATGGCCCGCCTGGCATTAT

GCCCAGTACATGACCTTATGGGACTTTCCTACTTGGCAGTACATCTACG

TATTAGTCATCGCTATTACCA

Neural retinal basic leucine zipper factor
(SEQ ID NO: 30)
TTTCTGCAGCGGGGATTAATATGATTATGAACACCCCCAATCTCCCAGA

TGCTGATTCAGCCAGGA

What is claimed is:

1. A nucleic acid comprising an intron derived from an MVM comprising SEQ ID NO:23 and a promoter.
2. The nucleic acid of claim 1, wherein the promoter is located 5' to the MVM intron.
3. An expression construct comprising the nucleic acid of claim 1.
4. A vector comprising the nucleic acid of claim 1.
5. A cell comprising the nucleic acid of claim 1.
6. The nucleic acid of claim 1, further comprising an enhancer.
7. The nucleic acid of claim 2, further comprising an enhancer.
8. An expression construct comprising the nucleic acid of claim 2.
9. An expression construct comprising the nucleic acid of claim 7.
10. A vector comprising the expression construct of claim 3.
11. A vector comprising the expression construct of claim 8.
12. A vector comprising the expression construct of claim 9.
13. A cell comprising the expression construct of claim 3.
14. A cell comprising the expression construct of claim 9.
15. A cell comprising the vector of claim 4.
16. A cell comprising the vector of claim 12.

* * * * *